United States Patent [19]

Makino et al.

[11] Patent Number: 5,500,406
[45] Date of Patent: Mar. 19, 1996

[54] IMINOSULFONYLUREA DIRIVATIVES AND HERBICIDES

[75] Inventors: Kenzi Makino; Shigeaki Akiyama; Hideaki Suzuki; Takeshi Nagaoka; Toshio Niki, all of Funabashi; Koichi Suzuki, Shiraoka; Tsutomu Nawamaki, Shiraoka; Shigeomi Watanabe, Shiraoka; Kimihiro Ishikawa, Shiraoka, all of Japan

[73] Assignee: Nissan Chemical Industries Ltd., Tokyo, Japan

[21] Appl. No.: 170,222

[22] PCT Filed: Jun. 25, 1992

[86] PCT No.: PCT/JP92/00808

§ 371 Date: Apr. 15, 1994

§ 102(e) Date: Apr. 15, 1994

[87] PCT Pub. No.: WO93/00336

PCT Pub. Date: Jul. 1, 1993

[30] Foreign Application Priority Data

| Jun. 28, 1991 | [JP] | Japan | 3-158106 |
| Aug. 14, 1991 | [JP] | Japan | 3-204294 |
| Sep. 25, 1991 | [JP] | Japan | 3-245876 |
| Dec. 3, 1991 | [JP] | Japan | 3-319422 |
| Jan. 20, 1992 | [JP] | Japan | 4-007397 |
| Mar. 24, 1992 | [JP] | Japan | 4-066277 |
| Apr. 30, 1992 | [JP] | Japan | 4-111494 |

[51] Int. Cl.$^6$ .......... C07D 403/12; C07D 413/12; H01N 43/54

[52] U.S. Cl. .......... 504/215; 540/601; 544/320; 544/321; 544/323; 544/324; 544/331; 544/332

[58] Field of Search .......... 504/215; 544/320, 544/323, 324, 331, 332, 321; 540/601

[56] References Cited

PUBLICATIONS

Chemical Abstracts, vol. 104, No. 13, Mar. 31, 1986, AN 109685u, JP–A–60 214 785, Oct. 28, 1985.

*Primary Examiner*—John M. Ford
*Attorney, Agent, or Firm*—Oblon, Spivak, McClelland, Maier & Neustadt

[57] ABSTRACT

The present invention provides novel iminosulfonylurea derivatives which are useful as herbicides with excellent activity and selectivity. These derivatives can be used to protect rice, wheat, corn, soybean, cotton and sugar beet from weeds.

18 Claims, No Drawings

IMINOSULFONYLUREA DIRIVATIVES AND HERBICIDES

TECHNICAL FIELD

This application is a 371 of PCT/JP92/00808 filed Jun. 25, 1992.

The present invention relates to novel iminosulfonylurea derivatives, and herbicides containing them as active ingredients.

BACKGROUND TECHNIQUE

It is indispensable to use herbicides to protect important crop plants such as rice, wheat, corn, soybean, cotton and sugar beet from weeds and thereby to increase the harvest. Especially in recent years, a selective herbicide is desired which is capable of selectively killing weeds without showing any phytotoxicity against crop plants when applied to the foliages of crop plants and weeds simultaneously in a field where such useful crop plants and weeds are coexistent. Further, with a view to avoiding environmental pollution and reducing the costs for transportation and application, researches and developments have been conducted for many years for compounds having high herbicidal effects at low doses. Some of the compounds having such properties are presently used as selective herbicides. However, there still exists a need for better new compounds having such properties.

As the prior art showing a chemical structure similar to that of the compounds of the present invention, Japanese Unexamined Patent Publications No. 15962/1983, No. 103371/1983, No. 126859/1983, No. 48973/1985, No. 214785/1985, No. 134377/1986, No. 151577/1989, No. 45473/1990, No. 91060/1990, No. 7284/1991 and No. 68562/1991, and U.S. Pat. Nos. 4,559,081, 4,592,776, 4,602,939, 4,622,065, 4,666,508, 4,696,695 and 4,741,762, disclose compounds having sulfonylurea bonded to a nitrogen atom. However, compounds having sulfonylurea bonded to a nitrogen atom of an imino structure like the compounds of the present invention have not been known at all, and they are novel compounds.

DISCLOSURE OF THE INVENTION

The present inventors have conducted extensive researches over years to develop selective herbicides for important crop plants and have studied herbicidal properties of many compounds with an aim to find out compounds having higher herbicidal activities as well as selectivity. As a result, it has been found that an iminosulfonylurea derivative of the formula (1) or an agriculturally suitable salt thereof:

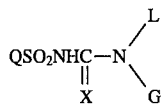

(1)

wherein Q is

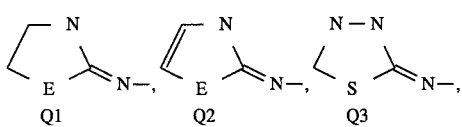

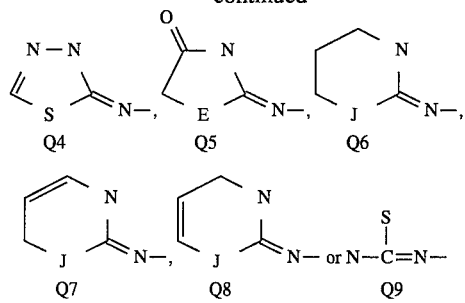

wherein in Q1, Q2 and Q5, E is a sulfur atom, an oxygen atom or a nitrogen atom mono-substituted by an optional substituent other than a hydrogen atom; in Q6, Q7 and Q8, J is a sulfur atom or an oxygen atom; in Q1 to Q8, a nitrogen atom in the ring of Q is substituted by an optional substituent other than a hydrogen atom, and a carbon atom in the ring of Q may be substituted by an optional substituent; and in Q9, the sulfur atom and the nitrogen atom on the carbon atom to which the imino group of Q is bonded, are substituted by optional substituents other than hydrogen atoms, wherein Q is preferably

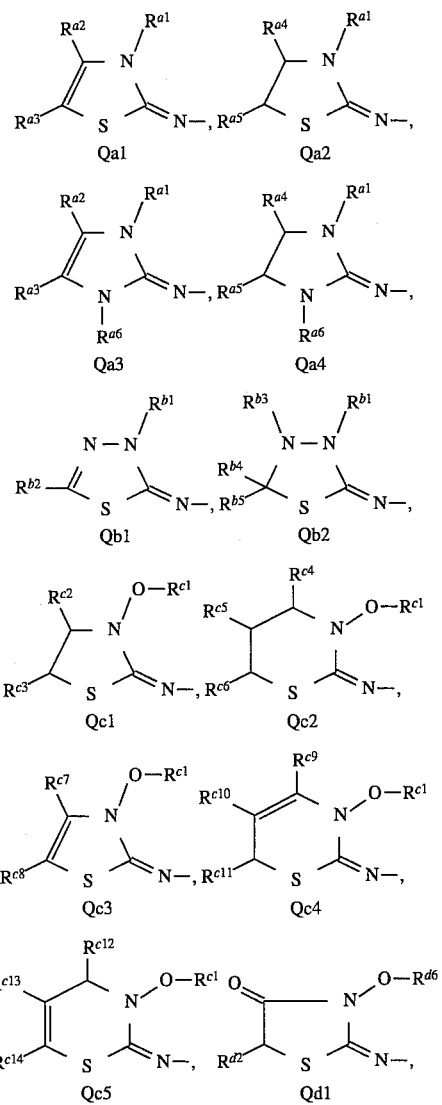

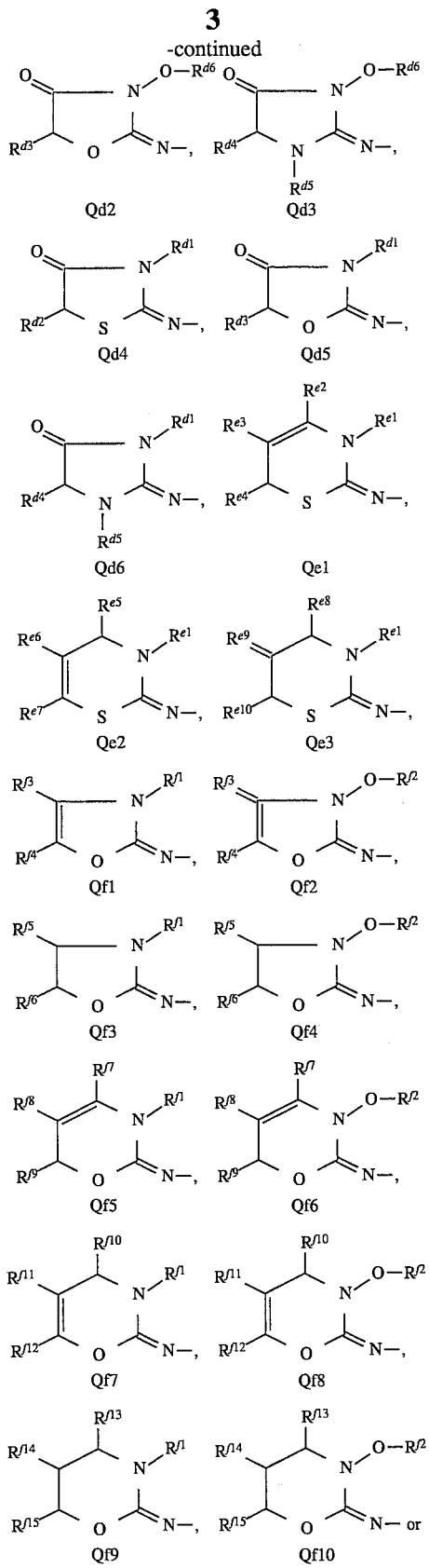

$R^{a1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-(C$_{2-7}$ alkylcarbonyl)-N-(C$_{1-6}$ alkoxy)amino group, a C$_{1-6}$ alkyl group substituted by an N-(C$_{1-6}$ alkylsulfonyl)-N-(C$_{1-6}$ alkyl)amino group, a C$_{1-6}$ alkyl group substituted by an N-(C$_{1-6}$ alkylsulfonyl)-N-(C$_{1-6}$ alkoxy)amino group, a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{2-7}$ alkenyl group substituted by a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{2-6}$ alkynyl group substituted by a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenoxy group (provided that such a phenoxy group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenylthio group (provided that such a phenylthio group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a benzylthio group (provided that the phenyl group of such a benzylthio group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), a C$_{1-6}$ alkyl group substituted by an amino group substituted by a C$_{1-4}$ alkylsulfonyl group, or a C$_{1-6}$ alkyl group substituted by an amino group substituted by a C$_{2-4}$ alkylcarbonyl group, each of $R^{a2}$ and $R^{a3}$ which are independent of each other, is a hydrogen atom, a C$_{1-6}$ alkyl group, a mono-, di- or poly-halogeno C$_{1-6}$ alkyl group, a C$_{1-6}$ alkoxy group, a mono-, di or poly-halogeno C$_{1-6}$ alkoxy group, a C$_{1-6}$ alkylthio group, a C$_{1-6}$ alkylsulfinyl group, a C$_{1-6}$ alkylsulfonyl group, a C$_{2-7}$ alkoxycarbonyl group, a C$_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), each of $R^{a4}$ and $R^{a5}$ which are independent of each other, is a hydrogen atom, a C$_{1-8}$ alkyl group, a C$_{2-8}$ alkenyl group, a C$_{2-8}$ alkynyl group, or a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), $R^{a6}$ is a C$_{1-8}$ alkyl group, a C$_{2-8}$ alkenyl group, a C$_{2-8}$ alkynyl group or a phenyl group (provided that such a phenyl group may be substituted by one or more substituents selected from the group consisting of a halogen atom, a trifluoromethyl group, a nitro group, a C$_{1-6}$ alkyl group, a C$_{1-6}$ alkoxy group and a C$_{2-7}$ alkoxycarbonyl group), $R^{b1}$ is a C$_{1-8}$ alkyl group, a C$_{3-7}$ cycloalkyl group, a C$_{1-6}$ alkyl group substituted by a C$_{3-7}$ cycloalkyl group, a C$_{3-7}$ cycloalkenyl group, a C$_{1-6}$ alkyl group substituted by a C$_{3-7}$ cycloalkenyl group, a C$_{2-8}$ alkenyl group, a C$_{2-8}$ alkynyl group, a C$_{1-6}$ alkyl group substituted by a C$_{1-6}$ alkoxy group, a C$_{1-6}$ alkyl group substituted by a C$_{2-6}$ alkenyloxy group, a C$_{1-6}$ alkyl group substituted by a C$_{2-6}$ alkynyloxy group, a C$_{1-6}$ alkyl group substituted by a mono-, di or poly-halogeno C$_{1-6}$ alkoxy group, a C$_{1-6}$ alkyl group substituted by a mono-, di- or poly-halogeno C$_{2-6}$ alkenyloxy group, a C$_{1-6}$ alkyl group substituted by a mono-, di- or poly-halogeno C$_{2-6}$ alkynyloxy group, a C$_{1-6}$ alkyl group substituted by a C$_{1-6}$ alkylthio group, a C$_{1-6}$ alkyl group substituted by a C$_{1-6}$ alkylsulfinyl group, a C$_{1-6}$ alkyl group substituted by a C$_{1-6}$ alkylsulfonyl group, a mono-, di- or poly-halogeno C$_{1-8}$ alkyl group, a mono-, di- or poly-halogeno C$_{2-8}$ alkenyl group, a mono-, di- or poly-halogeno C$_{2-8}$ alkynyl group, a C$_{1-6}$ alkyl group substituted by a cyano group, a C$_{2-6}$ alkenyl group substituted by a cyano group, a C$_{2-6}$ alkynyl group substituted by a cyano group, a C$_{1-6}$ alkyl group substituted by a nitro group, a C$_{2-6}$ alkenyl group substituted by a nitro group, a C$_{2-6}$ alkynyl group substituted by a nitro group, a C$_{1-6}$ alkyl group substituted by a C$_{2-7}$ alkoxycarbonyl group, a C$_{2-6}$ alkenyl group substituted by a C$_{2-7}$ alkoxycarbonyl group, a C$_{2-6}$ alkynyl group substituted by a C$_{2-7}$ alkoxycarbonyl group, a C$_{1-6}$ alkyl group substituted by a $C_{2-7}$ alkylcarbonyl group, a $C_{1-6}$ alkyl group substituted by a mono-, di- or polyhalogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, $R^{b2}$ is a hydrogen atom, a $C_{1-6}$ alkyl group, a mono-, di- or poly-halogeno $C_{1-6}$ alkyl group, a $C_{1-6}$ alkoxy group, a mono-, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{b3}$ is a $C_{1-6}$ alkyl group, a $C_{2-6}$ alkenyl group or a $C_{2-6}$ alkynyl group, $R^{b4}$ is a hydrogen atom, or a $C_{1-6}$ alkyl group, $R^{b5}$ is a hydrogen atom, or a $C_{1-6}$ alkyl group, $R^{c1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{c2}$, $R^{c3}$, $R^{c4}$, $R^{c5}$, $R^{c6}$, $R^{c11}$ and $R^{c12}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{c7}$, $R^{c8}$, $R^{c9}$, $R^{c10}$, $R^{c13}$ and $R^{c14}$ which are independent of one another, is a hydrogen atom, a $C_{1-6}$ alkyl group, a mono-, di- or poly-halogeno $C_{1-6}$ alkyl group, a $C_{1-6}$ alkoxy group, a mono, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{d2}$, $R^{d3}$ and $R^{d4}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d5}$ is a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d6}$ is a $C_{1-8}$ alkyl group, a $C_{2-8}$ alkenyl group, a $C_{2-8}$ alkynyl group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a $C_{1-6}$ alkyl group substituted by a $C_{1-6}$ alkoxy group, a $C_{1-6}$ alkyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a cyano group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{e1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{e2}$, $R^{e3}$, $R^{e6}$ and $R^{e7}$ which are independent of one another, is a hydrogen atom, a $C_{1-6}$ alkyl group, a mono-, di- or poly-halogeno $C_{1-6}$ alkyl group, a $C_{1-6}$ alkoxy group, a mono-, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{e4}$, $R^{e5}$, $R^{e8}$, $R^{e9}$ and $R^{e10}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{f1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, $R^{f2}$ is a $C_{1-8}$ alkyl group, a $C_{2-8}$ alkenyl group, a $C_{2-8}$ alkynyl group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a $C_{1-6}$ alkyl group substituted by a $C_{1-6}$ alkoxy group, a $C_{1-6}$ alkyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a cyano group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{f3}$, $R^{f4}$, $R^{f7}$, $R^{f8}$, $R^{f11}$ and $R^{f12}$ which are independent of one another, is a hydrogen atom, a $C_{1-6}$ alkyl group, a mono-, di- or poly-halogeno $C_{1-6}$ alkyl group, a $C_{1-6}$ alkoxy group, a mono-, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{f5}$, $R^{f6}$, $R^{f9}$, $R^{f10}$, $R^{f13}$, $R^{f14}$ and $R^{f15}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{g1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{g2}$ and $R^{g3}$ which are independent of each other, is a $C_{1-6}$ alkyl group, a $C_{2-6}$ alkenyl group, a $C_{2-6}$ alkynyl group, a mono-, di- or poly-halogeno $C_{1-6}$ alkyl group, a $C_{1-6}$ alkoxy group, a $C_{1-6}$ alkylsulfonyl group, a $C_{1-6}$ alkylsulfamoyl group, a di($C_{1-3}$ alkyl)sulfamoyl group, a $C_{2-7}$ alkoxycarbonyl group, a $C_{2-7}$ alkylcarbonyl group, a $C_{2-7}$ alkylcarbamoyl group, a di($C_{1-3}$ alkyl)carbamoyl group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a benzyl group (provided that the phenyl group of such a benzyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or $R^{g2}$ and $R^{g3}$ form a saturated 3- to 7-membered heterocyclic ring together with the nitrogen atom to which they are bonded, X is an oxygen atom or a sulfur atom, L is a hydrogen atom, a $C_{1-6}$ alkyl group, a $C_{2-6}$ alkenyl group or a $C_{2-6}$ alkynyl group, G is

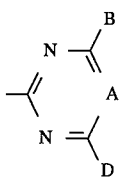

A is a CH group, or a nitrogen atom, and each of B and D which are independent of each other, is a $C_{1-4}$ alkyl group, a $C_{1-4}$ alkoxy group, a mono-, di- or poly-halogeno $C_{1-4}$ alkyl group, a mono-, di- or poly-halogeno $C_{1-4}$ alkoxy group, a halogen atom, a $C_{1-4}$ alkylamino group, or a di($C_{1-4}$ alkyl)amino group, (hereinafter referred to as the compound of the present invention) exhibits remarkably strong herbicidal activities against many weeds in soil treatment, in soil admixing treatment or in foliage treatment and at the same time has a high level of safety for important crop plants such as wheat, corn, cotton, soybean, sugar beet and rice, etc. The present invention has been accomplished on the basis of this discovery.

Examples for the substituents $R^{a1}$, $R^{a2}$, $R^{a3}$, $R^{a4}$, $R^{a5}$, $R^{a6}$, $R^{b1}$, $R^{b2}$, $R^{b3}$, $R^{b4}$, $R^{b5}$, $R^{c1}$, $R^{c2}$, $R^{c3}$, $R^{c4}$, $R^{c5}$, $R^{c6}$, $R^{c7}$, $R^{c8}$, $R^{c9}$, $R^{c10}$, $R^{c11}$, $R^{c12}$, $R^{c13}$, $R^{c14}$, $R^{d1}$, $R^{d2}$, $R^{d3}$, $R^{d4}$, $R^{d5}$, $R^{d6}$, $R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{f1}$, $R^{f2}$, $R^{f3}$, $R^{f4}$, $R^{f5}$, $R^{f6}$, $R^{f7}$, $R^{f8}$, $R^{f9}$, $R^{f10}$, $R^{f11}$, $R^{f12}$, $R^{f13}$, $R^{f14}$, $R^{f15}$, $R^{g1}$, $R^{g2}$, $R^{g3}$ L, B and D of the compound of the present invention are as follows. However, symbols have the following meanings.

Me: methyl group, Et: ethyl group, Pr-n: n-propyl group, Pr-iso: isopropyl group, Bu-n: n-butyl group, Bu-iso: isobutyl group, Bu-sec: sec-butyl group, Bu-tert: tert-butyl group, Pen-n: n-pentyl group, Hex-n: n-hexyl group, Hep-n: n-heptyl group, Pr-cyc: cyclopropyl group, Bu-cyc: cyclobutyl group, Pen-cyc: cyclopentyl group, Hex-cyc: cyclohexyl group, and Ph: phenyl group.

Specific examples for the substituents $R^{a1}$, $R^{b1}$, $R^{d1}$, $R^{e1}$ and $R^{f1}$ of the compound of the present invention Me, Et, Pr-n, Pr-iso, Bu-n, Bu-iso, Bu-sec, Bu-tert, Pen-n, Hex-n, Hep-n, Pr-cyc, Bu-cyc, Pen-cyc, Hex-cyc, $CH_2$Pr-cyc, $CH_2CH_2$ Pr-cyc, CHMe-Pr-cyc, $CH_2$CHMe-Pr-cyc, CHMe$CH_2$Pr-cyc, $CH_2$Bu-cyc, $CH_2CH_2$Bu-cyc, $CH_2$ Pen-cyc, $CH_2$Hex-cyc, $CH_2$ CH=$CH_2$, $CH_2$CH=CHMe, $CH_2$CH=CHEt, $CH_2$ $CH_2$CH=$CH_2$, $CH_2CH_2$CH=CHMe, $CH_2$CH=$CMe_2$, CHMeCH=$CH_2$, $CH_2$CMe=$CH_2$, $CH_2$CMe=CHMe, CHMeCH=CHMe, $CH_2$CMe=CHEt, $CH_2CH_2$CH=$CMe_2$, $CH_2$CMe=$CMe_2$, $CH_2$C≡CH, $CH_2$C≡CMe, $CH_2$C≡CEt, $CH_2CH_2$C≡CH, $CH_2CH_2$C≡CMe, CHMeC≡CH, CHMeC≡CMe, $CH_2$OMe, $CH_2$OEt, $CH_2$OPr-n, $CH_2$OPr-iso, $CH_2CH_2$OMe, $CH_2CH_2$OEt, $CH_2CH_2$OPr-n, CHMeOMe, CHMeOEt, $CH_2$CHMeOMe, $CH_2$CHMeOEt, $CH_2CH_2CH_2$OMe, $CH_2CH_2CH_2$OEt, $CH_2$O$CH_2$CH=$CH_2$, $CH_2$O$CH_2$CH=CHMe, $CH_2CH_2$O$CH_2$CH=$CH_2$, $CH_2CH_2$ O$CH_2$ CH=CHMe, $CH_2$O$CH_2$ C≡CH, $CH_2$ $CH_2$ O$CH_2$ C≡CMe, $CH_2$ OCHMeC≡CH, $CH_2$ O$CMe_2$C≡CH, $CH_2$ $CH_2$ O$CH_2$ C≡CH, $CH_2CH_2$ O$CH_2$ C≡CMe, $CH_2$ $CH_2$ OCHMeC≡CH, $CH_2$ $CH_2$O$CMe_2$C≡CH, $CH_2$ O$CHF_2$, $CH_2$ O$CF_3$, $CH_2$ O$CF_2CF_3$, $CH_2$ $CH_2$O$CHF_2$, $CH_2$ $CH_2$ O$CF_3$, $CH_2CH_2$ O$CF_2$ $CF_3$, $CH_2$O$CH_2CF_3$, $CH_2$ $CH_2$ O$CH_2$ $CF_3$, $CH_2$O$CH_2$ $CHF_2$, $CH_2$ $CH_2$ O$CH_2$ $CHF_2$, $CH_2$ O$CH_2$ $CH_2$ F, $CH_2$O$CH_2$ $CH_2$ Cl, $CH_2$ O$CH_2$ $CH_2$ Br, $CH_2$ $CH_2$ O$CH_2$ $CH_2$ F, $CH_2$ $CH_2$O$CH_2$ $CH_2$ Cl, $CH_2CH_2$ O$CH_2$ $CH_2$ Br, $CH_2$O$CH_2$CH=CHCl, $CH_2$ $CH_2$ O$CH_2$ CH=CHCl, $CH_2$O$CH_2$ CH=CHBr, $CH_2$ $CH_2$ O$CH_2$ CH=CHBr, $CH_2$ O$CH_2$ CF=$CF_2$, $CH_2CH_2$ O$CH_2$ CF=$CF_2$, $CH_2$ OCH=CHCl, $CH_2CH_2$O$CH$=CHCl, $CH_2$O$CF$=$CF_2$, $CH_2$ OCF=$CF_2$, $CH_2$ $CH_2$ OCF=$CF_2$, $CH_2CH_2$O$CF_2$CF=$CF_2$, $CH_2$O$CH_2$CH=$CF_2$, $CH_2CH_2$O$CH_2$CH=$CF_2$, $CH_2$O$CH_2$CH=$CHCF_3$, $CH_2CH_2$O$CH_2$CH=$CHCF_3$, $CH_2$O$CH_2$C≡CI, $CH_2$O$CH_2CH_2$C≡CI, $CH_2CH_2$O$CH_2$C≡CI, $CH_2$ O$CH_2$C≡$CCF_3$, $CH_2$O$CH_2$ C≡$CCF_3$, $CH_2$ O$CMe_2$C≡CI, $CH_2$ $CH_2$ O$CMe_2$ C≡CI, $CH_2$ O$CMe_2$C≡$CCF_3$, $CH_2$ $CH_2$ O$CMe_2$C≡$CCF_3$, $CH_2$SMe, $CH_2$SEt, $CH_2$ SPr-n, $CH_2$ $CH_2$SMe, $CH_2$ $CH_2$ SEt, $CH_2$ $CH_2$SPr-n, CHMeSMe, CHMeSEt, $CH_2$CHMeSMe, $CH_2$ CHMeSEt, $CH_2$ SOMe, $CH_2$ SOEt, $CH_2$SOPr-n, $CH_2$ $CH_2$ SOMe, $CH_2CH_2$ SOEt, $CH_2$ $CH_2$ SOPr-n, CHMeSOMe, CHMeSOEt, $CH_2$ CHMeSOMe, $CH_2$CHMeSOEt, $CH_2$$SO_2$Me, $CH_2$$SO_2$Et, $CH_2$$SO_2$Pr-n, $CH_2CH_2$$SO_2$Me, $CH_2CH_2$$SO_2$Et, $CH_2CH_2$$SO_2$Pr-n, CHMe$SO_2$Me, CHMe$SO_2$Et, $CH_2$CHMe$SO_2$Me, $CH_2$CHMe$SO_2$Et, $CH_2CH_2$F, $CH_2$$CHF_2$, $CH_2$$CF_3$, $CH_2CH_2$Cl, $CH_2CH_2$Br, $CH_2$$CCl_3$, $CH_2CH_2$$CF_3$, $CH_2CH_2$$CCl_3$, $CH_2CH_2CH_2$F, $CH_2CH_2CH_2$Cl, $CF_2$$CF_3$, $CH_2$$CF_2$$CF_3$, $CH_2$CH=CHCl, $CH_2$CH=CHBr, $CH_2$CH=$CF_2$, $CH_2$CF=$CF_2$, $CH_2$CH=$CHCF_3$, $CH_2$CH=CBrMe, $CH_2$CH=CClMe, $CH_2$CH=$C(CF_3)$Me, $CF_2$CF=$CF_2$, $CH_2$C≡CI, $CH_2$$CH_2$C≡CI, $CH_2$C≡$CCF_3$, $CH_2CH_2$C≡$CCF_3$, $CH_2$CN, $CH_2CH_2$CN, CHMeCN, $CH_2$CHMeCN, $CH_2$$CMe_2$CN, $CH_2$CH=CHCN, $CH_2$CH(CN)CH=$CH_2$, $CH_2$ C(CN)=$CH_2$, $CH_2$ C(CN)=CHMe, $CH_2$CH(CN)C≡CH, $CH_2$CH(CN)C≡C-Me, CH(CN)C≡CH, $CH_2$$NO_2$, $CH_2$ $CH_2$ $NO_2$, $CH_2$CHMe$NO_2$, $CH_2$ $CMe_2$$NO_2$, $CH_2$ $CH_2$ $CH_2$ $NO_2$, $CH_2$ CH=CHN$O_2$, $CH_2$CH($NO_2$)CH=$CH_2$, $CH_2$ C($NO_2$)=$CH_2$, $CH_2$ C($NO_2$)=CHMe, $CH_2$ CH($NO_2$)C≡CH, $CH_2$ CH($NO_2$)C≡CMe, $CH_2$ $CO_2$Me, $CH_2$ $CO_2$Et, $CH_2$ $CO_2$Pr-n, $CH_2$ $CO_2$Pr-iso, $CH_2$ $CO_2$ Bu-n, CHMe$CO_2$Me, CHMe$CO_2$Et, $CH_2$ $CH_2$ $CO_2$Me, $CH_2CH_2$ $CO_2$Et, $CH_2$ CHMe$CO_2$Me, $CH_2CH_2$ $CH_2$$CO_2$Me, $CH_2$ CH=$CHCO_2$Me, $CH$=$CHCO_2$Et, $CH_2$CH=$CHCO_2$Pr-n, $CH_2$ CH=$CMeCO_2$Me, $CH_2$CMe=$CHCO_2$Me, CHMeCH=$CHCO_2$Me, CHMeCH=$CHCO_2$Et, $CH_2$ $CH_2$ CH=$CHCO_2$Me, $CH_2$CH=$CHCH_2$ $CO_2$Me, $CH_2$ C≡$CCO_2$Me, $CH_2$C≡$CCO_2$Et, $CH_2$ C≡$CCO_2$Pr-n, $CH_2CH_2$ C≡$CCO_2$Me, $CH_2$ CHMeC≡$CCO_2$Me, $CH_2$ CMeC≡$CCO_2$Me, $CH_2$ C≡CCH $CO_2$Me, $CH_2$COMe, $CH_2$ COEt, $CH_2$COPr-n, $CH_2$ $CH_2$ COMe, $CH_2CH_2$ COEt, $CH_2$ CHMeCOMe, $CH_2$ $CMe_2$COMe, $CH_2$ COC$F_3$, $CH_2$COC$Cl_3$, $CH_2CH_2$ COC$F_3$, $CH_2$COC$H_2$ $CF_3$, $CH_2$COC$H_2$$CHF_2$, $CH_2$COC$H_2$ $CHCl_2$, $CH_2$COC$H_2$F, $CH_2$ COC$H_2$Cl, $CH_2$ COC$H_2$Br, $CH_2$ COCH=$CH_2$, $CH_2$ CH=CHMe, $CH_2$ COCH$_2$ CH=$CH_2$, $CH_2$ $CH_2$ COCH=$CH_2$, $CH_2$ $CH_2$ COCH=CHMe, $CH_2$COC≡CH, $CH_2$ COC≡CMe, $CH_2$ COC$H_2$ C≡CH, $CH_2$ $CH_2$ COC≡CH, $CH_2CH_2$ COC≡CMe, $CH_2$COC$H_2$ OMe, $CH_2$COC$H_2$OEt, $CH_2$COC$H_2CH_2$ OMe, $CH_2$COC$H_2$ $CH_2$ OEt, $CH_2$ $CH_2$ COC$H_2$OMe, $CH_2CH_2$COC$H_2$ OEt, $CH_2$COC$H_2$ SMe, $CH_2$COC$H_2$ SEt, $CH_2$ COC$H_2CH_2$SMe, $CH_2$COC$H_2CH_2$ SEt, $CH_2CH_2$COC$H_2$SMe, $CH_2CH_2$COC$H_2$SEt, $CH_2$COC$H_2$SOMe, $CH_2$COC$H_2$SOEt, $CH_2$ COC$H_2CH_2$ SOMe, $CH_2$COC$H_2$ $CH_2$SOEt, $CH_2$ $CH_2$ COC$H_2$SOMe, $CH_2CH_2$COC$H_2$SOEt, $CH_2CH_2$COC$H_2$$SO_2$Me, $CH_2CH_2$COC$H_2$$SO_2$Et, $CH_2$COC$H_2$ $SO_2$Me, $CH_2$ COC$H_2$$SO_2$Et, $CH_2CH_2$ COC$H_2$$SO_2$Me, $CH_2CH_2$COC$H_2$$SO_2$Et, $CH_2$ CH=CHCOMe, $CH_2$CH=CHCOEt, CHMeCH=CHCOMe, CHMeCH=CHCOEt, $CH_2$ C≡CCOMe, $CH_2$C≡CCOEt, CHMeC≡CCOMe, CHMeC≡CCOEt, $CH_2$$SO_2$NHMe, $CH_2$ $SO_2$NHEt, $CH_2$$SO_2$NHPr-n, $CH_2$ $CH_2SO_2$NHMe, $CH_2$ $CH_2$ $SO_2$NHEt, $CH_2$ $CH_2SO_2$NHPr-n, $CH_2SO_2$NHOMe, $CH_2SO_2$NHOEt, $CH_2SO_2$NHOPr-n, $CH_2CH_2SO_2$NHOMe, $CH_2$ $CH_2SO_2$NHOEt, $CH_2CH_2SO_2$NHOPr-n, $CH_2SO_2$ $NMe_2$, $CH_2SO_2$NMeEt, $CH_2SO_2$$NEt_2$, $CH_2CH_2$ $SO_2NMe_2$, $CH_2CH_2SO_2$NMeEt, $CH_2$ $CH_2SO_2$$NEt_2$, $CH_2SO_2$N(OMe)Me, $CH_2$ $SO_2$N(OMe)Et, $CH_2SO_2$N(OEt)Me, $CH_2CH_2$ $SO_2$N(OMe)Me, $CH_2$ $CH_2$ $SO_2$N(OMe)Et, $CH_2$ $CH_2SO_2$N(OEt)Me, $CH_2SO_2$N(OEt)Et, $CH_2CH_2SO_2$N(OEt)Et, $CH_2$ CONHMe, $CH_2$CONHEt, $CH_2$CONHPr-n, $CH_2CH_2$ CONHMe, $CH_2$ $CH_2$ CONHEt, $CH_2CH_2$CONHPr-n, $CH_2$CON$Me_2$, $CH_2$CONMeEt, $CH_2$CON$Et_2$, $CH_2CH_2$CON$Me_2$, $CH_2$ $CH_2$ CONMeEt, CH$_2$ CH$_2$ CONEt$_2$, CH$_2$ CONHOMe, CH$_2$CONHOEt, CH$_2$ CONHOPr-n, CH$_2$ CH$_2$ CONHOMe, CH$_2$CH$_2$ CONHOEt, CH$_2$CH$_2$CONHOPr-n, CH$_2$ CON(OMe)Me, CH$_2$ CON(OMe)Et, CH$_2$ CON(OEt)Me, CH$_2$ CH$_2$ CON(OMe)Me, CH$_2$CH$_2$CON(OMe)Et, CH$_2$ CH$_2$ CON(OEt)Me, CH$_2$ CH$_2$ CON(OEt)Et, CH$_2$ CON(OEt)Et, CH$_2$ NHMe, CH$_2$ NHEt, CH$_2$ NHPr-n, CH$_2$ CH$_2$ NHMe, CH$_2$ CH$_2$ NHEt, CH$_2$ CH$_2$ NHPr-n, CH$_2$ CHMeNHMe, CH$_2$CHMeNHEt, CH$_2$ CHMeNHPr-n, CH$_2$ CH$_2$ CH$_2$ NHMe, CH$_2$ NHOMe, CH$_2$ NHOEt, CH$_2$ NHOPr-n, CH$_2$ CH$_2$NHOMe, CH$_2$ CH$_2$ NHOEt, CH$_2$ CH$_2$NHOPr-n, CH$_2$ CHMeNHOMe, CH$_2$ CHMeNHOEt, CH$_2$CHMeNHOPr-n, CH$_2$ NMe$_2$, CH$_2$ NMeEt, CH$_2$ NMePr-n, CH$_2$ CH$_2$ NMe$_2$, CH$_2$ CH$_2$ NMeEt, CH$_2$CH$_2$ NMePr-n, CH$_2$ NEt$_2$, CH$_2$CH$_2$NEt$_2$, CH$_2$ N(OMe)Et, CH$_2$ N(OMe)Et, CH$_2$ N(OEt)Me, CH$_2$ N(OEt)Et, CH$_2$CH$_2$N(OMe)Me, CH$_2$CH$_2$N(OMe)Et, CH$_2$ CH$_2$N(OEt)Me, CH$_2$CH$_2$N(OEt)Et, CH$_2$ NMeCOMe, CH$_2$NEtCOMe, CH$_2$NMeCOEt, CH$_2$ CH$_2$ NMeCOMe, CH$_2$ CH$_2$ NEtCOMe, CH$_2$CH$_2$ NMeCOEt, CH$_2$N(OMe)COMe, CH$_2$N(OEt)COMe, CH$_2$ N(OMe)COEt, CH$_2$CH$_2$N(OMe)COMe, CH$_2$CH$_2$N(OEt)COMe, CH$_2$ CH$_2$N(OMe)COEt, CH$_2$NMeSO$_2$Me, CH$_2$NEtSO$_2$Me, CH$_2$ NMeSO$_2$Et, CH$_2$ CH$_2$ NMeSO$_2$Me, CH$_2$ CH$_2$ NEtSO$_2$Me, CH$_2$ CH$_2$ NMeSO$_2$Et, CH$_2$ N(OMe)SO$_2$Me, CH$_2$ N(OEt)SO$_2$Me, CH$_2$ N(OMe)SO$_2$Et, CH$_2$ CH$_2$ N(OMe)SO$_2$Me, CH$_2$ CH$_2$ N(OEt)SO$_2$Me, CH$_2$ CH$_2$ N(OMe)SO$_2$Et, CH$_2$ Ph, CH$_2$ CH$_2$ Ph, CH$_2$ CH$_2$ CH$_2$ Ph, CHMePh, CH$_2$ CHMePh, CH$_2$ CMe$_2$Ph, CH$_2$ CH=CHPh, CH$_2$ CH=CMePh, CHMeCH=CHPh, CH$_2$ CMe=CMePh, CHMeCMe=CMePh, CH$_2$ C≡CPh, CHMeC≡CPh, CH$_2$CMe$_2$C≡CPh, CH$_2$CH$_2$OPh, CH$_2$CHMeOPh, CH$_2$CMe$_2$OPh, CH$_2$OPh, CH$_2$CH$_2$SPh, CH$_2$CHMeSPh, CH$_2$CMe$_2$SPh, CH$_2$SPh, CH$_2$ CH$_2$ SOPh, CH$_2$ CHMeSOPh, CH$_2$ CMe$_2$SOPh, CH$_2$ CH$_2$SO$_2$Ph, CH$_2$ CMe$_2$SO$_2$Ph, CH$_2$ OCH$_2$ Ph, CH$_2$ CH$_2$ OCH$_2$ Ph, CH$_2$ CHMeOCH$_2$ Ph, CH$_2$ SCH$_2$ Ph, CH$_2$ CH$_2$ SCH$_2$ Ph, CH$_2$ CHMeSCH$_2$ Ph, CH$_2$ SOCH$_2$ Ph, CH$_2$ CH$_2$SOCH$_2$ Ph, CH$_2$CHMeSOCH$_2$ Ph, CH$_2$ SO$_2$CH$_2$ Ph, CH$_2$ CH$_2$ SO$_2$CH$_2$ Ph, CHMeSO$_2$CH$_2$ Ph, CH$_2$ COPh, CH$_2$ CH$_2$ COPh, CHMeCOPh, CH$_2$ COCH$_2$ Ph, CH$_2$ CH$_2$ COCH$_2$Ph, CHMeCOCH$_2$ Ph, CH$_2$ C(Cl)=CH$_2$, Ph, CH$_2$ SOPh, CH$_2$ SO$_2$Ph, CH$_2$ Ph-4-OMe, CH$_2$Ph-4-Cl, CH$_2$C(Br)=CH$_2$, CH$_2$ C(Cl)=CHCl, CH$_2$ CH=C(I)Me, CH$_2$ CH=CHI, CH$_2$ C(F)=CHMe, CH$_2$ C(F)=CHBr, CH=CBr$_2$, CH$_2$ CH=CHF, CH$_2$ C(Cl)=CHMe, CH$_2$ C(F)=CHBr, CH$_2$C(Br)=CHCl, CH$_2$ C(Br)=CCl$_2$, CH$_2$CH=CHCH$_2$ F, CH$_2$ C(I)=CH$_2$, CH$_2$ C(Br)=C(Cl)Me, CH$_2$C(I)=CHMe, CH$_2$C(Cl)=CCl$_2$, CH$_2$CH=CHCCl$_3$, CH$_2$C(Br)=CHMe, CH$_2$ C(Cl)=CHF, CH$_2$ C(Br)=CHF, CH$_2$ CH=C(Cl)Br, CH$_2$ C(F)=C(Cl)CF$_3$, CH$_2$C(Cl)=C(Cl)Me, CH$_2$ C(Br)=CHBr, CH$_2$CH=C(F)CF$_2$Cl, CH$_2$C(Br)=C(Br)Me, CH$_2$CH=C(F)CF$_3$, CH$_2$ CH=CCl$_2$, CH$_2$ C(F)=CH$_2$, CH$_2$CH=CHCCl$_3$, CH$_2$ CH=C(F)Cl, CH$_2$ C(Cl)=C(F)Cl, CH$_2$ C(F)=CCl$_2$, CH$_2$ C(Cl)=CF$_2$, CH$_2$ C(CF$_3$)=CH$_2$, CMe$_2$CH=CH$_2$, CMe$_2$C=CH, CH$_2$CH$_2$ I, CH$_2$C=C-CN, CH$_2$NHBu-n, CH$_2$ NHSO$_2$Me, CH$_2$NHSO$_2$Et, CH$_2$CH$_2$NHSO$_2$Me, CH$_2$CH$_2$ NHSO$_2$Et, CH$_2$ NHCOMe, CH$_2$ NHCOEt, CH$_2$ CH$_2$ NHCOMe, CH$_2$CH$_2$NHCOEt Specific examples for the substituents $R^{a2}$ and $R^{a3}$ of the compound of the present invention H, Me, Et, Pr-n, Pr-iso, Bu-n, Bu-iso, Bu-sec, Bu-tert, CH$_2$F, CHF$_2$, CF$_3$, CH$_2$Cl, CH$_2$ Br, CH$_2$CF$_3$, CH$_2$ CH$_2$F, CH$_2$ CH$_2$Cl, CH$_2$ CH$_2$Br, CF$_2$ CF$_3$, OMe, OEt, OPr-n, OPr-iso, OCF$_3$, OCH$_2$CF$_3$, SMe, SEt, SPr-n, SPr-iso, SOMe, SOEt, SOPr-n, SOPr-iso, SO$_2$Me, SO$_2$Et, SO$_2$Pr-n, SO$_2$Pr-iso, CO$_2$Me, CO$_2$Et, CO$_2$Pr-n, CO$_2$Pr-iso, CO$_2$Bu-n, COMe, COEt, COPr-n, COPr-iso, COBu-n, F, Cl, Br, I, NO$_2$, CN, Ph Specific examples for the substituents $R^{a4}$ and $R^{a5}$ of the compound of the present invention H, Me, Et, Pr-n, Pr-iso, Bu-n, Bu-iso, Bu-sec, Bu-tert, Pen-n, Hex-n, Hep-n, CH=CH$_2$, CH=CHMe, CH=CHEt, CMe=CH$_2$, CH=CMe$_2$, CMe=CHMe, CMe=CMe$_2$, CH$_2$CH=CH$_2$, CH$_2$CH$_2$ CHMe, CHMeCH=CH$_2$, CHMeCH=CHMe, CMe$_2$CH=CH$_2$, CMe$_2$CH=CHMe, C≡CH, C≡CMe, C≡CEt, CH$_2$ C≡CH, CH$_2$ C≡CMe, CHMeC≡CH, CHMeC≡CMe, CMe$_2$C≡CH, CMe$_2$C≡CMe, Ph Specific examples for the substituent $R^{a6}$ of the compound of the present invention Me, Et, Pr-n, Pr-iso, Bu-n, Bu-iso, Bu-sec, Bu-tert, Pen-n, Hex-n, Hep-n, CH$_2$CH=CH$_2$, CH$_2$ CH=CHMe, CH$_2$CH=CHEt, CH$_2$CH$_2$CH=CH$_2$, CH$_2$ CH$_2$ CH=CHMe, CH$_2$ CH=CMe$_2$, CHMeCH=CH$_2$, CH$_2$CMe=CH$_2$, CH$_2$CMe=CHMe, CHMeCH=CHMe, CH$_2$ CMe=CHEt, CH$_2$CH$_2$ CH=CMe$_2$, CH$_2$CMe=CMe$_2$, CH$_2$ C≡CH, CH$_2$ C≡CMe, CH$_2$ C≡CEt, CH$_2$ CH$_2$ C≡CH, CH$_2$ CH$_2$ C≡CMe, CHMeC≡CH, CHMeC≡CMe, CMe$_2$C≡CH, CMe$_2$C≡CMe, Ph Specific examples for the substituent $R^{b2}$ of the compound of the present invention H, Me, Et, Pr-n, Pr-iso, Bu-n, Bu-iso, Bu-sec, Bu-tert, CH$_2$F, CHF$_2$, CF$_3$, CH$_2$Cl, CH$_2$Br, CH$_2$ CF$_3$, CH$_2$CH$_2$F, CH$_2$CH$_2$Cl, CH$_2$ CH$_2$ Br, CF$_2$CF$_3$, OMe, OEt, OPr-n, OPr-iso, OCF$_3$, OCH$_2$ CF$_3$, SMe, SEt, SPr-n, SPr-iso, SOMe, SOEt, SOPr-n, SOPr-iso, SO$_2$Me, SO$_2$Et, SO$_2$Pr-n, SO$_2$Pr-iso, CO$_2$Me, CO$_2$Et, CO$_2$Pr-n, CO$_2$Pr-iso, CO$_2$Bu-n, COMe, COEt, COPr-n, COPr-iso, COBu-n, F, Cl, Br, I, NO$_2$, CN, Ph Specific examples for the substituent $R^{b3}$ of the compound of the present invention Me, Et, Pr-n, Pr-iso, Bu-n, Bu-iso, Bu-sec, Bu-tert, Pen-n, Hex-n, CH$_2$CH=CH$_2$, CH$_2$ CH=CHMe, CH$_2$CH=CHEt, CH$_2$ CH$_2$ CH=CH$_2$, CH$_2$ CH$_2$ CH=CHMe, CH$_2$ CH=CMe$_2$, CHMeCH=CH$_2$, CH$_2$CMe=CH$_2$, CH$_2$CMe=CHMe, CHMeCH=CHMe, CH$_2$ CMe=CHEt, CH$_2$CH$_2$CH=CMe$_2$, CH$_2$CMe=CME$_2$, CH$_2$ C≡CH, CH$_2$ C≡CMe, CH$_2$ C≡CEt, CH$_2$ CH$_2$ C≡CH, CH$_2$ CH$_2$ C≡CMe, CHMeC≡CH, CHMeC≡CMe Specific examples for the substituent $R^{b4}$ of the compound of the present invention H, Me, Et, Pr-n, Pr-iso, Bu-n, Pen-n, Hex-n Specific examples for the substituent $R^{b5}$ of the compound of the present invention H, Me, Et, Pr-n, Pr-iso, Bu-n, Pen-n, Hex-n Specific examples for the substituent $R^{c1}$ of the compound of the present invention Me, Et, Pr-n, Pr-iso, Bu-n, Bu-iso, Bu-sec, Bu-tert, Pen-n, Hex-n, Hep-n, Pr-cyc, Bu-cyc, Pen-cyc, Hex-cyc, CH$_2$ Pr-cyc, CH$_2$CH$_2$Pr-cyc, CHMe-Pr-cyc, CH$_2$CHMe-Pr-cyc, CHMeCH$_2$Pr-cyc, CH$_2$Bu-cyc, CH$_2$CH$_2$Bu-cyc, CH$_2$Pen-cyc, CH$_2$Hex-cyc,

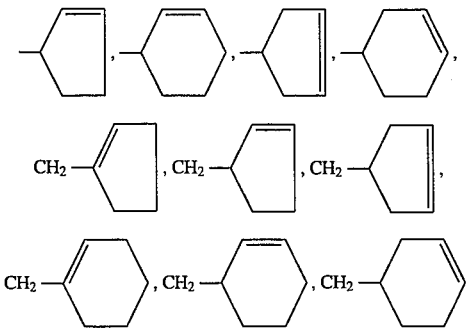

CH$_2$CH=CH$_2$, CH$_2$ CH=CHMe, CH$_2$ CH=CHEt, CH$_2$ CH$_2$ CH=CH$_2$, CH$_2$CH$_2$CH=CHMe, CH$_2$CH=CMe$_2$, CHMeCH=CH$_2$, CH$_2$ CMe=CH$_2$, CH$_2$ CMe=CHMe, CHMeCH=CHMe, CH$_2$ CMe=CHEt, CH$_2$ CH$_2$ CH=CMe$_2$, CH$_2$ CMe=CMe$_2$, CH$_2$ C≡CH, CH$_2$ C≡CMe, CH$_2$C≡CEt, CH$_2$CH$_2$C≡CH, CH$_2$ CH$_2$ C≡CMe, CHMeC≡CH, CHMeC≡CMe, CH$_2$OMe, CH$_2$ OEt, CH$_2$OPr-n, CH$_2$OPr-iso, CH$_2$ CH$_2$ OMe, CH$_2$CH$_2$ OEt, CH$_2$ CH$_2$OPr-n, CHMeOMe, CHMeOEt, CH$_2$CHMeOMe, CH$_2$ CHMeOEt, CH$_2$CH$_2$ CH$_2$OMe, CH$_2$ CH$_2$CH$_2$OEt, CH$_2$ OCH$_2$CH=CH$_2$, CH$_2$OCH$_2$CH=CHMe, CH$_2$ CH$_2$ OCH$_2$ CH=CH$_2$, CH$_2$CH$_2$ OCH$_2$CH=CHMe, CH$_2$ OCH$_2$ C≡CH, CH$_2$OCH$_2$C≡CMe, CH$_2$ OCHMeC≡CH, CH$_2$ OCMe$_2$C≡CH, CH$_2$ CH$_2$OCH$_2$C≡CH, CH$_2$CH$_2$OCH$_2$C≡CMe, CH$_2$CH$_2$ OCHMeC≡CH, CH$_2$OCMe$_2$C≡CH, CH$_2$ OCHF$_2$, CH$_2$OCF$_3$, CH$_2$ OCF$_2$CF$_3$, CH$_2$ CH$_2$ OCHF$_2$, CH$_2$ CH$_2$ OCF$_3$, CH$_2$ CH$_2$ OCF$_2$C$_3$, CH$_2$ OCH$_2$ CF$_3$, CH$_2$ CH$_2$ OCH$_2$CF$_3$, CH$_2$ OCH$_2$CHF$_2$, CH$_2$CH$_2$ OCH$_2$CHF$_2$, CH$_2$OCH$_2$CH$_2$F, CH₂OCH₂ CH₂ Cl, CH₂ OCH₂CH₂Br, CH₂ CH₂ OCH₂CH₂F, CH₂ CH₂OCH₂ CH₂ Cl, CH₂CH₂OCH₂ CH₂Br, CH₂ OCH₂CH=CHCl, CH₂CH₂OCH₂CH=CHCl, CH₂OCH₂ CH=CHBr, CH₂ CH₂OCH₂CH=CHBr, CH₂OCH₂ CF=CF₂, CH₂ CH₂ OCH₂ CF=CF₂, CH₂OCH=CHCl, CH₂CH₂ OCH=CHCl, CH₂ OCF=CF₂, CH₂CH₂ OCF=CF₂, CH₂ OCF₂CF=CF₂, CH₂CH₂OCF₂CF=CF₂, CH₂ OCH₂ CH=CF₂, CH₂CH₂ OCH₂ CH=CF₂, CH₂ OCH₂ CH=CHCF₃, CH₂ CH₂ OCH₂CH=CHCF₃, CH₂ OCH₂ C≡CI, CH₂ OCH₂ CH₂ C≡CI, CH₂ CH₂ OCH₂ C≡CI, CH₂ OCH₂ C≡CCF₃, CH₂ CH₂ OCH₂ C≡CCF₃, CH₂ OCMe₂ C≡CI, CH₂ CH₂ OCMe₂C≡CI, CH₂ OCMe₂C≡CCF₃, CH₂ CH₂ OCMe₂ C≡CCF₃, CH₂ SMe, CH₂ SEt, CH₂SPr-n, CH₂ CH₂ SMe, CH₂ CH₂ SEt, CH₂ CH₂ SPr-n, CHMeSMe, CHMeSEt, CH₂ CHMeSMe, CH₂ CHMeSEt, CH₂ SOMe, CH₂ SOEt, CH₂ SOPr-n, CH₂ CH₂SOMe, CH₂ CH₂ SOEt, CH₂ CH₂ SOPr-n, CHMeSOMe, CHMeSOEt, CH₂ CHMeSOMe, CH₂ CHMe-SOEt, CH₂SO₂Me, CH₂ SO₂Et, CH₂ SO₂Pr-n, CH₂CH₂ SO₂ Me, CH₂ CH₂ SO₂Et, CH₂CH₂SO₂Pr-n, CHMeSO₂Me, CHMeSO₂Et, CH₂ CHMeSO₂Me, CH₂ CHMeSO₂Et, CH₂ CH₂ F, CH₂ CHF₂, CH₂ CF₃, CH₂ CH₂ Cl, CH₂ CH₂ Br, CH₂ CCl₃, CH₂ CH₂ CF₃, CH₂ CH₂ CCl₃, CH₂ CH₂ CH₂ F, CH₂ CH₂ CH₂ Cl, CF₂CF₃, CH₂ CF₂CF₃, CH₂ CH=CHCl, CH₂ CH=CHBr, CH₂ CH=CF₂, CH₂ CF=CF₂, CH₂ CH=CHCF₃, CH₂ CH=CBrMe, CH₂ CH=CClMe, CH₂ CH=C(CF₃)Me, CF₂CF=CF₂, CH₂C≡CI, CH₂ CH₂ C≡CI, CH₂C≡CCF₃, CH₂CH₂C≡CCF₃, CH₂ CN, CH₂CH₂CN, CHMeCN, CH₂CHMeCN, CH₂ CMe₂ CN, CH₂CH=CHCN, CH₂ CH(CN)CH=CH₂, CH₂ C(CN)=CH₂, CH₂ C(CN)=CHMe, CH₂ CH(CN)C≡CH, CH₂ CH(CN)C≡C-Me, CH(CN)C≡CH, CH₂NO₂, CH₂CH₂ NO₂, CH₂ CHMeNO₂, CH₂ CMe₂NO₂, CH₂CH₂CH₂NO₂, CH₂ CH=CHNO₂, CH₂CH(NO₂)CH=CH₂, CH₂C(NO₂)=CH₂, CH₂ C(NO₂)=CHMe, CH₂CH(NO₂)C≡CH, CH₂CH(NO₂)C≡CMe, CH₂ CO₂Me, CH₂CO₂Et, CH₂ CO₂Pr-n, CH₂CO₂Pr-iso, CH₂ CO₂ Bu-n, CHMeCO₂Me, CHMeCO₂Et, CH₂CH₂CO₂Me, CH₂CH₂CO₂Et, CH₂ CHMeCO₂Me, CH₂CH₂CH₂CO₂Me, CH₂CH=CHCO₂Me, CH₂ CH=CHCO₂Et, CH₂ CH=CHCO₂Pr-n, CH₂ CH=CMeCO₂Me, CH₂ CMe=CHCO₂Me, CHMeCH=CHCO₂Me, CHMeCH=CHCO₂Et, CH₂ CH₂ CH=CHCO₂Me, CH₂CH=CHCH₂ CO₂Me, CH₂C≡CCO₂Me, CH₂C≡CCO₂Et, CH₂ C≡CCO₂ Pr-n, CH₂CH₂C≡CCO₂Me, CH₂ CHMeC≡CCO₂Me, CH₂CMe₂C≡CCO₂Me, CH₂ C≡CCH₂CO₂Me, CH₂ COMe, CH₂ COEt, CH₂ COPr-n, CH₂CH₂ COMe, CH₂ CH₂COEt, CH₂ CHMeCOMe, CH₂CMe₂COMe, CH₂ COCF₃, CH₂COCCl₃, CH₂CH₂COCF₃, CH₂COCH₂CF₃, CH₂ COCH₂CHF₂, CH₂COCH₂ CHCl₂, CH₂ COCH₂F, CH₂COCH₂Cl, CH₂ COCH₂ Br, CH₂COCH=CH₂, CH₂COCH=CHMe, CH₂COCH₂CH=CH₂, CH₂ CH₂ COCH=CH₂, CH₂CH₂ COCH=CHMe, CH₂ COC≡CH, CH₂ COC≡CMe, CH₂COCH₂ C≡CH, CH₂CH₂ COC≡CH, CH₂ CH₂ COC≡CMe, CH₂COCH₂OMe, CH₂ COCH₂ OEt, CH₂COCH₂ CH₂ OMe, CH₂ COCH₂ CH₂OEt, CH₂ CH₂COCH₂ OMe, CH₂ CH₂ COCH₂ OEt, CH₂ COCH₂ SMe, CH₂ COCH₂ SEt, CH₂ COCH₂ CH₂ SMe, CH₂COCH₂ CH₂ SEt, CH₂ CH₂COCH₂SMe, CH₂ CH₂ COCH₂SEt, CH₂ COCH₂SOMe, CH₂COCH₂ SOEt, CH₂COCH₂ CH₂SOMe, CH₂COCH₂CH₂SOEt, CH₂CH₂COCH₂SOMe, CH₂ CH₂ COCH₂ SOEt, CH₂COCH₂SO₂Me, CH₂COCH₂ SO₂Et, CH₂ COCH₂ CH₂ SO₂Me, CH₂COCH₂ CH₂ SO₂Et, CH₂ CH₂ COCH₂ SO₂Me, CH₂CH₂COCH₂ SO₂Et, CH₂CH=CHCOMe, CH₂CH=CHCOEt, CHMeCH=CHCOMe, CHMeCH=CHCOEt, CH₂ C≡CCOMe, CH₂C≡CCOEt, CHMeC≡CCOMe, CHMeC≡CCOEt, CH₂SO₂NHMe, CH₂SO₂NHEt, CH₂ SO₂NHPr-n, CH₂ CH₂SO₂NHMe, CH₂CH₂ SO₂NHEt, CH₂ CH₂ SO₂NHPr-n, CH₂SO₂NHOMe, CH₂ SO₂NHOEt, CH₂SO₂ NHOPr-n, CH₂ CH₂SO₂NHOMe, CH₂CH₂ SO₂NHOEt, CH₂ CH₂SO₂NHOPr-n, CH₂ SO₂NMe₂, CH₂SO₂NMeEt, CH₂ SO₂NEt₂, CH₂ CH₂SO₂NMe₂, CH₂CH₂SO₂NMeEt, CH₂ CH₂SO₂NEt₂, CH₂SO₂N(OMe)Me, CH₂ SO₂N(OMe)Et, CH₂ SO₂N(OEt)Me, CH₂CH₂SO₂ N(OMe)Me, CH₂CH₂ SO₂N(OMe)Et, CH₂CH₂SO₂N(OEt)Me, CH₂SO₂N(OEt)Et, CH₂CH₂ SO₂ N(OEt)Et, CH₂CONHMe, CH₂CONHEt, CH₂ CONHPr-n, CH₂CH₂CONHMe, CH₂CH₂CONHEt, CH₂CH₂ CONHPr-n, CH₂ CONMe₂, CH₂ CONMeEt, CH₂ CONEt₂, CH₂CH₂CONMe₂, CH₂CH₂CONMeEt, CH₂ CH₂CONEt₂, CH₂ CONHOMe, CH₂ CONHOEt, CH₂CONHOPr-n, CH₂ CH₂ CONHOMe, CH₂ CH₂ CONHOEt, CH₂ CH₂ CONHOPr-n, CH₂ CON(OMe)Me, CH₂CON(OMe)Et, CH₂ CON(OEt)Me, CH₂CH₂ CON(OMe)Me, CH₂CH₂ CON(OMe)Et, CH₂CON(OEt)Me, CH₂ CON(OEt)Et, CH₂ CH₂ CON(OEt)Et, CH₂NHMe, CH₂NHEt, CH₂ NHPr-n, CH₂ CH₂NHMe, CH₂ CH₂ NHEt, CH₂CH₂NHPr-n, CH₂ CHMeNHMe, CH₂ CHMeNHEt, CH₂ CHMeNHPr-n, CH₂ CH₂CH₂ NHMe, CH₂NHOMe, CH₂ NHOEt, CH₂ NHOPr-n, CH₂CH₂ NHOMe, CH₂ NHOEt, CH₂CH₂NHOPr-n, CH₂CHMeNHOMe, CH₂CHMeNHOEt, CH₂CHMeNHOPr-n, CH₂NMe₂, CH₂NMeEt, CH₂NMePr-n, CH₂CH₂ NMe₂, CH₂ CH₂ NMeEt, CH₂CH₂ NMePr-n, CH₂ NEt₂, CH₂ CH₂ NEt₂, CH₂N(OMe)Me, CH₂N(OMe)Et, CH₂N(OEt)Me, CH₂ N(OEt)Et, CH₂ CH₂ N(OMe)Me, CH₂ CH₂ N(OMe)Et, CH₂CH₂N(OEt)Me, CH₂ CH₂ N(OEt)Et, CH₂ NMeCOMe, CH₂ NEtCOMe, CH₂ NMeCOEt, CH₂ CH₂ NMeCOMe, CH₂ CH₂ NEtCOMe, CH₂ CH₂ NMeCOEt, CH₂ N(OMe)COMe, CH₂ N(OEt)COMe, CH₂ N(OMe)COEt, CH₂CH₂ N(OMe)COMe, CH₂CH₂N(OEt)COMe, CH₂ CH₂ N(OMe)COEt, CH₂ NMeSO₂ Me, CH₂ NEtSO₂Me, CH₂ NMeSO₂Et, CH₂ CH₂ NMeSO₂ Me, CH₂ CH₂ NEtSO₂Me, CH₂ CH₂ NMeSO₂Et, CH₂N(OMe)SO₂Me, CH₂ N(OEt)SO₂ Me, CH₂N(OMe)SO₂Et, CH₂CH₂ N(OMe)SO₂Me, CH₂ CH₂N(OEt)SO₂ Me, CH₂CH₂ N(OMe)SO₂Et, CH₂ Ph, CH₂ CH₂ Ph, CH₂CH₂ CH₂ Ph, CHMePh, CH₂ CHMePh, CH₂ CMe₂Ph, CH₂CH=CHPh, CH₂ CH=CMePh, CHMeCH=CHPh, CH₂ CMe=CMePh, CHMeCMe=CMePh, CH₂ C≡CPh, CHMeC≡CPh, CH₂ CMe₂C≡CPh, CH₂ CH₂ OPh, CH₂ CHMeOPh, CH₂ CMe₂OPh, CH₂ OPh, CH₂ CH₂ SPh, CH₂ CHMeSPh, CH₂ CMe₂ SPh, CH₂ SPh, CH₂CH₂SOPh, CH₂CHMeSOPh, CH₂CMe₂SOPh, CH₂ CH₂ SO₂Ph, CH₂ CHMeSO₂Ph, CH₂ CMe₂SO₂Ph, CH₂OCH₂ Ph, CH₂CH₂OCH₂Ph, CH₂CHMeOCH₂Ph, CH₂ SCH₂ Ph, CH₂CH₂SCH₂Ph, CH₂CHMeSCH₂Ph, CH₂SOCH₂Ph, CH₂CH₂SOCH₂Ph, CH₂CHMeSOCH₂Ph, CH₂SO₂CH₂ Ph, CH₂ CH₂ SO₂CH₂ Ph, CH₂CHMeSO₂CH₂ Ph, CH₂ COPh, CH₂ CH₂ COPh, CHMeCOPh, CH₂COCH₂Ph, CH₂ CH₂COCH₂Ph, CHMeCOCH₂Ph, CH₂ C(Cl)=CH₂, Ph, CH₂SOPh, CH₂SO₂Ph, CH₂C(Cl)=CHCl, CH₂CH=C(I)Me, CH₂ CH=CHI, CH₂C(F)=CHCl, CH₂CH=CBr₂, CH₂ CH=CHF, CH₂ C(Cl)=CHMe, CH₂C(F)=CHBr, CH₂C(Br)=CHCl, CH₂C(Br)=CCl₂, CH₂ CH=CHCH₂F, CH₂C(Br)=CH₂, CH₂ C(I)=CH₂, CH₂C(Br)=C(Cl)Me, CH₂C(I)=CHMe, CH₂ C(Cl)=CCl₂, CH₂CH=CHCCl₃, CH₂C(Br)=CHMe, CH₂C(Cl)=CHF, CH₂ C(Br)=CHF, CH₂ CH=C(Cl)Br, CH₂ C(F)=C(Cl)CF₃, CH₂C(Cl)=C(Cl)Me, CH₂ C(Br)=CHBr, CH₂

CH=C(F)CF₂Cl, CH₂ C(Br)=C(Br)Me, CH₂ CH=C(F)CF₃, CH₂ CH=CCl₂, CH₂ C(F)=CH₂, CH₂ CH=CHCCl₃, CH₂ CH=C(F)Cl, CH₂ C(Cl)=C(F)Cl, CH₂ C(F)=CCl₂, CH₂ C(Cl)=CF₂, CH₂ C(CF₃)=CH₂, CMe₂CH=CH₂, CMe₂C≡CH, CH₂ CH₂I, CH₂ C≡C-CN, CH₂NHBu-n, CH₂ NHSO₂Me, CH₂ NHSO₂Et, CH₂ CH₂ NHSO₂Me, CH₂ CH₂NHSO₂Et, CH₂ NHCOMe, CH₂NHCOEt, CH₂ CH₂ NHCOMe, CH₂ CH₂ NHCOEt

Specific examples for the substituents $R^{c2}$, $R^{c3}$, $R^{c4}$, $R^{c5}$, $R^{c6}$, $R^{c11}$, and $R^{c12}$ of the compound of the present invention H, Me, Et, Pr-n, Pr-iso, Bu-n, Bu-iso, Bu-sec, Bu-tert, Pen-n, Hex-n, Hep-n, CH=CH₂, CH=CHMe, CMe=CH₂, CH=CMe₂, CH=CHEt, CMe=CHMe, CMe=CMe₂, CH₂CH=CH₂, CH₂ CH=CHMe, CHMeCH=CH₂, CMe₂CH=CH₂, C≡CH, C≡CMe, C≡CEt, CH₂ C≡CH, CHMeC≡CH, CMe₂C≡CH, Ph Specific examples for the substituents $R^{c7}$, $R^{c8}$, $R^{c9}$, $R^{c10}$, $R^{c13}$, and $R^{c14}$ of the compound of the present invention H, Me, Et, Pr-n, Pr-iso, Bu-n, Bu-iso, Bu-sec, Bu-tert, Pen-n, Hex-n, CH₂ F, CHF₂, CF₃, CH₂Cl, CH₂ Br, CH₂CF₃, CH₂CH₂F, CH₂ CH₂ Cl, CH₂ CH₂Br, CF₂CF₃, OMe, OEt, OPr-n, OPr-iso, OCF₃, OCH₂ CF₃, SMe, SEt, SPr-n, SPr-iso, SOMe, SOEt, SOPr-n, SOPr-iso, SO₂Me, SO₂Et, SO₂Pr-n, SO₂Pr-iso, CO₂Me, CO₂Et, CO₂Pr-n, CO₂Pr-iso, CO₂Bu-n, COMe, COEt, COPr-n, COPr-iso, COBu-n, F, Cl, Br, I, NO₂, CN, Ph Specific examples for the substituents $R^{d2}$, $R^{d3}$ and $R^{d4}$ of the compound of the present invention H, Me, Et, Pr-n, Pr-iso, Bu-n, Bu-iso, Bu-sec, Bu-tert, Pen-n, Hex-n, Hep-n, CH=CH₂, CH=CHMe, CH=CHEt, CMe=CH₂, CH=CMe₂, CMe=CHMe, CMe=CMe₂, CH₂CH=CH₂, CH₂ CH=CHMe, CHMeCH=CH₂, CHMeCH=CHMe, CMe₂CH=CH₂, CMe₂CH=CHMe, C≡CH, C≡CMe, C≡CEt, CH₂ C≡CH, CH₂ C≡CMe, CHMeC≡CH, CHMeC≡CMe, CMe₂C≡CH, CMe₂C≡CMe, Ph Specific examples for the substituent $R^{d5}$ of the compound of the present invention Me, Et, Pr-n, Pr-iso, Bu-n, Bu-iso, Bu-sec, Bu-tert, Pen-n, Hex-n, Hep-n, CH₂CH=CH₂, CH₂CH=CHMe, CH₂ CH=CHEt, CH₂CH₂CH=CH₂, CH₂ CH₂CH=CHMe, CH₂CH=CMe₂, CHMeCH=CH₂, CH₂CMe=CH₂, CH₂CMe=CHMe, CHMeCH=CHMe, CH₂ CMe=CHEt, CH₂CH₂ CH=CMe₂, CH₂ CMe=CMe₂, CMe₂CH=CH₂, CMe₂CH=CHMe, CH₂ C≡CH, CH₂ C≡CMe, CH₂ C≡CEt, CH₂CH₂ C≡CH, CH₂ CH₂C≡CMe, CHMeC≡CH, CHMeC≡CMe, CMe₂C≡CH, CMe₂C≡CMe, Ph Specific examples for the substituents $R^{d6}$ and $R^{f2}$ of the compound of the present invention Me, Et, Pr-n, Pr-iso, Bu-n, Bu-iso, Bu-sec, Bu-tert, Pen-n, Hex-n, Hep-n, CH₂CH=CH₂, CH₂ CH=CHMe, CH₂CH=CHEt, CH₂CH₂ CH=CH₂, CH₂CH₂CH=CHMe, CH₂ CH=CMe₂, CHMeCH=CH₂, CH₂ CMe=CH₂, CH₂ CMe=CHMe, CHMeCH=CHMe, CH₂ CMe=CHEt, CH₂CH₂CH=CMe₂, CH₂ CMe=CMe₂, CMe₂CH=CH₂, CMe₂CH=CHMe, CH₂C≡CH, CH₂C≡CMe, CH₂C≡CEt, CH₂CH₂ C≡CH, CH₂CH₂ C≡CMe, CHMeC≡CH, CHMeC≡CMe, CMe₂C≡CH, CMe₂C≡CMe, CH₂ SMe, CH₂SEt, CH₂SPr-n, CH₂ SBu-n, CH₂CH₂ SMe, CH₂CH₂SEt, CH₂CH₂SPr-n, CH₂SOMe, CH₂ SOEt, CH₂ SOPr-n, CH₂CH₂SOMe, CH₂CH₂SOEt, CH₂CH₂SOPr-n, CH₂ SO₂Me, CH₂SO₂Et, CH₂SO₂Pr-n, CH₂SO₂Bu-n, CH₂CH₂SO₂Me, CH₂CH₂SO₂Et, CH₂CH₂SO₂Pr-n, CH₂OMe, CH₂ OEt, CH₂ OPr-n, CH₂ OBu-n, CH₂ CH₂OMe, CH₂CH₂OEt, CH₂CH₂ OPr-n, CH₂ CO₂Me, CH₂ CO₂Et, CH₂CO₂Pr-n, CH₂ CO₂Bu-n, CHMeCO₂Me, CHMeCO₂Et, CHMeCO₂Pr-n, CMe₂CO₂Me, CMe₂CO₂Et, CH₂ COMe, CH₂ COEt, CH₂ COPr-n, CH₂COBu-n, CH₂ CH₂COMe, CH₂ CH₂ COEt, CH₂ CH₂ COPr-n, CH₂ CN, CH₂ CH₂CN, CH₂CH₂ CH₂ CN, Ph, CH₂ Ph, CH₂ CH₂ Ph, CHMePh Specific examples for the substituents $R^{e2}$, $R^{e3}$, $R^{e6}$ and $R^{e7}$ of the compound of the present invention H, Me, Et, Pr-n, Pr-iso, Bu-n, Bu-iso, Bu-sec, Bu-tert, Pen-n, Hex-n, CH₂F, CHF₂, CF₃, CH₂Cl, CH₂Br, CH₂CF₃, CH₂CH₂ F, CH₂CH₂Cl, CH₂CH₂Br, CF₂CF₃, OMe, OEt, OPr-n, OPr-iso, OCF₃, OCH₂CF₃, SMe, SEt, SPr-n, SPr-iso, SOMe, SOEt, SOPr-n, SOPr-iso, SO₂Me, SO₂Et, SO₂Pr-n, SO₂Pr-iso, CO₂Me, CO₂Et, CO₂Pr-n, CO₂Pr-iso, CO₂Bu-n, COMe, COEt, COPr-n, COPr-iso, COBu-n, F, Cl, Br, I, NO₂, CN, Ph Specific examples for the substituents $R^{e4}$, $R^{e5}$, $R^{e8}$, $R^{e9}$ and $R^{e10}$ of the compound of the present invention H, Me, Et, Pr-n, Pr-iso, Bu-n, Bu-iso, Bu-sec, Bu-tert, Pen-n, Hex-n, CH=CH₂, CH=CHMe, CH=CHEt, CMe=CH₂, CH=CMe₂, CMe=CHMe, CMe=CMe₂, CH₂ CH=CH₂, CH₂ CH=CHMe, CHMeCH=CH₂, CHMeCH=CHMe, CMe₂CH=CH₂, CMe₂CH=CHMe, C≡CH, C≡CMe, C≡CEt, CH₂ C≡CH, CH₂ C≡CMe, CHMeC≡CH, CHMeC≡CMe, CMe₂C≡CH, CMe₂C≡CMe, Ph Specific examples for the substituents $R^{f3}$, $R^{f4}$, $R^{f7}$, $R^{f8}$, $R^{f11}$ and $R^{f12}$ of the compound of the present invention H, Me, Et, Pr-n, Pr-iso, Bu-n, Bu-iso, Bu-sec, Bu-tert, CH₂ F, CHF₂, CF₃, CH₂ Cl, CH₂Br, CH₂CF₃, CH₂CH₂F, CH₂CH₂Cl, CH₂ CH₂Br, CF₂CF₃, OMe, OEt, OPr-n, OPr-iso, OCF₃, OCH₂CF₃, SMe, SEt, SPr-n, SPr-iso, SOMe, SOEt, SOPr-n, SOPr-iso, SO₂Me, SO₂Et, SO₂Pr-n, SO₂Pr-iso, CO₂Me, CO₂Et, CO₂Pr-n, CO₂Pr-iso, CO₂Bu-n, COMe, COEt, COPr-n, COPr-iso, COBu-n, F, Cl, Br, I, NO₂, CN, Ph Specific examples for the substituents $R^{f5}$, $R^{f6}$, $R^{f9}$, $R^{f10}$, $R^{f13}$, $R^{f14}$ and $R^{f15}$ of the compound of the present invention H, Me, Et, Pr-n, Pr-iso, Bu-n, Bu-iso, Bu-sec, Bu-tert, Pen-n, Hex-n, Hep-n, CH=CH₂, CH=CHMe, CH=CHEt, CMe=CH₂, CH=CMe₂, CMe=CHMe, CMe=CMe₂, CH₂CH=CH₂, CH₂CH=CHMe, CHMeCH=CH₂, CHMeCH=CHMe, CMe₂CH=CH₂, CMe₂CH=CHMe, C≡CH, C≡CMe, C≡CEt, CH₂C≡CH, CH₂C≡CMe, CHMeC≡CH, CHMeC≡CMe, CMe₂C≡CH, CMe₂C≡CMe, Ph Specific examples for the substituent $R^{g1}$ of the compound of the present invention Me, Et, Pr-n, Pr-iso, Bu-n, Bu-iso, Bu-sec, Bu-tert, Pen-n, Hex-n, Hep-n, Pr-cyc, Bu-cyc, Pen-cyc, Hex-cyc, CH₂ Pr-cyc, CH₂CH₂Pr-cyc, CHMe-Pr-cyc, CH₂ CHMe-Pr-cyc, CHMeCH₂Pr-cyc, CH₂ Bu-cyc, CH₂CH₂Bu-cyc, CH₂Pen-cyc, CH₂ Hex-cyc,

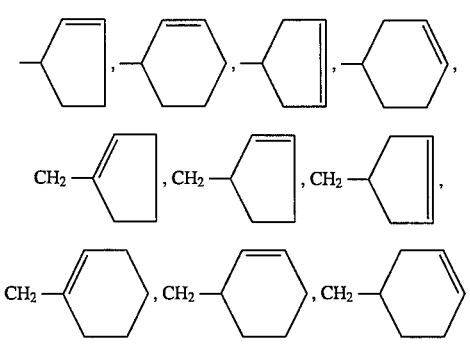

CH₂ CH=CH₂, CH₂CH=CHMe, CH₂CH=CHEt,

CH₂CH₂CH=CH₂, CH₂CH₂CH=CHMe, CH₂CH=CMe₂, CHMeCH=CH₂, CH₂CMe=CH₂, CH₂CMe=CHMe, CHMeCH=CHMe, CH₂ CMe=CHEt, CH₂CH₂ CH=CMe₂, CH₂ CMe=CMe₂, CH₂ C≡CH, CH₂ C≡CMe, CH₂ C≡CEt, CH₂ CH₂ C≡CH, CH₂ CH₂ C≡CMe, CHMeC≡CH, CHMeC≡CMe, CH₂ OMe, CH₂ OEt, CH₂ OPr-n, CH₂ OPr-iso, CH₂ CH₂ OMe, CH₂ CH₂ OEt, CH₂ CH₂ OPr-n, CHMeOMe, CHMeOEt, CH₂CHMeOMe, CH₂ CHMeOEt, CH₂ CH₂ CH₂ OMe, CH₂ CH₂ CH₂OEt, CH₂ OCH₂ CH=CH₂, CH₂ OCH₂ CH=CHMe, CH₂ CH₂ OCH₂CH=CH₂, CH₂ CH₂ OCH₂CH=CHMe, CH₂ OCH₂ C≡CH, CH₂ OCH₂ C≡CMe, CH₂ OCHMeC≡CH, CH₂ OCMe₂C≡CH, CH₂ CH₂ OCH₂ C≡CH, CH₂ CH₂ OCH₂ C≡CMe, CH₂CH₂ OCHMeC≡CH, CH₂ CH₂ OCMe₂C≡CH, CH₂ OCHF₂, CH₂ OCF₃, CH₂ OCF₂CF₃, CH₂ CH₂ OCHF₂, CH₂ CH₂ OCF₃, CH₂ CH₂ OCF₂ CF₃, CH₂ OCH₂ CF₃, CH₂CH₂ OCH₂CF₃, CH₂ OCH₂ CHF₂, CH₂ CH₂ OCH₂ CHF₂, CH₂ OCH₂CH₂ F, CH₂ OCH₂CH₂Cl, CH₂ OCH₂ CH₂ Br, CH₂ CH₂OCH₂CH₂ F, CH₂ CH₂ OCH₂ CH₂ Cl, CH₂ CH₂ OCH₂ CH₂ Br, CH₂ OCH₂ CH=CHCl, CH₂ CH₂ OCH₂ CH=CHCl, CH₂ OCH₂ CH=CHBr, CH₂ CH₂ OCH₂CH=CHBr, CH₂ OCH₂ CF=CF₂, CH₂ CH₂ OCH₂ CF=CF₂, CH₂ OCH=CHCl, CH₂ CH₂ OCH=CHCl, CH₂ OCF=CF₂, CH₂CH₂ OCF=CF₂, CH₂ OCF₂ CF=CF₂, CH₂ CH₂ OCF₂ CF=CF₂, CH₂OCH₂ CH=CF₂, CH₂OCH₂CH=CF₂, CH₂ OCH₂ CH=CHCF₃, CH₂OCH₂ OCH₂ CH=CHCF₃, CH₂OCH₂C≡CI, CH₂ OCH₂ CH₂ C≡CI, CH₂CH₂, OCH₂ C≡CI, CH₂ OCH₂ C≡CCF₃, CH₂ CH₂ OCH₂ C≡CCF₃, CH₂ OCMe₂C≡CI, CH₂ CH₂ OCMe₂C≡CI, CH₂OCMe₂C≡CCF₃, CH₂CH₂OCMe₂C≡CCF₃, CH₂SMe, CH₂ SEt, CH₂SPr-n, CH₂ CH₂SMe, CH₂CH₂SEt, CH₂ CH₂SPr-n, CHMeSMe, CHMeSEt, CH₂ CHMeSMe, CH₂ CHMeSEt, CH₂ SOMe, CH₂ SOEt, CH₂ SOPr-n, CH₂CH₂ SOMe, CH₂ CH₂ SOEt, CH₂ CH₂SOPr-n, CHMeSOMe, CHMeSOEt, CH₂ CHMeSOMe, CH₂ CHMeSOEt, CH₂ SO₂Me, CH₂SO₂Et, CH₂ SO₂Pr-n, CH₂ CH₂SO₂Me, CH₂ CH₂ SO₂Et, CH₂CH₂ SO₂Pr-n, CHMeSO₂Me, CHMeSO₂Et, CH₂ CHMeSO₂Me, CH₂ CHMeSO₂Et, CH₂ CH₂F, CH₂CHF₂, CH₂ CF₃, CH₂ CH₂Cl, CH₂ CH₂ Br, CH₂ CCl₃, CH₂ CH₂CF₃, CH₂CH₂ CCl₃, CH₂ CH₂ CH₂ F, CH₂ CH₂ CH₂ Cl, CF₂CF₃, CH₂ CF₂CF₃, CH₂CH=CHCl, CH₂ CH=CHBr, CH₂ CH=CF₂, CH₂ CF=CF₂, CH₂ CH=CHCF₃, CH₂ CH=CBrMe, CH₂ CH=CClMe, CH₂ CH=C(CF₃)Me, CF₂CF=CF₂, CH₂ C≡CI, CH₂ CH₂ C≡CI, CH₂C≡CCF₃, CH₂ CH₂ C≡CCF₃, CH₂ CN, CH₂ CH₂ CN, CHMeCN, CH₂ CHMeCN, CH₂ CMe₂CN, CH₂CH=CHCN, CH₂ CH(CN)CH=CH₂, CH₂ C(CN)=CH₂, CH₂ C(CN)=CHMe, CH₂ CH(CN)C≡CH, CH₂ CH(CN)C≡CMe, CH(CN)C≡CH, CH₂ NO₂, CH₂CH₂ NO₂, CH₂CHMeNO₂, CH₂CMe₂NO₂, CH₂ CH₂ CH₂ NO₂, CH₂ CH=CHNO₂, CH₂ CH(NO₂)CH=CH₂, CH₂C(NO₂)=CH₂, CH₂ C(NO₂)=CHMe, CH₂ CH(NO₂)C≡CH, CH₂ CH(NO₂)C≡CMe, CH₂ CO₂Me, CH₂CO₂Et, CH₂ CO₂Pr-n, CH₂ CO₂Pr-iso, CH₂ CO₂Bu-n, CHMeCO₂ Me, CHMeCO₂Et, CH₂ CH₂ CO₂Me, CH₂ CH₂ CO₂Et, CH₂CHMeCO₂Me, CH₂CH₂ CH₂ CO₂Me, CH₂ CH=CHCO₂Me, CH₂ CH=CHCO₂Et, CH₂CH=CHCO₂Pr-n, CH₂ CH=CMeCO₂Me, CH₂ CMe=CHCO₂Me, CHMeCH=CHCO₂Me, CHMeCH=CHCO₂Et, CH₂ CH₂CH=CHCO₂Me, CH₂ CH=CHCH₂ CO₂Me, CH₂ C≡CCO₂Me, CH₂ C≡CCO₂Et, CH₂C≡CCO₂Pr-n, CH₂CH₂ C≡CCO₂Me, CH₂ CHMeC≡CCO₂Me, CH₂ CMe₂C≡CCO₂Me, CH₂C≡CCH₂CO₂Me, CH₂COMe, CH₂ COEt, CH₂ COPr-n, CH₂CH₂ COMe, CH₂CH₂ COEt, CH₂CHMeCOMe, CH₂CMe₂COMe, CH₂COCF₃, CH₂ COCCl₃, CH₂ CH₂ COCF₃, CH₂COCH₂ CF₃, CH₂COCH₂CHF₂, CH₂COCH₂ CHCl₂, CH₂ COCH₂F, CH₂ COCH₂ Cl, CH₂COCH₂Br, CH₂ COCH=CH₂, CH₂ COCH=CHMe, CH₂COCH₂CH=CH₂, CH₂CH₂ COCH=CH₂, CH₂CH₂COCH=CHMe, CH₂COC≡CH, CH₂ COC≡CMe, CH₂ COCH₂ C≡CH, CH₂ CH₂ COC≡CH, CH₂CH₂ COC≡CMe, CH₂COCH₂ OMe, CH₂COCH₂ OEt, CH₂ COCH₂ CH₂ OMe, CH₂ COCH₂CH₂ OEt, CH₂ CH₂ COCH₂OMe, CH₂ CH₂ COCH₂OEt, CH₂ COCH₂ SMe, CH₂ COCH₂SEt, CH₂ COCH₂CH₂SMe, CH₂COCH₂ CH₂ SEt, CH₂ CH₂COCH₂ SMe, CH₂CH₂COCH₂SEt, CH₂COCH₂SOMe, CH₂ COCH₂SOEt, CH₂COCH₂ SOMe, CH₂ COCH₂CH₂SOEt, CH₂CH₂COCH₂SOMe, CH₂CH₂COCH₂SOEt, CH₂ COCH₂ SO₂Me, CH₂ COCH₂SO₂Et, CH₂ COCH₂CH₂ SO₂Me, CH₂ COCH₂CH₂ SO₂ Et, CH₂ CH₂ COCH₂ SO₂Me, CH₂CH₂ COCH₂SO₂Et, CH₂ CH=CHCOMe, CH₂ CH=CHCOEt, CHMeCH=CHCOMe, CHMeCH=CHCOEt, CH₂ C≡CCOMe, CH₂C≡CCOEt, CHMeC≡CCOMe, CHMeC≡CCOEt, CH₂SO₂ NHMe, CH₂SO₂ NHEt, CH₂ SO₂NHPr-n, CH₂CH₂ SO₂NHMe, CH₂ CH₂ SO₂ NHEt, CH₂CH₂SO₂NHPr-n, CH₂ SO₂ NHOMe, CH₂SO₂ NHOEt, CH₂SO₂NHOPr-n, CH₂ CH₂SO₂ NHOMe, CH₂ CH₂ SO₂ NHOEt, CH₂CH₂SO₂NHOPr-n, CH₂ SO₂ NMe₂, CH₂SO₂NMeEt, CH₂ SO₂ NEt₂, CH₂ CH₂SO₂NMe₂, CH₂CH₂ SO₂NMeEt, CH₂ CH₂ SO₂NEt₂, CH₂SO₂N(OMe)Me, CH₂SO₂N(OMe)Et, CH₂SO₂N(OEt)Me, CH₂CH₂SO₂N(OMe)Me, CH₂CH₂ SO₂ N(OMe)Et, CH₂CH₂ SO₂N(OEt)Me, CH₂SO₂N(OEt)Et, CH₂CH₂SO₂ N(OEt)Et, CH₂CONHMe, CH₂CONHEt, CH₂ CONHPr-n, CH₂CH₂ CONHMe, CH₂ CH₂ CONHEt, CH₂ CH₂ CONHPr-n, CH₂ CONMe₂, CH₂CONMeEt, CH₂CONEt₂, CH₂CH₂CONMe₂, CH₂CH₂ CONMeEt, CH₂CH₂CONEt₂, CH₂CONHOMe, CH₂CONHOEt, CH₂CONHOPr-n, CH₂ CH₂CONHOMe, CH₂CH₂CONHOEt, CH₂ CH₂ CONHOPr-n, CH₂CON(OMe)Me, CH₂CON(OMe)Et, CH₂ CON(OEt)Me, CH₂CH₂CON(OMe)Me, CH₂ CH₂ CON(OMe)Et, CH₂CH₂ CON(OEt)Me, CH₂CON(OEt)Et, CH₂ CH₂CON(OEt)Et, CH₂ NHMe, CH₂ NHEt, CH₂ NHPr-n, CH₂CH₂ NHMe, CH₂CH₂NHEt, CH₂CH₂NHPr-n, CH₂CHMeNHMe, CH₂CHMeNHEt, CH₂CHMeNHPr-n, CH₂CH₂CH₂NHMe, CH₂NHOMe, CH₂NHOEt, CH₂ NHOPr-n, CH₂CH₂ NHOMe, CH₂CH₂NHOEt, CH₂CH₂ NHOPr-n, CH₂ CHMeNHOMe, CH₂CHMeNHOEt, CH₂ CHMeNHOPr-n, CH₂NMe₂, CH₂NMeEt, CH₂NMePr-n, CH₂ CH₂ NMe₂, CH₂CH₂NMeEt, CH₂ CH₂ NMePr-n, CH₂NEt₂, CH₂CH₂NEt₂, CH₂N(OMe)Me, CH₂N(OMe)Et, CH₂ N(OEt)Me, CH₂ N(OEt)Et, CH₂ CH₂N(OMe)Me, CH₂ CH₂ N(OMe)Et, CH₂CH₂ N(OEt)Me, CH₂ CH₂N(OEt)Et, CH₂NMeCOMe, CH₂NEtCOMe, CH₂NMeCOEt, CH₂CH₂ NMeCOMe, CH₂CH₂NEtCOMe, CH₂CH₂NMeCOEt, CH₂N(OMe)COMe, CH₂N(OEt)COMe, CH₂ N(OMe)COEt, CH₂CH₂N(OMe)COMe, CH₂CH₂N(OEt)COMe, CH₂ CH₂N(OMe)COEt, CH₂NMeSO₂Me, CH₂NEtSO₂Me, CH₂ NMeSO₂Et, CH₂CH₂NMeSO₂Me, CH₂CH₂NEtSO₂Me, CH₂CH₂ NMeSO₂Et, CH₂N(OMe)SO₂Me, CH₂ N(OEt)SO₂Me, CH₂N(OMe)SO₂Et, CH₂CH₂ N(OMe)SO₂Me, CH₂CH₂ N(OEt)SO₂Me, CH₂CH₂N(OMe)SO₂Et, CH₂Ph, CH₂CH₂Ph, CH₂ CH₂ CH₂ Ph, CHMePh, CH₂ CHMePh, CH₂ CMe₂Ph, CH₂ CH=CHPh, CH₂ CH=CMePh, CHMeCH=CHPh, CH₂ CMe=CMePh, CHMeCMe=CMePh, CH₂ C≡CPh, CHMeC≡CPh, CH₂CMe₂C≡CPh, CH₂CH₂OPh, CH₂CHMeOPh, CH₂CMe₂OPh, CH₂OPh, CH₂CH₂SPh, CH₂CHMeSPh, CH$_2$CMe$_2$SPh, CH$_2$SPh, CH$_2$CH$_2$SOPh, CH$_2$ CHMeSOPh, CH$_2$CMe$_2$SOPh, CH$_2$CH$_2$SO$_2$Ph, CH$_2$ CHMeSO$_2$Ph, CH$_2$CMe$_2$SO$_2$Ph, CH$_2$OCH$_2$ Ph, CH$_2$CH$_2$OCH$_2$ Ph, CH$_2$CHMeOCH$_2$Ph, CH$_2$SCH$_2$ Ph, CH$_2$CH$_2$SCH$_2$Ph, CH$_2$CHMeSCH$_2$Ph, CH$_2$SOCH$_2$Ph, CH$_2$CH$_2$SOCH$_2$Ph, CH$_2$CHMeSOCH$_2$Ph, CH$_2$SO$_2$CH$_2$Ph, CH$_2$CH$_2$SO$_2$CH$_2$Ph, CH$_2$CHMeSO$_2$CH$_2$Ph, CH$_2$ COPh, CH$_2$ CH$_2$COPh, CHMeCOPh, CH$_2$COCH$_2$Ph, CH$_2$CH$_2$COCH$_2$Ph, CHMeCOCH$_2$Ph Specific examples for the substituents $R^{g2}$ and $R^{g3}$ of the compound of the present invention Me, Et, Pr-n, Pr-iso, Bu-n, Bu-iso, Bu-sec, Bu-tert, Pen-n, Hex-n, CH$_2$CH=CH$_2$, CH$_2$CH=CHMe, CH$_2$CH=CHEt, CH$_2$CH$_2$CH=CH$_2$, CH$_2$ CH$_2$CH=CHMe, CH$_2$CH=CMe$_2$, CHMeCH=CH$_2$, CH$_2$ CMe=CH$_2$, CH$_2$CH=CMe$_2$, CHMeCH=CHMe, CH$_2$CMe=CHEt, CH$_2$CH$_2$CH=CMe$_2$, CH$_2$CMe=CMe$_2$, CH$_2$ C≡CH, CH$_2$C≡CMe, CH$_2$C≡CEt, CH$_2$CH$_2$C≡CH, CH$_2$CH$_2$C≡CMe, CHMeC≡CH, CHMeC≡CMe, CH$_2$ F, CHF$_2$, CF$_3$, CH$_2$ Cl, CH$_2$ Br, CH$_2$ CF$_3$, CH$_2$ CH$_2$ F, CH$_2$ CH$_2$ Cl, CH$_2$ CH$_2$ Br, CF$_2$CF$_3$, OMe, OEt, OPr-n, OPr-iso, SO$_2$Me, SO$_2$Et, SO$_2$Pr-n, SO$_2$Pr-iso, SO$_2$NHMe, SO$_2$NHEt, SO$_2$NHPr-n, SO$_2$NHPr-iso, SO$_2$NMe$_2$, SO$_2$NEt$_2$, SO$_2$N(Pr-n)$_2$, SO$_2$NMeEt, SO$_2$NMePr-n, CO$_2$Me, CO$_2$Et, CO$_2$Pr-n, CO$_2$Pr-iso, CO$_2$Bu-n, COMe, COEt, COPr-n, COPr-iso, COBu-n, CONHMe, CONHEt, CONHPr-n, CONHPr-iso, CONMe$_2$, CONEt$_2$, CON(Pr-n)$_2$, CONMeEt, CONMePr-n, Ph, PhCH$_2$ Specific examples of —NR$^{g2}$R$^{g3}$ wherein the substituents R$^{g2}$ and R$^{g3}$ of the compound of the present invention form a saturated 3- to 7-membered heterocyclic ring together with the nitrogen atom to which they are bonded

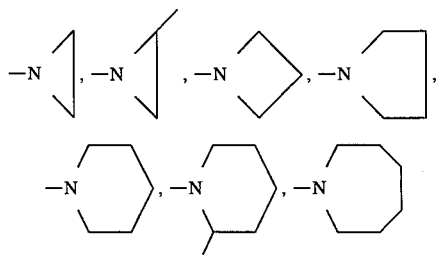

Specific examples for the substituent L of the compound of the present invention H, Me, Et, Pr-n, CH$_2$CH=CH$_2$, CH$_2$C≡CH Specific examples for the substituents B and D of the compound of the present invention Me, Et, Pr-n, OMe, OEt, CH$_2$ F, CHF$_2$, CF$_3$, OCHF$_2$, OCF$_3$, F, Cl, Br, NHMe, NHEt, NHPr-n, OCH$_2$ CF$_3$, NMe$_2$, OCBrF$_2$, CH$_2$ Cl, CH$_2$ F Now, examples of the compound covered by the present invention will be presented in the following Tables 1A, 1B, 1C, 2A, 2B, 2C, 3, 4A, 4B, 4C, 5, 6, 7, 8, 9, 10, 11 and 12. However, the compound of the present invention is not limited to such examples. The symbols in these Tables have the following meanings.

Me: methyl group, Et: ethyl group, Pr-n: n-propyl group, Pr-iso: isopropyl group, Bu-n: n-butyl group, Bu-iso: isobutyl group, Bu-sec: sec-butyl group, Bu-tert: tert-butyl group, Pen-n: n-pentyl group, Hex-n: n-hexyl group, Hep-n: n-heptyl group, Pr-cyc: cyclopropyl group, Bu-cyc: cyclobutyl group, Pen-cyc: cyclopentyl group, Hex-cyc: cyclohexyl group, and Ph: phenyl group,

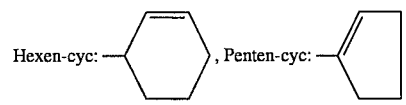

Gn is the same as above G and represents the following Ga, Gb and Gc.

Ga= G1 to G90 (i.e. represents any one of G1 to G90)

Gb= G1 to G13 (i.e. represents any one of G1 to G13)

Gc= G1 to G6 (i.e. represents any one of G1 to G6)

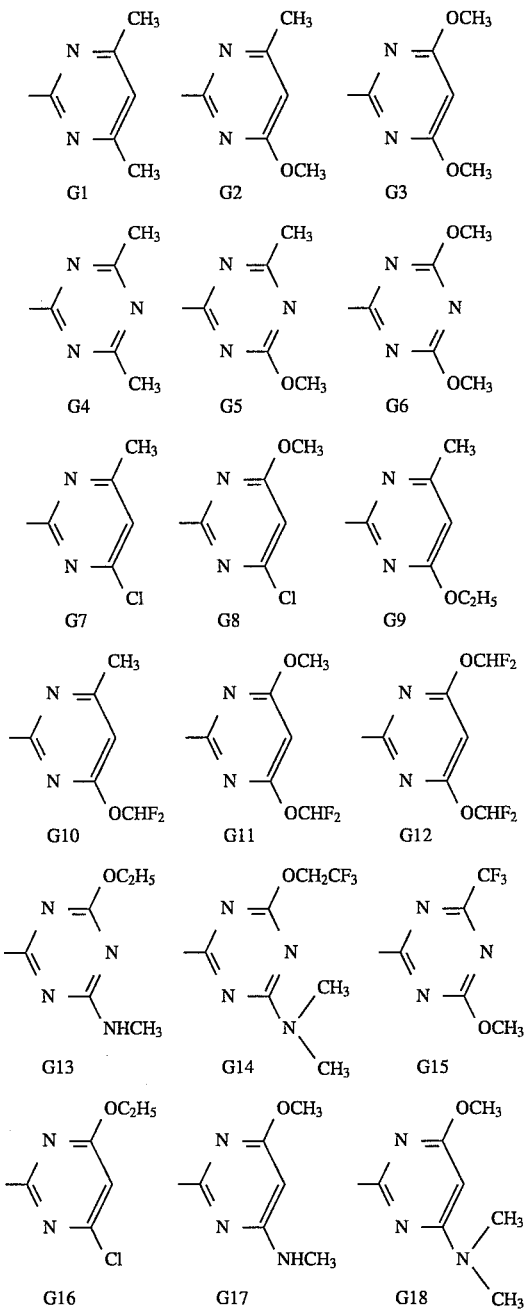

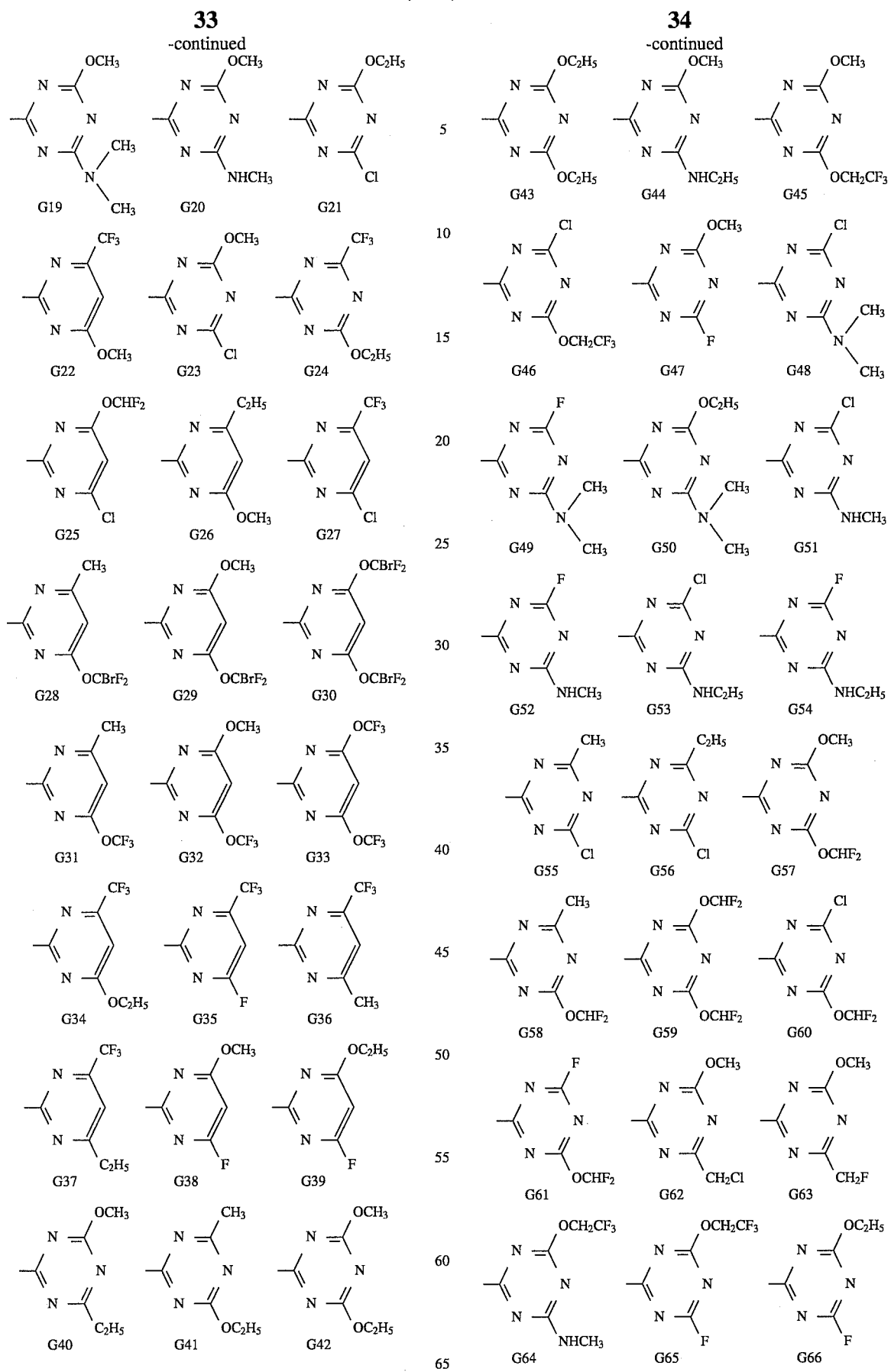

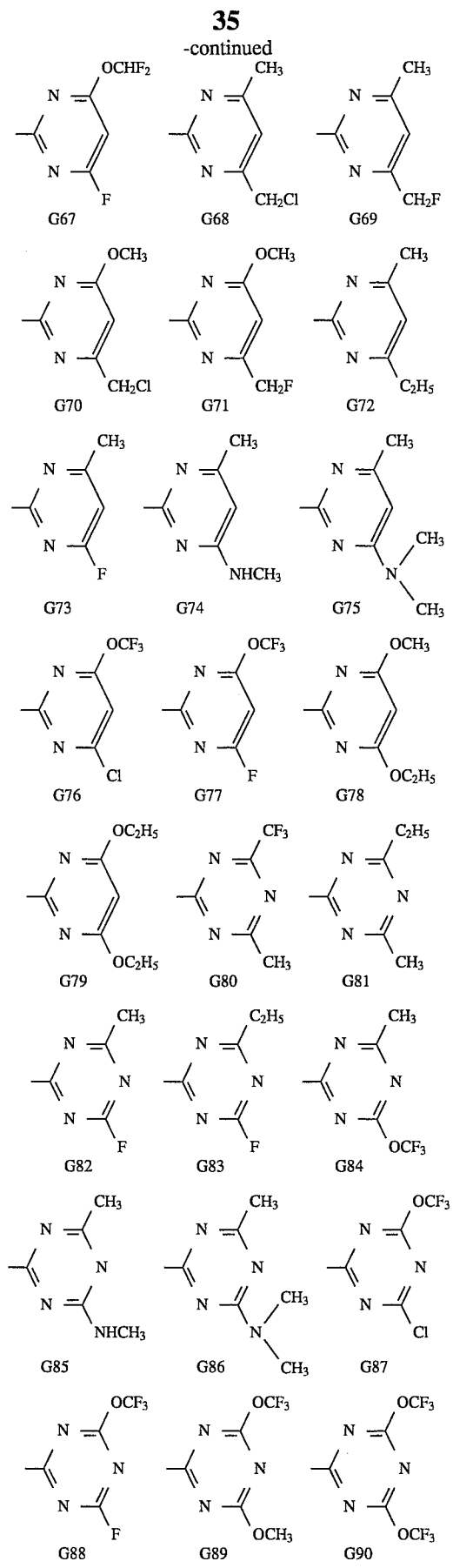
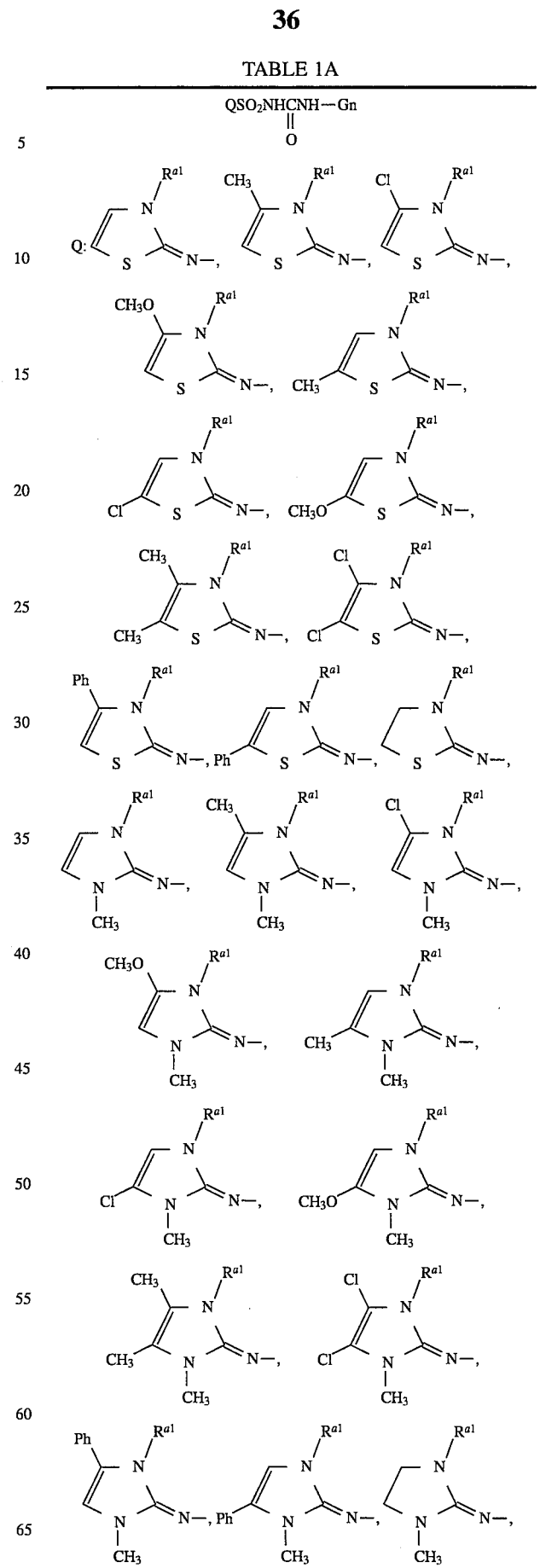

TABLE 1A-continued
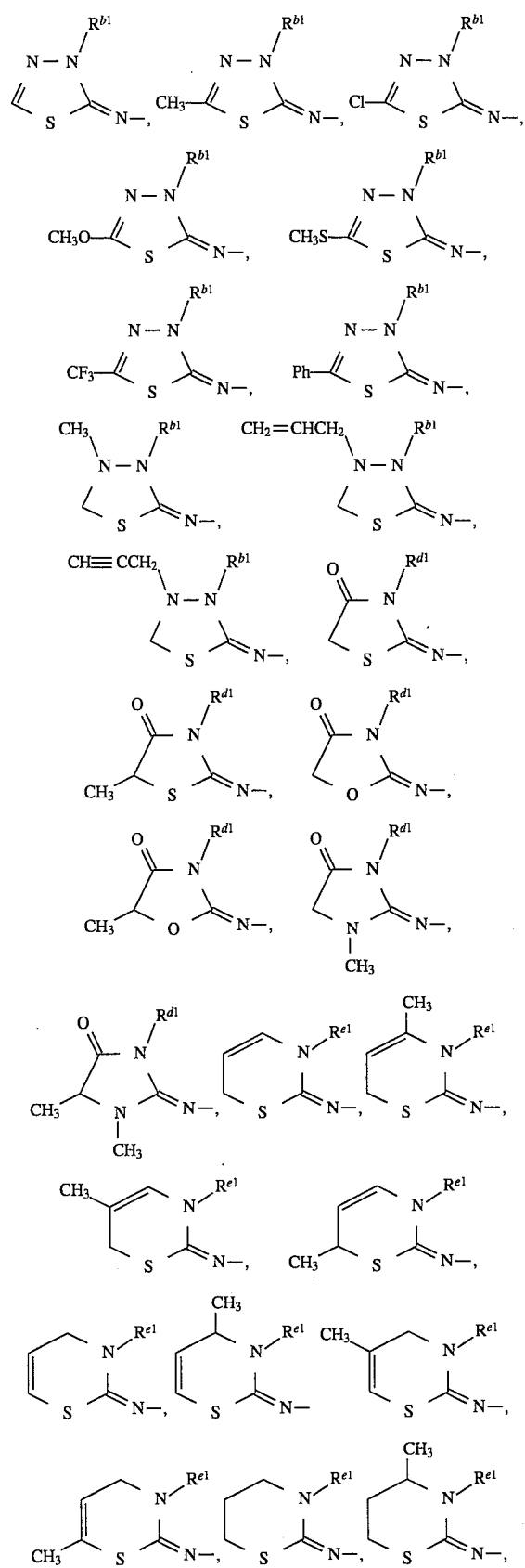
TABLE 1A-continued
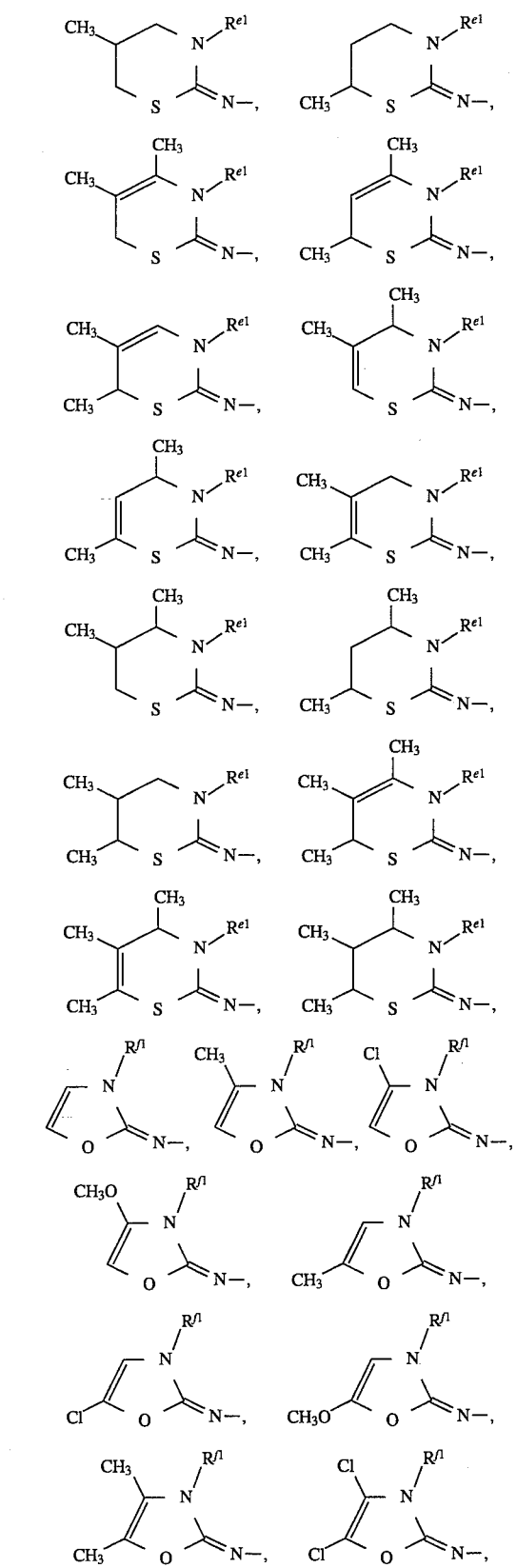

TABLE 1A-continued

[Structures omitted]

| $R^m$ | Gn |
|---|---|
| Me | Ga |
| Et | Ga |
| Pr-n | Ga |
| Pr-iso | Ga |
| Bu-n | Ga |
| Bu-iso | Ga |
| Bu-sec | Gb |
| Bu-tert | Gb |
| Pen-n | Ga |
| Hex-n | Gb |
| Hep-n | Gb |
| Pr-cyc | Ga |
| Hex-cyc | Ga |
| $CH_2$Pr-cyc | Ga |
| $CH_2CH_2$Pr-cyc | Ga |
| $CH_2$Bu-cyc | Gb |
| $CH_2$Pen-cyc | Gc |
| Hexen-cyc | Gb |
| $CH_2$Penten-cyc | Gb |
| $CH_2CH=CH_2$ | Ga |
| $CH_2CH=CHMe$ | Ga |
| $CH_2CH=CHEt$ | Ga |
| $CH_2CH=CMe_2$ | Gb |
| $CH_2CMe=CH_2$ | Ga |
| $CH_2CHMeCH=CHMe$ | Gc |
| $CH_2CH_2CH=CH_2$ | Ga |
| $CH_2CH_2CH=CHMe$ | Gb |
| $CH_2C\equiv CH$ | Ga |
| $CH_2C\equiv CMe$ | Ga |
| $CH_2C\equiv CEt$ | Ga |
| $CH_2CH_2C\equiv CH$ | Ga |
| $CH_2CH_2C\equiv CMe$ | Gb |
| $CHMeC\equiv CH$ | Gb |
| $CHMeC\equiv CMe$ | Gc |
| $CH_2OMe$ | Ga |
| $CH_2OEt$ | Ga |
| $CH_2OPr$-n | Gb |
| $CH_2CH_2OMe$ | Ga |
| $CH_2CH_2OEt$ | Ga |
| $CH_2CH_2OPr$-n | Gb |
| $CH_2CHMeOMe$ | Gb |
| $CH_2CH_2CH_2OMe$ | Ga |
| $CH_2CH_2CH_2OEt$ | Ga |
| $CH_2OCH_2CH=CH_2$ | Ga |
| $CH_2OCH_2CH=CHMe$ | Ga |
| $CH_2CH_2OCH_2CH=CH_2$ | Ga |
| $CH_2CH_2OCH_2CH=CHMe$ | Ga |
| $CH_2OCH_2C\equiv CH$ | Ga |
| $CH_2OCH_2C\equiv CMe$ | Ga |
| $CH_2CH_2OCH_2C\equiv CH$ | Ga |
| $CH_2CH_2OCH_2C\equiv CMe$ | Ga |
| $CH_2OCHF_2$ | Ga |
| $CH_2OCF_3$ | Ga |

TABLE 1A-continued

| | |
|---|---|
| $CH_2CH_2OCHF_2$ | Ga |
| $CH_2CH_2OCF_3$ | Ga |
| $CH_2OCH_2CF_3$ | Ga |
| $CH_2CH_2OCH_2CF_3$ | Ga |
| $CH_2OCH_2CH_2F$ | Ga |
| $CH_2OCH_2CH_2Cl$ | Ga |
| $CH_2CH_2OCH_2CH_2F$ | Ga |
| $CH_2CH_2OCH_2CH_2Cl$ | Ga |
| $CH_2OCH_2CH=CHCl$ | Gb |
| $CH_2CH_2OCH_2CH=CHCl$ | Gb |
| $CH_2OCH_2CH=CHBr$ | Gb |
| $CH_2CH_2OCH_2CH=CHBr$ | Gb |
| $CH_2OCH_2CH=CF_2$ | Gb |
| $CH_2CH_2OCH_2CH=CF_2$ | Gb |
| $CH_2OCH_2CH=CHCF_3$ | Gb |
| $CH_2CH_2OCH_2CH=CHCF_3$ | Gb |
| $CH_2OCH_2C \equiv Cl$ | Gb |
| $CH_2CH_2OCH_2C \equiv Cl$ | Gb |
| $CH_2OCH_2C \equiv CCF_3$ | Gb |
| $CH_2CH_2OCH_2C \equiv CCF_3$ | Gb |
| $CH_2SMe$ | Ga |
| $CH_2SEt$ | Ga |
| $CH_2SPr$-n | Gb |
| $CH_2CH_2SMe$ | Ga |
| $CH_2CH_2SEt$ | Ga |
| $CH_2CH_2SPr$-n | Gb |
| $CH_2SOMe$ | Gb |
| $CH_2SOEt$ | Gb |
| $CH_2CH_2SOMe$ | Gb |
| $CH_2CH_2SOEt$ | Gb |
| $CH_2SO_2Me$ | Ga |
| $CH_2SO_2Et$ | Ga |
| $CH_2SO_2Pr$-n | Gb |
| $CH_2CH_2SO_2Me$ | Ga |
| $CH_2CH_2SO_2Et$ | Ga |
| $CH_2CH_2SO_2Pr$-n | Gb |
| $CH_2CH_2F$ | Ga |
| $CH_2CHF_2$ | Ga |
| $CH_2CF_3$ | Ga |
| $CH_2CH_2Cl$ | Ga |
| $CH_2CH_2Br$ | Ga |
| $CH_2CH_2CF_3$ | Ga |
| $CH_2CF_2CF_3$ | Ga |
| $CH_2CH=CHCl$ | Ga |
| $CH_2CH=CHBr$ | Ga |
| $CH_2CH=CF_2$ | Ga |
| $CH_2CH=CHCF_3$ | Ga |
| $CH_2C \equiv Cl$ | Gb |
| $CH_2C \equiv CCF_3$ | Gb |
| $CH_2CN$ | Ga |
| $CH_2CH_2CN$ | Ga |
| $CHMeCN$ | Ga |
| $CH_2CH=CHCN$ | Ga |
| $CH(CN)C \equiv CH$ | Gb |
| $CH_2NO_2$ | Ga |
| $CH_2CH_2NO_2$ | Ga |
| $CH_2CH=CHNO_2$ | Gb |
| $CH_2CH(NO_2)CH=CH_2$ | Gc |
| $CH_2CH(NO_2)C \equiv CH$ | Gc |
| $CH_2CO_2Me$ | Gb |
| $CH_2CO_2Et$ | Gb |
| $CH_2CO_2Pr$-n | Gb |
| $CHMeCO_2Me$ | Gb |
| $CHMeCO_2Et$ | Gb |
| $CH_2CH_2CO_2Me$ | Ga |
| $CH_2CH_2CO_2Et$ | Ga |
| $CH_2CH_2CH_2CO_2Me$ | Gb |
| $CH_2CH=CHCO_2Me$ | Ga |
| $CH_2CH=CHCO_2Et$ | Ga |
| $CHMeCH=CHCO_2Me$ | Ga |
| $CHMeCH=CHCO_2Et$ | Ga |
| $CH_2C \equiv CCO_2Me$ | Ga |
| $CH_2C \equiv CCO_2Et$ | Ga |
| $CH_2COMe$ | Ga |
| $CH_2COEt$ | Ga |
| $CH_2COPr$-n | Gb |
| $CH_2CH_2COMe$ | Ga |
| $CH_2CH_2COEt$ | Ga |
| $CH_2COCF_3$ | Ga |
| $CH_2CH_2COCF_3$ | Ga |
| $CH_2COCH_2CF_3$ | Gb |
| $CH_2COCH_2F$ | Gb |
| $CH_2COCH=CH_2$ | Ga |
| $CH_2COCH=CHMe$ | Ga |
| $CH_2COCH_2CH=CH_2$ | Gb |
| $CH_2CH_2COCH=CH_2$ | Gb |
| $CH_2CH_2COCH=CHMe$ | Gb |
| $CH_2COC \equiv CH$ | Ga |
| $CH_2COC \equiv CMe$ | Ga |
| $CH_2COCH_2OMe$ | Ga |
| $CH_2COCH_2OEt$ | Ga |
| $CH_2COCH_2CH_2OMe$ | Ga |
| $CH_2COCH_2CH_2OEt$ | Ga |
| $CH_2COCH_2SMe$ | Ga |
| $CH_2COCH_2SEt$ | Ga |
| $CH_2COCH_2CH_2SMe$ | Ga |
| $CH_2COCH_2CH_2SEt$ | Ga |
| $CH_2COCH_2SOMe$ | Gb |
| $CH_2COCH_2CH_2SOMe$ | Gb |
| $CH_2COCH_2SO_2Me$ | Ga |
| $CH_2COCH_2SO_2Et$ | Ga |
| $CH_2COCH_2CH_2SO_2Me$ | Ga |
| $CH_2COCH_2CH_2SO_2Et$ | Ga |
| $CH_2CH=CHCOMe$ | Ga |
| $CH_2CH=CHCOEt$ | Ga |
| $CHMeCH=CHCOMe$ | Ga |
| $CHMeCH=CHCOEt$ | Ga |
| $CH_2C \equiv CCOMe$ | Ga |
| $CH_2C \equiv CCOEt$ | Ga |
| $CH_2SO_2NHMe$ | Ga |
| $CH_2SO_2NHEt$ | Ga |
| $CH_2CH_2SO_2NHMe$ | Ga |
| $CH_2CH_2SO_2NHEt$ | Ga |
| $CH_2SO_2NHOMe$ | Ga |
| $CH_2SO_2NHOEt$ | Ga |
| $CH_2CH_2SO_2NHOMe$ | Ga |
| $CH_2CH_2SO_2NHOEt$ | Ga |
| $CH_2SO_2NMe_2$ | Ga |
| $CH_2SO_2NMeEt$ | Ga |
| $CH_2SO_2NEt_2$ | Ga |
| $CH_2CH_2SO_2NMe_2$ | Ga |
| $CH_2CH_2SO_2NMeEt$ | Ga |
| $CH_2CH_2SO_2NEt_2$ | Ga |
| $CH_2SO_2N(OMe)Me$ | Ga |
| $CH_2SO_2N(OMe)Et$ | Ga |
| $CH_2SO_2N(OEt)Me$ | Ga |
| $CH_2CH_2SO_2N(OMe)Me$ | Ga |
| $CH_2CH_2SO_2N(OMe)Et$ | Ga |
| $CH_2CH_2SO_2N(OEt)Me$ | Ga |
| $CH_2CONHMe$ | Ga |
| $CH_2CONHEt$ | Ga |
| $CH_2CONHPr$-n | Gb |
| $CH_2CH_2CONHMe$ | Ga |
| $CH_2CH_2CONHEt$ | Ga |
| $CH_2CH_2CONHPr$-n | Gb |
| $CH_2CONMe_2$ | Ga |
| $CH_2CONMeEt$ | Ga |
| $CH_2CONEt_2$ | Ga |
| $CH_2CONHOMe$ | Ga |
| $CH_2CONHOEt$ | Ga |
| $CH_2CONHOPr$-n | Gb |
| $CH_2CON(OMe)Me$ | Ga |
| $CH_2CON(OMe)Et$ | Ga |
| $CH_2CON(OEt)Me$ | Ga |
| $CH_2CON(OEt)Et$ | Ga |

TABLE 1A-continued

| | |
|---|---|
| CH₂NHMe | Ga |
| CH₂NHEt | Ga |
| CH₂NHPr-n | Gb |
| CH₂CH₂NHMe | Ga |
| CH₂CH₂NHEt | Ga |
| CH₂CH₂NHPr-n | Gb |
| CH₂NHOMe | Ga |
| CH₂NHOEt | Ga |
| CH₂CH₂NHOMe | Ga |
| CH₂CH₂NHOEt | Ga |
| CH₂NMe₂ | Ga |
| CH₂NMeEt | Ga |
| CH₂CH₂NMe₂ | Ga |
| CH₂CH₂NMeEt | Ga |
| CH₂N(OMe)Me | Ga |
| CH₂N(OMe)Et | Ga |
| CH₂N(OEt)Me | Ga |
| CH₂CH₂N(OMe)Me | Ga |
| CH₂CH₂N(OMe)Et | Ga |
| CH₂CH₂N(OEt)Me | Ga |
| CH₂NMeCOMe | Ga |
| CH₂NEtCOMe | Ga |
| CH₂NMeCOEt | Ga |
| CH₂CH₂NMeCOMe | Ga |
| CH₂CH₂NEtCOMe | Ga |
| CH₂CH₂NMeCOEt | Ga |
| CH₂N(OMe)COMe | Ga |
| CH₂N(OEt)COMe | Ga |
| CH₂N(OMe)COEt | Ga |
| CH₂CH₂N(OMe)COMe | Ga |
| CH₂CH₂N(OEt)COMe | Ga |
| CH₂CH₂N(OMe)COEt | Ga |
| CH₂NMeSO₂Me | Ga |
| CH₂NEtSO₂Me | Ga |
| CH₂NMeSO₂Et | Ga |
| CH₂CH₂NMeSO₂Me | Ga |
| CH₂CH₂NEtSO₂Me | Ga |
| CH₂CH₂NMeSO₂Et | Ga |
| CH₂N(OMe)SO₂Me | Ga |
| CH₂N(OEt)SO₂Me | Ga |
| CH₂N(OMe)SO₂Et | Ga |
| CH₂CH₂N(OMe)SO₂Me | Ga |
| CH₂CH₂N(OEt)SO₂Me | Ga |
| CH₂CH₂N(OMe)SO₂Et | Ga |
| CH₂Ph | Gb |
| CH₂CH₂Ph | Gb |
| CH₂CH₂CH₂Ph | Gb |
| CHMePh | Gb |
| CH₂CH=CHPh | Ga |
| CHMeCH=CHPh | Ga |
| CH₂C≡CPh | Ga |
| CHMeC≡CPh | Ga |
| CH₂CH₂OPh | Ga |
| CH₂OPh | Ga |
| CH₂CH₂SPh | Ga |
| CH₂SPh | Ga |
| CH₂CH₂SOPh | Gb |
| CH₂CH₂SO₂Ph | Ga |
| CH₂OCH₂Ph | Ga |
| CH₂CH₂OCH₂Ph | Ga |
| CH₂SCH₂Ph | Ga |
| CH₂CH₂SCH₂Ph | Ga |
| CH₂SOCH₂Ph | Gb |
| CH₂CH₂SOCH₂Ph | Gb |
| CH₂SO₂CH₂Ph | Ga |
| CH₂CH₂SO₂CH₂Ph | Ga |
| CH₂COPh | Ga |
| CH₂CH₂COPh | Ga |
| CHMeCOPh | Ga |
| CH₂COCH₂Ph | Gb |
| CHMeCOCH₂Ph | Gb |
| CH₂CH₂CH₂F | Ga |
| CH₂CH₂CH₂Cl | Ga |
| CH₂C(Cl)=CH₂ | Ga |
| CH₂C(Br)=CH₂ | Ga |
| Ph | Ga |
| CH₂SOPh | Ga |
| CH₂SO₂Ph | Ga |
| CH₂Ph-4-OMe | Gb |
| CH₂Ph-4-Cl | Gb |
| CH₂C(Cl)=CHCl | Ga |
| CH₂C(F)=CHCl | Ga |
| CH₂CH=CHF | Ga |
| CH₂C(Cl)=CHMe | Ga |
| CH₂CH=C(Cl)Me | Ga |
| CH₂CF=CF₂ | Ga |
| CH₂CH=CHCH₂F | Ga |
| CH₂C(Br)=CHMe | Ga |
| CH₂C(Cl)=CHF | Ga |
| CH₂C(Br)=CHF | Ga |
| CH₂C(Cl)=C(Cl)Me | Ga |
| CH₂C(Br)=CHBr | Ga |
| CH₂C(Br)=C(Br)Me | Ga |
| CH₂CH=C(F)CF₃ | Ga |
| CH₂CH=CCl₂ | Ga |
| CH₂C(F)=CH₂ | Ga |
| CH₂CH=C(F)Cl | Ga |
| CH₂C(Cl)=C(F)Cl | Ga |
| CH₂C(F)=CCl₂ | Ga |
| CH₂CCl=CF₂ | Ga |
| CH₂C(CF₃)=CH₂ | Ga |
| CH₂NHSO₂Me | Gb |
| CH₂CH₂NHSO₂Me | Gb |
| CH₂NHCOMe | Gb |
| CH₂CH₂NHCOMe | Gb |

$R^m$ represents $R^{a1}$, $R^{b1}$, $R^{d1}$, $R^{e1}$ or $R^{f1}$.

TABLE 1B $$Q-SO_2NHCNH-Gn$$
$$\|$$
$$O$$

Q:

[Structures showing thiazoline rings with various substituents: C₂H₅, CF₃, CH₃S, CH₃SO₂, CH₃O₂C, CH₃CO, F, Br, O₂N, NC, C₂H₅, each with $R^{a1}$ group on nitrogen]

TABLE 1B-continued

TABLE 1B-continued

TABLE 1B-continued
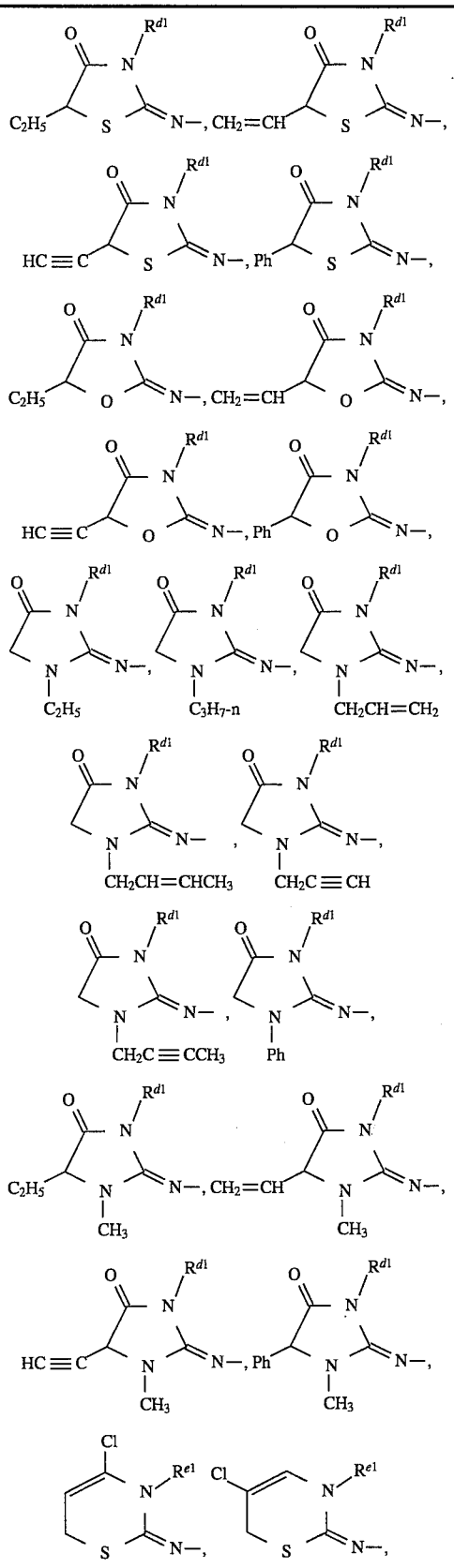
TABLE 1B-continued
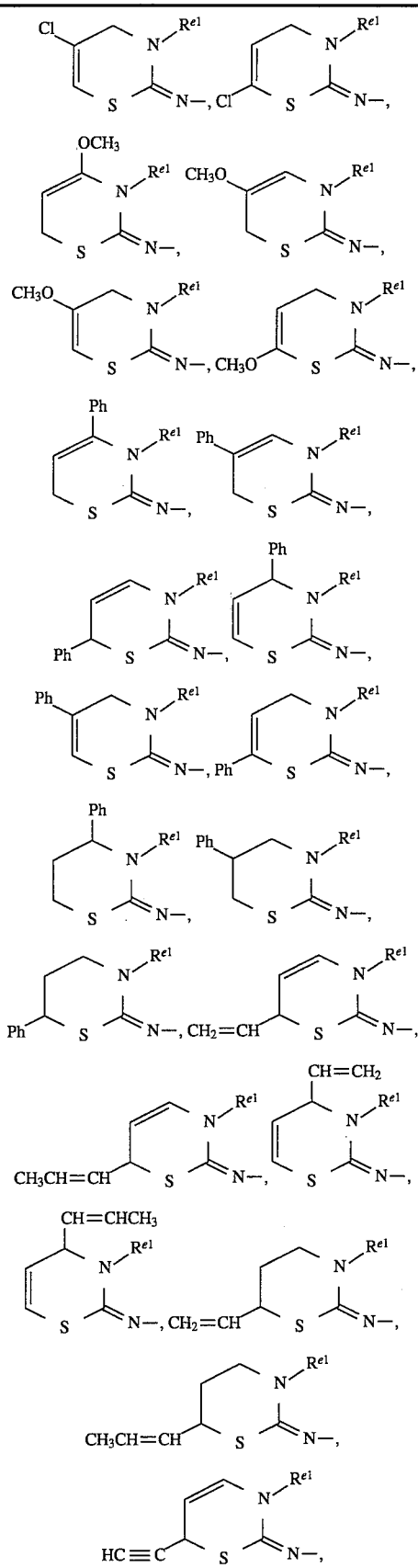

TABLE 1B-continued

TABLE 1B-continued

TABLE 1B-continued
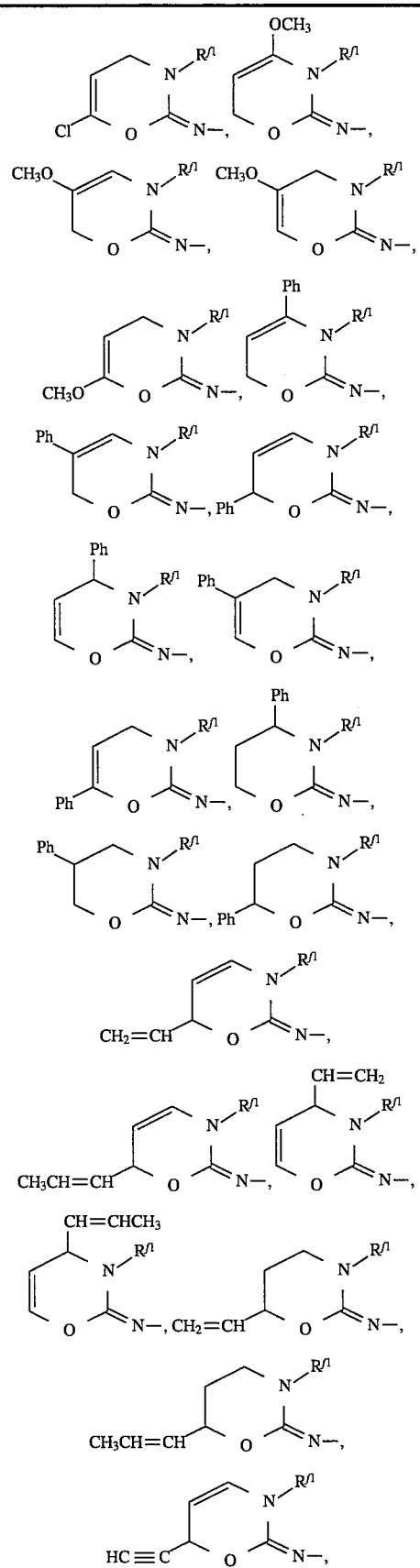
TABLE 1B-continued
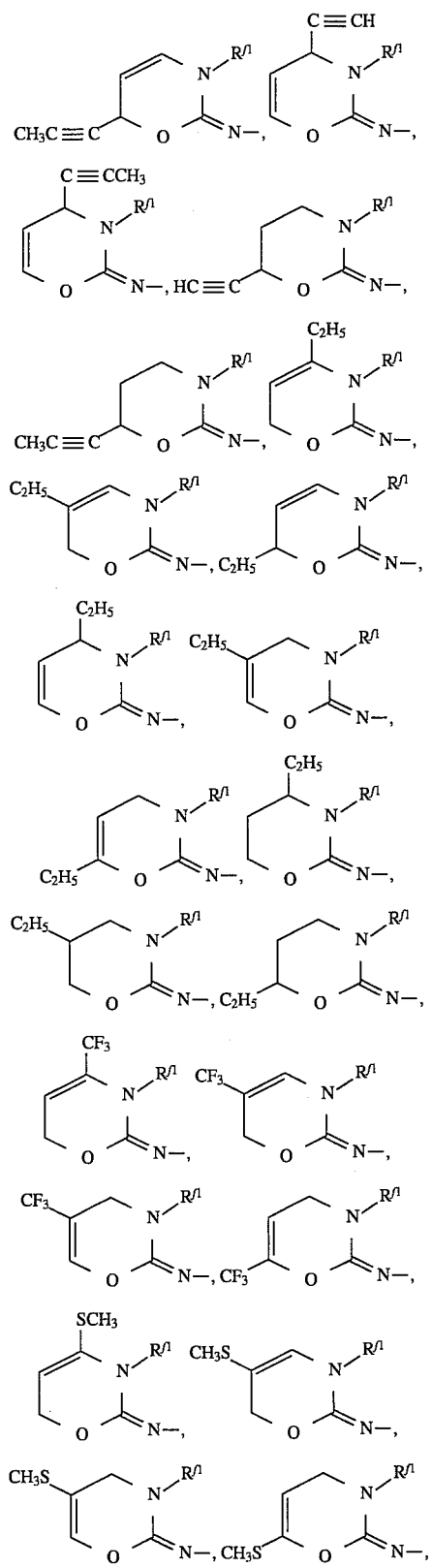

TABLE 1B-continued

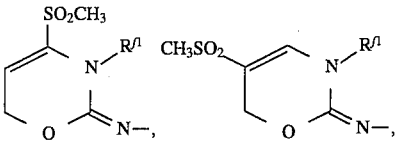

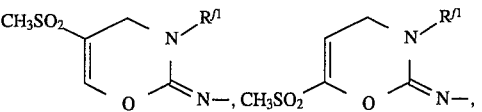

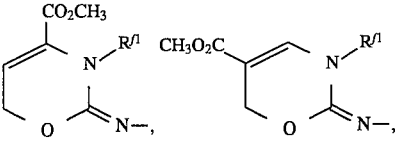

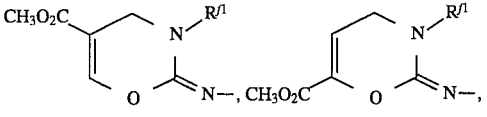

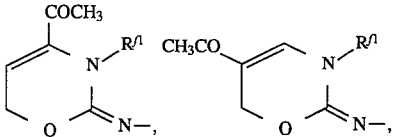

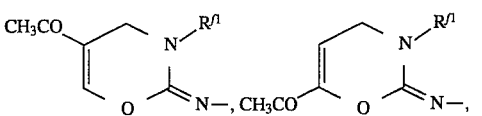

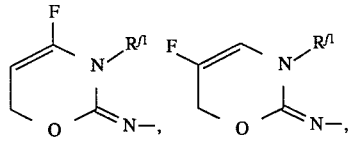

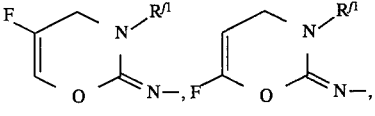

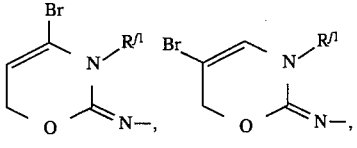

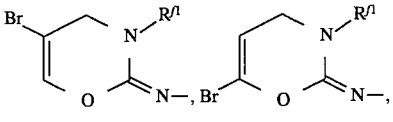

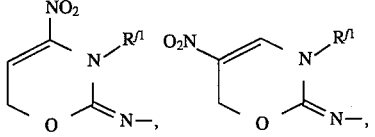

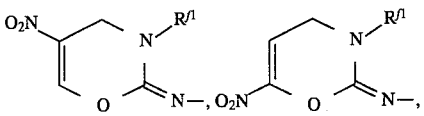

TABLE 1B-continued

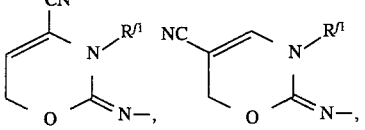

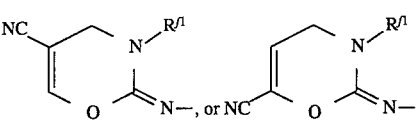

| $R^m$ | Gn |
|---|---|
| Me | Ga |
| Et | Ga |
| Pr-n | Ga |
| Pr-iso | Ga |
| Bu-n | Ga |
| Bu-iso | Gb |
| Pen-n | Gb |
| Hex-n | Gb |
| $CH_2Pr$-cyc | Ga |
| $CH_2CH_2Pr$-cyc | Ga |
| $CH_2CH=CH_2$ | Ga |
| $CH_2CH=CHMe$ | Ga |
| $CH_2C\equiv CH$ | Ga |
| $CH_2C\equiv CMe$ | Ga |
| $CH_2OMe$ | Ga |
| $CH_2OEt$ | Ga |
| $CH_2CH_2OMe$ | Ga |
| $CH_2CH_2OEt$ | Ga |
| $CH_2OCH_2CH=CH_2$ | Ga |
| $CH_2CH_2OCH_2CH=CH_2$ | Ga |
| $CH_2OCH_2C\equiv CH$ | Ga |
| $CH_2CH_2OCH_2C\equiv CH$ | Ga |
| $CH_2OCH_2CF_3$ | Ga |
| $CH_2CH_2OCH_2CF_3$ | Ga |
| $CH_2SMe$ | Ga |
| $CH_2SEt$ | Ga |
| $CH_2CH_2SMe$ | Ga |
| $CH_2CH_2SEt$ | Ga |
| $CH_2SO_2Me$ | Ga |
| $CH_2SO_2Et$ | Ga |
| $CH_2CH_2SO_2Me$ | Ga |
| $CH_2CH_2SO_2Et$ | Ga |
| $CH_2CH_2F$ | Ga |
| $CH_2CF_3$ | Ga |
| $CH_2CN$ | Ga |
| $CH_2CH_2CN$ | Ga |
| CHMeCN | Ga |
| $CH_2CH=CHCN$ | Ga |
| $CH_2NO_2$ | Ga |
| $CH_2CH_2NO_2$ | Ga |
| $CH_2CO_2Me$ | Gb |
| $CH_2CO_2Et$ | Gb |
| $CHMeCO_2Me$ | Gb |
| $CHMeCO_2Et$ | Gb |
| $CH_2CH_2CO_2Me$ | Ga |
| $CH_2CH_2CO_2Et$ | Ga |
| $CH_2CH=CHCO_2Me$ | Ga |
| $CH_2CH=CHCO_2Et$ | Ga |
| $CHMeCH=CHCO_2Me$ | Ga |
| $CH_2COMe$ | Ga |
| $CH_2COEt$ | Ga |
| $CH_2COPr$-n | Gb |
| $CH_2COCF_3$ | Ga |
| $CH_2COCH=CH_2$ | Ga |
| $CH_2COCH=CHMe$ | Ga |
| $CH_2COCH_2OMe$ | Ga |
| $CH_2COCH_2OEt$ | Ga |
| $CH_2COCH_2CH_2OMe$ | Ga |

TABLE 1B-continued

| | |
|---|---|
| CH₂COCH₂CH₂OEt | Ga |
| CH₂COCH₂SMe | Ga |
| CH₂COCH₂CH₂SMe | Ga |
| CH₂COCH₂SO₂Me | Ga |
| CH₂COCH₂CH₂SO₂Me | Ga |
| CH₂CH=CHCOMe | Ga |
| CHMeCH=CHCOMe | Ga |
| CH₂SO₂NHMe | Gb |
| CH₂CH₂SO₂NHMe | Gb |
| CH₂SO₂NHOMe | Gb |
| CH₂CH₂SO₂NHOMe | Gb |
| CH₂SO₂NMe₂ | Ga |
| CH₂CH₂SO₂NMe₂ | Ga |
| CH₂SO₂N(OMe)Me | Ga |
| CH₂CH₂SO₂N(OMe)Me | Ga |
| CH₂CONHMe | Gb |
| CH₂CH₂CONHMe | Gb |
| CH₂CONMe₂ | Ga |
| CH₂CH₂CONMe₂ | Ga |
| CH₂CONHOMe | Gb |
| CH₂CH₂CONHMe | Gb |
| CH₂CON(OMe)Me | Ga |
| CH₂CH₂CON(OMe)Me | Ga |
| CH₂NHMe | Gb |
| CH₂CH₂NHMe | Gb |
| CH₂CHOMe | Gb |
| CH₂CH₂NHOMe | Gb |
| CH₂NMe₂ | Ga |
| CH₂CH₂NMe₂ | Ga |
| CH₂N(OMe)Me | Ga |
| CH₂CH₂N(OMe)Me | Ga |
| CH₂NMeCOMe | Ga |
| CH₂CH₂NMeCOMe | Ga |
| CH₂N(OMe)COMe | Ga |
| CH₂CH₂N(OMe)COMe | Ga |
| CH₂NMeSO₂Me | Ga |
| CH₂CH₂NMeSO₂Me | Ga |
| CH₂N(OMe)SO₂Me | Ga |
| CH₂CH₂N(OMe)SO₂Me | Ga |
| CH₂Ph | Gb |
| CH₂CH₂Ph | Gb |
| CH₂CH₂CH₂Ph | Gb |
| CHMePh | Gb |
| CH₂CH=CHPh | Gb |
| CHMeCH=CHPh | Gb |
| CH₂CH₂OPh | Gb |
| CH₂OPh | GB |
| CH₂CH₂OPh | Gb |
| CH₂SPh | Gb |
| CH₂CH₂SO₂Ph | Gb |
| CH₂COPh | Gb |
| CH₂CH₂COPh | Gb |
| CH₂COCH₂Ph | Gb |
| CH₂CH₂COCH₂Ph | Gb |
| Ph | Gb |

TABLE 1C $$QSO_2NHCNH-Gn$$
$$\parallel$$
$$O$$

Q: 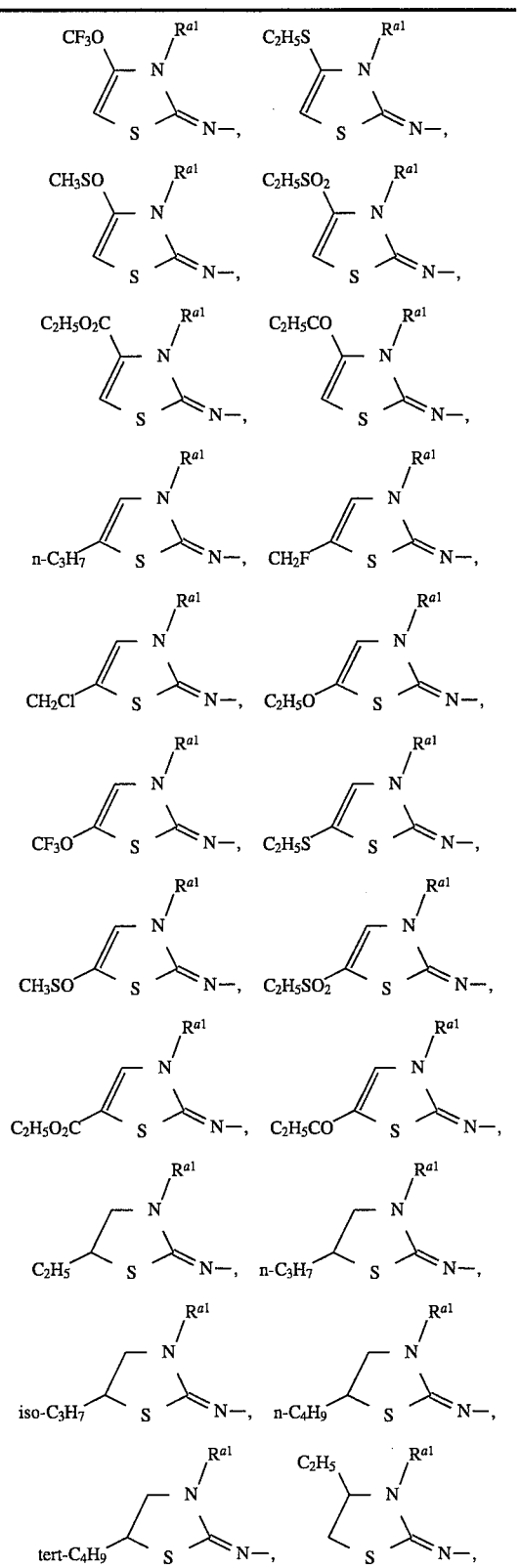

TABLE 1C-continued

TABLE 1C-continued

TABLE 1C-continued

TABLE 1C-continued
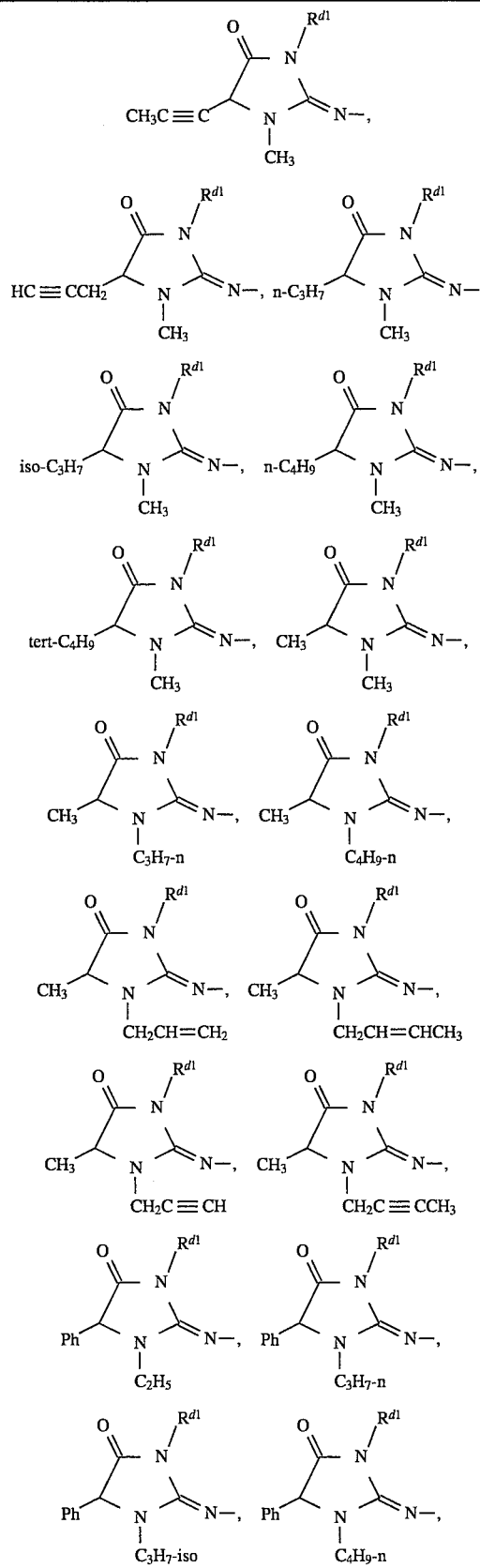
TABLE 1C-continued
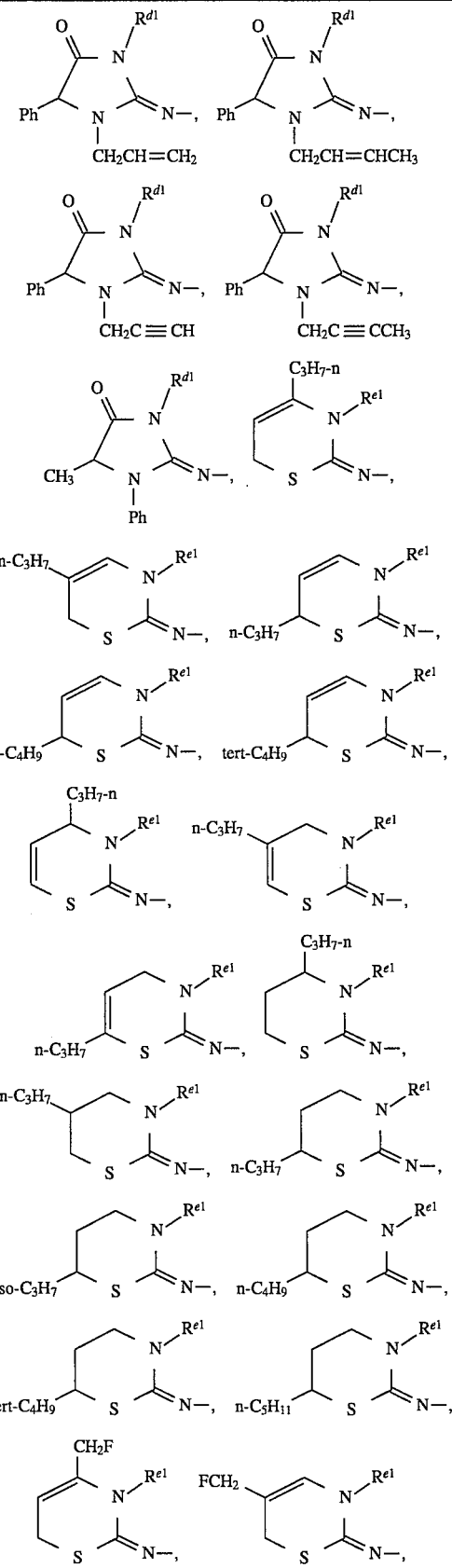

TABLE 1C-continued

TABLE 1C-continued

TABLE 1C-continued

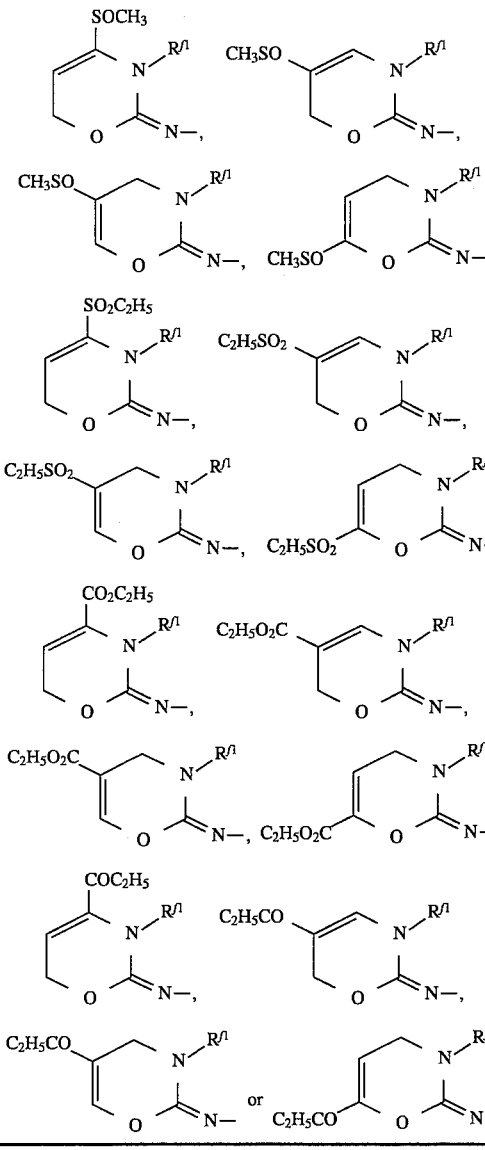

| $R^m$ | Gn |
|---|---|
| Me | Ga |
| Et | Ga |
| Pr-n | Ga |
| Pr-iso | Gb |
| Bu-n | Ga |
| Bu-iso | Ga |
| Pen-n | Gb |
| CH$_2$Pr-cyc | Ga |
| CH$_2$CH$_2$Pr-cyc | Gb |
| CH$_2$CH=CH$_2$ | Ga |
| CH$_2$CH=CHMe | Ga |
| CH$_2$C≡CH | Ga |
| CH$_2$C≡CMe | Ga |
| CH$_2$CH$_2$OMe | Ga |
| CH$_2$OMe | Ga |
| CH$_2$CH$_2$SMe | Ga |
| CH$_2$SMe | Ga |
| CH$_2$SO$_2$Me | Ga |
| CH$_2$CH$_2$SO$_2$Me | Ga |
| CH$_2$CF$_3$ | Ga |

TABLE 1C-continued

| | |
|---|---|
| CH$_2$CN | Ga |
| CH$_2$CH$_2$CN | Ga |
| CH$_2$NO$_2$ | Ga |
| CH$_2$CH$_2$NO$_2$ | Ga |
| CH$_2$COMe | Ga |
| CH$_2$COEt | Ga |
| CH$_2$COCH=CH$_2$ | Ga |
| CH$_2$CH=CHCOMe | Ga |
| CH$_2$CONMe$_2$ | Ga |

$R^m$ represents $R^{a1}$, $R^{b1}$, $R^{d1}$, $R^{e1}$, or $R^{f1}$.

TABLE 2A $$QSO_2NHCNH-Gn$$
$$\parallel$$
$$O$$

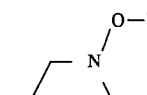

| $R^{c1}$ | Gn |
|---|---|
| Me | Ga |
| Et | Ga |
| Pr-n | Ga |
| Pr-iso | Ga |
| Bu-n | Ga |
| Bu-iso | Ga |
| Bu-sec | Ga |
| Bu-tert | Gb |
| Pen-n | Ga |
| Hex-n | Gb |
| Hep-n | Gb |
| Pr-cyc | Ga |
| Hex-cyc | Ga |
| CH$_2$Pr-cyc | Ga |
| CH$_2$CH$_2$Pr-cyc | Ga |
| CH$_2$Bu-cyc | Gb |
| CH$_2$Pen-cyc | Gc |
| Hexen-cyc | Gb |
| CH$_2$Penten-cyc | Gb |
| CH$_2$CH=CH$_2$ | Ga |
| CH$_2$CH=CHMe | Ga |
| CH$_2$CH=CHEt | Ga |
| CH$_2$CH=CMe$_2$ | Ga |
| CH$_2$CMe=CH$_2$ | Ga |
| CH$_2$CMeCH=CHMe | Ga |
| CH$_2$CH$_2$CH=CH$_2$ | Ga |
| CH$_2$CH$_2$CH=CHMe | Ga |
| CH$_2$C≡CH | Ga |
| CH$_2$C≡CMe | Ga |
| CH$_2$C≡CEt | Ga |
| CH$_2$CH$_2$C≡CH | Ga |
| CH$_2$CH$_2$C≡CMe | Ga |
| CHMeC≡CH | Ga |

TABLE 2A-continued $$QSO_2NHCNH-Gn$$
$$\parallel$$
$$O$$

Q: [structures with N-O-R^c1 groups on thiazoline/thiazine rings]

| R^c1 | Gn |
|---|---|
| CHMeC≡CMe | Ga |
| CH₂OMe | Ga |
| CH₂OEt | Ga |
| CH₂OPr-n | Gb |
| CH₂CH₂OMe | Ga |
| CH₂CH₂OEt | Ga |
| CH₂CH₂OPr-n | Gb |
| CH₂CHMeOMe | Ga |
| CH₂CH₂CH₂OMe | Ga |
| CH₂CH₂CH₂OEt | Ga |
| CH₂OCH₂CH=CH₂ | Ga |
| CH₂OCH₂CH=CHMe | Ga |
| CH₂CH₂OCH₂CH=CH₂ | Ga |
| CH₂CH₂OCH₂CH=CHMe | Ga |
| CH₂OCH₂C≡CH | Ga |
| CH₂OCH₂C≡CMe | Ga |
| CH₂CH₂OCH₂C≡CH | Ga |
| CH₂CH₂OCH₂C≡CMe | Ga |
| CH₂OCHF₂ | Ga |
| CH₂OCF₃ | Ga |
| CH₂CH₂OCHF₂ | Ga |
| CH₂CH₂OCF₃ | Ga |
| CH₂OCH₂CF₃ | Ga |
| CH₂CH₂OCH₂CF₃ | Ga |
| CH₂OCH₂CH₂F | Ga |
| CH₂OCH₂CH₂Cl | Ga |
| CH₂CH₂OCH₂CH₂F | Ga |
| CH₂CH₂OCH₂CH₂Cl | Ga |
| CH₂OCH₂CH=CHCl | Gb |
| CH₂CH₂OCH₂CH=CHCl | Gb |
| CH₂OCH₂CH=CHBr | Gb |
| CH₂CH₂OCH₂CH=CHBr | Gb |
| CH₂OCH₂CH=CF₂ | Gb |
| CH₂CH₂OCH₂CH=CF₂ | Gb |
| CH₂OCH₂CH=CHCF₃ | Gb |
| CH₂CH₂OCH₂CH=CHCF₃ | Gb |
| CH₂OCH₂C≡CI | Gb |
| CH₂CH₂OCH₂C≡CI | Gb |
| CH₂OCH₂C≡CCF₃ | Gb |
| CH₂CH₂OCH₂C≡CCF₃ | Gb |
| CH₂SMe | Ga |
| CH₂SEt | Ga |
| CH₂SPr-n | Gb |
| CH₂CH₂SMe | Ga |
| CH₂CH₂SEt | Ga |
| CH₂CH₂SPr-n | Gb |
| CH₂SOMe | Gb |
| CH₂SOEt | Gb |
| CH₂CH₂SOMe | Gb |
| CH₂CH₂SOEt | Gb |
| CH₂SO₂Me | Ga |
| CH₂SO₂Et | Ga |
| CH₂SO₂Pr-n | Gb |
| CH₂CH₂SO₂Me | Ga |
| CH₂CH₂SO₂Et | Ga |
| CH₂CH₂SO₂Pr-n | Gb |
| CH₂CH₂F | Ga |
| CH₂CHF₂ | Ga |
| CH₂CF₃ | Ga |
| CH₂CH₂Cl | Ga |
| CH₂CH₂Br | Ga |
| CH₂CH₂CF₃ | Ga |
| CH₂CF₂CF₃ | Ga |
| CH₂CH=CHCl | Ga |
| CH₂CH=CHBr | Ga |
| CH₂CH=CF₂ | Ga |
| CH₂CH=CHCF₃ | Ga |
| CH₂C≡CI | Gb |
| CH₂C≡CCF₃ | Gb |
| CH₂CN | Ga |
| CH₂CH₂CN | Ga |
| CHMeCN | Ga |
| CH₂CH=CHCN | Ga |
| CH(CN)C≡CH | Gb |
| CH₂NO₂ | Ga |
| CH₂CH₂NO₂ | Ga |
| CH₂CH=CHNO₂ | Gb |
| CH₂CH(NO₂)CH=CH₂ | Gc |
| CH₂CH(NO₂)C≡CH | Gc |
| CH₂CO₂Me | Ga |
| CH₂CO₂Et | Ga |
| CH₂CO₂Pr-n | Gb |
| CHMeCO₂Me | Ga |
| CHMeCO₂Et | Ga |
| CH₂CH₂CO₂Me | Ga |
| CH₂CH₂CO₂Et | Ga |
| CH₂CH₂CH₂CO₂Me | Gb |
| CH₂CH=CHCO₂Me | Ga |
| CH₂CH=CHCO₂Et | Ga |
| CHMeCH=CHCO₂Me | Ga |
| CHMeCH=CHCO₂Et | Ga |
| CH₂C≡CCO₂Me | Ga |
| CH₂C≡CCO₂Et | Ga |
| CH₂COMe | Ga |
| CH₂COEt | Ga |

TABLE 2A-continued $$QSO_2NHCNH-Gn$$
$$\parallel$$
$$O$$

[structures with Q: and R^cl, Gn substituents]

| R^cl | Gn |
|---|---|
| CH₂COPr-n | Gb |
| CH₂CH₂COMe | Ga |
| CH₂CH₂COEt | Ga |
| CH₂COCF₃ | Ga |
| CH₂CH₂COCF₃ | Ga |
| CH₂COCH₂CF₃ | Gb |
| CH₂COCH₂F | Gb |
| CH₂COCH=CH₂ | Ga |
| CH₂COCH=CHMe | Ga |
| CH₂COCH₂CH=CH₂ | Gb |
| CH₂CH₂COCH=CH₂ | Gb |
| CH₂CH₂COCH=CHMe | Gb |
| CH₂COC≡CH | Ga |
| CH₂COC≡CMe | Ga |
| CH₂COCH₂OMe | Ga |
| CH₂COCH₂OEt | Ga |
| CH₂COCH₂CH₂OMe | Ga |
| CH₂COCH₂CH₂OEt | Ga |
| CH₂COCH₂SMe | Ga |
| CH₂COCH₂SEt | Ga |
| CH₂COCH₂CH₂SMe | Ga |
| CH₂COCH₂CH₂SEt | Ga |
| CH₂COCH₂SOMe | Gb |
| CH₂COCH₂CH₂SOMe | Gb |
| CH₂COCH₂SO₂Me | Ga |
| CH₂COCH₂SO₂Et | Ga |
| CH₂COCH₂CH₂SO₂Me | Ga |
| CH₂COCH₂CH₂SO₂Et | Ga |
| CH₂CH=CHCOMe | Ga |
| CH₂CH=CHCOEt | Ga |
| CHMeCH=CHCOMe | Ga |
| CHMeCH=CHCOEt | Ga |
| CH₂C≡CCOMe | Ga |
| CH₂C≡CCOEt | Ga |
| CH₂SO₂NHMe | Ga |
| CH₂SO₂NHEt | Ga |
| CH₂CH₂SO₂NHMe | Ga |
| CH₂CH₂SO₂NHEt | Ga |
| CH₂SO₂NHOMe | Ga |
| CH₂SO₂NHOEt | Ga |
| CH₂CH₂SO₂NHOMe | Ga |
| CH₂CH₂SO₂NHOEt | Ga |
| CH₂SO₂NMe₂ | Ga |
| CH₂SO₂NMeEt | Ga |
| CH₂SO₂NEt₂ | Ga |
| CH₂CH₂SO₂NMe₂ | Ga |
| CH₂CH₂SO₂NMeEt | Ga |
| CH₂CH₂SO₂NEt₂ | Ga |
| CH₂SO₂N(OMe)Me | Ga |
| CH₂SO₂N(OMe)Et | Ga |
| CH₂SO₂N(OEt)Me | Ga |
| CH₂CH₂SO₂N(OMe)Me | Ga |
| CH₂CH₂SO₂N(OMe)Et | Ga |
| CH₂CH₂SO₂N(OEt)Me | Ga |
| CH₂CONHMe | Ga |
| CH₂CONHEt | Ga |
| CH₂CONHPr-n | Gb |
| CH₂CH₂CONHMe | Ga |
| CH₂CH₂CONHEt | Ga |
| CH₂CH₂CONHPr-n | Gb |
| CH₂CONMe₂ | Ga |
| CH₂CONMeEt | Ga |
| CH₂CONEt₂ | Ga |
| CH₂CONHOMe | Ga |
| CH₂CONHOEt | Ga |
| CH₂CONHOPr-n | Gb |
| CH₂CON(OMe)Me | Ga |
| CH₂CON(OMe)Et | Ga |
| CH₂CON(OEt)Me | Ga |
| CH₂CON(OEt)Et | Ga |
| CH₂NHMe | Ga |
| CH₂NHEt | Ga |
| CH₂NHPr-n | Gb |
| CH₂CH₂NHMe | Ga |
| CH₂CH₂NHEt | Ga |
| CH₂CH₂NHPr-n | Gb |
| CH₂NHOMe | Ga |
| CH₂NHOEt | Ga |
| CH₂CH₂NHOMe | Ga |
| CH₂CH₂NHOEt | Ga |
| CH₂NMe₂ | Ga |
| CH₂NMeEt | Ga |
| CH₂CH₂NMe₂ | Ga |
| CH₂CH₂NMeEt | Ga |
| CH₂N(OMe)Me | Ga |
| CH₂N(OMe)Et | Ga |
| CH₂N(OEt)Me | Ga |
| CH₂CH₂N(OMe)Me | Ga |
| CH₂CH₂N(OMe)Et | Ga |
| CH₂CH₂N(OEt)Me | Ga |
| CH₂NMeCOMe | Ga |
| CH₂NEtCOMe | Ga |
| CH₂NMeCOEt | Ga |
| CH₂CH₂NMeCOMe | Ga |
| CH₂CH₂NEtCOMe | Ga |
| CH₂CH₂NMeCOEt | Ga |
| CH₂N(OMe)COMe | Ga |
| CH₂N(OEt)COMe | Ga |
| CH₂N(OMe)COEt | Ga |
| CH₂CH₂N(OMe)COMe | Ga |
| CH₂CH₂N(OEt)COMe | Ga |
| CH₂CH₂N(OMe)COEt | Ga |
| CH₂NMeSO₂Me | Ga |

TABLE 2A-continued $$QSO_2NHCNH-Gn$$
$$\parallel$$
$$O$$

Q: [structures with N-O-R^{c1}, S, N substituents as shown]

| $R^{c1}$ | Gn |
|---|---|
| CH$_2$NEtSO$_2$Me | Ga |
| CH$_2$NMeSO$_2$Et | Ga |
| CH$_2$CH$_2$NMeSO$_2$Me | Ga |
| CH$_2$CH$_2$NEtSO$_2$Me | Ga |
| CH$_2$CH$_2$NMeSO$_2$Et | Ga |
| CH$_2$N(OMe)SO$_2$Me | Ga |
| CH$_2$N(OEt)SO$_2$Me | Ga |
| CH$_2$N(OMe)SO$_2$Et | Ga |
| CH$_2$CH$_2$N(OMe)SO$_2$Me | Ga |
| CH$_2$CH$_2$N(OEt)SO$_2$Me | Ga |
| CH$_2$CH$_2$N(OMe)SO$_2$Et | Ga |
| CH$_2$Ph | Gb |
| CH$_2$CH$_2$Ph | Gb |
| CH$_2$CH$_2$CH$_2$Ph | Gb |
| CHMePh | Gb |
| CH$_2$CH=CHPh | Ga |
| CHMeCH=CHPh | Ga |
| CH$_2$C≡CPh | Ga |
| CHMeC≡CPh | Ga |
| CH$_2$CH$_2$OPh | Ga |
| CH$_2$OPh | Ga |
| CH$_2$CH$_2$SPh | Ga |
| CH$_2$SPh | Ga |
| CH$_2$CH$_2$SOPh | Gb |
| CH$_2$CH$_2$SO$_2$Ph | Ga |
| CH$_2$OCH$_2$Ph | Ga |
| CH$_2$CH$_2$OCH$_2$Ph | Ga |
| CH$_2$SCH$_2$Ph | Ga |
| CH$_2$CH$_2$SCH$_2$Ph | Ga |
| CH$_2$SOCH$_2$Ph | Gb |
| CH$_2$CH$_2$SOCH$_2$Ph | Gb |
| CH$_2$SO$_2$CH$_2$Ph | Ga |
| CH$_2$CH$_2$SO$_2$CH$_2$Ph | Ga |
| CH$_2$COPh | Ga |
| CH$_2$CH$_2$COPh | Ga |
| CHMeCOPh | Ga |
| CH$_2$COCH$_2$Ph | Gb |
| CHMeCOCH$_2$Ph | Gb |
| CH$_2$CH$_2$CH$_2$F | Ga |
| CH$_2$CH$_2$CH$_2$Cl | Ga |
| CH$_2$C(Cl)=CH$_2$ | Ga |
| Ph | Ga |
| CH$_2$SOPh | Ga |
| CH$_2$SO$_2$Ph | Ga |
| CH$_2$C(Cl)=CHCl | Ga |
| CH$_2$C(F)=CHCl | Ga |
| CH$_2$CH=CHF | Ga |
| CH$_2$C(Cl)=CHMe | Ga |
| CH$_2$CH=C(Cl)Me | Ga |
| CH$_2$CF=CF$_2$ | Ga |
| CH$_2$CH=CHCH$_2$F | Ga |
| CH$_2$C(Br)=CHMe | Ga |

TABLE 2A-continued $$QSO_2NHCNH-Gn$$
$$\parallel$$
$$O$$

Q: [structures with N-O-R^{c1}, S, N substituents as shown]

| $R^{c1}$ | Gn |
|---|---|
| CH$_2$C(Cl)=CHF | Ga |
| CH$_2$C(Br)=CHF | Ga |
| CH$_2$C(Cl)=C(Cl)Me | Ga |
| CH$_2$C(Br)=CHBr | Ga |
| CH$_2$C(Br)=C(Br)Me | Ga |
| CH$_2$CH=C(F)CF$_3$ | Ga |
| CH$_2$CH=CCl$_2$ | Ga |
| CH$_2$C(F)=CH$_2$ | Ga |
| CH$_2$CH=C(F)Cl | Ga |
| CH$_2$C(Cl)=C(F)Cl | Ga |
| CH$_2$C(F)=CCl$_2$ | Ga |
| CH$_2$C(Cl)=CF$_2$ | Ga |
| CH$_2$C(CF$_3$)=CH$_2$ | Ga |
| CH$_2$CH=CHI | Ga |
| CH$_2$CH=CBr$_2$ | Ga |
| CH$_2$C(F)=CHBr | Ga |
| CH$_2$C(I)=CH$_2$ | Ga |
| CH$_2$C(Cl)=CCl$_2$ | Ga |
| CH$_2$C(F)=C(Cl)CF$_3$ | Ga |
| CH$_2$CH=C(F)CF$_2$Cl | Ga |
| CH$_2$C(Br)=CH$_2$ | Ga |
| CH$_2$NHSO$_2$Me | Gb |
| CH$_2$CH$_2$NHSO$_2$Me | Gb |
| CH$_2$NHCOMe | Gb |
| CH$_2$CH$_2$NHCOMe | Gb |

TABLE 2B $$QSO_2NHCNH-Gn$$
$$\parallel$$
$$O$$

Q: [structures with N-O-R^{c1}, S, N substituents as shown]

TABLE 2B-continued

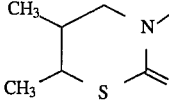

TABLE 2B-continued

| R$^{c1}$ | Gn |
|---|---|
| Me | Ga |
| Et | Ga |
| Pr-n | Ga |
| Pr-iso | Ga |
| Bu-n | Ga |
| Bu-iso | Gb |
| Pen-n | Gb |
| Hex-n | Gb |
| CH$_2$Pr-cyc | Ga |
| CH$_2$CH$_2$Pr-cyc | Ga |
| CH$_2$CH=CH$_2$ | Ga |
| CH$_2$CH=CHMe | Ga |
| CH$_2$C≡CH | Ga |
| CH$_2$C≡CMe | Ga |
| CH$_2$OMe | Ga |
| CH$_2$OEt | Ga |
| CH$_2$CH$_2$OMe | Ga |
| CH$_2$CH$_2$OEt | Ga |
| CH$_2$OCH$_2$CH=CH$_2$ | Ga |
| CH$_2$CH$_2$OCH$_2$CH=CH$_2$ | Ga |
| CH$_2$OCH$_2$C≡CH | Ga |
| CH$_2$CH$_2$OCH$_2$C≡CH | Ga |
| CH$_2$OCH$_2$CF$_3$ | Ga |
| CH$_2$CH$_2$OCH$_2$CF$_3$ | Ga |
| CH$_2$SMe | Ga |
| CH$_2$SEt | Ga |
| CH$_2$CH$_2$SMe | Ga |
| CH$_2$CH$_2$SEt | Ga |
| CH$_2$SO$_2$Me | Ga |
| CH$_2$SO$_2$Et | Ga |
| CH$_2$CH$_2$SO$_2$Me | Ga |
| CH$_2$CH$_2$SO$_2$Et | Ga |
| CH$_2$CH$_2$F | Ga |
| CH$_2$CF$_3$ | Ga |
| CH$_2$CN | Ga |
| CH$_2$CH$_2$CN | Ga |
| CHMeCN | Ga |
| CH$_2$CH=CHCN | Ga |
| CH$_2$NO$_2$ | Ga |
| CH$_2$CH$_2$NO$_2$ | Ga |
| CH$_2$CO$_2$Me | Gb |
| CH$_2$CO$_2$Et | Gb |
| CHMeCO$_2$Me | Gb |
| CHMeCO$_2$Et | Gb |
| CH$_2$CH$_2$CO$_2$Me | Ga |
| CH$_2$CH$_2$CO$_2$Et | Ga |
| CH$_2$CH=CHCO$_2$Me | Ga |
| CH$_2$CH=CHCO$_2$Et | Ga |
| CHMeCH=CHCO$_2$Me | Ga |
| CH$_2$COMe | Ga |
| CH$_2$COEt | Ga |
| CH$_2$COPr-n | Gb |
| CH$_2$COCF$_3$ | Ga |
| CH$_2$COCH=CH$_2$ | Ga |
| CH$_2$COCH=CHMe | Ga |
| CH$_2$COCH$_2$OMe | Ga |
| CH$_2$COCH$_2$OEt | Ga |
| CH$_2$COCH$_2$CH$_2$OMe | Ga |
| CH$_2$COCH$_2$CH$_2$OEt | Ga |
| CH$_2$COCH$_2$SMe | Ga |
| CH$_2$COCH$_2$CH$_2$SMe | Ga |
| CH$_2$COCH$_2$SO$_2$Me | Ga |
| CH$_2$COCH$_2$CH$_2$SO$_2$Me | Ga |
| CH$_2$CH=CHCOMe | Ga |
| CHMeCH=CHCOMe | Ga |
| CH$_2$SO$_2$NHMe | Gb |
| CH$_2$CH$_2$SO$_2$NHMe | Gb |
| CH$_2$SO$_2$NHMe | Gb |
| CH$_2$CH$_2$SO$_2$NHOMe | Gb |
| CH$_2$SO$_2$NMe$_2$ | Ga |
| CH$_2$CH$_2$SO$_2$NMe$_2$ | Ga |
| CH$_2$SO$_2$N(OMe)Me | Ga |
| CH$_2$CH$_2$SO$_2$N(OMe)Me | Ga |
| CH$_2$CONHMe | Gb |

TABLE 2B-continued

| | |
|---|---|
| CH$_2$CH$_2$CONHMe | Gb |
| CH$_2$CONMe$_2$ | Ga |
| CH$_2$CH$_2$CONMe$_2$ | Ga |
| CH$_2$CONHOMe | Gb |
| CH$_2$CH$_2$CONHOMe | Gb |
| CH$_2$CON(OMe)Me | Ga |
| CH$_2$CH$_2$CON(OMe)Me | Ga |
| CH$_2$NHMe | Gb |
| CH$_2$CH$_2$NHMe | Gb |
| CH$_2$NHOMe | Gb |
| CH$_2$CH$_2$NHOMe | Gb |
| CH$_2$NMe$_2$ | Ga |
| CH$_2$CH$_2$NMe$_2$ | Ga |
| CH$_2$N(OMe)Me | Ga |
| CH$_2$CH$_2$N(OMe)Me | Ga |
| CH$_2$NMeCOMe | Ga |
| CH$_2$CH$_2$NMeCOMe | Ga |
| CH$_2$N(OMe)COMe | Ga |
| CH$_2$CH$_2$N(OMe)COMe | Ga |
| CH$_2$NMeSO$_2$Me | Ga |
| CH$_2$CH$_2$NMeSO$_2$Me | Ga |
| CH$_2$N(OMe)SO$_2$Me | Ga |
| CH$_2$CH$_2$N(OMe)SO$_2$Me | Ga |
| CH$_2$Ph | Gb |
| CH$_2$CH$_2$Ph | Gb |
| CH$_2$CH$_2$CH$_2$Ph | Gb |
| CHMePh | Gb |
| CH$_2$CH=CHPh | Gb |
| CHMeCH=CHPh | Gb |
| CH$_2$CH$_2$OPh | Gb |
| CH$_2$OPh | Gb |
| CH$_2$CH$_2$SPh | Gb |
| CH$_2$SPh | Gb |
| CH$_2$CH$_2$SO$_2$Ph | Gb |
| CH$_2$COPh | Gb |
| CH$_2$CH$_2$COPh | Gb |
| CH$_2$COCH$_2$Ph | Gb |
| CH$_2$CH$_2$COCH$_2$Ph | Gb |
| Ph | Ga |

TABLE 2C

QSO$_2$NHCNH—Gn
‖
O

Q:

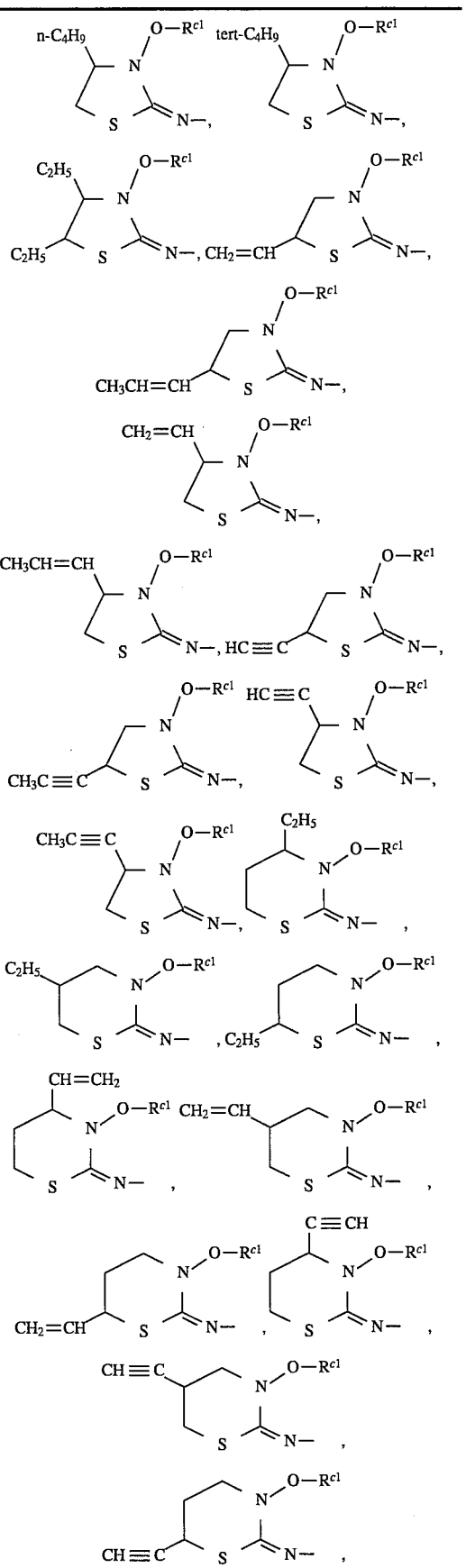

TABLE 2C-continued
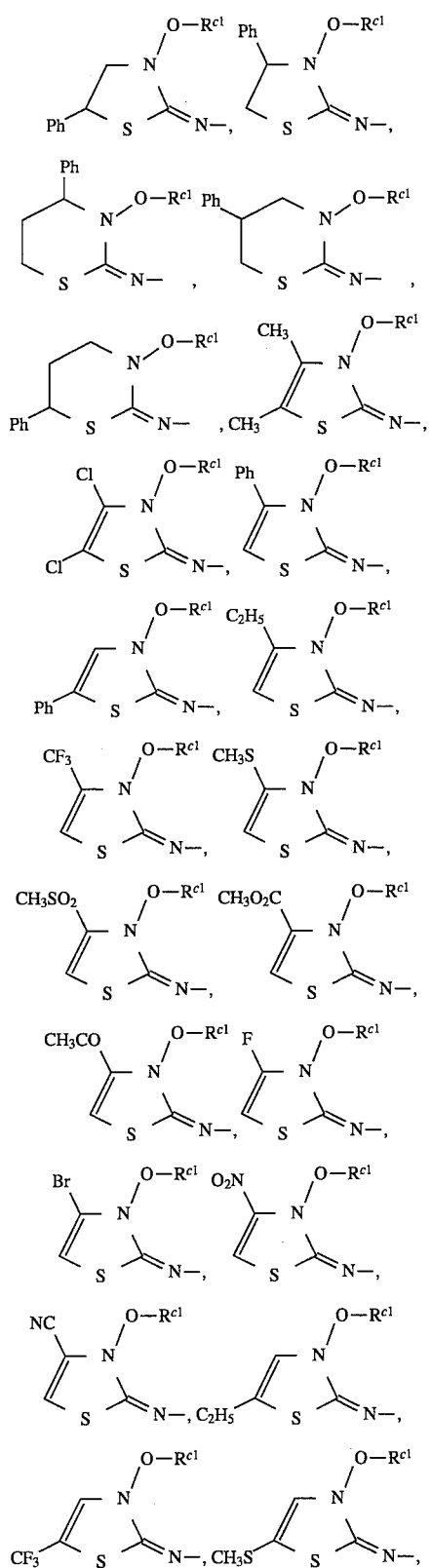
TABLE 2C-continued
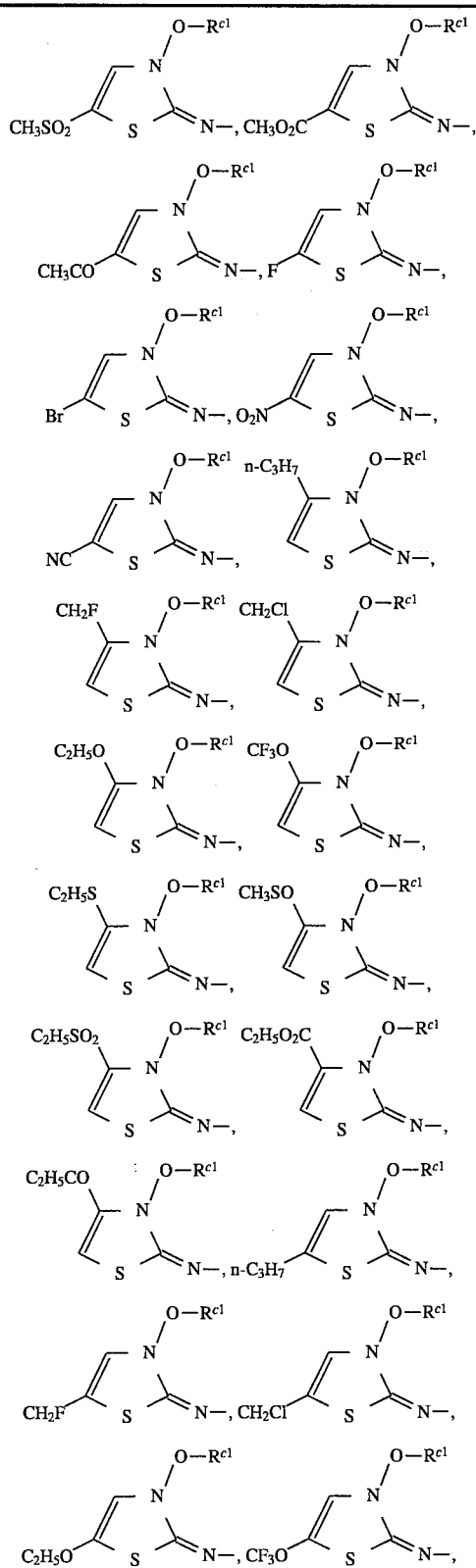

TABLE 2C-continued

TABLE 2C-continued

TABLE 2C-continued (Structures showing various thiocarbamate/oxime compounds with substituents including ClCH₂, C₂H₅O, CF₃O, C₂H₅S, CH₃SO, CH₃SO₂, C₂H₅SO₂, C₂H₅O₂C, C₂H₅CO, and OCF₃, OC₂H₅, SC₂H₅, SOCH₃, SO₂C₂H₅, CO₂C₂H₅, COC₂H₅ groups, each bearing N—O—R^{c1} and connected to S—C=N— moieties)

| R^{c1} | Gn |
| --- | --- |
| Me | Ga |
| Et | Ga |
| Pr-n | Ga |
| Pro-iso | Gb |
| Bu-n | Ga |
| Bu-iso | Ga |
| Pen-n | Gb |
| CH₂Pr-cyc | Ga |

TABLE 2C-continued

| | |
|---|---|
| CH$_2$CH$_2$Pr-cyc | Gb |
| CH$_2$CH=CH$_2$ | Ga |
| CH$_2$CH=CHMe | Ga |
| CH$_2$C≡CH | Ga |
| CH$_2$C≡CMe | Ga |
| CH$_2$CH$_2$OMe | Ga |
| CH$_2$OMe | Ga |
| CH$_2$CH$_2$SMe | Ga |
| CH$_2$SMe | Ga |
| CH$_2$SO$_2$Me | Ga |
| CH$_2$CH$_2$SO$_2$Me | Ga |
| CH$_2$CF$_3$ | Ga |
| CH$_2$CN | Ga |
| CH$_2$CH$_2$CN | Ga |
| CH$_2$NO$_2$ | Ga |
| CH$_2$CH$_2$NO$_2$ | Ga |
| CH$_2$COMe | Ga |
| CH$_2$COEt | Ga |
| CH$_2$COCH=CH$_2$ | Ga |
| CH$_2$CH=CHCOMe | Ga |
| CH$_2$CONMe$_2$ | Ga |
| Ph | Ga |

TABLE 3

$$QSO_2NHCNH-Gn$$
$$\underset{O}{\|}$$

Q:

TABLE 3-continued (Chemical structures, not transcribed as text.)

TABLE 3-continued
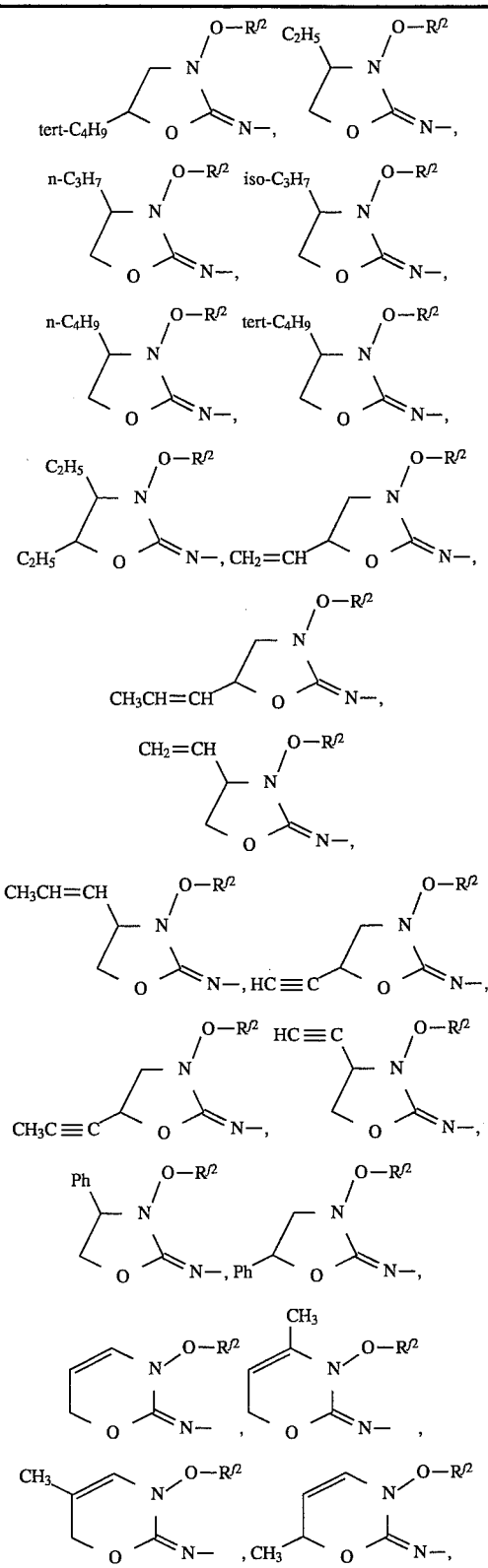
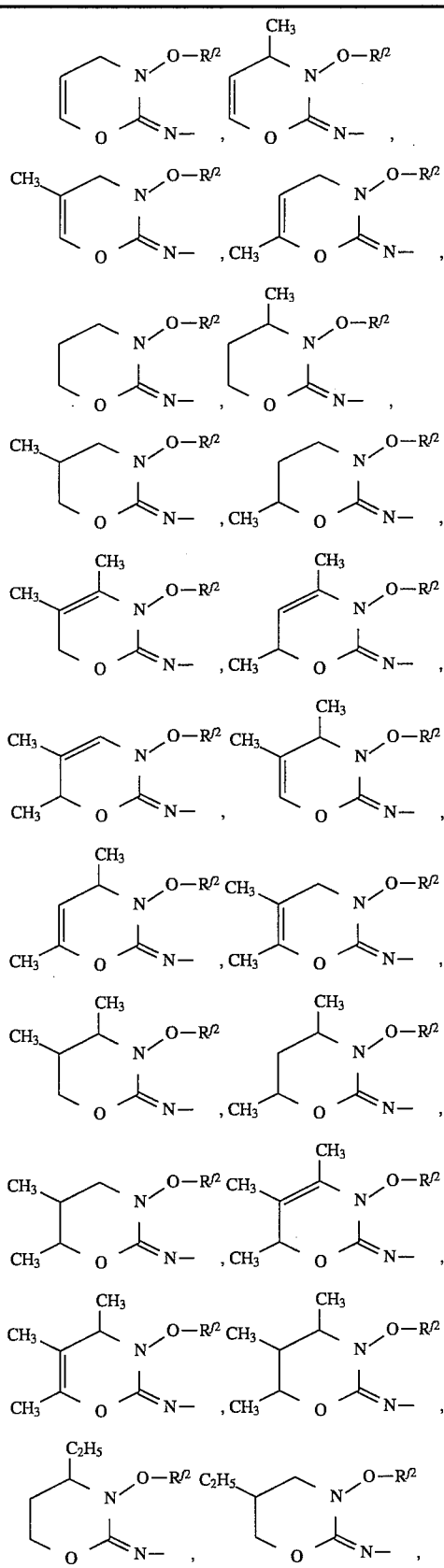

TABLE 3-continued

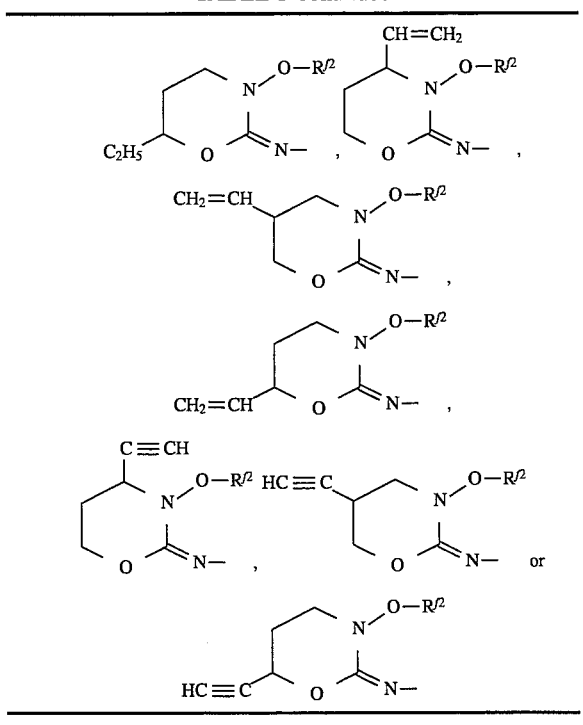

| $R^n$ | Gn |
|---|---|
| Me | Ga |
| Et | Ga |
| Pr-n | Ga |
| Pr-iso | Gb |
| Bu-n | Gb |
| Pen-n | Gb |
| Hex-n | Gb |
| $CH_2CH=CH_2$ | Ga |
| $CH_2CH=CHMe$ | Ga |
| $CH_2CH=CMe_2$ | Gb |
| $CHMeCH=CH_2$ | Gb |
| $CH_2C\equiv CH$ | Ga |
| $CH_2C\equiv CMe$ | Ga |
| $CHMeC\equiv CH$ | Gb |
| $CH_2SMe$ | Ga |
| $CH_2SEt$ | Ga |
| $CH_2SPr$-n | Gb |
| $CH_2CH_2SMe$ | Ga |
| $CH_2CH_2SEt$ | Ga |
| $CH_2SOMe$ | Gb |
| $CH_2SOEt$ | Gb |
| $CH_2CH_2SOMe$ | Gb |
| $CH_2CH_2SOEt$ | Gb |
| $CH_2SO_2Me$ | Ga |
| $CH_2SO_2Et$ | Ga |
| $CH_2SO_2Pr$-n | Gb |
| $CH_2CH_2SO_2Me$ | Ga |
| $CH_2CH_2SO_2Et$ | Ga |
| $CH_2OMe$ | Ga |
| $CH_2OEt$ | Ga |
| $CH_2OPr$-n | Gb |
| $CH_2CH_2OMe$ | Ga |
| $CH_2CH_2OEt$ | Ga |
| $CH_2CH_2OPr$-n | Gb |
| $CH_2CO_2Me$ | Ga |
| $CH_2CO_2Et$ | Ga |
| $CHMeCO_2Me$ | Ga |
| $CHMeCO_2Et$ | Ga |
| $CH_2COMe$ | Ga |
| $CH_2COEt$ | Ga |
| $CH_2COPr$-n | Gb |
| $CH_2CH_2COMe$ | Ga |
| $CH_2CH_2COEt$ | Ga |
| $CH_2CN$ | Ga |
| $CH_2CH_2CN$ | Ga |
| $CH_2CH_2CH_2CN$ | Ga |
| Ph | Ga |
| $CH_2Ph$ | Ga |
| $CH_2CH_2Ph$ | Ga |
| CHMePh | Ga |

$R^n$ represents $R^{d6}$ or $R^{f2}$.

TABLE 4A $QSO_2NHCNH-Gn$
$\parallel$
$O$

Q:

$\begin{array}{c} CH_3 \\ \diagdown \\ N-C \\ \diagup \\ CH_3 \end{array} \begin{array}{c} SR^{g1} \\ | \\ \\ N- \end{array}$, $\begin{array}{c} CH_3 \\ \diagdown \\ N-C \\ \diagup \\ C_2H_5 \end{array} \begin{array}{c} SR^{g1} \\ | \\ \\ N- \end{array}$, $\begin{array}{c} CH_3 \\ \diagdown \\ N-C \\ \diagup \\ n\text{-}C_3H_7 \end{array} \begin{array}{c} SR^{g1} \\ | \\ \\ N- \end{array}$, $\begin{array}{c} CH_3 \\ \diagdown \\ N-C \\ \diagup \\ CH_2=CHCH_2 \end{array} \begin{array}{c} SR^{g1} \\ | \\ \\ N- \end{array}$, $\begin{array}{c} CH_2=CHCH_2 \\ \diagdown \\ N-C \\ \diagup \\ CH_2=CHCH_2 \end{array} \begin{array}{c} SR^{g1} \\ | \\ \\ N- \end{array}$, $\begin{array}{c} CH_3 \\ \diagdown \\ N-C \\ \diagup \\ HC\equiv CCH_2 \end{array} \begin{array}{c} SR^{g1} \\ | \\ \\ N- \end{array}$, $\begin{array}{c} HC\equiv CCH_2 \\ \diagdown \\ N-C \\ \diagup \\ HC\equiv CCH_2 \end{array} \begin{array}{c} SR^{g1} \\ | \\ \\ N- \end{array}$, $\begin{array}{c} CH_3 \\ \diagdown \\ N-C \\ \diagup \\ CH_3O \end{array} \begin{array}{c} SR^{g1} \\ | \\ \\ N- \end{array}$, $\begin{array}{c} C_2H_5 \\ \diagdown \\ N-C \\ \diagup \\ CH_3O \end{array} \begin{array}{c} SR^{g1} \\ | \\ \\ N- \end{array}$, $\begin{array}{c} n\text{-}C_3H_7 \\ \diagdown \\ N-C \\ \diagup \\ CH_3O \end{array} \begin{array}{c} SR^{g1} \\ | \\ \\ N- \end{array}$, $\begin{array}{c} CH_3 \\ \diagdown \\ N-C \\ \diagup \\ C_2H_5O \end{array} \begin{array}{c} SR^{g1} \\ | \\ \\ N- \end{array}$, $\begin{array}{c} CH_3 \\ \diagdown \\ N-C \\ \diagup \\ CH_3SO_2 \end{array} \begin{array}{c} SR^{g1} \\ | \\ \\ N- \end{array}$, $\begin{array}{c} C_2H_5 \\ \diagdown \\ N-C \\ \diagup \\ CH_3SO_2 \end{array} \begin{array}{c} SR^{g1} \\ | \\ \\ N- \end{array}$, $\begin{array}{c} n\text{-}C_3H_7 \\ \diagdown \\ N-C \\ \diagup \\ CH_3SO_2 \end{array} \begin{array}{c} SR^{g1} \\ | \\ \\ N- \end{array}$, $\begin{array}{c} CH_3 \\ \diagdown \\ N-C \\ \diagup \\ CH_3NHSO_2 \end{array} \begin{array}{c} SR^{g1} \\ | \\ \\ N- \end{array}$, $\begin{array}{c} C_2H_5 \\ \diagdown \\ N-C \\ \diagup \\ CH_3NHSO_2 \end{array} \begin{array}{c} SR^{g1} \\ | \\ \\ N- \end{array}$, $\begin{array}{c} CH_3 \\ \diagdown \\ N-C \\ \diagup \\ (CH_3)_2NSO_2 \end{array} \begin{array}{c} SR^{g1} \\ | \\ \\ N- \end{array}$, $\begin{array}{c} C_2H_5 \\ \diagdown \\ N-C \\ \diagup \\ (CH_3)_2NSO_2 \end{array} \begin{array}{c} SR^{g1} \\ | \\ \\ N- \end{array}$, $\begin{array}{c} CH_3 \\ \diagdown \\ N-C \\ \diagup \\ CH_3O_2C \end{array} \begin{array}{c} SR^{g1} \\ | \\ \\ N- \end{array}$, $\begin{array}{c} C_2H_5 \\ \diagdown \\ N-C \\ \diagup \\ CH_3O_2C \end{array} \begin{array}{c} SR^{g1} \\ | \\ \\ N- \end{array}$, $\begin{array}{c} CH_3 \\ \diagdown \\ N-C \\ \diagup \\ C_2H_5O_2C \end{array} \begin{array}{c} SR^{g1} \\ | \\ \\ N- \end{array}$, $\begin{array}{c} C_2H_5 \\ \diagdown \\ N-C \\ \diagup \\ C_2H_5O_2C \end{array} \begin{array}{c} SR^{g1} \\ | \\ \\ N- \end{array}$,

TABLE 4A-continued $\begin{array}{c}CH_3\\ \diagdown\\ N-C\diagup SR^{g1}\\ CH_3CO\diagup \quad \diagdown N-,\end{array}$ $\begin{array}{c}C_2H_5\\ \diagdown\\ N-C\diagup SR^{g1}\\ CH_3CO\diagup \quad \diagdown N-,\end{array}$ $\begin{array}{c}CH_3\\ \diagdown\\ N-C\diagup SR^{g1}\\ C_2H_5CO\diagup \quad \diagdown N-,\end{array}$ $\begin{array}{c}C_2H_5\\ \diagdown\\ N-C\diagup SR^{g1}\\ C_2H_5CO\diagup \quad \diagdown N-,\end{array}$ $\begin{array}{c}CH_3\\ \diagdown\\ N-C\diagup SR^{g1}\\ CH_3NHCO\diagup \quad \diagdown N-,\end{array}$ $\begin{array}{c}C_2H_5\\ \diagdown\\ N-C\diagup SR^{g1}\\ CH_3NHCO\diagup \quad \diagdown N-,\end{array}$ $\begin{array}{c}CH_3\\ \diagdown\\ N-C\diagup SR^{g1}\\ C_2H_5NHCO\diagup \quad \diagdown N-,\end{array}$ $\begin{array}{c}C_2H_5\\ \diagdown\\ N-C\diagup SR^{g1}\\ (CH_3)_2NCO\diagup \quad \diagdown N-,\end{array}$ $\begin{array}{c}C_2H_5\\ \diagdown\\ N-C\diagup SR^{g1}\\ (CH_3)_2NCO\diagup \quad \diagdown N-,\end{array}$ $\begin{array}{c}CH_3\\ \diagdown\\ N-C\diagup SR^{g1}\\ Ph\diagup \quad \diagdown N-,\end{array}$ $\begin{array}{c}C_2H_5\\ \diagdown\\ N-C\diagup SR^{g1}\\ Ph\diagup \quad \diagdown N-,\end{array}$ $\begin{array}{c}CH_3\\ \diagdown\\ N-C\diagup SR^{g1}\\ PhCH_2\diagup \quad \diagdown N-,\end{array}$ $\begin{array}{c}C_2H_5\\ \diagdown\\ N-C\diagup SR^{g1}\\ PhCH_2\diagup \quad \diagdown N-,\end{array}$ $\begin{array}{c}\triangle\\ N-C\diagup SR^{g1}\\ \quad \diagdown N-,\end{array}$ or $\begin{array}{c}\square\\ N-C\diagup SR^{g1}\\ \quad \diagdown N-,\end{array}$

| $R^{g1}$ | Gn |
|---|---|
| Me | Ga |
| Et | Ga |
| Pr-n | Ga |
| Pr-iso | Ga |
| Bu-n | Ga |
| Bu-iso | Ga |
| Bu-sec | Gb |
| Bu-tert | Gb |
| Pen-n | Ga |
| Hex-n | Gb |
| Hep-n | Gb |
| Pr-cyc | Ga |
| Hex-cyc | Ga |
| $CH_2Pr$-cyc | Ga |
| $CH_2CH_2Pr$-cyc | Ga |
| $CH_2Bu$-cyc | Gb |
| $CH_2Pen$-cyc | Gc |
| Hexen-cyc | Gb |
| $CH_2Penten$-cyc | Gb |
| $CH_2CH=CH_2$ | Ga |
| $CH_2CH=CHMe$ | Ga |
| $CH_2CH=CHEt$ | Ga |
| $CH_2CH=CMe_2$ | Gb |
| $CH_2CMe=CH_2$ | Gb |
| $CH_2CMeCH=CHMe$ | Gc |
| $CH_2CH_2CHCH_2$ | Gb |
| $CH_2CH_2CH=CHMe$ | Gb |
| $CH_2C\equiv CH$ | Ga |
| $CH_2C\equiv CMe$ | Ga |
| $CH_2C\equiv CEt$ | Ga |
| $CH_2CH_2C\equiv CH$ | Gb |
| $CH_2CH_2C\equiv CMe$ | Gb |
| $CHMeC\equiv CH$ | Gb |
| $CHMeC\equiv CMe$ | Gc |
| $CH_2OMe$ | Ga |
| $CH_2OEt$ | Ga |
| $CH_2OPr$-n | Gb |
| $CH_2CH_2OMe$ | Ga |
| $CH_2CH_2OEt$ | Ga |
| $CH_2CH_2OPr$-n | Gb |
| $CH_2CHMeOMe$ | Gb |
| $CH_2CH_2CH_2OMe$ | Ga |
| $CH_2CH_2CH_2OEt$ | Ga |
| $CH_2OCH_2CH=CH_2$ | Ga |
| $CH_2OCH_2CH=CHMe$ | Ga |
| $CH_2CH_2OCH_2CH=CH_2$ | Ga |
| $CH_2CH_2OCH_2CH=CHMe$ | Ga |
| $CH_2OCH_2C\equiv CH$ | Ga |
| $CH_2OCH_2C\equiv CMe$ | Ga |
| $CH_2CH_2OCH_2C\equiv CH$ | Ga |
| $CH_2CH_2OCH_2C\equiv CMe$ | Ga |
| $CH_2OCHF_2$ | Ga |
| $CH_2OCF_3$ | Ga |
| $CH_2CH_2OCHF_2$ | Ga |
| $CH_2CH_2OCF_3$ | Ga |
| $CH_2OCH_2CF_3$ | Ga |
| $CH_2CH_2OCH_2CF_3$ | Ga |
| $CH_2OCH_2CH_2F$ | Ga |
| $CH_2OCH_2CH_2Cl$ | Ga |
| $CH_2CH_2OCH_2CH_2F$ | Ga |
| $CH_2CH_2OCH_2CH_2Cl$ | Ga |
| $CH_2OCH_2CH=CHCl$ | Gb |
| $CH_2CH_2OCH_2CH=CHCl$ | Gb |
| $CH_2OCH_2CH=CHBr$ | Gb |
| $CH_2CH_2OCH_2CH=CHBr$ | Gb |
| $CH_2OCH_2CH=CF_2$ | Gb |
| $CH_2CH_2OCH_2CH=CF_2$ | Gb |
| $CH_2OCH_2CH=CHCF_3$ | Gb |
| $CH_2CH_2OCH_2CH=CHCF_3$ | Gb |
| $CH_2OCH_2C\equiv Cl$ | Gb |
| $CH_2CH_2OCH_2C\equiv Cl$ | Gb |
| $CH_2OCH_2C\equiv CCF_3$ | Gb |
| $CH_2CH_2OCH_2C\equiv CCF_3$ | Gb |
| $CH_2SMe$ | Ga |
| $CH_2SEt$ | Ga |
| $CH_2SPr$-n | Gb |
| $CH_2CH_2SMe$ | Ga |
| $CH_2CH_2SEt$ | Ga |
| $CH_2CH_2SPr$-n | Gb |
| $CH_2SOMe$ | Gb |
| $CH_2SOEt$ | Gb |
| $CH_2CH_2SOMe$ | Gb |
| $CH_2CH_2SOEt$ | Gb |
| $CH_2SO_2Me$ | Ga |
| $CH_2SO_2Et$ | Ga |
| $CH_2SO_2Pr$-n | Gb |
| $CH_2CH_2SO_2Me$ | Ga |
| $CH_2CH_2SO_2Et$ | Ga |
| $CH_2CH_2SO_2Pr$-n | Gb |
| $CH_2CH_2F$ | Ga |
| $CH_2CHF_2$ | Ga |
| $CH_2CF_3$ | Ga |
| $CH_2CH_2Cl$ | Ga |
| $CH_2CH_2Br$ | Ga |
| $CH_2CH_2CF_3$ | Ga |
| $CH_2CF_2CF_3$ | Ga |

TABLE 4A-continued

| | |
|---|---|
| $CH_2CH=CHCl$ | Gb |
| $CH_2CH=CHBr$ | Gb |
| $CH_2CH=CF_2$ | Gb |
| $CH_2CH=CHCF_3$ | Gb |
| $CH_2C\equiv CI$ | Gb |
| $CH_2C\equiv CCF_3$ | Gb |
| $CH_2CN$ | Ga |
| $CH_2CH_2CN$ | Ga |
| $CHMeCN$ | Ga |
| $CH_2CH=CHCN$ | Ga |
| $CH(CN)C\equiv CH$ | Gb |
| $CH_2NO_2$ | Ga |
| $CH_2CH_2NO_2$ | Ga |
| $CH_2CH=CHNO_2$ | Gb |
| $CH_2CH(NO_2)CH=CH_2$ | Gc |
| $CH_2CH(NO_2)C\equiv CH$ | Gc |
| $CH_2CO_2Me$ | Gb |
| $CH_2CO_2Et$ | Gb |
| $CH_2CO_2Pr\text{-}n$ | Gb |
| $CHMeCO_2Me$ | Gb |
| $CHMeCO_2Et$ | Gb |
| $CH_2CH_2CO_2Me$ | Ga |
| $CH_2CH_2CO_2Et$ | Ga |
| $CH_2CH_2CH_2CO_2Me$ | Gb |
| $CH_2CH=CHCO_2Me$ | Ga |
| $CH_2CH=CHCO_2Et$ | Ga |
| $CHMeCH=CHCO_2Me$ | Ga |
| $CHMeCH=CHCO_2Et$ | Ga |
| $CH_2C\equiv CCO_2Me$ | Ga |
| $CH_2C\equiv CCO_2Et$ | Ga |
| $CH_2COMe$ | Ga |
| $CH_2COEt$ | Ga |
| $CH_2COPr\text{-}n$ | Gb |
| $CH_2CH_2COMe$ | Ga |
| $CH_2CH_2COEt$ | Ga |
| $CH_2COCF_3$ | Ga |
| $CH_2CH_2COCF_3$ | Ga |
| $CH_2COCH_2CF_3$ | Gb |
| $CH_2COCH_2F$ | Gb |
| $CH_2COCH=CH_2$ | Ga |
| $CH_2COCH=CHMe$ | Ga |
| $CH_2COCH_2CH=CH_2$ | Gb |
| $CH_2CH_2COCH=CH_2$ | Gb |
| $CH_2CH_2COCH=CHMe$ | Gb |
| $CH_2COC\equiv CH$ | Ga |
| $CH_2COC\equiv CMe$ | Ga |
| $CH_2COCH_2OMe$ | Ga |
| $CH_2COCH_2OEt$ | Ga |
| $CH_2COCH_2CH_2OMe$ | Ga |
| $CH_2COCH_2CH_2OEt$ | Ga |
| $CH_2COCH_2SMe$ | Ga |
| $CH_2COCH_2SEt$ | Ga |
| $CH_2COCH_2CH_2SMe$ | Ga |
| $CH_2COCH_2CH_2SEt$ | Ga |
| $CH_2COCH_2SOMe$ | Gb |
| $CH_2COCH_2CH_2SOMe$ | Gb |
| $CH_2COCH_2SO_2Me$ | Ga |
| $CH_2COCH_2SO_2Et$ | Ga |
| $CH_2COCH_2CH_2SO_2Me$ | Ga |
| $CH_2COCH_2CH_2SO_2Et$ | Ga |
| $CH_2CH=CHCOMe$ | Ga |
| $CH_2CH=CHCOEt$ | Ga |
| $CHMeCH=CHCOMe$ | Ga |
| $CHMeCH=CHCOEt$ | Ga |
| $CH_2C\equiv CCOMe$ | Ga |
| $CH_2C\equiv CCOEt$ | Ga |
| $CH_2SO_2NHMe$ | Ga |
| $CH_2SO_2NHEt$ | Ga |
| $CH_2CH_2SO_2NHMe$ | Ga |
| $CH_2CH_2SO_2NHEt$ | Ga |
| $CH_2SO_2NHOMe$ | Ga |
| $CH_2SO_2NHOEt$ | Ga |
| $CH_2CH_2SO_2NHOMe$ | Ga |
| $CH_2CH_2SO_2NHOEt$ | Ga |
| $CH_2SO_2NMe_2$ | Ga |
| $CH_2SO_2NMeEt$ | Ga |
| $CH_2SO_2NEt_2$ | Ga |
| $CH_2CH_2SO_2NMe_2$ | Ga |
| $CH_2CH_2SO_2NMeEt$ | Ga |
| $CH_2CH_2SO_2NEt_2$ | Ga |
| $CH_2SO_2N(OMe)Me$ | Ga |
| $CH_2SO_2N(OMe)Et$ | Ga |
| $CH_2SO_2N(OEt)Me$ | Ga |
| $CH_2CH_2SO_2N(OMe)Me$ | Ga |
| $CH_2CH_2SO_2N(OMe)Et$ | Ga |
| $CH_2CH_2SO_2N(OEt)Me$ | Ga |
| $CH_2CONHMe$ | Ga |
| $CH_2CONHEt$ | Ga |
| $CH_2CONHPr\text{-}n$ | Gb |
| $CH_2CH_2CONHMe$ | Ga |
| $CH_2CH_2CONHEt$ | Ga |
| $CH_2CH_2CONHPr\text{-}n$ | Gb |
| $CH_2CONMe_2$ | Ga |
| $CH_2CONMeEt$ | Ga |
| $CH_2CONEt_2$ | Ga |
| $CH_2CONHOMe$ | Ga |
| $CH_2CONHOEt$ | Ga |
| $CH_2CONHOPr\text{-}n$ | Gb |
| $CH_2CON(OMe)Me$ | Ga |
| $CH_2CON(OMe)Et$ | Ga |
| $CH_2CON(OEt)Me$ | Ga |
| $CH_2CON(OEt)Et$ | Ga |
| $CH_2NHMe$ | Ga |
| $CH_2NHEt$ | Ga |
| $CH_2NHPr\text{-}n$ | Gb |
| $CH_2CH_2NHMe$ | Ga |
| $CH_2CH_2NHEt$ | Ga |
| $CH_2CH_2NHPr\text{-}n$ | Gb |
| $CH_2NHOMe$ | Ga |
| $CH_2NHOEt$ | Ga |
| $CH_2CH_2NHOMe$ | Ga |
| $CH_2CH_2NHOEt$ | Ga |
| $CH_2NMe_2$ | Ga |
| $CH_2NMeEt$ | Ga |
| $CH_2CH_2NMe_2$ | Ga |
| $CH_2CH_2NMeEt$ | Ga |
| $CH_2N(OMe)Me$ | Ga |
| $CH_2N(OMe)Et$ | Ga |
| $CH_2N(OEt)Me$ | Ga |
| $CH_2CH_2N(OMe)Me$ | Ga |
| $CH_2CH_2N(OMe)Et$ | Ga |
| $CH_2CH_2N(OEt)Me$ | Ga |
| $CH_2NMeCOMe$ | Ga |
| $CH_2NEtCOMe$ | Ga |
| $CH_2NMeCOEt$ | Ga |
| $CH_2CH_2NMeCOMe$ | Ga |
| $CH_2CH_2NEtCOMe$ | Ga |
| $CH_2CH_2NMeCOEt$ | Ga |
| $CH_2N(OMe)COMe$ | Ga |
| $CH_2N(OEt)COMe$ | Ga |
| $CH_2N(OMe)COEt$ | Ga |
| $CH_2CH_2N(OMe)COMe$ | Ga |
| $CH_2CH_2N(OEt)COMe$ | Ga |
| $CH_2CH_2N(OMe)COEt$ | Ga |
| $CH_2NMeSO_2Me$ | Ga |
| $CH_2NEtSO_2Me$ | Ga |
| $CH_2NMeSO_2Et$ | Ga |
| $CH_2CH_2NMeSO_2Me$ | Ga |
| $CH_2CH_2NEtSO_2Me$ | Ga |
| $CH_2CH_2NMeSO_2Et$ | Ga |
| $CH_2N(OMe)SO_2Me$ | Ga |
| $CH_2N(OEt)SO_2Me$ | Ga |
| $CH_2N(OMe)SO_2Et$ | Ga |
| $CH_2CH_2N(OMe)SO_2Me$ | Ga |
| $CH_2CH_2N(OEt)SO_2Me$ | Ga |
| $CH_2CH_2N(OMe)SO_2Et$ | Ga |
| $CH_2Ph$ | Gb |
| $CH_2CH_2Ph$ | Gb |

TABLE 4A-continued

| | |
|---|---|
| CH₂CH₂CH₂Ph | Gb |
| CHMePh | Gb |
| CH₂CH=CHPh | Ga |
| CHMeCH=CHPh | Ga |
| CH₂C≡CPh | Ga |
| CHMeC≡CPh | Ga |
| CH₂CH₂OPh | Ga |
| CH₂OPh | Ga |
| CH₂CH₂SPh | Ga |
| CH₂SPh | Ga |
| CH₂CH₂SOPh | Gb |
| CH₂CH₂SO₂Ph | Ga |
| CH₂OCH₂Ph | Ga |
| CH₂CH₂OCH₂Ph | Ga |
| CH₂SCH₂Ph | Ga |
| CH₂CH₂SCH₂Ph | Ga |
| CH₂SOCH₂Ph | Gb |
| CH₂CH₂SOCH₂Ph | Gb |
| CH₂SO₂CH₂Ph | Ga |
| CH₂CH₂SO₂CH₂Ph | Ga |
| CH₂COPh | Ga |
| CH₂CH₂COPh | Ga |
| CHMeCOPh | Ga |
| CH₂COCH₂Ph | Gb |
| CHMeCOCH₂Ph | Gb |
| CH₂CH₂CH₂F | Ga |
| CH₂CH₂CH₂Cl | Ga |

TABLE 4B

QSO₂NHCNH—Gn
‖
O

Q: structures shown with various substituents including C₂H₅, n-C₄H₉, CH₂=CHCH₂, CH₃CH=CHCH₂, HC≡CCH₂, FCH₂, F₂CH, CF₃, CF₃CH₂, FCH₂CH₂, ClCH₂CH₂, BrCH₂CH₂, n-C₃H₇O, C₂H₅SO₂, CH₃NHSO₂, C₂H₅NHSO₂, (CH₃)₂NSO₂, (C₂H₅)₂NSO₂, CH₃O₂C, C₂H₅O₂C, CH₃CO, C₂H₅CO, CH₃NHCO, n-C₃H₇NHCO, (CH₃)₂NCO, (C₂H₅)₂NCO, Ph, PhCH₂, and cyclic (piperidine, azepane) groups.

| R^g1 | Gn |
|---|---|
| Me | Ga |
| Et | Ga |
| Pr-n | Ga |
| Pr-iso | Ga |
| Bu-n | Ga |
| Bu-iso | Gb |
| Pen-n | Gb |
| Hex-n | Gb |
| CH₂Pr-cyc | Ga |
| CH₂CH₂Pr-cyc | Ga |
| CH₂CH=CH₂ | Ga |
| CH₂CH=CHMe | Ga |
| CH₂C≡CH | Ga |
| CH₂C≡CMe | Ga |
| CH₂OMe | Ga |
| CH₂OEt | Ga |
| CH₂CH₂OMe | Ga |
| CH₂CH₂OEt | Ga |
| CH₂OCH₂CH=CH₂ | Ga |

TABLE 4B-continued

| | |
|---|---|
| CH₂CH₂OCH₂CH=CH₂ | Ga |
| CH₂OCH₂C≡CH | Ga |
| CH₂CH₂OCH₂C≡CH | Ga |
| CH₂OCH₂CF₃ | Ga |
| CH₂CH₂OCH₂CF₃ | Ga |
| CH₂SMe | Ga |
| CH₂SEt | Ga |
| CH₂CH₂SMe | Ga |
| CH₂CH₂SEt | Ga |
| CH₂SO₂Me | Ga |
| CH₂SO₂Et | Ga |
| CH₂CH₂SO₂Me | Ga |
| CH₂CH₂CO₂Et | Ga |
| CH₂CH₂F | Ga |
| CH₂CF₃ | Ga |
| CH₂CN | Ga |
| CH₂CH₂CN | Ga |
| CHMeCN | Ga |
| CH₂CH=CHCN | Ga |
| CH₂NO₂ | Ga |
| CH₂CH₂NO₂ | Ga |
| CH₂CO₂Me | Gb |
| CH₂CO₂Et | Gb |
| CHMeCO₂Me | Gb |
| CHMeCO₂Et | Gb |
| CH₂CH₂CO₂Me | Ga |
| CH₂CH₂CO₂Et | Ga |
| CH₂CH=CHCO₂Me | Ga |
| CH₂CH=CHCO₂Et | Ga |
| CHMeCH=CHCO₂Me | Ga |
| CH₂COMe | Ga |
| CH₂COEt | Ga |
| CH₂COPr-n | Gb |
| CH₂COCF₃ | Ga |
| CH₂COCH=CH₂ | Ga |
| CH₂COCH=CHMe | Ga |
| CH₂COCH₂OMe | Ga |
| CH₂COCH₂OEt | Ga |
| CH₂COCH₂CH₂OMe | Ga |
| CH₂COCH₂CH₂OEt | Ga |
| CH₂COCH₂SMe | Ga |
| CH₂COCH₂CH₂SMe | Ga |
| CH₂COCH₂SO₂Me | Ga |
| CH₂COCH₂CH₂SO₂Me | Ga |
| CH₂CH=CHCOMe | Ga |
| CHMeCH=CHCOMe | Ga |
| CH₂SO₂NHMe | Gb |
| CH₂CH₂SO₂NHMe | Gb |
| CH₂SO₂NHOMe | Gb |
| CH₂CH₂SO₂NHOMe | Gb |
| CH₂SO₂NMe₂ | Ga |
| CH₂CH₂SO₂NMe₂ | Ga |
| CH₂SO₂N(OMe)Me | Ga |
| CH₂CH₂SO₂N(OMe)Me | Ga |
| CH₂CONHMe | Gb |
| CH₂CH₂CONHMe | Gb |
| CH₂CONMe₂ | Ga |
| CH₂CH₂CONMe₂ | Ga |
| CH₂CONHOMe | Gb |
| CH₂CH₂CONHOMe | Gb |
| CH₂CON(OMe)Me | Ga |
| CH₂CH₂CON(OMe)Me | Ga |
| CH₂NHMe | Gb |
| CH₂CH₂NHMe | Gb |
| CH₂NHOMe | Gb |
| CH₂CH₂NHOMe | Gb |
| CH₂NMe₂ | Ga |
| CH₂CH₂NMe₂ | Ga |
| CH₂N(OMe)Me | Ga |
| CH₂CH₂N(OMe)Me | Ga |
| CH₂NMeCOMe | Ga |
| CH₂CH₂NMeCOMe | Ga |
| CH₂N(OMe)COMe | Ga |
| CH₂CH₂N(OMe)COMe | Ga |
| CH₂NMeSO₂Me | Ga |
| CH₂CH₂NMeSO₂Me | Ga |
| CH₂N(OMe)SO₂Me | Ga |
| CH₂CH₂N(OMe)SO₂Me | Ga |
| CH₂Ph | Gb |
| CH₂CH₂Ph | Gb |
| CH₂CH₂CH₂Ph | Gb |
| CHMePh | Gb |
| CH₂CH=CHPh | Gb |
| CHMeCH=CHPh | Gb |
| CH₂CH₂OPh | Gb |
| CH₂OPh | Gb |
| CH₂CH₂SPh | Gb |
| CH₂SPh | Gb |
| CH₂CH₂SO₂Ph | Gb |
| CH₂COPh | Gb |
| CH₂CH₂COPh | Gb |
| CH₂COCH₂Ph | Gb |
| CH₂CH₂COCH₂Ph | Gb |

TABLE 4C

QSO₂NHCNH—Gn
‖
O

Q:

$n\text{-}C_3H_7\diagdown N\diagup C\diagup SR^{g1}\diagdown N\text{-}$, with $n\text{-}C_3H_7$ on N, $n\text{-}C_5H_{11}\diagdown N\diagup C\diagup SR^{g1}\diagdown N\text{-}$, with $CH_3$ on N, $CH_3C\equiv CCH_2\diagdown N\diagup C\diagup SR^{g1}\diagdown N\text{-}$, with $CH_3$ on N, $n\text{-}C_3H_7SO_2\diagdown N\diagup C\diagup SR^{g1}\diagdown N\text{-}$, with $CH_3$ on N, $n\text{-}C_3H_7NHSO_2\diagdown N\diagup C\diagup SR^{g1}\diagdown N\text{-}$, with $CH_3$ on N, $n\text{-}C_3H_7O_2C\diagdown N\diagup C\diagup SR^{g1}\diagdown N\text{-}$, with $CH_3$ on N, $n\text{-}C_4H_9O_2C\diagdown N\diagup C\diagup SR^{g1}\diagdown N\text{-}$ or $n\text{-}C_3H_7CO\diagdown N\diagup C\diagup SR^{g1}\diagdown N\text{-}$, with $CH_3$ on N

| $R^{g1}$ | Gn |
|---|---|
| Me | Ga |
| Et | Ga |
| Pr-n | Ga |
| Pro-iso | Gb |
| Bu-n | Ga |
| Bu-iso | Ga |
| Pen-n | Gb |
| CH₂Pr-cyc | Ga |
| CH₂CH₂Pr-cyc | Gb |
| CH₂CH=CH₂ | Ga |
| CH₂CH=CHMe | Ga |
| CH₂C≡CH | Ga |
| CH₂C≡CMe | Ga |
| CH₂CH₂OMe | Ga |
| CH₂OMe | Ga |
| CH₂CH₂SMe | Ga |
| CH₂SMe | Ga |
| CH₂SO₂Me | Ga |
| CH₂CH₂SO₂Me | Ga |
| CH₂CF₃ | Ga |
| CH₂CN | Ga |
| CH₂CH₂CN | Ga |
| CH₂NO₂ | Ga |
| CH₂CH₂NO₂ | Ga |
| CH₂COMe | Ga |
| CH₂COEt | Ga |

TABLE 4C-continued
| | |
|---|---|
| CH₂COCH=CH₂ | Ga |
| CH₂CH=CHCOMe | Ga |
| CH₂CONMe₂ | Ga |
TABLE 5
$$QSO_2NHC(=O)-N(L)-Gn$$
Q:
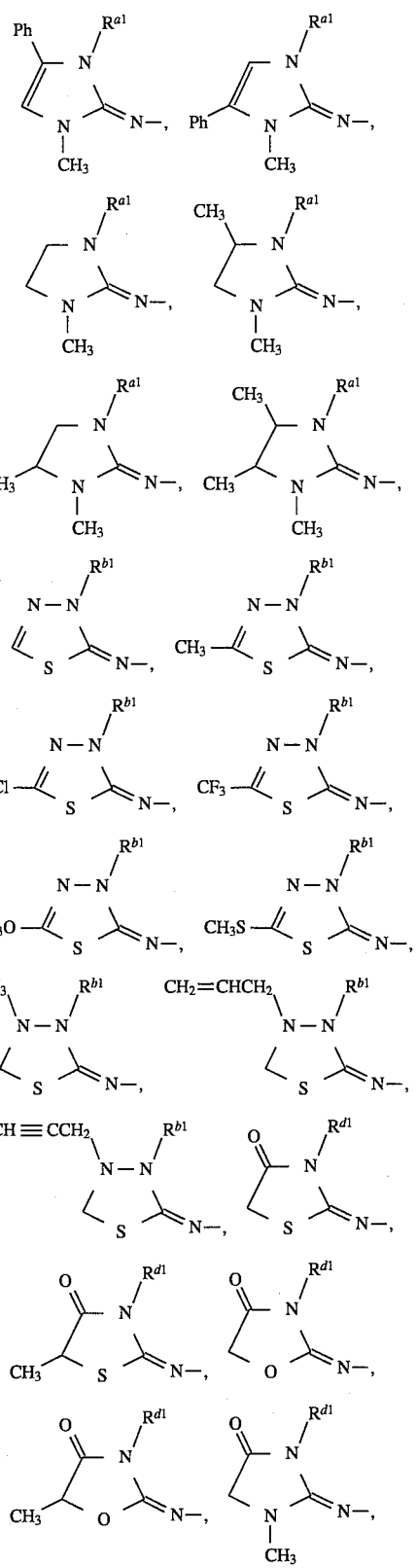
TABLE 5-continued TABLE 5-continued TABLE 5-continued

| $R^m$ | L | Gn |
|---|---|---|
| Me | Me | Ga |
| Me | Et | Gb |
| Et | Me | Ga |
| Et | Et | Gb |
| Pr-n | Me | Ga |
| Pr-n | Et | Gb |
| Pr-n | $CH_2CH=CH_2$ | Gb |
| Pr-n | $CH_2C\equiv CH$ | Gb |
| Bu-n | Me | Ga |
| Bu-n | Et | Gb |
| Bu-n | $CH_2CH=CH_2$ | Gb |
| Bu-n | $CH_2C\equiv CH$ | Gb |
| Pen-n | Me | Gb |
| $CH_2CH=CH_2$ | Me | Ga |
| $CH_2CH=CH_2$ | Et | Gb |
| $CH_2CH=CH_2$ | $CH_2CH=CH_2$ | Gb |
| $CH_2CH=CH_2$ | $CH_2C\equiv CH$ | Gb |
| $CH_2C\equiv CH$ | Me | Gb |
| $CH_2C\equiv CH$ | Et | Gb |
| $CH_2C\equiv CH$ | $CH_2CH=CH_2$ | Gb |
| $CH_2C\equiv CH$ | $CH_2C\equiv CH$ | Gb |
| $CH_2CH_2OMe$ | Me | Gb |
| $CH_2CH_2SMe$ | Me | Gb |
| $CH_2SO_2Me$ | Me | Gb |
| $CH_2CF_3$ | Me | Gb |
| $CH_2CF_3$ | Et | Gb |
| $CH_2CF_3$ | $CH_2CH=CH_2$ | Gb |
| $CH_2CF_3$ | $CH_2C\equiv CH$ | Gb |
| $CH_2CN$ | Me | Gb |
| $CH_2COMe$ | Me | Gb |
| $CH_2COMe$ | Et | Gb |
| $CH_2COMe$ | $CH_2CH=CH_2$ | Gb |
| $CH_2COMe$ | $CH_2C\equiv CH$ | Gb |
| $CH_2COCH=CH_2$ | Me | Gb |
| $CH_2CONMe_2$ | Me | Gb |

$R^m$ represents $R^{a1}$, $R^{b1}$, $R^{d1}$, $R^{e1}$, or $R^{f1}$.

TABLE 6

$$QSO_2NHC-N-Gn$$
$$\underset{O}{\|}\ \underset{L}{|}$$

Q:

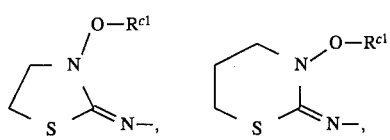

TABLE 6-continued

| R<sup>c1</sup> | L | Gn |
|---|---|---|
| Me | Me | Ga |
| Me | Et | Gb |
| Me | CH$_2$CH=CH$_2$ | Gb |
| Me | CH$_2$C≡CH | Gb |
| Et | Me | Ga |
| Et | Et | Gb |
| Et | CH$_2$CH=CH$_2$ | Gb |
| Et | CH$_2$C≡CH | Gb |
| Pr-n | Me | Ga |
| Pr-n | Et | Gb |
| Bu-n | Me | Ga |
| Bu-n | Et | Gb |
| Pen-n | Me | Gb |
| CH$_2$CH=CH$_2$ | Me | Ga |
| CH$_2$CH=CH$_2$ | Et | Gb |
| CH$_2$CH=CH$_2$ | CH$_2$CH=CH$_2$ | Gb |
| CH$_2$CH=CH$_2$ | CH$_2$C≡CH | Gb |
| CH$_2$C≡CH | Me | Gb |
| CH$_2$C≡CH | Et | Gb |
| CH$_2$C≡CH | CH$_2$CH=CH$_2$ | Gb |
| CH$_2$C≡CH | CH$_2$C≡CH | Gb |
| CH$_2$CH$_2$OMe | Me | Gb |
| CH$_2$CH$_2$SMe | Me | Gb |
| CH$_2$SO$_2$Me | Me | Gb |
| CH$_2$CF$_3$ | Me | Gb |
| CH$_2$CF$_3$ | Et | Gb |
| CH$_2$CF$_3$ | CH$_2$CH=CH$_2$ | Gb |

TABLE 6-continued
| | | |
|---|---|---|
| CH$_2$CF$_3$ | CH$_2$C≡CH | Gb |
| CH$_2$CN | Me | Gb |
| CH$_2$COMe | Me | Gb |
| CH$_2$COMe | Et | Gb |
| CH$_2$COMe | CH$_2$CH=CH$_2$ | Gb |
| CH$_2$COMe | CH$_2$C≡CH | Gb |
| CH$_2$COCH=CH$_2$ | Me | Gb |
| CH$_2$CONMe$_2$ | Me | Gb |
| Ph | Me | Gb |
TABLE 7
$$QSO_2NH\underset{O}{\overset{\|}{C}}-\underset{L}{N}-Gn$$
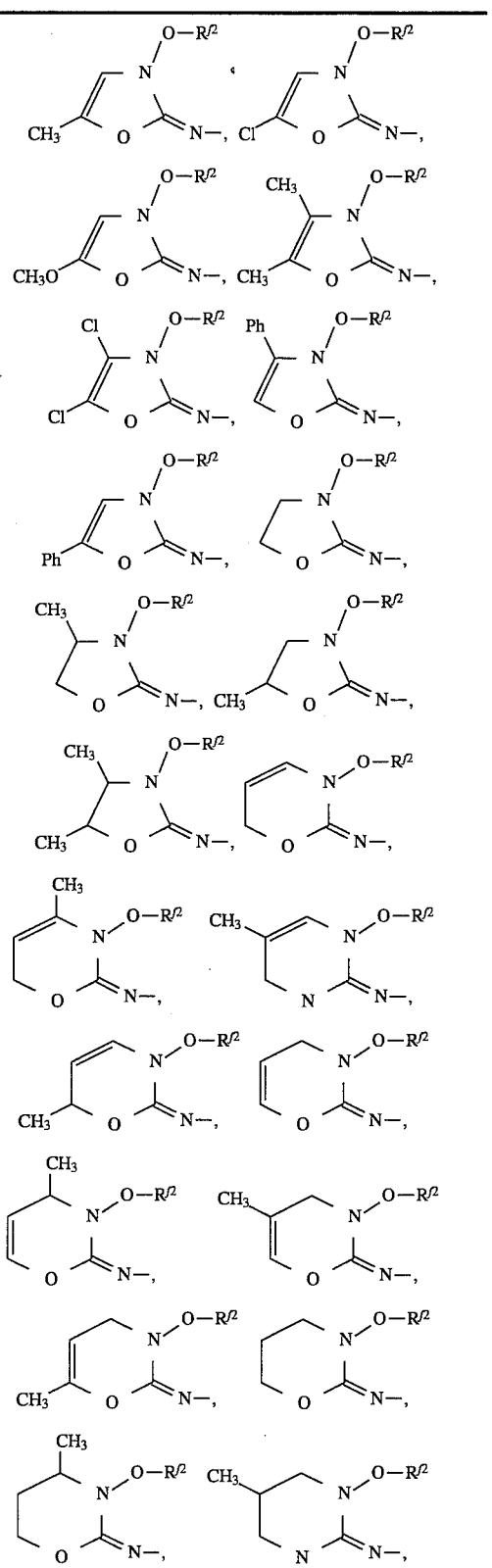

TABLE 7-continued

[Structures showing various N-O-R^f2 oxime/carbamate groups with CH3 substituents]

| R^n | L | Gn |
|---|---|---|
| Me | Me | Ga |
| Me | Et | Gb |
| Me | CH₂CH=CH₂ | Gb |
| Me | CH₂C≡CH | Gb |
| Et | Me | Ga |
| Et | Et | Gb |
| Et | CH₂CH=CH₂ | Gb |
| Et | CH₂C≡CH | Gb |
| Pr-n | Me | Ga |
| Pr-n | Et | Gb |
| Pr-n | CH₂CH=CH₂ | Gb |
| Pr-n | CH₂C≡CH | Gb |
| CH₂CH=CH₂ | Me | Gb |
| CH₂C≡CH | Me | Gb |
| CH₂SMe | Me | Gb |
| CH₂CH₂SMe | Me | Gb |
| CH₂SO₂Me | Me | Gb |
| CH₂CH₂SO₂Me | Me | Gb |
| CH₂OMe | Me | Gb |
| CH₂CH₂OMe | Me | Gb |
| CH₂CO₂Me | Me | Gb |
| CH₂COMe | Me | Gb |
| CH₂CH₂COMe | Me | Gb |
| CH₂CN | Me | Gb |
| CH₂CH₂CN | Me | Gb |
| Ph | Me | Gb |
| CH₂Ph | Me | Gb |
| CH₂CH₂Ph | Me | Gb |
| CHMePh | Me | Gb |

R^n represents R^d6 or R^f2.

TABLE 8

$$QSO_2NHC(=O)-N(L)-Gn$$

Q: [Various guanidine-type structures with SR^g1 substituents and combinations of CH₃, C₂H₅, n-C₃H₇, CH₂=CHCH₂, HC≡CCH₂, CH₃O, C₂H₅O, CH₃SO₂, CH₃NHSO₂, (CH₃)₂NSO₂, CH₃O₂C, CH₃CO, CH₃NHCO groups on nitrogen atoms]

TABLE 8-continued

[Structures shown:
- CH₃((CH₃)₂NCO)N-C(SR^g1)=N-
- CH₃(Ph)N-C(SR^g1)=N-
- CH₃(PhCH₂)N-C(SR^z1)=N-
- cyclopropyl-N-C(SR^g1)=N-
- or pyrrolidinyl-N-C(SR^g1)=N-]

| R^g1 | L | Gn |
|---|---|---|
| Me | Me | Ga |
| Me | Et | Gb |
| Et | Me | Ga |
| Et | Et | Gb |
| Pr-n | Me | Ga |
| Pr-n | Et | Gb |
| Pr-n | CH₂CH=CH₂ | Gb |
| Pr-n | CH₂C≡CH | Gb |
| Bu-n | Me | Ga |
| Bu-n | Et | Gb |
| Bu-n | CH₂CH=CH₂ | Gb |
| Bu-n | CH₂C≡CH | Gb |
| Pen-n | Me | Gb |
| CH₂CH=CH₂ | Me | Ga |
| CH₂CH=CH₂ | Et | Gb |
| CH₂CH=CH₂ | CH₂CH=CH₂ | Gb |
| CH₂CH=CH₂ | CH₂C≡CH | Gb |
| CH₂C≡CH | Me | Gb |
| CH₂C≡CH | Et | Gb |
| CH₂C≡CH | CH₂CH=CH₂ | Gb |
| CH₂C≡CH | CH₂C≡CH | Gb |
| CH₂CH₂OMe | Me | Gb |
| CH₂CH₂SMe | Me | Gb |
| CH₂SO₂Me | Me | Gb |
| CH₂CF₃ | Me | Gb |
| CH₂CF₃ | Et | Gb |
| CH₂CF₃ | CH₂CH=CH₂ | Gb |
| CH₂CF₃ | CH₂C≡CH | Gb |
| CH₂CN | Me | Gb |
| CH₂COMe | Me | GB |
| CH₂COMe | Et | Gb |
| CH₂COMe | CH₂CH=CH₂ | Gb |
| CH₂COMe | CH₂C≡CH | Gb |
| CH₂COCH=CH₂ | Me | Gb |
| CH₂CONMe₂ | Me | Gb |

TABLE 9

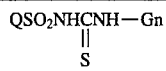

Q: 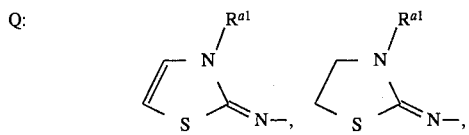

TABLE 9-continued

[Structures showing various Q groups with R^a1, R^b1, R^d1, R^e1, R^f1 substituents on imidazoline, thiazoline, oxazoline and related heterocyclic rings]

| R^m | Gn |
|---|---|
| Me | Gc |
| Et | Gc |
| Pr-n | Gc |
| Pr-iso | Gc |
| Bu-n | Gc |
| Bu-iso | Gc |
| Pen-n | Gc |
| CH₂Pr-cyc | Gc |
| CH₂CH₂Py-cyc | Gc |
| CH₂CH=CH₂ | Gc |
| CH₂CH=CHMe | Gc |
| CH₂C≡CH | Gc |
| CH₂C≡CMe | Gc |
| CH₂CH₂OMe | Gc |
| CH₂OMe | Gc |
| CH₂CH₂SMe | Gc |
| CH₂SMe | Gc |
| CH₂SO₂Me | Gc |
| CH₂CH₂SO₂Me | Gc |
| CH₂CF₃ | Gc |

TABLE 9-continued

| | |
|---|---|
| CH$_2$CN | Gc |
| CH$_2$CH$_2$CN | Gc |
| CH$_2$NO$_2$ | Gc |
| CH$_2$CH$_2$NO$_2$ | Gc |
| CH$_2$COMe | Gc |
| CH$_2$COEt | Gc |
| CH$_2$COCH=CH$_2$ | Gc |
| CH$_2$CH=CHCOMe | Gc |
| CH$_2$CONMe$_2$ | Gc |

R$^m$ represents R$^{a1}$, R$^{b1}$, R$^{d1}$, R$^{e1}$ or R$^{f1}$.

TABLE 10

QSO$_2$NHCNH—Gn
‖
S

[Chemical structures showing Q: connected to various ring systems with N—O—R$^{c1}$ groups]

| R$^{c1}$ | Gn |
|---|---|
| Me | Gc |
| Et | Gc |
| Pr-n | Gc |
| Pr-iso | Gc |
| Bu-n | Gc |
| Bu-iso | Gc |
| Pen-n | Gc |
| CH$_2$Pr-cyc | Gc |
| CH$_2$CH$_2$Py-cyc | Gc |
| CH$_2$CH=CH$_2$ | Gc |
| CH$_2$CH=CHMe | Gc |
| CH$_2$C≡CH | Gc |
| CH$_2$C≡CMe | Gc |
| CH$_2$CH$_2$OMe | Gc |
| CH$_2$OMe | Gc |
| CH$_2$CH$_2$SMe | Gc |
| CH$_2$SMe | Gc |
| CH$_2$SO$_2$Me | Gc |
| CH$_2$CH$_2$SO$_2$Me | Gc |
| CH$_2$CF$_3$ | Gc |
| CH$_2$CN | Gc |
| CH$_2$CH$_2$CN | Gc |
| CH$_2$NO$_2$ | Gc |
| CH$_2$CH$_2$NO$_2$ | Gc |
| CH$_2$COMe | Gc |
| CH$_2$COEt | Gc |
| CH$_2$COCH=CH$_2$ | Gc |
| CH$_2$CH=CHCOMe | Gc |
| CH$_2$CONMe$_2$ | Gc |
| Ph | Gc |

TABLE 11

QSO$_2$NHCNH—Gn
‖
S

[Chemical structures showing Q: connected to various ring systems with N—O—R$^{d6}$ and N—O—R$^{f2}$ groups]

R$^n$ represents R$^{d6}$ or R$^{f2}$.

| Rn | Gn |
|---|---|
| Me | Gc |
| Et | Gc |
| Pr-n | Gc |
| CH$_2$CH=CH$_2$ | Gc |
| CH$_2$C≡CH | Gc |
| CH$_2$SMe | Gc |
| CH$_2$CH$_2$SMe | Gc |
| CH$_2$SO$_2$Me | Gc |
| CH$_2$CH$_2$SO$_2$Me | Gc |
| CH$_2$OMe | Gc |
| CH$_2$CH$_2$OMe | Gc |
| CH$_2$CO$_2$Me | Gc |
| CH$_2$COMe | Gc |
| CH$_2$CH$_2$COMe | Gc |
| CH$_2$CN | Cc |
| CH$_2$CH$_2$CN | Gc |
| Ph | Gc |
| CH$_2$Ph | Gc |

TABLE 12

QSO$_2$NHCNH—Gn
‖
S

[Chemical structures showing Q: CH$_3$, CH$_2$=CHCH$_2$, HC≡CCH$_2$, CH$_3$O, CH$_3$SO$_2$, CH$_3$O$_2$C, CH$_3$CO, Ph — each connected to guanidine-type structure with N(CH$_3$)—C(SR$^{z1}$)=N—]

TABLE 12-continued $$\begin{array}{cc} CH_3 & SR^{z1} \\ \diagdown & | \\ N{-}C \\ \diagup & \diagdown \\ PhCH_2 & N{-} \\ & R^{g1} \end{array} \quad \text{or} \quad \begin{array}{c} SR^{z1} \\ | \\ \boxed{\phantom{x}}N{-}C \\ \diagdown \\ N{-} \\ Gn \end{array}$$

| | |
|---|---|
| Me | Gc |
| Et | Gc |
| Pr-n | Gc |
| Pr-iso | Gc |
| Bu-n | Gc |
| Bu-iso | Gc |
| Pen-n | Gc |
| CH$_2$Pr-cyc | Gc |
| CH$_2$CH$_2$Py-cyc | Gc |
| CH$_2$CH=CH$_2$ | Gc |
| CH$_2$CH=CHMe | Gc |
| CH$_2$C≡CH | Gc |
| CH$_2$C≡CMe | Gc |
| CH$_2$CH$_2$OMe | Gc |
| CH$_2$OMe | Gc |
| CH$_2$CH$_2$SMe | Gc |
| CH$_2$SMe | Gc |
| CH$_2$SO$_2$Me | Gc |
| CH$_2$CH$_2$SO$_2$Me | Gc |
| CH$_2$CF$_3$ | Gc |
| CH$_2$CN | Gc |
| CH$_2$CH$_2$CN | Gc |
| CH$_2$NO$_2$ | Gc |
| CH$_2$CH$_2$NO$_2$ | Gc |
| CH$_2$COMe | Gc |
| CH$_2$COEt | Gc |
| CH$_2$COCH=CH$_2$ | Gc |
| CH$_2$CH=CHCOMe | Gc |
| CH$_2$CONMe$_2$ | Gc |

The compound of the present invention can be used as a herbicide for upland fields by any treating method such as soil treatment, soil admixing treatment or foliage treatment.

The dose of the compound of the present invention varies depending upon the application site, the season for application, the manner of application, the type of weeds to be controlled, the type of crop plants, etc. However, the dose is usually within a range of from 0.0001 to 10 kg, preferably from 0.005 to 5 kg, per hectare (ha), as the amount of the active ingredient.

Further, the compound of the present invention may be combined with other herbicides, various insecticides, fungicides, plant growth regulating agents, synergism agents and safeners at the time of the preparation of the formulations or at the time of the application, as the case requires.

Particularly, by the combined application with other herbicide, it can be expected to reduce the cost due to a decrease of the dose or to enlarge the herbicidal spectrum or obtain higher herbicidal effects due to a synergistic effect of the combined herbicides. In such a case, a plurality of known herbicides may be simultaneously combined. The herbicides of the type which can be used in combination with the compound of the present invention, may, for example, be compounds disclosed in Farm Chemicals Handbook (1990).

When the compound of the present invention is to be used as a herbicide, it is usually mixed with a suitable carrier, for instance, a solid carrier such as clay, talc, bentonite, diatomaceous earth or fine silica powder, or a liquid carrier such as water, an alcohol (such as isopropanol, butanol, benzyl alcohol or furfuryl alcohol), an aromatic hydrocarbon (such as toluene or xylene), an ether (such as anisole), a ketone (such as cyclohexanone or isophorone), an ester (such as butyl acetate), an acid amide (such as N-methylpyrrolidone), or a halogenated hydrocarbon (such as chlorobenzene). If desired, a surfactant, an emulsifier, a dispersing agent, a penetrating agent, a spreader, a thickener, an antifreezing agent, a coagulation preventing agent or a stabilizer may be added to prepare an optional formulation such as a liquid formulation, an emulsifiable concentrate, a wettable powder, a dry flowable, a flowable, a dust or a granule.

Cropland weeds to be controlled by the compound of the present invention include, for example, Solanaceae weeds such as *Solanum nigrum* and *Datura stramonium*, Malvaceae weeds such as *Abutilon theophrasti* and *Side spinosa*, Convolvulaceae weeds such as Ipomoea spps. e.g. *Ipomoea purpurea*, and Calystegia spps., Amaranthaceae weeds such as *Amaranthus lividus* and *Amaranthus viridis*, Compositae weeds such as *Xanthium strumarium*, *Ambrosia artemisiaefolia*, *Helianthus annuu*, *Galinsoga ciliat*, *Cirsium arvense*, *Senecio vulgaris* and *Erigeron annus*, Cruciferae weeds such as *Rorippa indica*, *Sinapis arvensis* and *Capsella Bursapastris*, Polygonaceae weeds such as *Polygonum Blumei* and *Polygonum convolvulus*, Portulacaceae weeds such as *Portulaca oleracea*, Chenopodiaceae weeds such as *Chenopodium album*, *Chenopodium ficifolium* and *Kochia scoparis*, Caryophyllaceae weeds such as *Stellaria media*, Scrophulariaceae weeds such as *Veronica persica*, Commelinaceae weeds such as *Commelina communis*, Labiatae weeds such as *Lamium amplexicaule* and *Lamium purpureum*, Euphorbiaceae weeds such as *Euphorbia supina* and *Euphorbia maculata*, Rubiaceae weeds such as *Galium spurium*, *Galium aparine* and *Rubia akane*, Violaceae weeds such as *Viola arvensis*, Leguminosae weeds such as *Sesbania exaltata* and *Cassia obtusifolia*, Graminaceous weeds such as *Sorgham bicolor*, *Panicum dichotomiflorum*, *Sorghum halepense*, *Echinochloa crus-galli*, *Digitaria adscendens*, *Avena fatua*, *Eleusine indica*, *Setaria viridis* and *Alopecurus aegualis*, and Cyperaceous weeds such as *Cyperus rotundus* and *Cyperus esculentus*.

Further, the compound of the present invention can be used as a paddy field herbicide by any treating method such as irrigated soil treatment or foliage treatment. Paddy weeds include, for example, Alismataceae weeds such as *Alisma canaliculatum*, *Sagittaria trifolia* and *Sagittaria pygmaea*, Cyperaceae weeds such as *Cyperus difformis*, *Cyperus serotinus*, *Scirpus juncoides* and *Eleocharis kuroguwai*, Scrothulariaceae weeds such as *Lindemia pyxidaria*, Potenderiaceae weeds such as *Monochoria vaginalis*, Potamogetonaceae weeds such as *Potamogeton distinctus*, Lythraceae weeds such as *Rotala indica*, and Gramineae weeds such as *Echinochloa crus-galli*.

The compound of the present invention can be applied to control various weeds not only in the agricultural and horticultural fields such as upland fields, paddy fields or orchards, but also in non-agricultural fields such as play grounds, non-used vacant fields or railway sides.

The compound of the present invention can easily be produced by selecting any one of the following reaction schemes 1 to 5.

Reaction Scheme 1

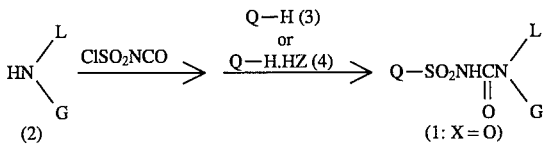

In the above formulas, Q, G and L are as defined above, and Z is a halogen atom.

Namely, the amine (2) is reacted with chlorosulfonyl isocyanate in a solvent such as tetrahydrofuran, dimethoxyethane, acetonitrile, propionitrile, dimethylformamide, dichloromethane, dichloroethane, benzene or toluene and then reacted with the imine (3) or (4) in the presence of a base such as triethylamine, pyridine, sodium hydride, sodium methoxide, sodium ethoxide, sodium hydroxide, potassium hydroxide or potassium carbonate, to obtain the compound of the present invention (1:X=O).

Reaction Scheme 2

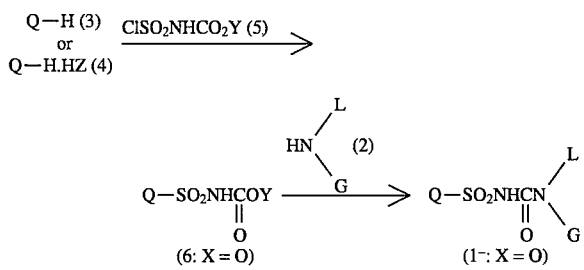

In the above formulas, Q, G, L and Z are as defined above, and Y is a $C_{1-6}$ alkyl group or a phenyl group.

Namely, the reaction of the imine (3) or (4) with phenyl N-chlorosulfonyl carbamate (5:Y=phenyl group) or an alkyl N-chlorosulfonyl carbamate (5:Y= lower alkyl group), is conducted by using the carbamate derivative (5) in an amount of from 0.5 to 3.0 mols, per mol of the imine (3) or (4). Preferably, the amount is within a range of from 0.9 to 1.2 mols.

The reaction temperature may be selected optionally within a range of from −50° C. to 100° C., but it is preferably within a range of from −20° C. to 30° C.

This reaction can be carried out by using various bases. The amount of the base is from 0.5 to 4.0 mols per mol of the imine (3) or (4).

A suitable base may, for example, be an organic base such as triethylamine or pyridine, a metal hydride such as sodium hydride, an inorganic base such as sodium hydroxide, potassium hydroxide or potassium carbonate, or a metal alkoxide such as sodium methoxide or sodium ethoxide.

A suitable solvent for this reaction is a solvent inert to this reaction, for example, an aromatic hydrocarbon such as benzene, toluene or xylene, a halogenated hydrocarbon such as dichloromethane, chloroform or carbon tetrachloride, an ether such as ethyl ether, isopropyl ether, dioxane or tetrahydrofuran, a nitrile such as acetonitrile or propionitrile, a hydrocarbon such as petroleum ether, petroleum benzine or n-hexane, a ketone such as acetone or methyl ethyl ketone, an ester such as ethyl acetate, or an amide such as dimethylformamide, dimethylacetamide or hexamethyl phosphorous triamide.

These solvents may be used alone or in combination as a mixture.

Particularly preferred is an ether or an amide.

Then, the phenyl N-substituted iminosulfonyl carbamate (6:X=O, Y= phenyl group) or the alkyl N-substituted iminosulfonyl carbamate (6:X=O, Y= lower alkyl group) and the compound (2) are heated in a solvent such as benzene, toluene or dioxane to obtain the compound of the present invention (1:X=O).

Reaction Scheme 3

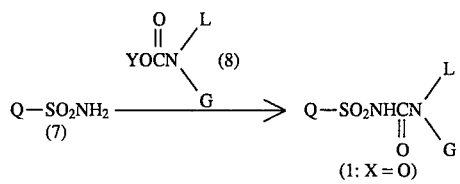

In the above formulas, Q, G, L and Y are as defined above.

Namely, the substituted iminosulfonamide derivative (7) is reacted with the carbamate derivative (8) in a solvent such as acetone, acetonitrile or dioxane in the presence of an inorganic base such as potassium carbonate or an organic base such as triethylamine or 1,8-diazabicyclo[5.4.0]-7-undecene (DBU) to obtain the compound of the present invention (1:X=O).

Reaction Scheme 4

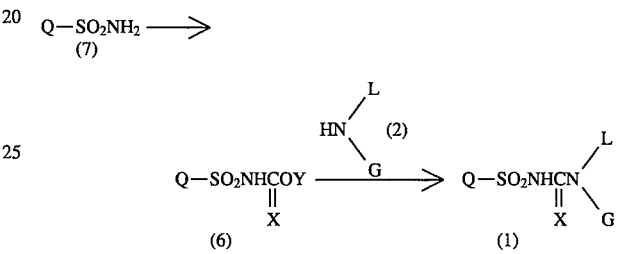

In the above formulas, Q, G, L, X and Y are as defined above.

Namely, the substituted iminosulfonamide derivative (7) is reacted with chloroformic acid (thio)ester or carbonic acid (thio)ester in a solvent such as acetone, methyl ethyl ketone, acetonitrile, dioxane or tetrahydrofuran in the presence of a base such as potassium carbonate, triethylamine or pyridine to obtain the compound (6), which is then heated together with the compound (2) in a solvent such as toluene, benzene or dioxane to obtain the compound of the present invention (1).

Reaction Scheme 5

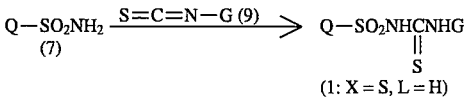

In the above formulas, Q and G are as defined above.

Namely, the substituted iminosulfonamide derivative (7) is reacted with the isothiocyanate derivative (9) in a solvent such as acetone, acetonitrile, dioxane or tetrahydrofuran in the presence of an inorganic base such as potassium carbonate or an organic base such as triethylamine or DBU, to obtain the compound of the present invention (1:X=S, L= H).

The intermediates to be used in the present invention, i.e. the substituted iminosulfonamide derivative (7), the phenyl N-substituted iminosulfonyl(thio)carbamate (6:Y= phenyl group) and the alkyl N-substituted iminosulfonyl(thio)carbamate (6: Y= $C_{1-6}$ alkyl group) are also novel compounds.

The substituted iminosulfonamide derivative (7) can be synthesized from an imine (3) or (4) by the methods of the following Reaction Schemes 6 and 7.

Reaction Scheme 6

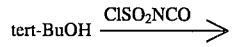

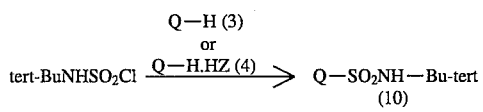

In the above formulas, Q and Z are as defined above.

In the Reaction Scheme 6, the reaction of tert-butanol with chlorosulfonyl isocyanate can be conducted by a method per se known, for example, in accordance with Japanese Unexamined Patent Publication No. 101323/1975.

The reaction of the imine (3) or (4) with tert-butylsulfamoyl chloride is carried out by using tert-butylsulfamoyl chloride in an amount of from 0.5 to 3.0 mols per mol of the imine (3) or (4). Preferably the amount is within a range of from 0.9 to 1.2 mols.

The reaction temperature may be selected optionally within a range of from −50° C. to 100° C. However, the temperature is preferably within a range of from −20° C. to 30° C.

This reaction can be conducted by using various bases. The amount of the base is from 0.5 to 4.0 mols per mol of the imine (3) or (4). Preferably, the amount is within a range of from 0.8 to 2.5 mols. A suitable base may, for example, be a metal hydride such as sodium hydride, an organic base such as triethylamine or pyridine, an inorganic base such as sodium hydroxide, potassium hydroxide or potassium carbonate, or a metal alkoxide such as sodium methoxide or sodium ethoxide.

A suitable solvent for the reaction is a solvent inert to this reaction, for example, an aromatic hydrocarbon such as benzene, toluene or xylene, a halogenated hydrocarbon such as dichloromethane, chloroform or carbon tetrachloride, an ether such as ethyl ether, isopropyl ether, dioxane or tetrahydrofuran, a nitrile such as acetonitrile or propionitrile, a hydrocarbon such as petroleum ether, petroleum benzine or n-hexane, a ketone such as acetone or methyl ethyl ketone, an ester such as ethyl acetate, or an amide such as dimethylformamide, dimethylacetamide or hexamethylphosphorous triamide.

These solvents may be used alone or in combination as a mixture. Particularly preferred is an ether or an amide.

Reaction Scheme 7

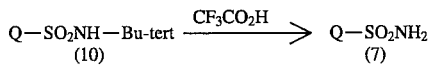

In the above formulas, Q is as defined above.

In the Reaction Scheme 7, removal of the tert-butyl group is carried out by using trifluoroacetic acid.

The amount of trifluoroacetic acid may be selected optionally within a range of an equimolar amount to an excess amount. Trifluoroacetic acid may be used as a solvent without any particular problem.

The reaction temperature may be selected optionally within a range of from −50° C. to 80° C. The temperature is preferably within a range of from −20° C. to 30° C.

When a solvent is used for this reaction, a solvent inert to this reaction, for example, an aromatic hydrocarbon such as benzene, toluene or xylene, a halogenated hydrocarbon such as dichloromethane, chloroform or carbon tetrachloride, an ether such as ethyl ether, isopropyl ether, dioxane or tetrahydrofuran, a nitrile such as acetonitrile or propionitrile, a hydrocarbon such as petroleum ether, petroleum benzine or n-hexane, a ketone such as acetone or methyl ethyl ketone, an ester such as ethyl acetate, or an amide such as dimethylformamide, dimethylacetamide or hexamethylphosphorous triamide, may be used. These solvents may be used alone or in combination as a mixture.

In Reaction Scheme 2, the phenyl N-chlorosulfonyl carbamate (5:Y= phenyl group) and the alkyl N-chlorosulfonyl carbamate (5:Y= lower alkyl group) can be synthesized by a method known per se, for example, in accordance with Chemische Berichte, vol. 96, p. 56 (1963).

The imines (3) and (4) to be used as the starting materials for the above reaction, can be synthesized, for example, in accordance with U.S. Pat. No. 4,237,302, Journal of Chemical Society, p. 307 (1956), Chemical and Pharmaceutical Bulletin, vol. 26, p. 3658 (1978), Journal of Organic Chemistry, vol. 30, p. 4298 (1965), East German Patent 291,757, Journal of American Chemical Society, vol. 93, p. 5552 (1971), U.S. Pat. No. 4,054,652, British Patent 752,003, Chemische Berichte, vol. 92, p. 1928 (1959), Journal of Medicinal Chemistry, vol. 6, p. 266 (1963), Chemical Abstracts, vol. 64, 14171e (1966), and Belgian Patent 654,416.

As representative examples, synthetic schemes for 2-imino-3-ethoxythiazolidine hydrobromide, 2-imino-3-n-propoxythiazolidine hydrobromide and 2-imino-3-methoxy-4,5-dimethylthiazoline hydrochloride will be shown as Reaction Schemes 8, 9 and 10.

Reaction Scheme 8

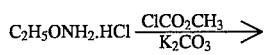

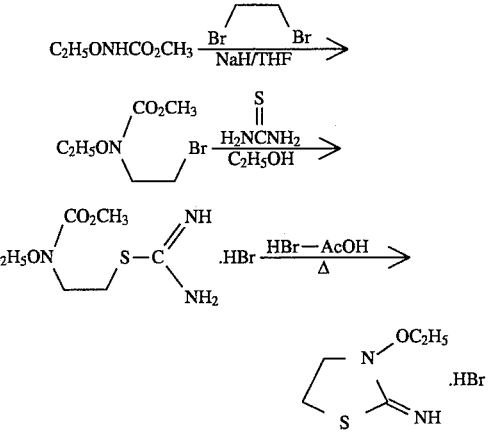

Reaction Scheme 9

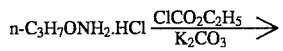

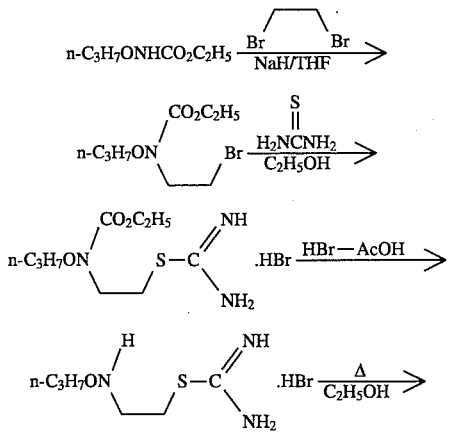

-continued

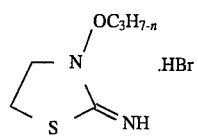

Reaction Scheme 10

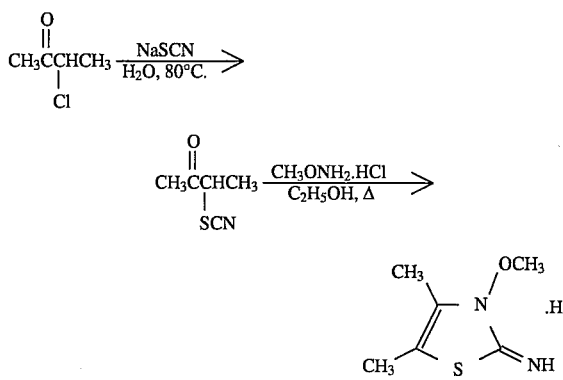

THE BEST MODE FOR CARRYING OUT THE INVENTION

Now, syntheses of the compounds of the present invention will be described in detail as Reference Examples and working Examples. However, the present invention is by no means restricted to such specific Examples.

REFERENCE EXAMPLE a-1

Preparation of 2-imino-3-methylthiazol-4-ine hydroiodide

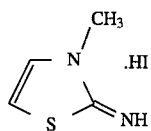

In 125 ml of dimethylformamide, 50 g (0.5 mol) of 2-aminothiazole was dissolved, and 90 g (0.63 mol) of methyl iodide was added thereto at room temperature. The mixture was further stirred at room temperature for 48 hours. Then, 1000 ml of ethyl acetate was added to the reaction mixture. Formed crystals were collected by filtration, washed with ethyl acetate and then dried to obtain 105 g of 2-imino-3-methylthiazol-4-ine hydroiodide.

Melting point: 181°–183° C.

The 2-imino-3-methylthiazol-4-ine hydroiodide was neutralized with potassium carbonate to obtain 2-imino-3-methylthiazol-4-ine.

Boiling point 55°–60° C./1 mmHg

REFERENCE EXAMPLE a-2

Preparation of 2-imino-3-n-butylthiazolidine

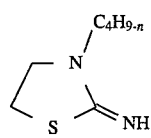

In 25 ml of dimethylformamide, 8.2 g (80 mmol) of 2-amino-2-thiazolidine was dissolved, and 18.4 g (100 mmol) of n-butyl iodide was added thereto at room temperature. The reaction mixture was heated and stirred at 60° C. for 10 hours and then left to cool to room temperature. The reaction mixture was added to 300 ml of ethyl acetate, and the mixture was stirred at room temperature for 10 minutes. A formed oily substance was separated by decantation from the ethyl acetate solution, and the same operation was repeated twice. Then, ethyl acetate contained in the oily substance was distilled off under reduced pressure to obtain 2-imino-3-n-butylthiazolidine hydroiodide as a crude product.

Then, the 2-imino-3-n-butylthiazolidine hydroiodide was stirred together with 5.28 g (80 mmol) of 85% potassium hydroxide in 300 ml of methanol at room temperature for one hour. Methanol was distilled off under reduced pressure. Then, 200 ml of chloroform was added to the residue, and precipitated insoluble matters were removed by filtration. Chloroform was distilled off under reduced pressure, and 6.9 g of 2-imino-3-n-butylthiazolidine was obtained by distillation under reduced pressure.

Boiling point: 85°–89° C./0.26 torr

REFERENCE EXAMPLE a-3

Preparation of 2-imino-1,3-dimethylimidazol-4-ine hydrochloride

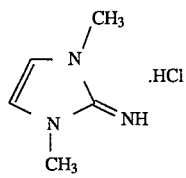

16.9 g (150 mmol) of creatinine was dissolved in 100 ml of N,N-dimethylformamide. Then, 27.6 g (194 mmol) of methyl iodide was added thereto, and the mixture was heated to 50° C. and stirred at that temperature for 2 hours and further at room temperature overnight. To the reaction mixture, 500 ml of ethyl acetate was added, and crystals were collected by filtration. The obtained crystals were washed with ethyl acetate and dried to obtain 26.2 g of 2-imino-1,3-dimethylimidazolidin-4-one hydroiodide as white crystals.

Then, to 150 ml of a methanol solution containing 5.17 g (78.4 mmol) of 85% potassium hydroxide, 20 g (78.4 mmol) of 2-imino-1,3-dimethylimidazolidin-4-one hydroiodide was added, and the mixture was stirred at room temperature for 20 minutes. The solvent was distilled off under reduced pressure. Then, to the residue, 200 ml of chloroform was added, and insoluble matters were filtered off. The filtrate was dried over anhydrous magnesium sulfate, and the solvent was distilled off under reduced pressure to obtain 9.0 g of 2-imino-1,3-dimethylimidazolidin-4-one.

800 mg (21.0 mmol) of lithium aluminum hydride was suspended in 20 ml of dry tetrahydrofuran, and 200 ml of a dry tetrahydrofuran solution containing 1.5 g (11.8 mmol) of 2-imino-1,3-dimethylimidazolidin-4-one, was added thereto at room temperature. The mixture was stirred at the same temperature overnight. Then, to the reaction mixture, 10 ml of ethyl acetate and then 5 ml of water were carefully added, and insoluble matters were filtered off. The filtrate was adjusted to pH 3 with concentrated hydrochloric acid, and then the solvent was distilled off under reduced pressure. Obtained crystals were washed with a solvent mixture of ethyl ether and ethanol to obtain 1.2 g of 2-imino-1,3-dimethylimidazol- 4-ine hydrochloride.

Melting point: 168°–171° C.

The structures and the physical property values or characteristics of the compounds prepared by the same methods as the above Reference Examples a-1 to a-3 are presented in Tables 13a-1, 13a-2 and 13a-3.

TABLE 13a-1

$$\underset{R^{a3}}{\overset{R^{a2}}{\diagup}}C=C\underset{S}{\overset{N(R^{a1})}{\diagdown}}C(=NH)\cdot HZ$$

| $R^{a1}$ | $R^{a2}$ | $R^{a3}$ | HZ | Physical property values or characteristics |
|---|---|---|---|---|
| $C_2H_5$ | H | H | HI | m.p. 113–114° C. |
| $C_3H_7$-n | H | H | HI | m.p. 99–101° C. |
| $CH_2Ph$ | H | H | HBr | m.p. 153–155° C. |
| $CH_2CO_2CH_3$ | H | H | HBr | m.p. 174–177° C. |
| $CH_2CH=CH_2$ | H | H | HI | m.p. 113–116° C. |
| $CH_2C\equiv CH$ | H | H | HBr | m.p. 148–153° C. |
| $CH_2CO_2C_2H_5$ | H | H | HBr | m.p. 166–167° C. |
| $CH(CH_3)CO_2C_2H_5$ | H | H | HBr | m.p. 138–141° C. |
| $CH_2COCH_3$ | H | H | HBr | m.p. 139–141° C. |
| $CH_3$ | $CH_3$ | H | HI | m.p. 157–160° C. |
| $CH_3$ | $CH_3$ | $CH_3$ | HI | m.p. 208–210° C. |
| $C_3H_7$-n | $CH_3$ | H | HI | m.p. 166–168° C. |
| $C_4H_9$-n | H | H | HI | m.p. 55–58° C. |
| $C_5H_{11}$-n | H | H | — | b.p. 97–100° C./0.9 torr |
| $CH_2CH=CHCH_3$ | H | H | HBr | m.p. 127–128° C. |
| $CH_2CH=CHPh$ | H | H | HBr | m.p. 125–129° C. |
| $CH_2CH_2OCH_3$ | H | H | HBr | m.p. 141–142° C. |
| $C_3H_7$-n | $CH_3$ | $CH_3$ | HI | m.p. 135–138° C. |
| $CH_3$ | Ph | H | HI | m.p. 235–238° C. |
| $CH_3$ | H | Cl | HI | m.p. 225–228° C. |
| $CH_2COPh$ | H | H | HBr | m.p. 207–208° C. |
| $CH_2OCH_2Ph$ | H | H | HCl | m.p. 99–104° C. |
| $CH_3$ | H | Br | HI | m.p. 223–225° C. |
| $C_3H_7$-n | H | Cl | HI | m.p. 182–184° C. |
| $CH(CH_3)_2$ | H | H | — | b.p. 75–78° C./0.3 torr |
| $CH_2CN$ | H | H | HBr | m.p. 154–155° C. |
| $CH_2CH(CH_3)_2$ | H | H | — | b.p. 78–81° C./0.3 torr |
| $C_6H_{13}$-n | H | H | — | b.p. 110–112° C./0.45 torr |
| $CH(CH_3)C_2H_5$ | H | H | — | b.p. 83–90° C./0.4 torr |
| $CH_2OCH_3$ | H | H | — | b.p. 80–81° C./0.5 torr |
| $CH_2C(Cl)=CH_2$ | H | H | HCl | m.p. 155–159° C. |
| $CH_2CH=CHCl$ | H | H | HCl | m.p. 60–66° C. |
| $CH_2SCH_3$ | H | H | — | b.p. 82–85° C./0.6 torr |
| $CH_2C(CH_3)=CH_2$ | H | H | HCl | m.p. 114–118° C. |
| $CH_2CH=C(CH_3)_2$ | H | H | — | b.p. 90–102° C./0.3 torr |
| $CH_3$ | H | $CH_3$ | HI | m.p. 179–181° C. |
| $C_3H_7$-n | H | $CH_3$ | HI | m.p. 152–154° C. |
| $CH_3$ | H | $OCH_3$ | HI | m.p. 158–160° C. |
| $CH_2Ph$-OMe-p | H | H | HCl | m.p. 163–165° C. |
| $CH_2Ph$-Cl-p | H | H | HCl | m.p. 157–159° C. |
| $CH_2C(Br)=CH_2$ | H | H | HBr | m.p. 165–168° C. |
| $CH_2CH_2Ph$ | H | H | HBr | m.p. 144–145° C. |
| $CH_2OC_2H_5$ | H | H | HCl | m.p. 95–97° C. |
| $CH_2C\equiv CCH_3$ | H | H | HBr | m.p. 167–169° C. |

TABLE 13a-2

$$\underset{R^{a5}}{\overset{R^{a4}}{\diagup}}CH-CH\underset{S}{\overset{N(R^{a1})}{\diagdown}}C(=NH)\cdot HZ$$

| $R^{a1}$ | $R^{a4}$ | $R^{a5}$ | HZ | Physical property values or characteristics |
|---|---|---|---|---|
| $CH_3$ | H | H | HI | m.p. 147–150° C. |
| $C_3H_7$-n | H | H | HI | m.p. 119–123° C. |
| $CH_2CH=CH_2$ | H | H | HI | m.p. 111–116° C. |
| $CH_2C\equiv CH$ | H | H | HBr | m.p. 118–122° C. |
| $C_2H_5$ | H | H | — | b.p. 78–83° C./0.9 torr |
| $CH_2COCH_3$ | H | H | HBr | m.p. 233–237° C. |
| $C_5H_{11}$-n | H | H | — | b.p. 95–96° C./0.25 torr |
| $CH_2CH=CHCH_3$ | H | H | — | b.p. 85–90° C./0.2 torr |
| $C_6H_{13}$-n | H | H | — | b.p. 109–110° C./0.4 torr |
| $CH_3$ | H | $CH_3$ | — | Pale yellow oil |
| $C_3H_7$-n | H | $CH_3$ | — | Pale yellow oil |
| $CH_2OCH_3$ | H | H | HCl | White solid |
| $CH_2C(Cl)=CH_2$ | H | H | HCl | m.p. 150–155° C. |
| $CH_2CH=CHCl$ | H | H | HCl | m.p. 131–133° C. |
| Ph | H | H | HCl | m.p. 224–226° C. |

TABLE 13a-3

$$\underset{R^{a3}}{\overset{R^{a2}}{\diagup}}C=C\underset{N(R^{a6})}{\overset{N(R^{a1})}{\diagdown}}C(=NH)\cdot HZ$$

| $R^{a1}$ | $R^{a2}$ | $R^{a3}$ | $R^{a6}$ | HZ | Physical property values or characteristics |
|---|---|---|---|---|---|
| $C_2H_5$ | H | H | $CH_3$ | HCl | Pale yellow solid |
| $C_3H_7$-n | H | H | $CH_3$ | HCl | Pale yellow solid |

REFERENCE EXAMPLE b-1

Preparation of 2-imino-3-n-propylthiadiazol-4-ine hydroiodide

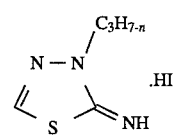

In 40 ml of dimethylformamide, 8.1 g (80 mmol) of 2-aminothiadiazole was dissolved, and 17.0 g (100 mmol) of n-propyl iodide was added thereto at room temperature. The mixture was heated at 60° C. for 30 minutes and then left to cool, and then it was stirred at room temperature for 24 hours. Then, to the reaction mixture, 500 ml of ethyl acetate was added. Formed crystals were collected by filtration, washed with ethyl acetate and then dried to obtain 13.1 g of desired 2-imino-3-n-propylthiadiazol- 4-ine hydroiodide.

Melting point: 121°–124° C.

The structures and the physical property values of the compounds prepared by the same method as in the above Reference Example b-1 are presented in Table 13b.

TABLE 13b $$\underset{R^{b2}}{\overset{R^{b1}}{\underset{S}{\bigvee}}}\underset{NH}{\overset{N-N}{\bigvee}}\cdot HZ$$

| $R^{b1}$ | $R^{b2}$ | HZ | Physical property values or characteristics |
|---|---|---|---|
| CH₃ | H | HI | m. p. 221–227° C. |
| CH₂CH=CH₂ | H | HBr | m. p. 131–132° C. |
| CH₂C≡CH | H | HBr | m. p. 114–117° C. |
| CH₂COCH₃ | H | HBr | m. p. 198–200° C. |
| CH₃ | CH₃ | HI | m. p. 117–121° C. |

REFERENCE EXAMPLE c-1

Preparation of 2-imino-3-n-propoxythiazolidine hydrobromide

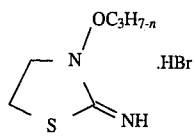

22 g (197 mmol) of n-propoxyamine hydrochloride was dissolved in 100 ml of water, and 200 ml of ethylene dichloride was added thereto. Then, 27.2 g (197 mmol) of potassium carbonate was added in several times under cooling, and then 21.3 g (196 mmol) of ethyl chloroformate was dropwise added thereto at a temperature of not higher than 10° C. After raising the temperature to room temperature, the mixture was further stirred at the same temperature for 4 hours. The ethylene dichloride layer was separated, and then the aqueous layer was extracted twice with 100 ml of chloroform. The ethylene dichloride layer and the chloroform layer were put together, and washed with a saturated sodium chloride aqueous solution, and then dried over anhydrous sodium sulfate. Then, the solvent was distilled off under reduced pressure. 27 g of ethyl N-n-propoxycarbamate was obtained by distillation under reduced pressure.

Boiling point: 88° C./2.5 mmHg 8.73 g (218 mmol) of 60% sodium hydride was suspended in 200 ml of dry tetrahydrofuran, and 50 ml of a dry tetrahydrofuran solution containing 26.7 g (182 mmol) of ethyl N-n-propoxycarbamate, was dropwise added thereto under cooling with ice at a temperature of not higher than 10° C. After raising the temperature to room temperature, the mixture was stirred at the same temperature for 20 minutes and again cooled with ice. Then, 121.4 g (646 mmol) of 1,2-dibromoethane was added all at once. The temperature was gradually raised and then the mixture was refluxed under heating for 2 hours. The mixture was left to cool to room temperature, and the solvent was partially distilled off under reduced pressure. The residue was poured into 100 ml of ice water and extracted three times with 100 ml of chloroform. The chloroform layer was washed with a saturated sodium chloride aqueous solution and then dried over anhydrous sodium sulfate. The solvent was distilled off under reduced pressure, and then 42.0 g of ethyl N-(2-bromoethyl)-N-n-propoxycarbamate was obtained by distillation under reduced pressure.

Boiling point: 97° C./0.4 mmHg

A mixture comprising 41.7 g (164 mmol) of ethyl N-(2-bromoethyl)-N-n-propoxycarbamate, 16.2 g (213 mmol) of thiourea and 200 ml of ethanol, was refluxed under heating for 5 hours. The mixture was left to cool, and then the solvent was distilled off under reduced pressure. Then, 300 ml of chloroform was added to the residue, and the mixture was stirred at room temperature for 10 minutes. After removing insoluble matters by filtration, chloroform was distilled off under reduced pressure. To the residue, ethyl ether and a small amount of water were added for crystallization. Then, the crystals were collected by filtration to obtain 50 g of S-[2-(N-ethoxycarbonyl-N-n-propoxy)aminoethyl]isothiuronium hydrobromide.

Melting point: 74°–76° C.

5.0 g (15.2 mmol) of S-[2-(N-ethoxycarbonyl-N-n-propoxy)aminoethyl] isothiuronium hydrobromide and 0.27 g (15.0 mmol) of water were added to 30 ml of a 30% hydrogen bromide/acetic acid solution, and the mixture was heated and stirred at 55° C. for 4 hours. The mixture was left to cool, and acetic acid was distilled off under reduced pressure. To the residue, ethyl ether and a small amount of ethanol were added for crystallization. The crystals were collected by filtration to obtain 3.8 g of S-[2-(N-n-propoxy)aminoethyl]isothiuronium hydrobromide.

Melting point: 112°–113° C.

3.8 g (14.7 mmol) of S-[2-(N-n-propoxy)aminoethyl] isothiuronium hydrobromide was added to 60 ml of ethanol, and the mixture was refluxed under heating for 3 hours. The mixture was left to cool, and then ethanol was distilled off under reduced pressure. To the residue, ethyl ether and a small amount of ethanol were added for crystallization. The crystals were collected by filtration to obtain 3.2 g of 2-imino-3-n-propoxythiazolidine hydrobromide.

Melting point: 117°–119° C.

REFERENCE EXAMPLE c-2

Preparation of 2-imino-3-methoxy-4-methylthiazol-4-ine hydrochloride

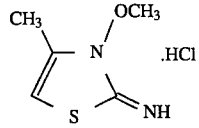

5.67 g (70 mmol) of sodium thiocyanate was dissolved in 12 ml of water, and the solution was heated to 80° C. 5.55 g (60 mmol) of chloroacetone was dropwise added thereto over a period of one hour, and the mixture was stirred at the same temperature for 3 hours. The mixture was cooled to room temperature, and then 60 ml of ethyl ether was added thereto. The aqueous layer was separated and removed. The ethyl ether layer was washed twice with 10 ml of water, and then the solvent was distilled off under reduced pressure to obtain 6.0 g of thiocyanoacetone.

2.30 g (20 mmol) of thiocyanoacetone and 1.67 g (20 mmol) of methoxyamine hydrochloride were dissolved in 10 ml of ethanol, and the solution was refluxed under heating for 5 hours. Ethanol was distilled off under reduced pressure. Then, to the obtained residue, 50 ml of ethyl acetate was added. Precipitated crystals were collected by filtration to obtain 3.34 g of 2-imino-3-methoxy-4-methylthiazol-4-ine hydrochloride.

Melting point: 145°–155° C. (decomposed)

The structures and the physical property values of the compounds prepared by the same methods as in Reference Examples c-1 and c-2 are presented in Tables 13c-1, 13c-2 and 13c-3.

TABLE 13c-1

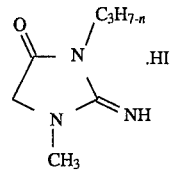

| $R^{c1}$ | $R^{c2}$ | $R^{c3}$ | HZ | Physical property values or characteristics |
|---|---|---|---|---|
| $C_2H_5$ | H | H | HBr | m.p. 175–176° C. |
| $CH(CH_3)_2$ | H | H | HBr | m.p. 150–152° C. |
| $CH_3$ | H | H | HBr | Pale yellow glassy |
| $C_4H_9$-n | H | H | HBr | m.p. 97–98° C. |
| $CH_2C\equiv CH$ | H | H | HBr | m.p. 139–140° C. |
| $CH_2CH=CH_2$ | H | H | HBr | m.p. 139–140° C. |
| $CH_2CH=CHCl$ | H | H | HBr | m.p. 145–150° C. |
| $CH_2CH(CH_3)_2$ | H | H | HBr | m.p. 110–111° C. |
| $C_5H_{11}$-n | H | H | HBr | Oil |
| $CH_2C(Cl)=CH_2$ | H | H | HBr | m.p. 169–170° C. |
| $CH_2Ph$ | H | H | HBr | m.p. 167–169° C. |

TABLE 13c-2

| $R^{c1}$ | $R^{c4}$ | $R^{c5}$ | $R^{c6}$ | HZ | Physical property values or characteristics |
|---|---|---|---|---|---|
| $C_2H_5$ | H | H | H | HBr | m.p. 209–210° C. |

TABLE 13c-3

| $R^{c1}$ | $R^{c7}$ | $R^{c8}$ | HZ | Physical property values or characteristics |
|---|---|---|---|---|
| $CH_3$ | $CH_3$ | $CH_3$ | HCl | m. p. 150–155° C. (decomposed) |

REFERENCE EXAMPLE d-1

Preparation of 3-methyl-2-iminothiazolidin-4-one hydroiodide

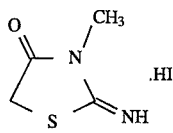

11.6 g (0.1 mol) of pseudothiohydantoin was suspended in 150 ml of dimethylformamide, and 17 g (0.12 mol) of methyl iodide was added thereto. Then, the mixture was stirred at 60° C. for one hour. After being left to cool, the reaction mixture was poured into 1000 ml of ethyl acetate, and precipitated crystals were collected by filtration to obtain 15 g of 3-methyl-2-iminothiazolidin- 4-one hydroiodide as pale yellow crystals.

Melting point: 237°–238° C.

REFERENCE EXAMPLE d-2

Preparation of 1-methyl-3-n-propyl-2-iminoimidazolidin-4-one hydroiodide 9.04 g (80 mmol) of creatinine was suspended in 50 ml of dimethylformamide, and 17.0 g (100 mmol) of n-propyl iodide was added thereto. Then, the mixture was heated and stirred within a range of from 70° C. to 80° C. until creatinine was completely dissolved. The mixture was left to cool, and 500 ml of ethyl acetate was added thereto. Precipitated crystals were collected by filtration to obtain 10.6 g of 1-methyl-3-n-propyl-2 -iminoimidazolidin-4-one hydroiodide.

Melting point: 159°–161° C.

The 1-methyl-3-n-propyl-2-iminoimidazolidin-4-one hydroiodide was neutralized in accordance with the following method to obtain 1-methyl-3-n-propyl-2 -iminoimidazolidin-4-one.

2.83 g (10 mmol) of the 1-methyl-3-n-propyl-2 -iminoimidazolidin-4-one hydroiodide was added to 25 ml of methanol containing 0.66 g (10 mmol) of 85% potassium hydroxide, and the mixture was stirred at room temperature for one hour. Methanol was distilled off under reduced pressure, and chloroform was added to the residue. Precipitated crystals were removed by filtration. Chloroform was distilled off under reduced pressure to obtain 1.16 g of 1-methyl-3-n-propyl-2 -iminoimidazolidin-4-one as an oily substance.

The structures and the physical property values of the compounds prepared by the same methods as in Reference Examples d-1 and d-2, are presented in Table 13d.

TABLE 13d

| $R^{d1}$ | $R^{d4}$ | $R^{d5}$ | HZ | Physical property values or characteristics |
|---|---|---|---|---|
| $CH_3$ | H | $CH_3$ | HI | m.p. 215–216° C. |
| $C_2H_5$ | H | $CH_3$ | HI | m.p. 220–222° C. |
| $CH_2CH=CH_2$ | H | $CH_3$ | HBr | m.p. 117–119° C. |
| $CH_2C\equiv CH$ | H | $CH_3$ | HBr | m.p. 228–230° C. |
| $CH_2COCH_3$ | H | $CH_3$ | HBr | m.p. 188–190° C. |
| $CH_2CO_2CH_3$ | H | $CH_3$ | HBr | m.p. 201–203° C. |
| $CH_2OCH_3$ | H | $CH_3$ | HCl | m.p. 198–199° C. |
| $CH_2SCH_3$ | H | $CH_3$ | HCl | m.p. 200–210° C. (decomposed) |

REFERENCE EXAMPLE e-1

Preparation of 3,6-dihydro-3-n-propyl-2H-1,3-thiazin-2-imine

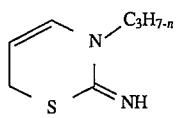

1.3 g (11.4 mmol) of 2-amino-6H-1,3-thiazine was dissolved in 4 ml of dimethylformamide, and 2.4 g (14.1 mmol) of n-propyl iodide was added thereto. The mixture was heated at 50° C. for one hour and then stirred at room temperature overnight. To the reaction solution, 100 ml of ethyl acetate was added, and the mixture was stirred and then left to stand still. Then, the ethyl acetate layer was separated and removed by decantation. Then, the residual oily substance was dissolved in 50 ml of methanol, and 30 ml of a methanol solution containing 0.75 g (11.4 mmol) of 85% potassium hydroxide, was added thereto at room temperature. The mixture was further stirred at the same temperature for one hour, and then methanol was distilled off under reduced pressure. To the residue, 60 ml of chloroform was added, and insoluble matters were removed by filtration. Then, the filtrate was concentrated under reduced pressure. The residual oily substance was purified by alumina column chromatography (eluent: chloroform) to obtain 0.4 g of 3,6-dihydro-3-n-propyl-2H-1,3-thiazin-2-imine as an oily substance.

REFERENCE EXAMPLE 2-e

Preparation of 3,4,5,6-tetrahydro-3-methyl-2H-1,3-thiazin-2-imine

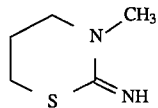

3.13 g (27 mmol) of 2-amino-4,5-dihydro-6H-1,3-thiazine was dissolved in 20 ml of isopropyl alcohol, and 4.26 g (30 mmol) of methyl iodide was added thereto. The mixture was refluxed under heating for one hour, and then left to cool. The solvent was distilled off under reduced pressure. Then, the residual oily substance was dissolved in 200 ml of methanol, and a 70 ml of a methanol solution containing 1.68 g (25.5 mmol) of 85% potassium hydroxide, was added thereto at room temperature. The mixture was stirred at the same temperature for 5 minutes, and then methanol was distilled off under reduced pressure. To the residue, 300 ml of chloroform was added and then dried over anhydrous sodium sulfate. Inorganic substances were removed by filtration, and then chloroform was distilled off under reduced pressure to obtain 3 g of 3,4,5,6-tetrahydro-3-methyl-2H-1,3-thiazin-2-imine as a pale red oily substance.

The structures and the characteristics of the compounds prepared by the same methods as in Reference Examples e-1 and e-2, are presented in Tables 13e-1 and 13e-2.

TABLE 13e-1

| $R^{e1}$ | $R^{e2}$ | $R^{e3}$ | $R^{e4}$ | Physical property values or characteristics |
|---|---|---|---|---|
| $CH_3$ | H | H | H | Oil |
| $CH_2OCH_3$ | H | H | H | Oil |

TABLE 13e-2

| $R^{e1}$ | $R^{e8}$ | $R^{e9}$ | $R^{e10}$ | Physical property values or characteristics |
|---|---|---|---|---|
| $C_3H_7$-n | H | H | H | Oil |

REFERENCE EXAMPLE f-1

Preparation of 2-imino-3-methyloxazolidine hydroiodide

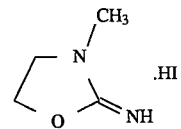

15 g (122 mmol) of 2-amino-2-oxazoline hydrochloride was stirred with 8.4 g (128 mmol) of 85% potassium hydroxide in 400 ml of methanol at room temperature for one hour. Methanol was distilled off under reduced pressure, and then 500 ml of chloroform was added. Precipitated insoluble substances were removed by filtration. Chloroform was distilled off under reduced pressure to obtain 10.5 g of 2-amino-2-oxazoline.

Then, 10.5 g of 2-amino-2-oxazoline was dissolved in 40 ml of dimethylformamide, and 22 g (155 mmol) of methyl iodide was added thereto at room temperature. The mixture was further stirred at room temperature for 48 hours. Then, 1000 ml of ethyl acetate was added to the reaction mixture. Formed crystals were collected by filtration, washed with ethyl acetate and then dried to obtain 23 g of 2-imino-3-methyloxazolidine hydroiodide.

Melting point: 165°–169° C.

The structures and characteristics of the compounds prepared by the same method as in Reference Example f-1 are presented in Table 13f.

TABLE 13f

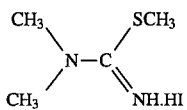

| $R^{f1}$ | $R^{f5}$ | $R^{f6}$ | HZ | Physical property values or characteristics |
|---|---|---|---|---|
| $CH_2CH=CH_2$ | H | H | HBr | Glassy |

REFERENCE EXAMPLE g-1

Preparation of N,N-dimethyl-S-methylisothiourea hydroiodide

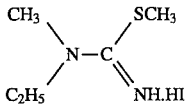

35 g (0.5 mol) of N,N-dimethylcyanamide was dissolved in a mixed solution of 70 ml of pyridine and 70 ml of triethylamine, and the solution was heated to 60° C. Hydrogen sulfide gas was introduced thereinto for 30 minutes. Then, the reaction mixture was left to cool to room temperature, and 300 ml of ethyl ether was added thereto. Precipitated crystals were collected by filtration and then washed with ethyl ether to obtain 48 g of N,N-dimethylthiourea as pale brown crystals.

Melting point: 163°–164° C.

10.4 g (0.1 mol) of N,N-dimethylthiourea was suspended in 80 ml of ethanol, and 17 g (0.12 mol) of methyl iodide was added thereto. The mixture was refluxed under heating for 30 minutes. The reaction mixture was left to cool to room temperature, and then the solvent was distilled off under reduced pressure. The obtained crystals were washed with ethyl ether, collected by filtration and dried to obtain 20 g of N,N-dimethyl-S-methylisothiourea hydroiodide as yellow crystals.

Melting point: 84°–85° C.

REFERENCE EXAMPLE g-2

Preparation of N-ethyl-N-methyl-S-methylisothiourea hydroiodide $$\begin{array}{c} CH_3 \\ \phantom{xx}\diagdown \\ \phantom{xxx}N-C \\ \phantom{xx}\diagup \phantom{xxx}\diagdown \\ C_2H_5 \phantom{xxxxx} NH.HI \end{array} \phantom{x} \begin{array}{c} SCH_3 \\ \diagup \\ \\ \diagdown \end{array}$$

7.08 g (120 mmol) of N-ethyl-N-methylamine was dissolved in 80 ml of dry acetone, and the solution was cooled to 0° C. 13.1 g (100 mmol) of ethoxycarbonyl isothiocyanate was dropwise added thereto. Then, the reaction temperature was raised to room temperature, and the mixture was further stirred at the same temperature for 2 hours. The solvent was distilled off under reduced pressure. To the obtained residue, 80 ml of concentrated hydrochloric acid was added. The reaction temperature was raised to 80° C., and the mixture was further stirred at the same temperature for 5 hours. Then, it was cooled to 0° C., and then ammonium carbonate was gradually added to neutralize the reaction mixture (pH= 6 to 7). After adding a small amount of water, the mixture was extracted three times with 100 ml of ethyl acetate. The ethyl acetate layer was washed with water and then dried over anhydrous sodium sulfate. Then, the solvent was distilled off under reduced pressure. Obtained crystals were washed with a solvent mixture of ethanol/n-hexane to obtain 5.8 g of N-ethyl-N-methylthiourea as white crystals. Melting point: 124°–125° C.

5.8 g (49 mmol) of N-ethyl-N-methylthiourea was dissolved in 10 ml of N,N-dimethylformamide. 8.8 g (62 mmol) of methyl iodide was added at room temperature, and the mixture was stirred at room temperature for 15 hours. 500 ml of ethyl acetate was added to the mixture, and precipitated crystals were collected by filtration and then washed with ethyl acetate to obtain 3.1 g of N-ethyl-N-methyl-S-methylisothiourea hydroiodide as pale yellow crystals.

Melting point: 94°–97° C.

REFERENCE EXAMPLE g-3

Preparation of N-methoxy-N-methyl-S-methylisothiourea hydroiodide

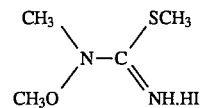

1.83 g (30 mmol) of N-methoxy-N-methylamine was dissolved in 20 ml of dichloromethane, and the solution was cooled to 0° C. 3.93 g (30 mmol) of ethoxycarbonyl isothiocyanate was dropwise added thereto. Then, the reaction temperature was raised to room temperature, and the mixture was further stirred at the same temperature for 15 hours. The solvent was distilled off under reduced pressure, and to the obtained residue, 20 ml of concentrated hydrochloric acid was added. The reaction temperature was raised to 80° C., and the mixture was further stirred at the same temperature for 5 hours. Then, the mixture was cooled to 0° C., and then ammonium carbonate was gradually added to neutralize the reaction mixture (pH= 6 to 7). After adding 10 ml of water, the mixture was extracted three times with 50 ml of ethyl acetate. The ethyl acetate layer was washed with water and then dried over anhydrous magnesium sulfate. Then, the solvent was distilled off under reduced pressure to obtain 2.0 g of N-methoxy-N-methylthiourea as pale yellow crystals. Melting point: 30°–32° C.

1.76 g (14.7 mmol) of N-methoxy-N-methylthiourea was dissolved in 5 ml of N,N-dimethylformamide. 2.09 g (14.7 mmol) of methyl iodide was added thereto at room temperature, and the mixture was stirred at room temperature for 15 hours. 500 ml of ethyl acetate was added thereto, and precipitated crystals were collected by filtration and then washed with ethyl acetate to obtain 2.7 g of N-methoxy-N-methyl-S-methylisothiourea hydroiodide as pale yellow crystals.

Melting point: 122°–124° C.

The structures and physical property values or characteristics of the compounds prepared by the same methods as in Reference Examples g-1 to g-3 are presented in Table 13g.

TABLE 13g $$\begin{array}{c} R^{g2} \\ \diagdown \\ R^{g3} \end{array} N-C \begin{array}{c} S-R^{g1} \\ \diagup \\ \diagdown NH \end{array} \cdot HZ$$

| $R^{g1}$ | $R^{g2}$ | $R^{g3}$ | HZ | Physical property values or characteristics |
|---|---|---|---|---|
| $C_2H_5$ | $CH_3$ | $CH_3$ | HI | m. p. 93–94° C. |
| $C_3H_7$-n | $CH_3$ | $CH_3$ | HI | m. p. 54–55° C. |
| $CH_2CH=CH_2$ | $CH_3$ | $CH_3$ | HBr | m. p. 148–149° C. |
| $CH_2C\equiv CH$ | $CH_3$ | $CH_3$ | HBr | m. p. 113–114° C. |
| $CH_3$ | $CH_3CO$ | $CH_3$ | — | Glassy |
| $CH_3$ | $-(CH_2)_4-$ | | HI | m. p. 121–123° C. |
| $CH_3$ | $C_3H_7$-n | $CH_3$ | HI | m. p. 126–127° C. |
| $CH_3$ | Ph | $CH_3$ | HI | m. p. 170–173° C. |
| $CH_3$ | $C_2H_5O$ | $CH_3$ | HI | m. p. 114–115° C. |
| $CH_3$ | n-$C_3H_7O$ | $CH_3$ | HI | m. p. 75–76° C. |
| $CH_3$ | $CH_2=CHCH_2$ | $CH_3$ | HI | m. p. 116–118° C. |

EXAMPLE a-1

Preparation of 1-(3-methyl-4-thiazoline-2-sulfonylimino)-3-(4,6-dimethoxypyrimidin-2-yl)urea

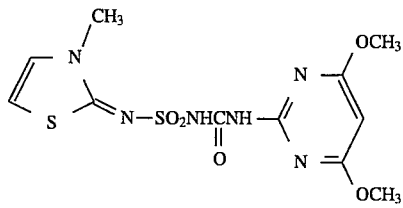

No. 1-a 1.55 g (10 mmol) of 2-amino-4,6-dimethoxypyrimidine was dissolved in 20 ml of dry tetrahydrofuran, and 1.42 g (10 mmol) of chlorosulfonyl isocyanate was dropwise added thereto within a range of from −10° C. to −5° C. The reaction temperature was raised to 0° C., and the mixture was stirred for 5 minutes. The reaction mixture was again cooled to −30° C., and 1.14 g (10 mmol) of 2-imino-3-methylthiazol-4-ine and 1.11 g (11 mmol) of triethylamine dissolved in 10 ml of dry tetrahydrofuran were dropwise added thereto. The reaction temperature was raised to room temperature, and the mixture was further stirred at the same temperature for one hour. Then, the solvent was distilled off under reduced pressure. Then, water was added to the obtained residue. Precipitated crystals were collected by filtration and washed with acetonitrile to obtain 1.5 g of desired 1-(3-methyl-4-thiazoline-2-sulfonylimino)-3-(4,6 -dimethoxypyrimidin-2-yl)urea.

Melting point: 214°–215° C.

EXAMPLE a-2

Preparation of 1-(3-n-propyl-4-thiazoline-2-sulfonylimino)-3-(4,6-dimethoxypyrimidin-2-yl)urea

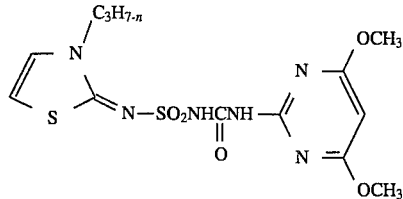

No. 2-a 1.55 g (10 mmol) of 2-amino-4,6-dimethoxypyrimidine was dissolved in 30 ml of dry tetrahydrofuran, and 1.42 g (10 mmol) of chlorosulfonyl isocyanate was dropwise added thereto at a temperature of not higher than −20° C. The reaction temperature was raised to 0° C., and then the mixture was cooled again to a temperature of not higher than −20° C. Then, 2.70 g (10 mmol) of 2-imino-3-n-propylthiazoyl- 4-ine hydroiodide and 2.22 g (22 mmol) of triethylamine dissolved in 30 ml of dry tetrahydrofuran were dropwise added thereto. The reaction temperature was raised to room temperature, and the mixture was further stirred at the same temperature for one hour. Then, the solvent was distilled off under reduced pressure. Then, water was added to the residue, and the mixture was extracted three times with chloroform. The chloroform layer was washed sequentially with water and a saturated sodium chloride aqueous solution and then dried over anhydrous sodium sulfate. Then, the solvent was distilled off under reduced pressure. The obtained crystals were washed with ethyl ether to obtain 3 g of desired 1-(3-n-propyl-4-thiazoline-2-sulfonylimino)-3-( 4,6-dimethoxypyrimidin-2-yl)urea.

Melting point: 166°–167° C.

EXAMPLE a-3

Preparation of 1-(3-n-butylthiazolidine-2-sulfonylimino)-3-(4,6-dimethoxypyrimidin-2-yl)urea

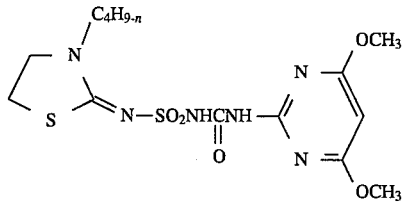

No. 40-a 1.55 g (10 mmol) of 2-amino-4,6-dimethoxypyrimidine was dissolved in 40 ml of dry tetrahydrofuran, and 1.42 g (10 mmol) of chlorosulfonyl isocyanate was dropwise added thereto at − 40° C. The reaction temperature was raised to 0° C., and then the reaction mixture was cooled again to −60° C. Then, 1.90 g (12 mmol) of 2-imino-3-n-butylthiazolidine suspended in 40 ml of dry tetrahydrofuran containing 1.33 g (13 mmol) of triethylamine, was added thereto. The reaction temperature was raised to room temperature, and the mixture was further stirred at the same temperature for one hour. Then, the solvent was distilled off under reduced pressure. Then, water was added to the residue, and the mixture was extracted three times with chloroform. The chloroform layer was washed sequentially with water and a saturated sodium chloride aqueous solution, and then dried over anhydrous sodium sulfate. Then, the solvent was distilled off under reduced pressure. The obtained crystals were washed with ethyl ether to obtain 2.8 g of desired 1-(3-n-butylthiazolidine- 2-sulfonylimino)-3-(4,6-dimethoxypyrimidin-2-yl)urea.

Melting point: 139°–140° C.

EXAMPLE a-4

Preparation of 1-(1,3-dimethyl-4-imidazoline-2-sulfonylimino)- 3-(4,6-dimethoxypyrimidin-2-yl)urea

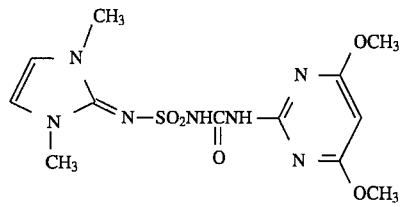

No. 66-a 540 mg (3.46 mmol) of 2-amino-4,6-dimethoxypyrimidine was dissolved in 30 ml of dry tetrahydrofuran, and 490 mg (3.46 mmol) of chlorosulfonyl isocyanate was dropwise added in a range of from − 20° C. to − 15° C. The reaction temperature was raised to 0° C., and then the mixture was cooled again to − 20° C. Then, a mixture comprising 600 mg (4.07 mmol) of 2-imino-1,3-dimethylimidazol-4-ine hydrochloride, 820 mg (8.13 mmol) of triethylamine and 30 ml of dry tetrahydrofuran, was added thereto. The reaction temperature was raised to room temperature, and the mixture was further stirred at the same temperature for 3 hours. Then, the solvent was distilled off under reduced pressure. Then, 60 ml of water was added to the obtained residue, and crystals were collected by filtration. The obtained crystals were washed with a solvent mixture of ethyl ether, acetonitrile and acetone to obtain 200 mg of desired 1-(1,3-dimethyl-4-imidazoline-2-sulfonylimino)-3-(4,6-dimethoxypyrimidin-2-yl)urea.

Melting point: 201°–203° C.

The structures and the physical property values of the compounds prepared by the same methods as in Examples a-1 to a-4 are presented in Tables 14a-1, 14a-2 and 14a-3.

TABLE 14a-1

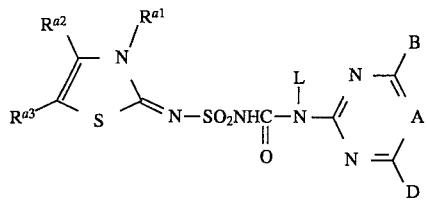

| Compound No. | $R^{a1}$ | $R^{a2}$ | $R^{a3}$ | L | A | B | D | m.p. (°C.) |
|---|---|---|---|---|---|---|---|---|
| 4-a | $CH_2CO_2CH_3$ | H | H | H | CH | $OCH_3$ | $OCH_3$ | 166–167 |
| 5-a | $CH_2Ph$ | H | H | H | CH | $OCH_3$ | $OCH_3$ | 177–178 |
| 6-a | $C_2H_5$ | H | H | H | CH | $OCH_3$ | $OCH_3$ | 189–190 |
| 7-a | $CH_2CH=CH_2$ | H | H | H | CH | $OCH_3$ | $OCH_3$ | 165–166 |
| 8-a | $CH_2C\equiv CH$ | H | H | H | CH | $OCH_3$ | $OCH_3$ | 183–184 |
| 9-a | $CH_2CO_2C_2H_5$ | H | H | H | CH | $OCH_3$ | $OCH_3$ | 137–138 |
| 10-a | $CH_2COCH_3$ | H | H | H | CH | $OCH_3$ | $OCH_3$ | 180–181 |
| 11-a | $CH(CH_3)CO_2C_2H_5$ | H | H | H | CH | $OCH_3$ | $OCH_3$ | 131–132 |
| 12-a | $C_3H_7$-n | H | H | H | CH | $OCH_3$ | $CH_3$ | 167–170 |
| 13-a | $C_3H_7$-n | H | H | H | CH | $CH_3$ | $CH_3$ | 155–158 |
| 14-a | $C_3H_7$-n | H | H | H | CH | $OCHF_2$ | $OCHF_2$ | 152–154 |
| 15-a | $C_3H_7$-n | H | H | H | CH | $OCHF_2$ | $CH_3$ | 143–145 |
| 16-a | $C_3H_7$-n | H | H | H | N | $OCH_3$ | $CH_3$ | 174–176 |
| 17-a | $CH_3$ | $CH_3$ | H | H | CH | $OCH_3$ | $OCH_3$ | 211–213 |
| 18-a | $CH_3$ | $CH_3$ | $CH_3$ | H | CH | $OCH_3$ | $OCH_3$ | 203–205 |
| 19-a | $C_3H_7$-n | $CH_3$ | H | H | CH | $OCH_3$ | $OCH_3$ | 176–178 |
| 20-a | $C_4H_9$-n | H | H | H | CH | $OCH_3$ | $OCH_3$ | 149–151 |
| 21-a | $C_5H_{11}$-n | H | H | H | CH | $OCH_3$ | $OCH_3$ | 160–161 |
| 22-a | $CH_2CH=CHCH_3$ | H | H | H | CH | $OCH_3$ | $OCH_3$ | 123–125 |
| 23-a | $CH_2CH=CH-Ph$ | H | H | H | CH | $OCH_3$ | $OCH_3$ | 180–181 |
| 27-a | $CH_2CH_2OCH_3$ | H | H | H | CH | $OCH_3$ | $OCH_3$ | 137.5–138.5 |
| 28-a | $C_3H_7$-n | $CH_3$ | $CH_3$ | H | CH | $OCH_3$ | $OCH_3$ | 199–201 |
| 29-a | $CH_3$ | Ph | H | H | CH | $OCH_3$ | $OCH_3$ | 196–198 |
| 30-a | $CH_3$ | H | Cl | H | CH | $OCH_3$ | $OCH_3$ | 198–201 |
| 31-a | $CH_3$ | H | Br | H | CH | $OCH_3$ | $OCH_3$ | 209–211 |
| 32-a | $C_3H_7$-n | H | Cl | H | CH | $OCH_3$ | $OCH_3$ | 139–142 |
| 33-a | $CH_2OCH_2Ph$ | H | H | H | CH | $OCH_3$ | $OCH_3$ | 168–169 |
| 35-a | $C_6H_{13}$-n | H | H | H | CH | $OCH_3$ | $OCH_3$ | 173–175 |
| 36-a | $CH_2CH(CH_3)_2$ | H | H | H | CH | $OCH_3$ | $OCH_3$ | 177–179 |
| 37-a | $CH(CH_3)_2$ | H | H | H | CH | $OCH_3$ | $OCH_3$ | 175.5–176.5 |
| 38-a | $CH_2OCH_3$ | H | H | H | CH | $OCH_3$ | $OCH_3$ | 173–174 |
| 39-a | $CH(CH_3)C_2H_5$ | H | H | H | CH | $OCH_3$ | $OCH_3$ | 81–82 |
| 43-a | $CH_2SCH_3$ | H | H | H | CH | $OCH_3$ | $OCH_3$ | 181–183 |
| 44-a | $CH_2CN$ | H | H | H | CH | $OCH_3$ | $OCH_3$ | 183–183.5 |
| 45-a | $CH_2C(Cl)=CH_2$ | H | H | H | CH | $OCH_3$ | $OCH_3$ | 174–175 |
| 46-a | $C_3H_7$-n | H | H | $CH_3$ | CH | $OCH_3$ | $OCH_3$ | 172–173 |
| 47-a | $C_4H_9$-n | H | H | H | CH | $OCH_3$ | $CH_3$ | 147–149 |
| 48-a | $CH_2CH=CHCl$ | H | H | H | CH | $OCH_3$ | $OCH_3$ | 165–167 |
| 49-a | $CH_2C(CH_3)=CH_2$ | H | H | H | CH | $OCH_3$ | $OCH_3$ | 177–179 |
| 52-a | $CH_3$ | H | $CH_3$ | H | CH | $OCH_3$ | $OCH_3$ | 206–208 |
| 53-a | $C_3H_7$-n | H | $CH_3$ | H | CH | $OCH_3$ | $OCH_3$ | 152–154 |
| 54-a | $CH_3$ | H | $OCH_3$ | H | CH | $OCH_3$ | $OCH_3$ | 187–190 |
| 55-a | $CH_2CH=C(CH_3)_2$ | H | H | H | CH | $OCH_3$ | $OCH_3$ | 170–171 |

TABLE 14a-1-continued

| Compound No. | $R^{a1}$ | $R^{a2}$ | $R^{a3}$ | L | A | B | D | m.p. (°C.) |
|---|---|---|---|---|---|---|---|---|
| 57-a | CH$_2$CH$_2$Ph | H | H | H | CH | OCH$_2$ | OCH$_3$ | 182–184 |
| 58-a | CH$_2$Ph—OMe—P | H | H | H | CH | OCH$_3$ | OCH$_3$ | 109–110 |
| 60-a | CH$_2$Ph—Cl—P | H | H | H | CH | OCH$_3$ | OCH$_3$ | 182–183 |
| 61-a | CH$_2$C(Br)=CH$_2$ | H | H | H | CH | OCH$_3$ | OCH$_3$ | 167–168 |
| 63-a | CH$_2$OC$_2$H$_5$ | H | H | H | CH | OCH$_3$ | OCH$_3$ | 177–178 |
| 65-a | CH$_2$C≡CCH$_3$ | H | H | H | CH | OCH$_3$ | OCH$_3$ | 184–186 |
| 68-a | C$_3$H$_7$-n | H | H | H | CH | OCH$_3$ | Cl | 165–168 |
| 72-a | C$_3$H$_7$-n | H | H | H | CH | OCH$_3$ | OCHF$_2$ | 193–195 |
| 73-a | C$_3$H$_7$-n | H | H | H | N | OCH$_3$ | OCH$_3$ | 156–158 |
| 79-a | C$_3$H$_7$-n | H | H | H | N | OC$_2$H$_5$ | CH$_3$ | 151–153 |
| 80-a | C$_3$H$_7$-n | H | H | H | N | OCH$_3$ | C$_2$H$_5$ | 141–143 |
| 82-a | C$_3$H$_7$-n | H | H | H | N | OCH$_3$ | CH$_2$Cl | 144–146 |
| 83-a | C$_3$H$_7$-n | H | H | H | CH | CF$_3$ | Cl | 146–148 |
| 84-a | C$_3$H$_7$-n | H | H | H | N | OCH$_3$ | C$_3$H$_7$-n | 159–160 |
| 85-a | C$_3$H$_7$-n | H | H | H | N | OCH$_3$ | CF$_3$ | 149–150 |
| 86-a | C$_3$H$_7$-n | H | H | H | N | OC$_3$H$_7$-n | CH$_3$ | 176–178 |

TABLE 14a-2

| Compound No. | $R^{a1}$ | $R^{a4}$ | $R^{a5}$ | A | B | D | m.p. (°C.) |
|---|---|---|---|---|---|---|---|
| 3-a | CH$_3$ | H | H | CH | OCH$_3$ | OCH$_3$ | 204–206 |
| 24-a | C$_3$H$_7$-n | H | H | CH | OCH$_3$ | OCH$_3$ | 172–173 |
| 25-a | CH$_2$CH=CH$_2$ | H | H | CH | OCH$_3$ | OCH$_3$ | 177–178 |
| 26-a | CH$_2$C≡CH | H | H | CH | OCH$_3$ | OCH$_3$ | 188–190 |
| 34-a | C$_2$H$_5$ | H | H | CH | OCH$_3$ | OCH$_3$ | 170–172 |
| 41-a | CH$_2$CH=CHCH$_3$ | H | H | CH | OCH$_3$ | OCHS | 133–134 |
| 42-a | C$_5$H$_{11}$-n | H | H | CH | OCH$_3$ | OCH$_3$ | 132–134 |
| 50-a | CH$_2$COCH$_3$ | H | H | CH | OCH$_3$ | OCH$_3$ | 186–188 |
| 51-a | C$_6$H$_{13}$-n | H | H | CH | OCH$_3$ | OCH$_3$ | 163–165 |
| 56-a | CH$_3$ | H | CH$_3$ | CH | OCH$_3$ | OCH$_3$ | 190–191 |
| 59-a | CH$_2$CH=CHCl | H | H | CH | OCH$_3$ | OCH$_3$ | 155–156 |
| 62-a | CH$_2$C(Cl)=CH$_2$ | H | H | CH | OCH$_3$ | OCH$_3$ | 190–191 |
| 64-a | CH$_2$OCH$_3$ | H | H | CH | OCH$_3$ | OCH$_3$ | 169–170 |
| 70-a | C$_3$H$_7$-n | H | H | CH | OCH$_3$ | Cl | 144–146 |
| 71-a | C$_3$H$_7$-n | H | H | CH | OCH$_3$ | OCHF$_2$ | 144–145 |
| 74-a | C$_3$H$_7$-n | H | H | CH | OCH$_3$ | CH$_3$ | 175–177 |
| 75-a | C$_3$H$_7$-n | H | H | CH | CH$_3$ | CH$_3$ | 166–168 |
| 76-a | C$_3$H$_7$-n | H | H | CH | OCHF$_2$ | OCHF$_2$ | 173–174 |
| 77-a | C$_3$H$_7$-n | H | H | CH | CH$_3$ | Cl | 155–158 |
| 78-a | C$_3$H$_7$-n | H | H | N | OCH$_3$ | CH$_3$ | 184–186 |
| 81-a | Ph | H | H | CH | OCH$_3$ | OCH$_3$ | 178–180 |

TABLE 14a-3

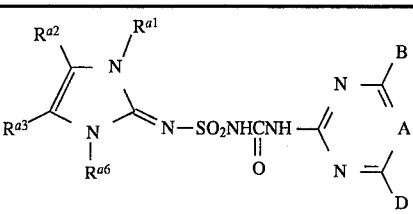

| Compound No. | R^a1 | R^a2 | R^a3 | R^a6 | A | B | D | m.p. (°C.) |
|---|---|---|---|---|---|---|---|---|
| 67-a | $C_2H_5$ | H | H | $CH_3$ | CH | $OCH_3$ | $OCH_3$ | 178–180 |
| 69-a | $C_3H_7$-n | H | H | $CH_3$ | CH | $OCH_3$ | $OCH_3$ | 167–169 |

EXAMPLE b-1

Preparation of 1-(3-n-propyl-4-thiadiazoline-2-sulfonylimino)-3-(4,6-dimethoxypyrimidin-2-yl)urea

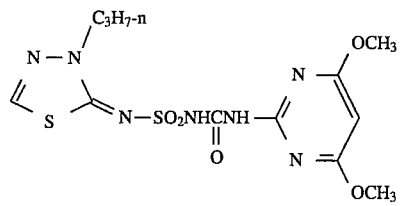

No. 1-b 1.55 g (10 mmol) of 2-amino-4,6-dimethoxypyrimidine was dissolved in 40 ml of dry tetrahydrofuran, and 1.42 g (10 mmol) of chlorosulfonyl isocyanate was dropwise added at −40° C. The reaction temperature was raised to 0° C., and then the mixture was cooled again to −40° C. Then, 2.58 g (9.5 mmol) of 2-imino-3-n-propylthiadiazol-4-ine hydroiodide suspended in 40 ml of dry tetrahydrofuran containing 2.22 g (22 mmol) of triethylamine, was added thereto. The reaction temperature was raised to room temperature, and the mixture was further stirred at the same temperature for one hour. Then, the solvent was distilled off under reduced pressure, and then water was added to the obtained residue. The mixture was extracted three times with chloroform. The chloroform layer was washed sequentially with water and a saturated sodium chloride aqueous solution and then dried over anhydrous sodium sulfate. Then, the solvent was distilled off under reduced pressure. Obtained crystals were washed with acetonitrile to obtain 2.25 g of desired 1-(3-n-propyl-4-thiadiazoline-2-sulfonylimino)-3-(4,6-dimethoxypyrimidin-2-yl)urea.

Melting point: 189°–190° C.

The structures and the physical property values of the compounds prepared by the same method as in Example b-1 are presented in Table 14b.

TABLE 14b

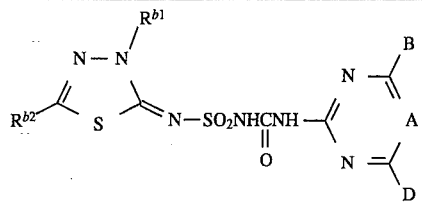

| Compound No. | R^b1 | R^b2 | A | B | D | m.p. (°C.) |
|---|---|---|---|---|---|---|
| 2-b | $CH_3$ | H | CH | $OCH_3$ | $OCH_3$ | 216–217 |
| 3-b | $CH_2CH=CH_2$ | H | CH | $OCH_3$ | $OCH_3$ | 197–198 |
| 4-b | $CH_2C\equiv CH$ | H | CH | $OCH_3$ | $OCH_3$ | 196–198 |
| 5-b | $CH_2COCH_3$ | H | CH | $OCH_3$ | $OCH_3$ | 206–208 |
| 6-b | $CH_3$ | $CH_3$ | CH | $OCH_3$ | $OCH_3$ | 203.5–204.5 |

EXAMPLE c-1

Preparation of 1-(3-ethoxythiazolidine-2-sulfonylimino)-3-(4,6-dimethoxypyrimidin-2-yl)urea

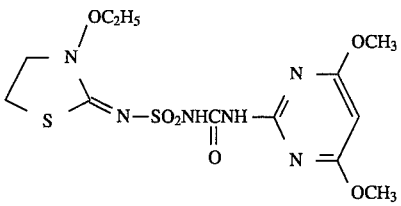

No. 1-c 1.55 g (10 mmol) of 2-amino-4,6-dimethoxypyrimidine was dissolved in 20 ml of dry tetrahydrofuran, and 1.42 g (10 mmol) of chlorosulfonyl isocyanate was dropwise added thereto in a range of −10° C. to −5° C. The reaction temperature was raised to 0° C., and the mixture was stirred for 5 minutes. The reaction mixture was cooled again to −30° C., and 2.72 g (12 mmol) of 2-imino-3-ethoxythiazolidine hydrobromide and 2.43 g (24 mmol) of triethylamine suspended in 10 ml of dry tetrahydrofuran were gradually added thereto. The reaction temperature was raised to room temperature, and the mixture was further stirred at the same temperature for 20 minutes. Then, the solvent was distilled off under reduced pressure, and then water was added to the obtained residue. Precipitated crystals were extracted three times with 100 ml of chloroform, and the extract was washed once with 100 ml of water and dried over anhydrous sodium sulfate. Then, the solvent was distilled off under reduced pressure. Obtained crystals were washed with ethyl ether and acetonitrile to obtain 2.1 g of desired 1-(3-ethoxythiazolidine-2-sulfonylimino)-3-(4,6-dimethoxypyridimin-2-yl)urea.

Melting point: 175°–176° C.

EXAMPLE c-2

Preparation of 1-(3-n-propoxythiazolidine-2 -sulfonylimino)-3-(4,6-dimethoxypyrimidin-2-yl)urea

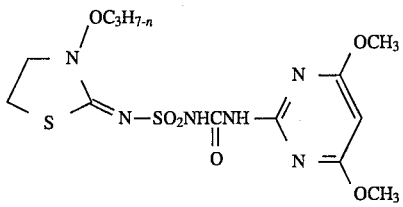

No. 12-c 0.62 g (4.0 mmol) of 2-amino-4,6-dimethoxypyrimidine was dissolved in 30 ml of dry tetrahydrofuran, and 0.57 g (4.0 mmol) of chlorosulfonyl isocyanate was dropwise added at −50° C. The reaction temperature was raised to room temperature, and then the reaction mixture was cooled again to −50° C. Then, 1.2 g (5.0 mmol) of 2 -imino-3-n-propoxythiazolidine hydrobromide suspended in 20 ml of dry tetrahydrofuran containing 1.01 g (10.0 mmol) of triethylamine, was added thereto. The reaction temperature was gradually raised to room temperature, and the mixture was further stirred at the same temperature for 10 minutes. Then, the solvent was distilled off under reduced pressure, and then water was added to the obtained residue. The mixture was extracted three times with 50 ml of chloroform. The chloroform layer was washed with a saturated sodium chloride aqueous solution and then dried over anhydrous sodium sulfate. Then, the solvent was distilled off under reduced pressure. To the obtained residue, ethyl ether and a small amount of acetonitrile were added for crystallization. The crystals were collected by filtration to obtain 0.65 g of desired 1-(3-n-propoxythiazolidine-2-sulfonylimino)-3-(4,6-dimethoxypyridimin-2-yl)urea.

Melting point: 173°–175° C.

EXAMPLE c-3

Preparation of 1-(3-n-propoxythiazolidine-2 -sulfonylimino)-3-(4,6-dimethoxytriazin-2-yl)urea

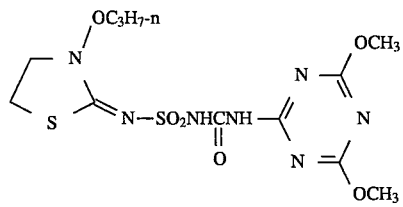

No. 24-c 3.76 g (40.0 mmol) of phenol was dissolved in 40 ml of dry tetrahydrofuran, and 5.66 g (40.0 mmol) of chlorosulfonyl isocyanate was dropwise added thereto at −50° C. The reaction temperature was raised to room temperature, and then the reaction mixture was cooled again to −50° C. Then, 10.6 g (44 mmol) of 2-imino-3-n-propoxythiazolidine hydrobromide suspended in 20 ml of dry acetonitrile containing 8.08 g (80 mmol) of triethylamine, was added thereto. The reaction temperature was gradually raised to room temperature, and the mixture was further stirred at the same temperature for 10 minutes. Then, the solvent was distilled off under reduced pressure, and then water was added to the obtained residue. The mixture was extracted three times with 70 ml of chloroform. The chloroform layer was washed with a saturated sodium chloride aqueous solution and then dried over anhydrous sodium sulfate. Then, the solvent was distilled off under reduced pressure. To the obtained residue, ethyl ether and a small amount of acetonitrile were added for crystallization. Then, the crystals were collected by filtration to obtain 14 g of phenyl N-(3-n-propoxythiazolidine-2 -sulfonylimino)carbamate. Then, 0.72 g (2.0 mmol) of the obtained carbamate was dissolved in 30 ml of dry dioxane, and 0.23 g (1.5 mmol) of 2-amino-4,6-dimethoxytriazine was added thereto. The mixture was refluxed under heating for 4 hours. The solvent was distilled off under reduced pressure, and ethyl ether and a small amount of acetonitrile were added for crystallization. Then, the crystals were collected by filtration to obtain 0.3 g of desired 1-(3-n-propoxythiazolidine-2-sulfonylimino)-3-( 4,6-dimethoxytriazin-2-yl)urea.

Melting point: 166°–167° C.

EXAMPLE c-4

Preparation of 1-[3-(3-chloroallyloxy)thiazolidine-2 -sulfonylimino]-3-(4-methyl-6-methoxytriazin-2-yl)urea

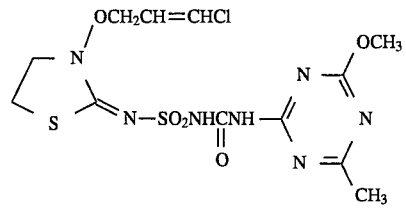

No. 37-c 0.84 g (6 mmol) of 2-amino-4-methyl-6-methoxytriazine was suspended in 20 ml of dry tetrahydrofuran, and 0.85 g (6 mmol) of chlorosulfonyl isocyanate was dropwise added thereto at room temperature. A heat was generated mildly, and the reaction mixture turned to a pale yellow solution. Then, 1.64 g (6 mmol) of 2-imino-3-(3-chloroallyloxy)thiazolidine hydrobromide and 1.43 g (14 mmol) of triethylamine suspended in 15 ml of dry tetrahydrofuran were gradually added thereto, and the mixture was further stirred at room temperature for 30 minutes. The solvent was distilled off under reduced pressure, and then water was added to the obtained residue. The resulting oily substance was extracted three times with 80 ml of chloroform. The extract solution was washed once with 100 ml of water and dried over anhydrous sodium sulfate. Then, the solvent was distilled off under reduced pressure. Obtained crystals were washed with ethyl ether and acetonitrile to obtain 1.2 g of desired 1-[3-(3-chloroallyloxy)thiazolidine-2-sulfonylimino] -3-(4-methyl-6-methoxytriazin-2-yl)urea.

Melting point: 145°–147° C.

EXAMPLE c-5

Preparation of 1-(3-methoxy-4-methyl-4-thiazoline-2 -sulfonylimino)-3-(4,6-dimethoxypyrimidin-2-yl)urea

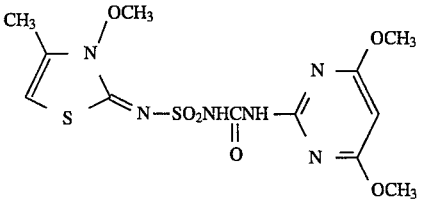

No. 45-c 0.78 g (5 mmol) of 2-amino-4,6-dimethoxypyrimidine was dissolved in 10 ml of dry tetrahydrofuran, and 0.71 g (5 mmol) of chlorosulfonyl isocyanate was dropwise added thereto in a range of −20° C. to −15° C. The reaction temperature was raised to 0° C., and the mixture was stirred for 5 minutes. The mixture was cooled again to −20° C., and 0.90 g (5 mmol) of 2-imino-3-methoxy-4 -methylthiazol-4- ine hydrochloride and 1.11 g (11 mmol) of triethylamine suspended in 10 ml of dry tetrahydrofuran, was gradually added thereto. The reaction temperature was raised to room temperature, and the mixture was further stirred at the same temperature for 20 minutes. The solvent was distilled off under reduced pressure, and then water was added to the obtained residue. Precipitated crystals were extracted three times with 50 ml of chloroform. The extract solution was washed once with 50 ml of water and dried over anhydrous sodium sulfate. Then, the solvent was distilled off under reduced pressure. Obtained crystals were washed with ethyl ether and acetonitrile to obtain 1.02 g of desired 1-(3-methoxy-4-methyl-4-thiazolidine-2-sulfonylimino)-3-( 4,6-dimethoxypyrimidin-2-yl)urea.

Melting point: 183°–185° C.

The structures and the physical property values of the compounds prepared by the same methods as in Examples c-1 to c-5 are presented in Tables 14c-1, 14c-2 and 14c-3.

TABLE 14c-1

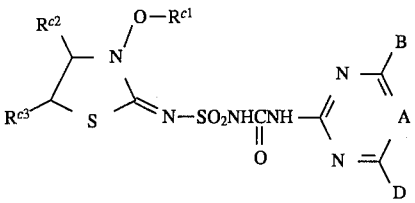

| Compound No. | $R^{c1}$ | $R^{c2}$ | $R^{c3}$ | A | B | D | m.p. (°C.) |
|---|---|---|---|---|---|---|---|
| 2-c | $C_2H_5$ | H | H | CH | $OCH_3$ | $CH_3$ | 182–183 |
| 3-c | $C_2H_5$ | H | H | N | $OCH_3$ | $CH_3$ | 155–156 |
| 4-c | $C_2H_5$ | H | H | CH | $CH_3$ | $CH_3$ | 152–153 |
| 5-c | $CH(CH_3)_2$ | H | H | CH | $OCH_3$ | $OCH_3$ | 175–178 |
| 6-c | $CH_3$ | H | H | CH | $OCH_3$ | $OCH_3$ | 193–194 |
| 7-c | $CH_3$ | H | H | CH | $OCH_3$ | $CH_3$ | 183–185 |
| 11-c | $CH(CH_3)_2$ | H | H | CH | $OCH_3$ | $CH_3$ | 150–152 |
| 13-c | $C_3H_7$-n | H | H | CH | $OCH_3$ | $CH_3$ | 161.5–162.5 |
| 14-c | $C_3H_7$-n | H | H | N | $OCH_3$ | $CH_3$ | 163–165 |
| 15-c | $C_3H_7$-n | H | H | CH | $CH_3$ | $CH_3$ | 145.5–146.5 |
| 16-c | $C_4H_9$-n | H | H | CH | $OCH_3$ | $OCH_3$ | 159–160 |
| 17-c | $CH_2C\equiv CH$ | H | H | CH | $OCH_3$ | $OCH_3$ | 172–173 |
| 18-c | $CH_2CH=CH_2$ | H | H | CH | $OCH_3$ | $OCH_3$ | 175.5–176.5 |
| 19-c | $CH_2CH=CH_2$ | H | H | CH | $OCH_3$ | $CH_3$ | 165–166 |
| 20-c | $C_3H_7$-n | H | H | CH | $OCHF_2$ | $OCHF_2$ | 118–119 |
| 21-c | $CH_2CH=CH_2$ | H | H | CH | $CH_3$ | $CH_3$ | 95–96 |
| 22-c | $CH_2Ph$ | H | H | CH | $OCH_3$ | $OCH_3$ | 159–161 |
| 23-c | $C_3H_7$-n | H | H | CH | $OCHF_2$ | $CH_3$ | 151–152 |
| 25-c | $C_3H_7$-n | H | H | CH | $OCHF_2$ | Cl | 225–226 |
| 26-c | $C_2H_5$ | H | H | N | $OCH_3$ | $OCH_3$ | 159–160 |
| 27-c | $C_2H_5$ | H | H | CH | $OCHF_2$ | $CH_3$ | 148–149 |
| 28-c | $C_2H_5$ | H | H | CH | $OCHF_2$ | $OCHF_2$ | 161–162 |
| 29-c | $C_3H_7$-n | H | H | CH | $OCH_3$ | $OCHF_2$ | 75–77 |
| 30-c | $C_2H_5$ | H | H | CH | $OCH_3$ | $OCHF_2$ | 149–151 |
| 31-c | $C_2H_5$ | H | H | CH | $OCH_3$ | Cl | 141–143 |
| 32-c | $C_3H_7$-n | H | H | CH | $OCH_3$ | Cl | 157–158 |
| 33-c | $C_2H_5$ | H | H | CH | $CH_3$ | Cl | 163–164 |
| 34-c | $C_3H_7$-n | H | H | CH | $CH_3$ | Cl | 153–156 |
| 35-c | $CH_2CH=CHCl$ | H | H | CH | $OCH_3$ | $OCH_3$ | 184–185 |
| 36-c | $CH_2CH=CHCl$ | H | H | CH | $OCH_3$ | $CH_3$ | 168–169 |
| 38-c | $CH_2CH(CH_3)_2$ | H | H | CH | $OCH_3$ | $OCH_3$ | 175.5–176.5 |
| 39-c | $CH_2CH(CH_3)_2$ | H | H | CH | $OCH_3$ | $CH_3$ | 151–152 |
| 40-c | $CH_2CH(CH_3)_2$ | H | H | N | $OCH_3$ | $CH_3$ | 148.5–149.5 |
| 41-c | $CH_2CH(CH_3)_2$ | H | H | N | $OCH_3$ | $OCH_3$ | 172–173 |
| 43-c | $CH_2CH=CHCl$ | H | H | CH | $CH_3$ | $CH_3$ | 164–165 |
| 44-c | $CH_2CH=CHCl$ | H | H | N | $OCH_3$ | $OCH_3$ | 158–163 |
| 46-c | $C_5H_{11}$-n | H | H | CH | $OCH_3$ | $OCH_3$ | 121–122 |
| 47-c | $CH_2CH(CH_3)_2$ | H | H | CH | $CH_3$ | $CH_3$ | 154–155 |
| 48-c | $CH_2CH=CHCl$ | H | H | CH | $OCH_3$ | $OCHF_2$ | 142–143 |
| 49-c | $CH_2C(Cl)=CH_2$ | H | H | CH | $OCH_3$ | $OCH_3$ | 178–179 |
| 50-c | $CH_2C(Cl)=CH_2$ | H | H | CH | $OCH_3$ | $CH_3$ | 159–160 |
| 51-c | $CH_2C(Cl)=CH_2$ | H | H | N | $OCH_3$ | $CH_3$ | 157–158 |
| 52-c | $CH_2C(Cl)=CH_2$ | H | H | N | $OCH_3$ | $OCH_3$ | 181–182 |
| 53-c | $C_3H_7$-n | H | H | N | $OC_2H_5$ | $CH_3$ | 134–135 |
| 54-c | $C_3H_7$-n | H | H | N | $OCH_3$ | $C_2H_5$ | 143.5–144.5 |
| 55-c | $CH_2CH=CHCl$ | H | H | N | $OC_2H_5$ | $CH_3$ | 131–133 |
| 56-c | $CH_2CH=CHCl$ | H | H | N | $OCH_3$ | $C_2H_5$ | 128–130 |
| 57-c | $CH_2CH=CHCl$ | H | H | N | $OCH_3$ | $CH_2Cl$ | 133–135 |
| 58-c | $C_3H_7$-n | H | H | N | $OCH_3$ | $CH_2Cl$ | 154–155 |
| 59-c | $CH_2CH=CHCl$ | H | H | CH | $OCHF_2$ | $CH_3$ | 136–137 |
| 60-c | $C_3H_7$-n | H | H | CH | $CF_3$ | Cl | 133–134 |
| 61-c | $C_2H_5$ | H | H | N | $OC_2H_5$ | $CH_3$ | 161–162 |
| 62-c | $C_3H_7$-n | H | H | N | $OCH_3$ | $C_3H_7$-n | 157–158 |

TABLE 14c-1-continued $$\text{R}^{c2}\text{-CH(R}^{c3}\text{)-S-C(=N-SO}_2\text{NHC(O)NH-pyrimidine(A,B,D))-N(O-R}^{c1}\text{)}$$

| Compound No. | $R^{c1}$ | $R^{c2}$ | $R^{c3}$ | A | B | D | m.p. (°C.) |
|---|---|---|---|---|---|---|---|
| 63-c | $C_3H_7$-n | H | H | N | $OC_3H_7$-n | $CH_3$ | 124–125 |
| 64-c | $CH_2CH=CHCl$ | H | H | CH | $CF_3$ | Cl | 183–186 |
| 65-c | $CH_2CH=CHCl$ | H | H | N | $OCH_3$ | $C_3H_7$-n | 114–115 |
| 66-c | $CH_2CH=CHCl$ | H | H | N | $OC_3H_7$-n | $CH_3$ | 128–130 |
| 67-c | $CH_2CH=CHCl$ | H | H | N | $OCH_3$ | $CF_3$ | 138–140 |
| 68-c | $CH_2C(Cl)=CH_2$ | H | H | N | $OC_2H_5$ | $CH_3$ | 139–140 |
| 69-c | $CH_2C(Cl)=CH_2$ | H | H | N | $OCH_3$ | $C_2H_5$ | 149–150 |
| 70-c | $CH_2C(Cl)=CH_2$ | H | H | N | $OCH_3$ | $CF_3$ | 152–154 |
| 71-c | $CH_2C(Cl)=CH_2$ | H | H | CH | $OCH_3$ | $OCHF_2$ | 86–87 |

TABLE 14c-2

| Compound No. | $R^{c1}$ | $R^{c4}$ | $R^{c5}$ | $R^{c6}$ | A | B | D | m.p. (°C.) |
|---|---|---|---|---|---|---|---|---|
| 8-c | $C_2H_5$ | H | H | H | CH | $OCH_3$ | $OCH_3$ | 189–190 |
| 9-c | $C_2H_5$ | H | H | H | CH | $OCH_3$ | $CH_3$ | 165–166 |
| 10-c | $C_2H_5$ | H | H | H | CH | $CH_3$ | $CH_3$ | 178–179 |

TABLE 14c-3

| Compound No. | $R^{c1}$ | $R^{c7}$ | $R^{c8}$ | A | B | D | m.p. (°C.) |
|---|---|---|---|---|---|---|---|
| 42-c | $CH_3$ | $CH_3$ | $CH_3$ | CH | $OCH_3$ | $OCH_3$ | 180–192 (decomposed) |

EXAMPLE d-1

Preparation of 1-(3-methylthiazolidin-4-one-2-sulfonylimino)-3-(4,6-dimethoxypyrimidin-2-yl)urea No. 1-d 1.55 g (10 mmol) of 2-amino-4,6-dimethoxypyrimidine was dissolved in 30 ml of dry tetrahydrofuran, and 1.42 g (10 mmol) of chlorosulfonyl isocyanate was dropwise added thereto in a range of from −20° C. to −15° C. The reaction temperature was raised to 0° C., and the mixture was further stirred at the same temperature for 10 minutes. The reaction mixture was cooled again to −30° C., and a mixture comprising 2.84 g (11 mmol) of 3-methyl-2-iminothiazolidin-4-one hydroiodide, 2.22 g (22 mmol) of triethylamine and 30 ml of dry tetrahydrofuran, was added thereto. The reaction temperature was raised to room temperature, and the mixture was further stirred at the same temperature for 20 minutes. Then, the solvent was distilled off under reduced pressure, and then 100 ml of water was added to the obtained residue. Precipitated crystals were extracted three times with 100 ml of chloroform. The chloroform layer was washed with water and then dried over anhydrous sodium sulfate. Then, the solvent was distilled off under reduced pressure. Obtained crystals were washed with a solvent mixture of ethyl ether/acetonitrile and collected by filtration to obtain 1.5 g of desired 1-(3-methylthiazolidin-4-one-2-sulfonylimino)-3-(4,6-dimethoxypyrimidin-2-yl)urea as colorless crystals.

Melting point: 200°–201° C.

EXAMPLE d-2

Preparation of 1-(1-methyl-3-n-propylimidazolidin-4-one-2-sulfonylimino)-3-(4,6-dimethoxypyrimidin-2-yl)urea

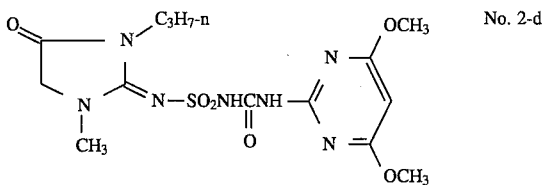

No. 2-d 1.16 g (7.5 mmol) of 2-amino-4,6-dimethoxypyrimidine was dissolved in 20 ml of dry tetrahydrofuran, and 1.07 g (7.5 mmol) of chlorosulfonyl isocyanate was dropwise added thereto at −40° C. The reaction temperature was raised to 0° C., and then the reaction mixture was cooled again to −40° C. Then, a mixture comprising 1.16 g (7.5 mmol) of 1-methyl-3-n-propyl-2-iminoimidazolidin-4-one, 0.83 g (8.2 mmol) of triethylamine and 20 ml of dry tetrahydrofuran, was added thereto. The reaction temperature was raised to room temperature, and the mixture was further stirred at the same temperature for 2 hours. Then, the solvent was distilled off under reduced pressure, and then 100 ml of water was added to the obtained residue. The mixture was extracted three times with 100 ml of chloroform. Then, the chloroform layer was washed with water and then dried over anhydrous sodium sulfate. The solvent was distilled off under reduced pressure, and precipitated crystals were washed with a solvent mixture of ethyl ether/acetonitrile and collected by filtration to obtain 0.16 g of desired 1-(1-methyl-3-n-propylimidazolidin-4-one-2-sulfonylimino)-3-( 4,6-dimethoxypyrimidin-2-yl)urea.

Melting point: 96°–98° C.

The structures and the physical property values of the compounds prepared by the same methods as in Examples d-1 and d-2 are presented in Table 14d.

TABLE 14d

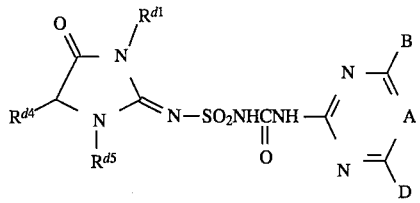

| Compound No. | $R^{d1}$ | $R^{d4}$ | $R^{d5}$ | A | B | D | m.p. (°C.) |
|---|---|---|---|---|---|---|---|
| 3-d | $CH_3$ | H | $CH_3$ | CH | $OCH_3$ | $OCH_3$ | 188–189 |
| 4-d | $C_2H_5$ | H | $CH_3$ | CH | $OCH_3$ | $OCH_3$ | 111–113 |
| 5-d | $CH_2CH=CH_2$ | H | $CH_3$ | CH | $OCH_3$ | $OCH_3$ | 156–158 |
| 6-d | $CH_2C\equiv CH$ | H | $CH_3$ | CH | $OCH_3$ | $OCH_3$ | 181–182 |
| 7-d | $CH_2COCH_3$ | H | $CH_3$ | CH | $OCH_3$ | $OCH_3$ | 190–192 |
| 8-d | $CH_2CO_2CH_3$ | H | $CH_3$ | CH | $OCH_3$ | $OCH_3$ | 188–190 |
| 9-d | $CH_2OCH_3$ | H | $CH_3$ | CH | $OCH_3$ | $OCH_3$ | 155–156 |
| 10-d | $CH_2SCH_3$ | H | $CH_3$ | CH | $OCH_3$ | $OCH_3$ | 115–120 (decomposed) |

EXAMPLE e-1

Preparation of 1-(3,6-dihydro-3-n-propyl-2H-1,3-thiazine-2-sulfonylimino)-3-(4,6-dimethoxypyrimidin-2-yl)urea

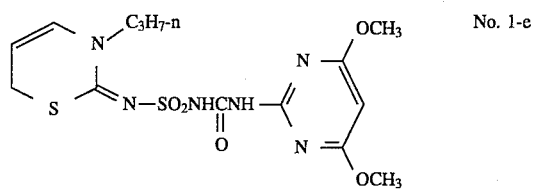

No. 1-e 0.32 g (2.06 mmol) of 2-amino-4,6-dimethoxypyrimidine was dissolved in 40 ml of dry tetrahydrofuran, and the solution was cooled to −40° C. At the same temperature, 0.29 g (2.05 mmol) of chlorosulfonyl isocyanate was dropwise added thereto. Then, the temperature was raised to 0° C. The mixture was cooled again to −40° C., and then a mixed solution comprising 0.4 g (2.56 mmol) of 3,6-dihydro-3-n-propyl-2H-1,3-thiazin-2-imine, 0.26 g (2.57 mmol) of triethylamine and 40 ml of dry tetrahydrofuran, was dropwise added thereto. The mixture was gradually heated to room temperature with stirring, and then the solvent was distilled off under reduced pressure. 100 ml of water was added to the residue, and then the mixture was extracted twice with 50 ml of chloroform. The chloroform layer was washed with water and then dried over anhydrous sodium sulfate. Then, chloroform was distilled off under reduced pressure. Obtained crystals were washed with acetonitrile and then with ethyl ether to obtain 0.3 g of desired 1-(3,6-dihydro-3-n-propyl-2H- 1,3-thiazine-2-sulfonylimino)-3-(4, 6-dimethoxypyrimidin- 2-yl) urea.

Melting point: 161°–163° C.

EXAMPLE e-2

Preparation of 1-(3,4,5,6-tetrahydro-3-methyl-2H-1,3-thiazine-2-sulfonylimino)-3-(4,6-dimethoxypyrimidin-2yl)urea

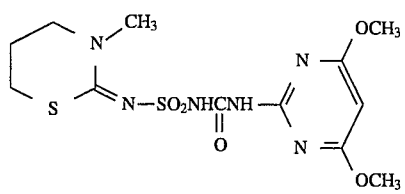
No. 2-e 1.55 g (10 mmol) of 2-amino-4,6-dimethoxypyrimidine was dissolved in 30 ml of dry tetrahydrofuran, and 1.42 g (10 mmol) of chlorosulfonyl isocyanate was dropwise added thereto in a range of from −15° C. to −5° C. The reaction solution was heated to 0° C. and then further stirred at the same temperature for 15 minutes. Then, the reaction solution was cooled again to −30° C., and a mixed solution comprising 1.56 g (12 mmol) of 3,4,5,6-tetrahydro-3-methyl-2H-1,3-thiazin-2-imine, 1.21 g (12 mmol) of triethylamine and 10 ml of dry tetrahydrofuran, was dropwise added thereto. The reaction solution was gradually heated to room temperature with stirring, and then the solvent was distilled off under reduced pressure. 80 ml of water was added to the residue, and precipitated crystals were extracted three times with 60 ml of chloroform. The chloroform layer was washed with water and dried over anhydrous sodium sulfate. Then, chloroform was distilled off under reduced pressure.

Obtained crystals were washed with a solvent mixture of ethyl ether/acetonitrile to obtain 1.2 g of desired 1-( 3,4,5,6-tetrahydro-3-methyl-2H-1,3-thiazine-2-sulfonylimino)-3-(4,6-dimethoxypyrimidin-2-yl)urea.

Melting point: 188°–190° C.

The structures and the physical property values of the compounds prepared by the same methods as in Examples e-1 and e-2 are presented in Tables 14e-1 and 14e-2.

TABLE 14e-1

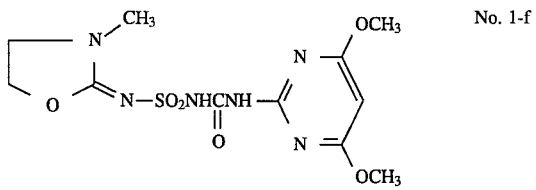

| Compound No. | $R^{e1}$ | $R^{e2}$ | $R^{e3}$ | $R^{e4}$ | A | B | D | m.p. (°C.) |
|---|---|---|---|---|---|---|---|---|
| 3-e | $CH_3$ | H | H | H | CH | $OCH_3$ | $OCH_3$ | 194–196 |
| 4-e | $CH_2OCH_3$ | H | H | H | CH | $OCH_3$ | $OCH_3$ | 158–160 |

TABLE 14e-2

| Compound No. | $R^{e1}$ | $R^{e8}$ | $R^{e9}$ | $R^{e10}$ | A | B | D | m.p. (°C.) |
|---|---|---|---|---|---|---|---|---|
| 5-e | $C_3H_7$-n | H | H | H | CH | $OCH_3$ | $OCH_3$ | 166–167 |

EXAMPLE f-1

Preparation of 1-(3-methyloxazolidine-2-sulfonylimino)-3-(4,6-dimethoxypyrimidin-2-yl)urea No. 1-f 1.55 g (10 mmol) of 2-amino-4,6-dimethoxypyrimidine was dissolved in 30 ml of dry tetrahydrofuran, and 1.42 g (10 mmol) of chlorosulfonyl isocyanate was dropwise added thereto at −20° C. The reaction temperature was raised to −5° C., and the mixture was stirred at the same temperature for 5 minutes. The reaction mixture was cooled again to −20° C., and a mixture comprising 2.28 g (10 mmol) of 2-imino-3-methyloxazolidine hydroiodide, 2.22 g (22 mmol) of triethylamine and 30 ml of dry tetrahydrofuran, was added thereto. The reaction temperature was raised to room temperature, and the mixture was further stirred at the same temperature for one hour. Then, the solvent was distilled off under reduced pressure, and then 100 ml of water was added to the obtained residue. Precipitated crystals were collected by filtration, washed with water and then with a solvent mixture of ethyl ether/acetonitrile and dried to obtain 0.8 g of desired 1-(3-methyloxazolidine-2-sulfonylimino)-3-(4,6-dimethoxypyrimidin-2-yl)urea.

Melting point: 174°–175° C.

The structures and the physical property values of the compounds prepared by the same method as in Example f-1

TABLE 14f

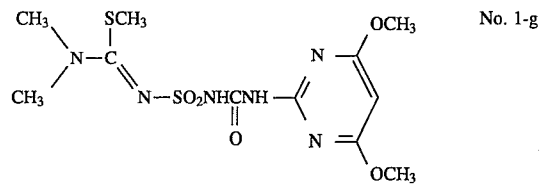

| Compound No. | $R^{f1}$ | $R^{f5}$ | $R^{f6}$ | A | B | D | m.p. (°C.) |
|---|---|---|---|---|---|---|---|
| 2-f | $CH_2CH=CH_2$ | H | H | CH | $OCH_3$ | $OCH_3$ | 157–159 |

EXAMPLE g-1

Preparation of 1-[N-((methylthio-N,N-dimethylamino)methylene)aminosulfonyl] -3-(4,6-dimethoxypyrimidin-2-yl)urea

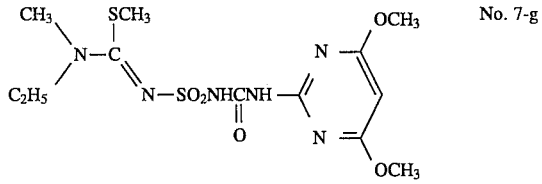

No. 1-g 1.55 g (10 mmol) of 2-amino-4,6-dimethoxypyrimidine was dissolved in 40 ml of dry tetrahydrofuran, and 1.42 g (10 mmol) of chlorosulfonyl isocyanate was dropwise added thereto in a range of from −20° C. to −15° C. The reaction temperature was raised to 0° C., and the mixture was cooled again to −20° C. Then, a mixture comprising 2.5 g (10.2 mmol) of N,N-dimethyl-S-methylisothiourea hydroiodide, 2.22 g (22 mmol) of triethylamine and 30 ml of dry tetrahydrofuran, was added thereto. The reaction temperature was raised to room temperature, and the mixture was further stirred at the same temperature for 10 minutes. Then, the solvent was distilled off under reduced pressure, and then 80 ml of water was added to the obtained residue. The mixture was extracted three times with 30 ml of chloroform. The chloroform layer was washed with water and then dried over anhydrous sodium sulfate. Then, solvent was distilled off under reduced pressure. Obtained crystals were washed with a solvent mixture of ethyl ether/acetonitrile to obtain 2 g of desired 1-[N-((methylthio-N,N-dimethylamino)methylene)aminosulfonyl] -3-(4,6-dimethoxypyrimidin-2-yl)urea.

Melting point: 167°–168° C.

EXAMPLE g-2

Preparation of 1-[N-((methylthio-N-ethyl-N-methylamino)methylene)aminosulfonyl] -3-(4,6-dimethoxypyrimidin-2 -yl)urea No. 7-g 1.55 g (10 mmol) of 2-amino-4,6-dimethoxypyrimidine was dissolved in 40 ml of dry tetrahydrofuran, and 1.42 g (10 mmol) of chlorosulfonyl isocyanate was dropwise added thereto in a range of from −20° C. to −15° C. The reaction temperature was raised to 0° C., and the mixture was cooled again to −20° C. Then, a mixture comprising 2.60 g (10 mmol) of N-ethyl-N-methyl-S-methylisothiourea hydroiodide, 2.22 g (22 mmol) of triethylamine and 30 ml of dry tetrahydrofuran, was added thereto. The reaction temperature was raised to room temperature, and the mixture was further stirred at the same temperature for one hour. Then, the solvent was distilled off under reduced pressure, and 80 ml of water was added to the obtained residue. The mixture was extracted three times with 50 ml of chloroform. The chloroform layer was washed with water, and then dried over anhydrous sodium sulfate. Then, the solvent was distilled off under reduced pressure. Obtained crystals were washed with acetonitrile to obtain 1.32 g of desired 1-[N-((methylthio-N-ethyl-N-methylamino)methylene)aminosulfonyl] -3-(4,6-dimethoxypyrimidin-2-yl)urea.

Melting point: 143°–144° C.

EXAMPLE g-3

Preparation of 1-[N-((methylthio-N-methoxy-N-methylamino)methylene)aminosulfonyl] -3-(4,6-dimethoxypyrimidin-2-yl)urea

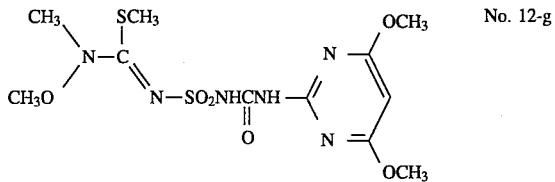

No. 12-g 0.78 g (5 mmol) of 2-amino-4,6-dimethoxypyrimidine was dissolved in 20 ml of dry tetrahydrofuran, and 0.71 g (5 mmol) of chlorosulfonyl isocyanate was dropwise added thereto in a range of from −20° C. to −15° C. The reaction temperature was raised to 0° C., and then the mixture was cooled again to −20° C. Then, a mixture comprising 1.31 g (5 mmol) of N-methoxy-N-methyl-S-methylisothiourea hydroiodide, 1.11 g (11 mmol) of triethylamine and 15 ml of dry tetrahydrofuran, was added thereto. The reaction temperature was raised to room temperature, and the mixture was further stirred at the same temperature for one hour. Then, the solvent was distilled off under reduced pressure, and then 40 ml of water was added to the obtained residue. The mixture was extracted three times with 25 ml of chloroform. The chloroform layer was washed with water, and then dried over anhydrous sodium sulfate. Then, the solvent was distilled off under reduced pressure. Obtained crystals were washed with acetonitrile to obtain 1.51 g of desired 1-[N-((methylthio-N-methoxy-N-methylamino)methylene)aminosulfonyl] -3-(4,6-dimethoxypyrimidin-2-yl)urea.

Melting point: 165°–167° C.

The structures and the physical property values of the compounds prepared by the same methods as in Examples g-1 to g-3 are presented in Table 14g.

TABLE 14g

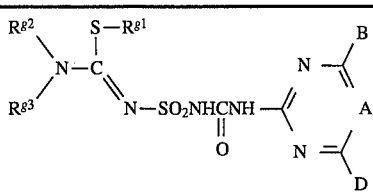

| Compound No. | $R^{g1}$ | $R^{g2}$ | $R^{g3}$ | A | B | D | m.p. (°C.) |
|---|---|---|---|---|---|---|---|
| 2-g | $C_2H_5$ | $CH_3$ | $CH_3$ | CH | $OCH_3$ | $OCH_3$ | 129–130 |
| 3-g | $C_3H_7$-n | $CH_3$ | $CH_3$ | CH | $OCH_3$ | $OCH_3$ | 115–116 |
| 4-g | $CH_2CH=CH_2$ | $CH_3$ | $CH_3$ | CH | $OCH_3$ | $OCH_3$ | 131–132 |
| 5-g | $CH_2C\equiv CH$ | $CH_3$ | $CH_3$ | CH | $OCH_3$ | $OCH_3$ | 140–141 |
| 6-g | $CH_3$ | $CH_3$ | $COCH_3$ | CH | $OCH_3$ | $OCH_3$ | 162–164 |
| 8-g | $CH_3$ | $-(CH_2)_4-$ | | CH | $OCH_3$ | $OCH_3$ | 184–186 |
| 9-g | $CH_3$ | $CH_3$ | $C_3H_7$-n | CH | $OCH_3$ | $OCH_3$ | 123–125 |
| 10-g | $CH_3$ | $CH_3$ | Ph | CH | $OCH_3$ | $OCH_3$ | 163–164 |
| 11-g | $CH_3$ | $CH_3$ | $CH_3$ | CH | $OCH_3$ | $CH_3$ | 178–179 |
| 13-g | $CH_3$ | $CH_3$ | $OC_2H_5$ | CH | $OCH_3$ | $OCH_3$ | 142–143 |
| 14-g | $CH_3$ | $CH_3$ | $OC_3H_7$-n | CH | $OCH_3$ | $OCH_3$ | 124–125 |
| 15-g | $CH_3$ | $CH_3$ | $OC_3H_7$-n | CH | $OCH_3$ | $CH_3$ | 142–143 |
| 16-g | $CH_3$ | $CH_3$ | $OC_2H_5$ | CH | $OCH_3$ | $CH_3$ | 141–142 |
| 17-g | $CH_3$ | $CH_3$ | $OC_2H_5$ | N | $OCH_3$ | $CH_3$ | 148–149 |
| 18-g | $CH_3$ | $CH_3$ | $OC_3H_7$-n | N | $OCH_3$ | $CH_3$ | 138–139 |
| 19-g | $CH_3$ | $CH_3$ | $CH_2CH=CH_2$ | CH | $OCH_3$ | $OCH_3$ | 138–141 |
| 20-g | $CH_3$ | $CH_3$ | $CH_3$ | N | $OCH_3$ | $CH_3$ | 166–167 |

Now, Formulation Examples of the herbicides containing the compounds of the present invention will be given specifically. However, it should be understood that the present invention is by no means restricted to such specific Examples. In the following Formulation Examples, "parts" means "parts by weight".

| Wettable powder | |
|---|---|
| Compound of the present invention | 5–80 parts |
| Solid carrier | 10–85 parts |
| Surfactant | 1–10 parts |
| Other | 1–5 parts |

As other, a coagulation preventing agent may, for example, be mentioned.

| Emulsifiable concentrate | |
|---|---|
| Compound of the present invention | 1–30 parts |
| Liquid carrier | 30–95 parts |
| Surfactant | 5–15 parts |

| Flowable | |
|---|---|
| Compound of the present invention | 5–70 parts |
| Liquid carrier | 15–65 parts |
| Surfactant | 5–12 parts |
| Other | 5–30 parts |

As other, an antifreezing agent and a thickener may, for example, be mentioned.

| Granular wettable powder (dry flowable) | |
|---|---|
| Compound of the present invention | 20–90 parts |
| Solid carrier | 10–60 parts |
| Surfactant | 1–20 parts |

| Granule | |
|---|---|
| Compound of the present invention | 0.1–10 parts |
| Solid carrier | 90–99.9 parts |
| Other | 1–5 parts |

FORMULATION EXAMPLE a-1: Wettable powder

| Compound No. 1-a of the present invention | 20 parts |
|---|---|
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE a-2: Wettable powder

| Compound No. 2-a of the present invention | 40 parts |
|---|---|
| Zeeklite A (tradename for a kaolin-type clay, manufactured by Zeeklite Industries, Co., Ltd.) | 54 parts |
| Sorpol 5039 (tradename for a mixture of a | 2 parts |

-continued

| | |
|---|---|
| nonionic surfactant and an anionic surfactant, manufactured by Toho Chemical Industry Co., Ltd.) | |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE a-3: Emulsifiable concentrate

| | |
|---|---|
| Compound No. 3-a of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE a-4: Flowable

| | |
|---|---|
| Compound No. 7-a of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE a-5: Flowable

| | |
|---|---|
| Compound No. 8-a of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE a-6: Granular wettable powder (dry flowable)

| | |
|---|---|
| Compound No. 10-a of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE a-7: Granule

| | |
|---|---|
| Compound No. 69-a of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE b-1: Wettable powder

| | |
|---|---|
| Compound No. 1-b of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE b-2: Wettable powder

| | |
|---|---|
| Compound No. 2-b of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE b-3: Emulsifiable concentrate

| | |
|---|---|
| Compound No. 3-b of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE b-4: Flowable

| | |
|---|---|
| Compound No. 1-b of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE b-5: Flowable

| | |
|---|---|
| Compound No. 4-b of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE b-6: Granular wettable powder (dry flowable)

| | |
|---|---|
| Compound No. 5-b of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE b-7: Granule

| | |
|---|---|
| Compound No. 6-b of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE c-1: Wettable powder

| | |
|---|---|
| Compound No. 1-c of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE c-2: Wettable powder

| | |
|---|---|
| Compound No. 2-c of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE c-3: Emulsifiable concentrate

| | |
|---|---|
| Compound No. 12-c of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE c-4: Flowable

| | |
|---|---|
| Compound No. 24-c of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE c-5: Flowable

| | |
|---|---|
| Compound No. 37-c of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE c-6: Granular wettable powder (dry flowable)

| | |
|---|---|
| Compound No. 45-c of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE c-7: Granule

| | |
|---|---|
| Compound No. 48-c of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE d-1: Wettable powder

| | |
|---|---|
| Compound No. 1-d of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon manufactured by Shionogi Pharmaceutical Co., Ltd.) | 2 parts |

The above ingredients are homogeneously pulverized and mixed to form a wettable powder.

FORMULATION EXAMPLE d-2: Wettable powder

| | |
|---|---|
| Compound No. 2-d of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE d-3: Emulsifiable concentrate

| | |
|---|---|
| Compound No. 3-d of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE d-4: Flowable

| | |
|---|---|
| Compound No. 4-d of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE d-5: Flowable

| | |
|---|---|
| Compound No. 5-d of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE d-6: Granular wettable powder (dry flowable)

| | |
|---|---|
| Compound No. 6-d of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE d-7: Granule

| | |
|---|---|
| Compound No. 9-d of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE e-1: Wettable powder

| | |
|---|---|
| Compound No. 1-e of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE e-2: Wettable powder

| | |
|---|---|
| Compound No. 2-e of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE e-3: Emulsifiable concentrate

| | |
|---|---|
| Compound No. 3-e of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE e-4: Flowable

| | |
|---|---|
| Compound No. 4-e of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE e-5: Flowable

| | |
|---|---|
| Compound No. 5-e of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE e-6: Granular wettable powder (dry flowable)

| | |
|---|---|
| Compound No. 1-e of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE e-7: Granule

| | |
|---|---|
| Compound No. 5-e of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE f-1: Wettable powder

| | |
|---|---|
| Compound No. 1-f of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE f-2: Wettable powder

| | |
|---|---|
| Compound No. 2-f of the present invention | 40 parts |
| Zeeklite A (tradename for a kaolin-type clay, manufactured by Zeeklite Industries, Co., Ltd.) | 54 parts |
| Sorpol 5039 (tradename for a mixture of a | 2 parts | nonionic surfactant and an anionic
surfactant, manufactured by Toho Chemical
Industry Co., Ltd.)

| | |
|---|---|
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE f-3: Emulsifiable concentrate

| | |
|---|---|
| Compound No. 1-f of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE f-4: Flowable

| | |
|---|---|
| Compound No. 2-f of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE f-5: Flowable

| | |
|---|---|
| Compound No. 2-f of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE f-6: Granular wettable powder (dry flowable)

| | |
|---|---|
| Compound No. 2-f of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE f-7: Granule

| | |
|---|---|
| Compound No. 2-f of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE g-1: Wettable powder

| | |
|---|---|
| Compound No. 1-g of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 2 parts |

The above ingredients are homogeneously pulverized and mixed to form a wettable powder.

FORMULATION EXAMPLE g-2: Wettable powder

| | |
|---|---|
| Compound No. 2-g of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a white carbon, manufactured by Shionogi Pharmaceutical Co., Ltd.) | 4 parts |

The above ingredients are homogeneously pulverized and mixed to form a wettable powder.

FORMULATION EXAMPLE g-3: Emulsifiable concentrate

| | |
|---|---|
| Compound No. 3-g of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE g-4: Flowable

| | |
|---|---|
| Compound No. 4-g of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE g-5: Flowable

| | |
|---|---|
| Compound No. 5-g of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE g-6: Granular wettable powder (dry flowable)

| | |
|---|---|
| Compound No. 12-g of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for a white carbon, manufactured by Shionogi Pharmaceutical Co., Ltd.) | 10 parts |

The above ingredients are uniformly mixed and pulverized to form a dry flowable.

FORMULATION EXAMPLE g-7: Granule

| | |
|---|---|
| Compound No. 19-g of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

In use, the above wettable powder, emulsifiable concentrate, flowable or granular wettable powder is diluted with water from 50 to 1,000 times and applied so that the active ingredient will be from 0.0001 to 10 kg per hectare (ha).

Now, the herbicidal activities of the compounds of the present invention will be described in detail with reference to the following Test Examples.

TEST EXAMPLE 1: Test-1 on the herbicidal effects in soil treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, Oryza sativa, Zea mays, Triticum aestivum, Glycine max* and *Gossypium* spp. were sown, and the soil was covered thereon in a thickness of about 1.5 cm, and then a herbicide solution was applied onto the surface of the soil uniformly so that the active ingredient was distributed at a predetermined concentration. The herbicide solution was prepared by diluting a wettable powder prepared in accordance with the foregoing Formulation Examples with water and applied by a small spray onto the entire soil surface. Four weeks after the application of the herbicidal solution, the herbicidal effects against each weed and the phytotoxicities against each crop plant were determined on the basis of the following standard ratings. The results are shown in Table 15.

Standard ratings:
- 5: Growth control rate of more than 90% (almost completely withered)
- 4: Growth control rate of from 70 to 90%
- 3: Growth control rate of from 40 to 70%
- 2: Growth control rate of from 20 to 40%
- 1: Growth control rate of from 5 to 20%
- 0: Growth control rate of less than 5% (almost non-effective)

The above growth control rates were calculated by the following equation:

$$\text{Growth control rate (\%)} = \left(1 - \frac{T}{N}\right) \times 100$$

where
- T: Weight of the weed grown above the soil surface of the treated area
- N: Weight of the weed grown above the soil surface of the non-treated area

TEST EXAMPLE 2: Test-1 on the herbicidal effects in foliage treatment

A plastic box having a length of 15 cm, a width of 22 cm and a depth of 6 cm was filled with a sterilized diluvial soil, and seeds of *Echinochloa crus-galli, Digitaria adscendens, Avena fatua, Cyperus microiria, Solanum nigrum, Galinsoga ciliata, Rorippa indica, Oryza sativa, Zea mays, Triticum aestivum, Glycine max,* Gossypium spp. and *Beta vulgaris* were spot-wisely sown, and the soil was covered thereon in a thickness of about 1.5 cm. When the various weeds and crop plants grew to the 2 or 3 leaf stage, a herbicidal solution was uniformly sprayed on the foliages so that the active ingredient was applied in a predetermined concentration. The herbicidal solution was prepared by diluting a wettable powder prepared in accordance with the above Formulation Examples with water and applied onto the entire surface of the foliages of the weeds and the crop plants by a small spray. Four weeks after the application of the herbicide solution, the herbicidal effects against each weed and the phytotoxicities against each crop plant were determined on the basis of the standard ratings described in Test Example 1. The results are shown in Table 16.

TEST EXAMPLE 3: Test-1 on the herbicidal effects in irrigation treatment

Into a Wagner pot of 1/5000a, alluvial soil was put, and then water was introduced and mixed to form an irrigated state with a water depth of 4 cm. Seeds of *Echinochloa crus-galli*, *Scirpus juncoides*, *Monochoria vaginalis* and *Rotala indica* were sown in the above pot, and tubers of *Sagittaria pygmaea* and *Cyperus serotinus* were embedded. Then, rice seedlings of 2.5 leaf stage were transplanted. The pot was placed in a greenhouse at a temperature of from 25° to 30° C., and the plants were cultured. On the third day after the seeding and plantation, a diluted solution of the herbicide was dropwise applied to the water surface by a measuring pipette, so that the dose would be a predetermined level. Three weeks after the dropwise application of the herbicide, the herbicidal effects against various weeds and rice were determined on the basis of the standard ratings described in Test Example 1. The results are shown in Table 17.

In Tables 15, 16 and 17, Compound Nos. correspond to Compound Nos. in the Examples, and symbols have the following meanings.

A: *Echinochloa crus-galli* (barnyardgrass)
B: *Digitaria adscendens* (large crabgrass)
C: *Avena fatua* (wild oat)
D: *Cyperus microiria* (annual sedge)
E: *Solanum nigrum* (black nightshade)
F: *Galinsoga ciliata* (hairy galinsoga)
G: *Rorippa indica* (fieldcress)
H: *Scirpus juncoides* (bulrush)
I: *Monochoria vaginalis* (ducksalad)
J: *Rotala indica* (toothcup)
K: *Sagittaria pygmaea* (arrowhead)
L: *Cyperus serotinus* (flat sedge)
a: *Oryza sativa* (rice)
b: *Zea mays* (corn)
c: *Triticum aestivum* (wheat)
d: *Glycine max* (soybean)
e: *Gossypium spp.* (cotton)
f: *Beta vulgaris* (sugar beet)

| No. | Dose (kg/ha) | A | B | D | E | F | G | a | b | c | d | e |
|---|---|---|---|---|---|---|---|---|---|---|---|---|
| 1-a | 2.5 | 4 | 4 | 5 | 1 | 3 | 5 | 5 | 5 | 5 | 4 | 3 |
| 2-a | 0.04 | 5 | 5 | 5 | 1 | 5 | 5 | 1 | 0 | 0 | 0 | 0 |
|  | 0.08 | 5 | 5 | 5 | 1 | 5 | 5 | 2 | 1 | 1 | 0 | 0 |
|  | 0.16 | 5 | 5 | 5 | 2 | 5 | 5 | 3 | 3 | 2 | 1 | 0 |
| 3-a | 2.5 | 4 | 4 | 1 | 1 | 0 | 4 | 3 | 0 | 2 | 1 | 0 |
| 6-a | 0.63 | 5 | 5 | 5 | 0 | 4 | 4 | 4 | 1 | 3 | 0 | 0 |
| 7-a | 0.04 | 4 | 5 | 5 | 0 | 3 | 4 | 0 | 0 | 0 | 0 | 0 |
|  | 0.08 | 5 | 5 | 5 | 0 | 4 | 5 | 0 | 0 | 0 | 0 | 0 |
|  | 0.16 | 5 | 5 | 5 | 2 | 5 | 5 | 2 | 0 | 0 | 0 | 0 |
| 8-a | 0.63 | 5 | 5 | 5 | 2 | 5 | 5 | 3 | 0 | 0 | 0 | 0 |
| 10-a | 0.16 | 4 | 5 | 5 | 0 | 2 | 4 | 0 | 0 | 0 | 0 | 0 |
|  | 0.32 | 5 | 5 | 5 | 0 | 4 | 5 | 1 | 0 | 0 | 0 | 0 |
|  | 0.63 | 5 | 5 | 5 | 0 | 5 | 5 | 3 | 0 | 0 | 0 | 0 |
| 12-a | 0.04 | 5 | 4 | 4 | 0 | 3 | 5 | 0 | 0 | 0 | 0 | 0 |
|  | 0.08 | 5 | 5 | 5 | 0 | 4 | 5 | 1 | 0 | 0 | 0 | 0 |
|  | 0.16 | 5 | 5 | 5 | 1 | 5 | 5 | 3 | 1 | 0 | 0 | 0 |
| 20-a | 0.04 | 4 | 2 | 5 | 0 | 3 | 3 | 1 | 0 | 0 | 0 | 0 |
|  | 0.08 | 5 | 3 | 5 | 0 | 4 | 4 | 2 | 0 | 0 | 0 | 0 |
|  | 0.16 | 5 | 4 | 5 | 1 | 5 | 5 | 3 | 1 | 0 | 0 | 0 |
| 22-a | 0.16 | 5 | 2 | 5 | 0 | 5 | 5 | 0 | 0 | 0 | 0 | 0 |
|  | 0.32 | 5 | 3 | 5 | 1 | 5 | 5 | 0 | 0 | 0 | 0 | 0 |
|  | 0.63 | 5 | 4 | 5 | 1 | 5 | 5 | 1 | 0 | 0 | 0 | 0 |
| 24-a | 0.16 | 5 | 5 | 4 | 0 | 3 | 4 | 0 | 0 | 0 | 0 | 0 |
|  | 0.32 | 5 | 5 | 5 | 0 | 4 | 5 | 2 | 0 | 0 | 0 | 0 |
|  | 0.63 | 5 | 5 | 5 | 0 | 5 | 5 | 3 | 1 | 1 | 0 | 0 |
| 25-a | 0.63 | 5 | 5 | 5 | 2 | 4 | 5 | 3 | 1 | 1 | 0 | 0 |

-continued

| No. | Dose (kg/ha) | A | B | D | E | F | G | a | b | c | d | e |
|---|---|---|---|---|---|---|---|---|---|---|---|---|
| 26-a | 0.63 | 4 | 3 | 4 | 0 | 4 | 5 | 0 | 0 | 0 | 0 | 0 |
| 30-a | 2.5 | 3 | 2 | 5 | 4 | 5 | 5 | 4 | 3 | 2 | 1 | 0 |
| 31-a | 2.5 | 2 | 2 | 5 | 4 | 4 | 5 | 2 | 0 | 1 | 0 | 0 |
| 34-a | 2.5 | 5 | 5 | 5 | 4 | 5 | 5 | 3 | 3 | 5 | 0 | 0 |
| 36-a | 2.5 | 5 | 4 | 5 | 5 | 5 | 5 | 1 | 0 | 0 | 0 | 0 |
| 38-a | 0.63 | 5 | 5 | 5 | 2 | 4 | 5 | 2 | 1 | 0 | 0 | 0 |
| 39-a | 2.5 | 5 | 5 | 5 | 4 | 4 | 5 | 3 | 1 | 0 | 0 | 0 |
| 40-a | 0.63 | 5 | 5 | 5 | 3 | 4 | 5 | 2 | 1 | 1 | 0 | 0 |
| 41-a | 2.5 | 5 | 5 | 5 | 4 | 5 | 5 | 4 | 1 | 1 | 0 | 0 |
| 43-a | 2.5 | 3 | 4 | 5 | 3 | 3 | 5 | 0 | 0 | 0 | 0 | 0 |
| 45-a | 0.63 | 5 | 5 | 5 | 0 | 5 | 5 | 0 | 0 | 0 | 0 | 0 |
| 47-a | 0.63 | 5 | 4 | 5 | 3 | 5 | 5 | 3 | 3 | 1 | 0 | 0 |
| 48-a | 0.63 | 5 | 4 | 5 | 1 | 5 | 5 | 5 | 3 | 2 | 0 | 0 |
| 49-a | 2.5 | 5 | 5 | 5 | 2 | 5 | 5 | 3 | 2 | 1 | 0 | 0 |
| 52-a | 2.5 | 5 | 5 | 5 | 3 | 3 | 5 | 4 | 1 | 1 | 0 | 0 |
| 53-a | 2.5 | 5 | 5 | 5 | 3 | 3 | 5 | 5 | 0 | 0 | 0 | 0 |
| 56-a | 2.5 | 5 | 5 | 5 | 3 | 5 | 5 | 4 | 3 | 3 | 3 | 0 |
| 59-a | 0.63 | 5 | 4 | 5 | 5 | 5 | 5 | 1 | 0 | 0 | 0 | 0 |
| 61-a | 2.5 | 5 | 5 | 5 | 4 | 5 | 5 | 1 | 2 | 1 | 0 | 0 |
| 63-a | 0.63 | 5 | 5 | 5 | 3 | 5 | 5 | 3 | 1 | 2 | 0 | 0 |
| 64-a | 2.5 | 5 | 5 | 5 | 2 | 5 | 5 | 3 | 2 | 3 | 1 | 0 |
| 73-a | 0.63 | 5 | 5 | 5 | 3 | 5 | 5 | 5 | 5 | 3 | 0 | 0 |
| 74-a | 0.63 | 5 | 5 | 5 | 2 | 5 | 5 | 3 | 2 | 2 | 0 | 0 |
| 1-b | 5 | — | — | 4 | — | 3 | 5 | — | 0 | 0 | 0 | — |
| 3-b | 5 | — | — | 3 | — | 2 | 4 | — | 0 | 0 | 0 | — |
| 1-c | 0.16 | 5 | 5 | 5 | 2 | 4 | 5 | 5 | 4 | 1 | 4 | 0 |
| 2-c | 0.16 | 5 | 5 | 5 | 4 | 5 | 5 | 5 | 4 | 2 | 0 | 0 |
| 3-c | 0.16 | 5 | 5 | 5 | 2 | 5 | 5 | 5 | 3 | 3 | 1 | 0 |
| 4-c | 0.63 | 4 | 5 | 5 | 2 | 4 | 5 | 1 | 1 | 0 | 0 | 0 |
| 5-c | 0.63 | 5 | 5 | 5 | 1 | 5 | 5 | 1 | 1 | 0 | 0 | 0 |
| 6-c | 0.63 | 2 | 3 | 5 | 0 | 4 | 5 | 1 | 0 | 0 | 0 | 0 |
| 7-c | 0.63 | 5 | 5 | 5 | 2 | 5 | 5 | 4 | 1 | 0 | 1 | 0 |
| 8-c | 10 | 2 | 4 | 5 | 5 | 4 | 5 | 1 | 0 | 0 | 0 | 0 |
| 11-c | 0.63 | 5 | 5 | 5 | 2 | 5 | 5 | 3 | 2 | 1 | 0 | 0 |
| 12-c | 0.16 | 5 | 5 | 5 | 2 | 5 | 5 | 4 | 3 | 0 | 0 | 0 |
| 13-c | 0.16 | 5 | 5 | 5 | 4 | 5 | 5 | 4 | 3 | 3 | 0 | 0 |
| 14-c | 0.63 | 5 | 5 | 5 | 0 | 5 | 5 | 2 | 0 | 0 | 0 | 0 |
| 15-c | 0.63 | 5 | 5 | 5 | 3 | 5 | 5 | 2 | 1 | 0 | 0 | 0 |
| 16-c | 0.63 | 5 | 5 | 5 | 4 | 5 | 5 | 4 | 4 | 3 | 0 | 0 |
| 17-c | 0.63 | 5 | 5 | 5 | 3 | 5 | 5 | 2 | 0 | 0 | 0 | 0 |
| 18-c | 0.16 | 5 | 5 | 5 | 3 | 5 | 5 | 5 | 2 | 0 | 0 | 0 |
| 20-c | 0.63 | 0 | 0 | 3 | 3 | 5 | 5 | 0 | 0 | 0 | 0 | 0 |
| 23-c | 0.63 | 4 | 3 | 5 | 5 | 5 | 5 | 1 | 2 | 0 | 0 | 0 |
| 24-c | 0.16 | 5 | 5 | 1 | 2 | 5 | 5 | 4 | 1 | 1 | 0 | 0 |
| 26-c | 0.63 | 5 | 5 | 4 | 2 | 5 | 5 | 3 | 5 | 3 | 0 | 0 |
| 35-c | 0.16 | 5 | 5 | 5 | 3 | 5 | 5 | 5 | 4 | 0 | 0 | 0 |
| 36-c | 0.16 | 5 | 5 | 5 | 3 | 5 | 5 | 5 | 4 | 4 | 0 | 0 |
| 37-c | 0.16 | 5 | 5 | 5 | 4 | 5 | 5 | 5 | 5 | 4 | 1 |
| 38-c | 0.63 | 5 | 5 | 5 | 3 | 5 | 5 | 5 | 2 | 0 | 1 |
| 39-c | 0.63 | 5 | 5 | 5 | 3 | 5 | 5 | 4 | 4 | 3 | 1 | 0 |
| 40-c | 0.16 | 5 | 5 | 5 | 4 | 5 | 5 | 5 | 5 | 2 | 2 |
| 2-d | 2.5 | 4 | 5 | 5 | 4 | 5 | 0 | 0 | 0 | 0 | 0 |
| 3-d | 2.5 | 5 | 5 | 5 | 5 | 0 | 5 | 0 | 0 | 0 | 0 | 0 |
| 5-d | 2.5 | 3 | 5 | 5 | 5 | 3 | 5 | 3 | 0 | 0 | 0 | 0 |
| 6-d | 10 | 2 | 4 | 5 | 5 | 5 | 5 | 1 | 0 | 0 | 0 | 1 |
| 9-d | 10 | 3 | 5 | 5 | 5 | 5 | 5 | 3 | 1 | 1 | 0 | 0 |
| 1-e | 5 | 5 | 5 | 5 | 2 | 2 | 5 | 5 | 1 | 0 | 0 | 0 |
| 2-e | 2.5 | 3 | 3 | 2 | 1 | 0 | 2 | 0 | 0 | 0 | 0 | 0 |
| 4-e | 5 | 3 | 5 | 5 | 3 | 3 | 5 | 1 | 0 | 0 | 0 | 0 |
| 2-f | 10 | 4 | 5 | 5 | 5 | 5 | 5 | 4 | 0 | 1 | 0 | 0 |
| 1-g | 0.63 | 5 | 5 | 5 | 5 | 5 | 5 | 3 | 0 | 1 | 1 | 0 |
| 7-g | 2.5 | 5 | 5 | 5 | 3 | 5 | 5 | 3 | 1 | 4 | 2 | 1 |
| 9-g | 2.5 | 5 | 5 | 5 | 5 | 5 | 5 | 0 | 0 | 0 | 0 | 0 |
| 11-g | 0.63 | 5 | 5 | 5 | 3 | 5 | 5 | 3 | 2 | 1 | 1 | 0 |
| 12-g | 2.5 | 5 | 4 | 5 | 3 | 5 | 5 | 1 | 1 | 1 | 0 | 0 |
| 13-g | 2.5 | 5 | 3 | 5 | 3 | 5 | 5 | 1 | 0 | 1 | 0 | 0 |
| 14-g | 2.5 | 4 | 4 | 5 | 3 | 5 | 5 | 0 | 0 | 0 | 0 | 0 |
| 15-g | 2.5 | 5 | 4 | 5 | 3 | 5 | 5 | 1 | 1 | 2 | 0 | 0 |
| 16-g | 2.5 | 5 | 4 | 5 | 3 | 5 | 5 | 3 | 3 | 4 | 0 | 0 |
| 17-g | 0.63 | 5 | 5 | 5 | 5 | 5 | 5 | 3 | 1 | 3 | 0 | 0 |
| 18-g | 0.63 | 5 | 5 | 5 | 5 | 5 | 5 | 4 | 2 | 2 | 0 | 0 |
| 19-g | 2.5 | 4 | 5 | 5 | 2 | 5 | 5 | 4 | 3 | 3 | 1 | 0 |

TABLE 16

| No. | Dose (kg/ha) | A | B | C | D | E | F | G | a | b | c | d | e | f |
|---|---|---|---|---|---|---|---|---|---|---|---|---|---|---|
| 1-a | 2.5 | 4 | 2 | 4 | 2 | 5 | 4 | 4 | 3 | 3 | 3 | 3 | 1 | 3 |
| 2-a | 0.16 | 5 | 2 | 4 | 3 | 4 | 4 | 4 | 2 | 3 | 2 | 3 | 0 | 1 |
| | 0.32 | 5 | 3 | 5 | 4 | 5 | 5 | 5 | 2 | 4 | 2 | 3 | 1 | 2 |
| | 0.63 | 5 | 3 | 5 | 4 | 5 | 5 | 5 | 3 | 4 | 3 | 4 | 2 | 2 |
| 3-a | 2.5 | 4 | 3 | 4 | 2 | 3 | 1 | 2 | 1 | 1 | 2 | 3 | 1 | 1 |
| 6-a | 2.5 | 5 | 3 | 5 | 2 | 3 | 3 | 4 | 4 | 4 | 3 | 3 | 1 | 0 |
| 7-a | 0.16 | 5 | 1 | 3 | 2 | 3 | 2 | 3 | 1 | 3 | 0 | 0 | 1 | 0 |
| | 0.32 | 5 | 2 | 3 | 3 | 5 | 3 | 4 | 2 | 3 | 1 | 1 | 1 | 0 |
| | 0.63 | 5 | 3 | 4 | 3 | 5 | 4 | 5 | 3 | 4 | 3 | 3 | 2 | 2 |
| 8-a | 2.5 | 5 | 1 | 5 | 2 | 5 | 4 | 4 | 3 | 4 | 2 | 4 | 2 | 2 |
| 10-a | 2.5 | 5 | 2 | 5 | 3 | 5 | 3 | 4 | 3 | 3 | 3 | 4 | 1 | 3 |
| 12-a | 0.16 | 4 | 3 | 4 | 3 | 2 | 4 | 4 | 1 | 3 | 0 | 0 | 0 | 0 |
| | 0.32 | 5 | 4 | 5 | 4 | 3 | 5 | 5 | 2 | 3 | 0 | 1 | 0 | 1 |
| | 0.63 | 5 | 5 | 5 | 5 | 4 | 5 | 5 | 3 | 4 | 1 | 2 | 1 | 1 |
| 20-a | 0.16 | 5 | 0 | 2 | 4 | 4 | 4 | 4 | 2 | 4 | 0 | 0 | 0 | 1 |
| | 0.32 | 5 | 1 | 2 | 5 | 5 | 5 | 5 | 3 | 5 | 1 | 1 | 0 | 1 |
| | 0.63 | 5 | 2 | 3 | 5 | 5 | 5 | 5 | 4 | 5 | 2 | 2 | 1 | 1 |
| 22-a | 0.63 | 5 | 1 | 2 | 5 | 5 | 5 | 5 | 2 | 4 | 1 | 2 | 0 | 3 |
| 24-a | 0.63 | 5 | 2 | 4 | 4 | 4 | 5 | 5 | 3 | 4 | 1 | 1 | 0 | 1 |
| 30-a | 2.5 | 3 | 0 | 5 | 4 | 4 | 2 | 5 | 3 | 5 | 1 | 3 | 1 | 3 |
| 31-a | 2.5 | 2 | 0 | 5 | 3 | 4 | 5 | 5 | 3 | 4 | 1 | 1 | 0 | 1 |
| 34-a | 2.5 | 5 | 5 | 3 | 5 | 5 | 4 | 4 | 2 | 5 | 1 | 1 | 0 | 3 |
| 36-a | 2.5 | 4 | 0 | 2 | 4 | 4 | 4 | 3 | 0 | 3 | 0 | 0 | 0 | 0 |
| 38-a | 2.5 | 5 | 3 | 4 | 5 | 5 | 3 | 4 | 4 | 5 | 2 | 3 | 0 | 1 |
| 40-a | 2.5 | 5 | 3 | 5 | 5 | 4 | 3 | 4 | 4 | 5 | 3 | 3 | 1 | 0 |
| 47-a | 2.5 | 5 | 2 | 5 | 5 | 3 | 5 | 5 | 4 | 5 | 1 | 3 | 1 | 3 |
| 48-a | 2.5 | 5 | 2 | 5 | 5 | 5 | 5 | 5 | 5 | 5 | 3 | 4 | 1 | 5 |
| 56-a | 2.5 | 5 | 3 | 5 | 3 | 5 | 3 | 5 | 3 | 4 | 1 | 3 | 0 | 3 |
| 59-a | 2.5 | 5 | 2 | 5 | 5 | 5 | 5 | 5 | 4 | 5 | 2 | 3 | 1 | 5 |
| 63-a | 2.5 | 5 | 3 | 3 | 5 | 5 | 5 | 5 | 3 | 5 | 1 | 4 | 1 | 4 |
| 64-a | 2.5 | 5 | 3 | 5 | 5 | 5 | 5 | 5 | 4 | 5 | 3 | 3 | 0 | 4 |
| 73-a | 0.16 | 5 | 5 | 5 | 4 | 2 | 5 | 5 | 4 | 5 | 4 | 4 | 1 | 0 |
| 74-a | 0.63 | 5 | 5 | 3 | 4 | 5 | 5 | 5 | 1 | 5 | 2 | 1 | 1 | 4 |
| 1-c | 0.16 | 5 | 5 | 5 | 5 | 5 | 5 | 5 | 4 | 5 | 1 | 4 | 1 | 5 |
| 2-c | 0.16 | 5 | 5 | 5 | 5 | 4 | 5 | 5 | 4 | 4 | 2 | 3 | 1 | 4 |
| 3-c | 0.16 | 5 | 5 | 5 | 5 | 5 | 5 | 5 | 5 | 4 | 2 | 4 | 1 | 5 |
| 4-c | 0.63 | 5 | 2 | 1 | 3 | 3 | 5 | 5 | 3 | 4 | 0 | 0 | 0 | 4 |
| 5-c | 0.63 | 5 | 5 | 5 | 5 | 5 | 5 | 5 | 3 | 5 | 3 | 3 | 3 | 5 |
| 6-c | 0.63 | 5 | 5 | 4 | 5 | 5 | 5 | 5 | 2 | 5 | 2 | 4 | 2 | 5 |
| 7-c | 0.63 | 5 | 5 | 4 | 5 | 5 | 5 | 5 | 3 | 4 | 1 | 3 | 3 | 4 |
| 8-c | 10 | 2 | 2 | 2 | 3 | 5 | 5 | 5 | 0 | 3 | 0 | 0 | 2 | 4 |
| 11-c | 0.63 | 5 | 5 | 5 | 5 | 5 | 5 | 5 | 3 | 4 | 3 | 3 | 4 | 5 |
| 12-c | 0.16 | 5 | 5 | 4 | 5 | 5 | 5 | 5 | 2 | 5 | 1 | 4 | 3 | 5 |
| 13-c | 0.16 | 5 | 5 | 5 | 5 | 5 | 5 | 5 | 3 | 5 | 3 | 5 | 4 | 5 |
| 14-c | 0.63 | 5 | 5 | 5 | 5 | 2 | 5 | 5 | 2 | 4 | 0 | 0 | 3 | 5 |
| 15-c | 0.63 | 5 | 5 | 4 | 5 | 5 | 5 | 5 | 3 | 5 | 0 | 0 | 2 | 5 |
| 16-c | 0.63 | 5 | 5 | 4 | 5 | 5 | 5 | 5 | 3 | 5 | 3 | 4 | 4 | 5 |
| 17-c | 0.63 | 5 | 4 | 3 | 5 | 5 | 5 | 5 | 1 | 5 | 1 | 3 | 3 | 4 |
| 18-c | 0.16 | 5 | 5 | 4 | 5 | 5 | 5 | 5 | 2 | 5 | 3 | 4 | 4 | 5 |
| 20-c | 0.63 | 1 | 1 | 0 | 0 | 5 | 5 | 5 | 0 | 0 | 0 | 0 | 1 | 2 |
| 21-c | 0.63 | 3 | 5 | 2 | 3 | 5 | 5 | 5 | 1 | 3 | 0 | 0 | 1 | 2 |
| 23-c | 0.63 | 5 | 4 | 3 | 5 | 5 | 5 | 5 | 1 | 1 | 0 | 0 | 1 | 1 |
| 24-c | 0.16 | 5 | 5 | 5 | 2 | 3 | 5 | 5 | 4 | 5 | 1 | 5 | 3 | 3 |
| 26-c | 0.63 | 5 | 5 | 5 | 3 | 4 | 5 | 5 | 5 | 5 | 5 | 5 | 0 | 3 |
| 35-c | 0.16 | 5 | 5 | 5 | 5 | 5 | 5 | 5 | 4 | 5 | 4 | 3 | 3 | 5 |
| 36-c | 0.16 | 5 | 5 | 5 | 5 | 5 | 5 | 5 | 4 | 5 | 4 | 4 | 3 | 5 |
| 37-c | 0.16 | 5 | 5 | 5 | 5 | 5 | 5 | 5 | 5 | 5 | 5 | 5 | 3 | 5 |
| 38-c | 0.63 | 5 | 5 | 5 | 3 | 5 | 5 | 5 | 3 | 5 | 2 | 4 | 2 | 5 |
| 39-c | 0.63 | 5 | 5 | 5 | 5 | 4 | 5 | 5 | 4 | 5 | 2 | 5 | 4 | 4 |
| 40-c | 0.16 | 5 | 5 | 5 | 5 | 5 | 5 | 5 | 5 | 5 | 5 | 5 | 4 | 5 |
| 5-d | 10 | 4 | 5 | 2 | 5 | 5 | 5 | 5 | 2 | 4 | 1 | 3 | 3 | 5 |
| 6-d | 10 | 3 | 4 | 4 | 5 | 5 | 5 | 5 | 2 | 3 | 1 | 2 | 3 | 5 |
| 9-d | 10 | 2 | 4 | 4 | 4 | 5 | 5 | 5 | 0 | 4 | 0 | 3 | 2 | 3 |
| 1-e | 5 | 4 | 2 | 2 | 3 | 5 | 5 | 5 | 3 | 5 | 1 | 2 | 0 | 3 |
| 2-e | 2.5 | 3 | 0 | 0 | 1 | 3 | 0 | 1 | 1 | 0 | 0 | 0 | 0 | 1 |
| 4-e | 5 | 2 | 0 | 4 | 4 | 5 | 5 | 3 | 2 | 3 | 0 | 0 | 0 | 4 |
| 2-f | 10 | 3 | 0 | 2 | 2 | 5 | 5 | 4 | 1 | 3 | 0 | 2 | 0 | 3 |
| 1-g | 2.5 | 5 | 4 | — | 5 | 5 | 5 | 5 | 4 | 4 | 2 | 4 | 1 | 4 |
| 7-g | 2.5 | 2 | 3 | 5 | 5 | 5 | 5 | 5 | 1 | 5 | 2 | 4 | 3 | 5 |
| 9-g | 2.5 | 2 | 3 | 4 | 5 | 5 | 4 | 5 | 0 | 3 | 1 | 5 | 2 | 5 |
| 11-g | 2.5 | 5 | 5 | 3 | 5 | 5 | 5 | 5 | 2 | 5 | 4 | 4 | 3 | 4 |
| 12-g | 2.5 | 4 | 3 | 3 | 3 | 5 | 5 | 5 | 0 | 4 | 1 | 4 | 1 | 3 |
| 13-g | 2.5 | 4 | 2 | 3 | 3 | 5 | 5 | 5 | 0 | 4 | 1 | 4 | 1 | 3 |
| 14-g | 2.5 | 3 | 1 | 3 | 3 | 5 | 5 | 5 | 0 | 4 | 1 | 4 | 1 | 3 |
| 15-g | 2.5 | 4 | 3 | 5 | 5 | 5 | 5 | 5 | 1 | 5 | 3 | 4 | 2 | 4 |
| 16-g | 2.5 | 5 | 3 | 5 | 5 | 5 | 5 | 5 | 2 | 5 | 3 | 5 | 2 | 4 |

TABLE 16-continued

| No. | Dose (kg/ha) | A | B | C | D | E | F | G | a | b | c | d | e | f |
|---|---|---|---|---|---|---|---|---|---|---|---|---|---|---|
| 17-g | 2.5 | 5 | 5 | 5 | 4 | 5 | 5 | 5 | 5 | 5 | 5 | 5 | 1 | 3 |
| 18-g | 2.5 | 5 | 5 | 5 | 4 | 5 | 5 | 5 | 5 | 5 | 5 | 5 | 3 | 5 |
| 19-g | 2.5 | 3 | 2 | 2 | 3 | 5 | 5 | 3 | 1 | 4 | 2 | 3 | 2 | 3 |

TABLE 17

| No. | Dose (kg/ha) | A | H | I | J | K | L | a |
|---|---|---|---|---|---|---|---|---|
| 74-a | 2.5 | 5 | 4 | 4 | 4 | 5 | 4 | 0 |
| 1-b | 4 | 4 | — | 5 | 5 | 5 | — | 0 |
| 1-c | 0.64 | 5 | 5 | 4 | 5 | 5 | 5 | 0 |
| 7-c | 2.5 | 5 | 0 | 4 | 4 | 4 | 4 | 0 |
| 13-c | 0.64 | 5 | 4 | 5 | 4 | 5 | 5 | 0 |
| 50-c | 0.64 | 5 | 4 | 5 | 5 | 5 | 4 | 0 |
| 53-c | 0.16 | 5 | 0 | 4 | 5 | 4 | 2 | 0 |
| 54-c | 0.16 | 5 | 2 | 4 | 4 | 5 | 5 | 0 |

TEST EXAMPLE 4: Test-2 on the herbicidal effects in soil treatment

A plastic box having a length of 21 cm, a width of 13 cm and a depth of 7 cm was filled with a sterilized diluvial soil, and seeds of *Echinochloa crus-galli, Setaria viridis, Avena fatua, Alopecurus myosuroides, Abutilon theophrasti, Xanthium strumarium, Amaranthus viridis,* Ipomoea spp., *Veronica persica, Stellaria media, Zea mays, Oryza sativa, Oryza sativa, Glycine max,* Gossypium spp., *Triticum aestivum* and *Beta vulgaris* were spot-wisely sown, and the soil was covered thereon in a thickness of about 1.5 cm, and then a herbicide solution was applied onto the surface of the soil uniformly so that the active ingredient was distributed at a predetermined concentration. The herbicide solution was prepared by diluting a wettable powder prepared in accordance with the foregoing Formulation Examples with water and applied onto the entire soil surface by a small spray. Three weeks after the application of the herbicidal solution, the herbicidal effects against each weed and the phytotoxicities against each crop plant were visually determined on the basis of the following standard ratings. The results are shown in Table 18.

Some of the compounds of the present invention show selectivity for certain crop plants.
Standard ratings:

5: Growth control rate of more than 90% (almost completely withered)

4: Growth control rate of from 70 to 90%

3: Growth control rate of from 40 to 70%

2: Growth control rate of from 20 to 40%

1: Growth control rate of from 5 to 20%

0: Growth control rate of less than 5% (almost non-effective)

TEST EXAMPLE 5: Test-2 on the herbicidal effects in foliage treatment

A plastic box having a length of 21 cm, a width of 13 cm and a depth of 7 cm was filled with a sterilized diluvial soil, and seeds of *Echinochloa crus-galli, Setaria viridis, Avena fatua, Alopecurus myosuroides, Abutilon theophrasti, Xanthium strumarium, Amaranthus viridis,* Ipomoea spp., *Veronica persica, Stellaria media, Zea mays, Oryza sativa, Glycine max,* Gossypium spp., *Triticum aestivum* and *Beta vulgaris* were spot-wisely sown and the soil was covered thereon in a thickness of about 1.5 cm. When the various weeds and crop plants grew to the 2 or 3 leaf stage, a herbicidal solution was uniformly sprayed on the foliages so that the active ingredient was applied in a predetermined concentration. The herbicidal solution was prepared by diluting a wettable powder prepared in accordance with the above Formulation Examples with water and applied onto the entire surface of the foliages of the weeds and the crop plants by a small spray. Three weeks after the application of the herbicide solution, the herbicidal effects against each weed and the phytotoxicities against each crop plant were visually determined on the basis of the standard ratings described in Test Example 4. The results are shown in Table 19.

TEST EXAMPLE 6: Test-2 on the herbicidal effects during the growing stage in irrigation treatment Into a Wagner pot of 1/5000a, alluvial soil was put, and then water was introduced and mixed to form an irrigated state with a water depth of 4 cm. Seeds of *Echinochloa crus-galli, Scirpus juncoides, Monochoria vaginalis* and *Rotala indica* were sown in the above pot. The pot was placed in a greenhouse at a temperature of from 25° to 30° C., and the plants were cultured. When *Echinochloa crus-galli, Scirpus juncoides, Monochoria vaginalis* and *Rotala indica* reached 1 to 2 leaf stage, a diluted solution of the herbicide was dropwise applied to the water surface by a measuring pipette, so that the dose would be a predetermined level. Three weeks after the dropwise application of the herbicide, the herbicidal effects to various weeds were visually determined on the basis of the standard ratings described in Test Example 4. The results are shown in Table 20.

In Tables 18, 19 and 20, Nos. correspond to Compound Nos. in the Examples, and symbols have the following meanings.

A: *Echinochloa crus-galli* (barnyardgrass)

B: *Setaria viridis* (green foxtail)

C: *Avena fatua* (wild oat)

D: *Alopecurus myosuroides* (black grass)

E: *Abutilon theophrasti* (velvetleaf)

F: *Xanthium strumarium* (common cocklebur)

G: *Amaranthus viridis* (slender amaranth)

H: Ipomoea spp. (mornigglory)

I: *Veronica persica* (Persian speedwell)

J: *Stellaria media* (common chickweed)

a: *Zea mays* (corn)

b: *Oryza sativa* (rice)

c: *Glycine max* (soybean)

d: Gossypium spp. (cotton)

e: *Triticum aestivum* (wheat)

f: *Beta vulgaris* (sugar beet)

TABLE 18

| No. | Dose (kg/ha) | A | B | C | D | E | F | G | H | I | J | a | b | c | d | e | f |
|---|---|---|---|---|---|---|---|---|---|---|---|---|---|---|---|---|---|
| 41-c | 0.16 | 5 | 5 | 3 | 5 | 5 | 5 | 5 | 4 | 2 | 5 | 4 | 5 | 3 | 0 | 3 | 4 |
| 43-c | 0.63 | 5 | 5 | 3 | 5 | 3 | 1 | 5 | 3 | 5 | 5 | 5 | 5 | 1 | 0 | 4 | 4 |
| 44-c | 0.63 | 5 | 5 | 5 | 5 | 5 | 3 | 5 | 5 | 5 | 5 | 5 | 5 | 4 | 0 | 4 | 4 |
| 49-c | 0.63 | 5 | 5 | 2 | 5 | 5 | 2 | 5 | 5 | 5 | 5 | 5 | 5 | 0 | 2 | 2 | 5 |
| 50-c | 0.63 | 5 | 5 | 4 | 5 | 5 | 2 | 5 | 5 | 5 | 5 | 5 | 5 | 1 | 1 | 3 | 5 |
| 51-c | 0.16 | 5 | 5 | 4 | 5 | 5 | 5 | 5 | 5 | 5 | 5 | 5 | 5 | 3 | 1 | 2 | 4 |
| 52-c | 0.63 | 5 | 5 | 5 | 5 | 2 | 5 | 5 | 5 | 5 | 5 | 5 | 5 | 3 | 3 | 4 | 4 |
| 53-c | 0.16 | 5 | 5 | 5 | 5 | 2 | 5 | 5 | 5 | 5 | 5 | 4 | 5 | 0 | 0 | 4 | 5 |
| 54-c | 0.63 | 5 | 5 | 5 | 5 | 5 | 5 | 5 | 5 | 5 | 5 | 5 | 5 | 3 | 1 | 4 | 5 |
| 55-c | 0.63 | 5 | 5 | 5 | 5 | 4 | 5 | 5 | 5 | 5 | 5 | 5 | 5 | 1 | 0 | 5 | 5 |
| 56-c | 0.63 | 5 | 5 | 5 | 5 | 5 | 5 | 5 | 5 | 5 | 5 | 5 | 5 | 3 | 1 | 5 | 5 |
| 20-g | 0.63 | 5 | 5 | 3 | 5 | 5 | 2 | 5 | 3 | 5 | 5 | 4 | 4 | 2 | 0 | 2 | 5 |

TABLE 19

| No. | Dose (kg/ha) | A | B | C | D | E | F | G | H | I | J | a | b | c | d | e | f |
|---|---|---|---|---|---|---|---|---|---|---|---|---|---|---|---|---|---|
| 41-c | 0.16 | 5 | 5 | 4 | 5 | 5 | 5 | 5 | 5 | 1 | 5 | 5 | 3 | 4 | 2 | 2 | 5 |
| 43-c | 0.63 | 5 | 5 | 4 | 5 | 5 | 5 | 5 | 3 | 2 | 5 | 5 | 3 | 0 | 1 | 2 | 5 |
| 44-c | 0.63 | 5 | 5 | 5 | 5 | 5 | 5 | 5 | 5 | 3 | 5 | 5 | 4 | 4 | 3 | 3 | 5 |
| 49-c | 0.63 | 5 | 5 | 2 | 5 | 5 | 5 | 5 | 5 | 5 | 5 | 5 | 2 | 4 | 2 | 1 | 5 |
| 50-c | 0.63 | 5 | 5 | 3 | 5 | 5 | 5 | 5 | 4 | 5 | 4 | 5 | 3 | 4 | 3 | 1 | 5 |
| 51-c | 0.16 | 5 | 5 | 3 | 4 | 5 | 5 | 5 | 5 | 5 | 5 | 4 | 5 | 1 | 2 | 5 | 5 |
| 52-c | 0.63 | 5 | 5 | 5 | 5 | 5 | 5 | 5 | 4 | 2 | 5 | 4 | 4 | 1 | 4 | 5 | 5 |
| 53-c | 0.16 | 5 | 5 | 5 | 5 | 5 | 5 | 5 | 5 | 5 | 5 | 5 | 5 | 5 | 3 | 4 | 5 |
| 54-c | 0.16 | 5 | 5 | 5 | 5 | 5 | 5 | 5 | 5 | 5 | 5 | 5 | 5 | 5 | 3 | 3 | 5 |
| 55-c | 0.16 | 5 | 5 | 5 | 5 | 5 | 5 | 5 | 3 | 5 | 5 | 5 | 5 | 1 | 5 | 5 | 5 |
| 56-c | 0.16 | 5 | 5 | 5 | 5 | 5 | 5 | 5 | 2 | 5 | 5 | 5 | 5 | 1 | 5 | 5 | 5 |
| 20-g | 0.63 | 5 | 5 | 5 | 5 | 5 | 5 | 5 | 4 | 5 | 5 | 5 | 5 | 5 | 3 | 4 | 5 |

TABLE 20

| No. | Dose (kg/ha) | A | H | I | J |
|---|---|---|---|---|---|
| 50-c | 0.64 | 5 | 4 | 4 | 4 |
| 53-c | 0.16 | 5 | 3 | 4 | 2 |
| 54-c | 0.16 | 5 | 4 | 4 | 4 |

INDUSTRIAL APPLICABILITY

Iminosulfonylurea derivatives of the formula (1) of the present invention can be used safely to important crop plants, and they are compounds showing high herbicidal effects against many weeds and thus useful as active ingredients of herbicides.

We claim:

1. An iminosulfonylurea derivative of formula (I) or its salt:

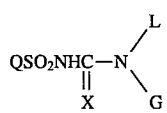

(1)

wherein Q is

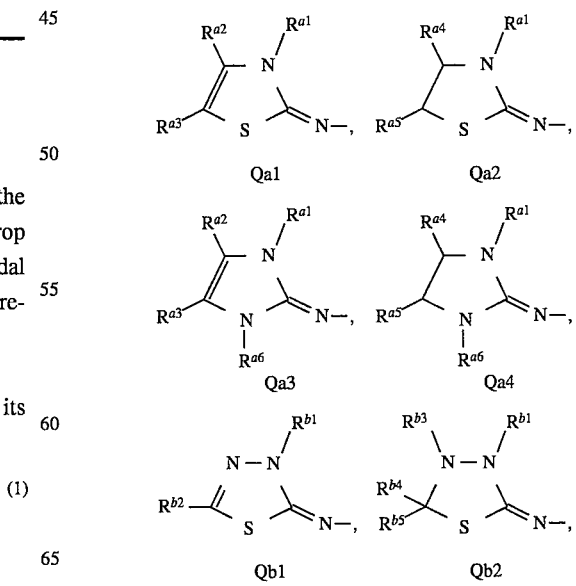

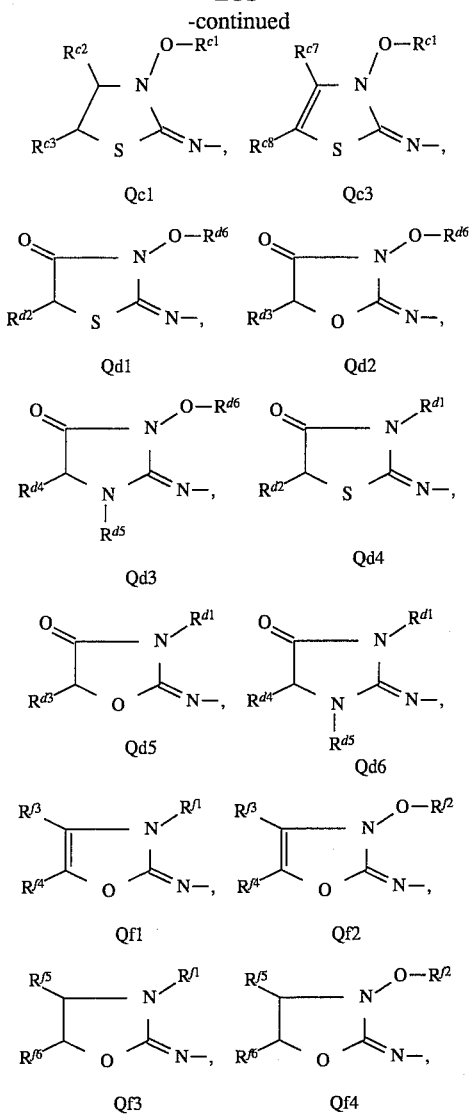

$R^{a1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{a2}$ and $R^{a3}$ which are independent of each other, is a hydrogen atom, a $C_{1-6}$ alkyl group, a mono-, di- or poly-halogeno $C_{1-6}$ alkyl group, a $C_{1-6}$ alkoxy group, a mono-, di or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{a4}$ and $R^{a5}$ which are independent of each other, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{a6}$ is a $C_{1-8}$ alkyl group, a $C_{2-8}$ alkenyl group, a $C_{2-8}$ alkynyl group or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{b1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, $R^{b2}$ is a hydrogen atom, a $C_{1-6}$ alkyl group, a mono-, di- or poly-halogeno $C_{1-6}$ alkyl group, a $C_{1-6}$ alkoxy group, a mono-, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{b3}$ is a $C_{1-6}$ alkyl group, a $C_{2-6}$ alkenyl group or a $C_{2-6}$ alkynyl group, $R^{b4}$ is a hydrogen atom, or a $C_{1-6}$ alkyl group, $R^{b5}$ is a hydrogen atom, or a $C_{1-6}$ alkyl group, $R^{c1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{c2}$ and $R^{c3}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{c7}$ and $R^{c8}$ which are independent of one another, is a hydrogen atom, a $C_{1-6}$ alkyl group, a mono-, di- or poly-halogeno $C_{1-6}$ alkyl group, a $C_{1-6}$ alkoxy group, a mono, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, each of $R^{d2}$, $R^{d3}$ and $R^{d4}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d5}$ is a $C_{1-8}$ alkyl group, a $C_{2-8}$ alkenyl group, a $C_{2-8}$ alkynyl group, or a phenyl group (provided that such a phenyl group may be substituted from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{d6}$ is a $C_{1-8}$ alkyl group, a $C_{2-8}$ alkenyl group, a $C_{2-8}$ alkynyl group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a $C_{1-6}$ alkyl group substituted by a $C_{1-6}$ alkoxy group, a $C_{1-6}$ alkyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a cyano group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), $R^{f1}$ is a $C_{1-8}$ alkyl group, a $C_{3-7}$ cycloalkyl group, a $C_{1-6}$ alkyl group substituted by a $C_{3-7}$ cycloalkyl group, a $C_{3-7}$ cycloalkenyl group, a $C_{1-6}$ alkyl group substituted by a $C_{3-7}$ cycloalkenyl group, a $C_{2-8}$ alkenyl group, a $C_{2-8}$ alkynyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a mono-, di- or poly-halogeno $C_{1-6}$ alkoxy group, a $C_{1-6}$ alkyl group substituted by a mono-, di- or poly-halogeno $C_{2-6}$ alkenyloxy group, a $C_{1-6}$ alkyl group substituted by a mono-, di- or poly-halogeno $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a mono-, di- or poly-halogeno $C_{1-8}$ alkyl group, a mono-, di- or poly-halogeno $C_{2-8}$ alkenyl group, a mono-, di- or poly-halogeno $C_{2-8}$ alkynyl group, a $C_{1-6}$ alkyl group substituted by a cyano group, a $C_{2-6}$ alkenyl group substituted by a cyano group, a $C_{2-6}$ alkynyl group substituted by a cyano group, a $C_{1-6}$ alkyl group substituted by a nitro group, a $C_{2-6}$ alkenyl group substituted by a nitro group, a $C_{2-6}$ alkynyl group substituted by a nitro group, a $C_{1-6}$ alkyl group substituted by a $C_{2-7}$ alkoxycarbonyl group, a $C_{2-6}$ alkenyl group substituted by a $C_{2-7}$ alkoxycarbonyl group, a $C_{2-6}$ alkynyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a mono-, di- or poly-halogeno $C_{2-7}$ alkylcarbonyl group, a $C_{1-6}$ alkyl group substituted by a $C_{3-7}$ alkenylcarbonyl group, a $C_{1-6}$ alkyl group substituted by a $C_{3-7}$ alkynylcarbonyl group, a $C_{1-6}$ alkyl group substituted by a $C_{2-5}$ alkylcarbonyl group substituted by a $C_{1-4}$ alkoxy group, a $C_{1-6}$ alkyl group substituted by a $C_{2-5}$ alkylcarbonyl group substituted by a $C_{1-4}$ alkylthio group, a $C_{1-6}$ alkyl group substituted by a $C_{2-5}$ alkylcarbonyl group substituted by a $C_{1-4}$ alkylsulfinyl group, a $C_{1-6}$ alkyl group substituted by a $C_{2-5}$ alkylcarbonyl group substituted by a $C_{1-4}$ alkylsulfonyl group, a $C_{2-6}$ alkenyl group substituted by a $C_{2-7}$ alkylcarbonyl group, a $C_{2-6}$ alkynyl group substituted by a $C_{2-7}$ alkylcarbonyl group, a $C_{1-6}$ alkyl group substituted by a $C_{1-6}$ alkylsulfamoyl group, a $C_{1-6}$ alkyl group substituted by a $C_{1-6}$ alkoxysulfamoyl group, a $C_{1-6}$ alkyl group substituted by a di($C_{1-3}$ alkyl)sulfamoyl group, a $C_{1-6}$ alkyl group substituted by an N-($C_{1-3}$ alkyl)-N-($C_{1-3}$ alkoxy)sulfamoyl group, a $C_{1-6}$ alkyl group substituted by a $C_{2-7}$ alkylcarbamoyl group, a $C_{1-6}$ alkyl group substituted by a di($C_{1-3}$ alkyl)carbamoyl group, a $C_{1-6}$ alkyl group substituted by a $C_{2-7}$ alkoxycarbamoyl group, a $C_{1-6}$ alkyl group substituted by an N-($C_{1-3}$ alkyl)-N-($C_{1-3}$ alkoxy)carbamoyl group, a $C_{1-6}$ alkyl group substituted by a $C_{1-6}$ alkylamino group, a $C_{1-6}$ alkyl group substituted by a $C_{1-6}$ alkoxyamino group, a $C_{1-6}$ alkyl group substituted by a di($C_{1-3}$ alkyl)amino group, a $C_{1-6}$ alkyl group substituted by an N-($C_{1-3}$ alkyl)-N-($C_{1-3}$ alkoxy)amino group, a $C_{1-6}$ alkyl group substituted by an N-($C_{2-7}$ alkylcarbonyl)-N-($C_{1-6}$ alkyl)amino group, a $C_{1-6}$ alkyl group substituted by an N-($C_{2-7}$ alkylcarbonyl)-N-($C_{1-6}$ alkoxy)amino group, a $C_{1-6}$ alkyl group substituted by an N-($C_{1-6}$ alkylsulfonyl)-N-($C_{1-6}$ alkyl)amino group, a $C_{1-6}$ alkyl group substituted by an N-($C_{1-6}$ alkylsulfonyl)-N-($C_{1-6}$ alkoxy)amino group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-7}$ alkenyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{2-6}$ alkynyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenoxy group (provided that such a phenoxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylthio group (provided that such a phenylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfinyl group (provided that such a phenylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylsulfonyl group (provided that such a phenylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzyloxy group (provided that the phenyl group of such a benzyloxy group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylthio group (provided that the phenyl group of such a benzylthio group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfinyl group (provided that the phenyl group of such a benzylsulfinyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylsulfonyl group (provided that the phenyl group of such a benzylsulfonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a phenylcarbonyl group (provided that such a phenylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by a benzylcarbonyl group (provided that the phenyl group of such a benzylcarbonyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), a $C_{1-6}$ alkyl group substituted by an amino group substituted by a $C_{1-4}$ alkylsulfonyl group, or a $C_{1-6}$ alkyl group substituted by an amino group substituted by a $C_{2-4}$ alkylcarbonyl group, $R^{/2}$ is a $C_{1-8}$ alkyl group, a $C_{2-8}$ alkenyl group, a $C_{2-8}$ alkynyl group, a $C_{1-6}$ alkyl group substituted by a $C_{1-6}$ alkylthio group, a $C_{1-6}$ alkyl group substituted by a $C_{1-6}$ alkylsulfinyl group, a $C_{1-6}$ alkyl group substituted by a $C_{1-6}$ alkylsulfonyl group, a $C_{1-6}$ alkyl group substituted by a $C_{1-6}$ alkoxy group, a $C_{1-6}$ alkyl group substituted by a $C_{2-7}$ alkoxycarbonyl group, a $C_{1-6}$ alkyl group substituted by a $C_{2-7}$ alkylcarbonyl group, a $C_{1-6}$ alkyl group substituted by a cyano group, a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), or a $C_{1-6}$ alkyl group substituted by a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{/3}$ and $R^{/4}$ which are independent of one another, is a hydrogen atom, a $C_{1-6}$ alkyl group, a mono-, di- or poly-halogeno $C_{1-6}$ alkyl group, a $C_{1-6}$ alkoxy group, a mono-, di- or poly-halogeno $C_{1-6}$ alkoxy group, a $C_{1-6}$ alkylthio group, a $C_{1-6}$ alkylsulfinyl group, a $C_{1-6}$ alkylsulfonyl group, a $C_{2-7}$ alkoxycarbonyl group, a $C_{2-7}$ alkylcarbonyl group, a halogen atom, a nitro group, a cyano group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), each of $R^{/5}$ and $R^{/6}$ which are independent of one another, is a hydrogen atom, a $C_{1-8}$ alkyl group, a $C_{2-8}$ alkenyl group, a $C_{2-8}$ alkynyl group, or a phenyl group (provided that such a phenyl group may be substituted by one or more substituents selected from the group consisting of a halogen atom, a trifluoromethyl group, a nitro group, a $C_{1-6}$ alkyl group, a $C_{1-6}$ alkoxy group and a $C_{2-7}$ alkoxycarbonyl group), X is an oxygen atom or a sulfur atom, L is a hydrogen atom, a $C_{1-6}$ alkyl group, a $C_{2-6}$ alkenyl group or a $C_{2-6}$ alkynyl group, G is

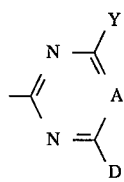

A is a CH group and each of Y and D which are independent of each other, is a $C_{1-4}$ alkyl group, a $C_{1-4}$ alkoxy group, a mono-, di- or poly-halogeno $C_{1-4}$ alkyl group, a mono-, di- or poly-halogeno $C_{1-4}$ alkoxy group, a halogen atom, a $C_{1-4}$ alkylamino group, or a di($C_{1-4}$ alkyl)amino group.

2. The iminosulfonylurea derivative or its salt according to claim 1, wherein Q is

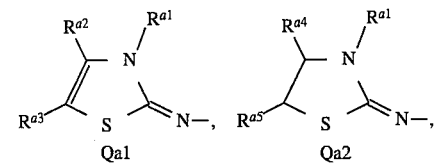

3. The iminosulfonylurea derivative or its salt according to claim 1, wherein Q is

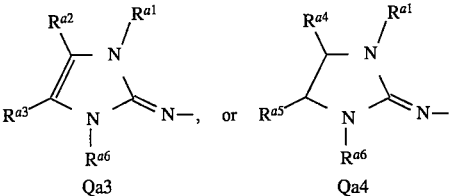

4. The iminosulfonylurea derivative or its salt according to claim 1, wherein Q is

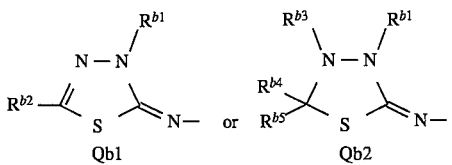

5. The iminosulfonylurea derivative or its salt according to claim 1, wherein Q is

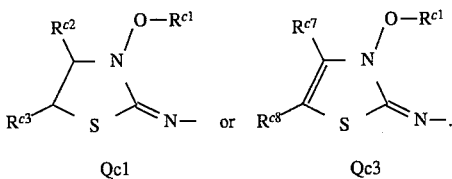

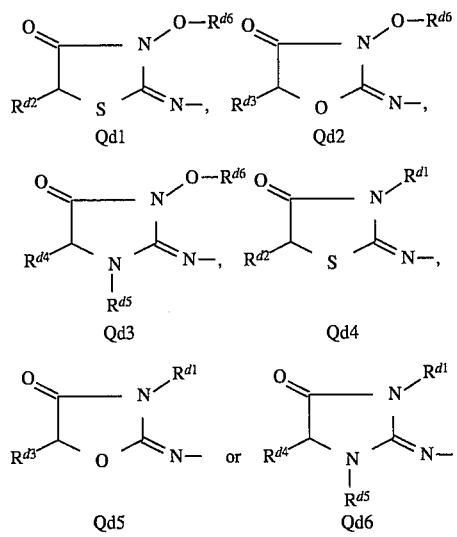

6. The iminosulfonylurea derivative or its salt according to claim 1, wherein Q is

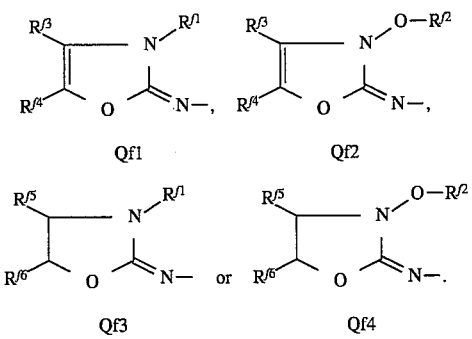

7. A herbicidal and growth control method against weeds, which comprises applying a herbicidally effective amount of an iminosulfonylurea derivative defined in claim 1.

8. A herbicidal and growth control method against weeds, which comprises applying a herbicidally effective amount of an iminosulfonylurea derivative defined in claim 2.

9. A herbicidal and growth control method against weeds, which comprises applying a herbicidally effective amount of an iminosulfonylurea derivative defined in claim 3.

10. A herbicidal and growth control method against weeds, which comprises applying a herbicidally effective amount of an iminosulfonylurea derivative defined in claim 4.

11. A herbicidal and growth control method against weeds, which comprises applying a herbicidally effective amount of an iminosulfonylurea derivative defined in claim 5.

12. A herbicidal and growth control method against weeds, which comprises applying a herbicidally effective amount of an iminosulfonylurea derivative defined in claim 6.

13. A herbicidal composition comprising an effective amount of a compound of the formula (I) as described in claim 1 and an inert carrier.

14. The herbicidal composition of claim 13 wherein Q, in said compound of the formula (I), is

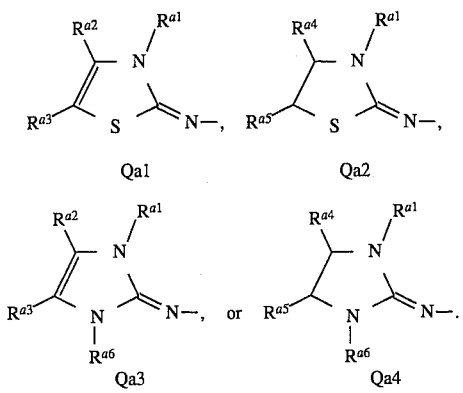
15. The herbicidal composition of claim 13 wherein Q, in said compound of the formula (I), is
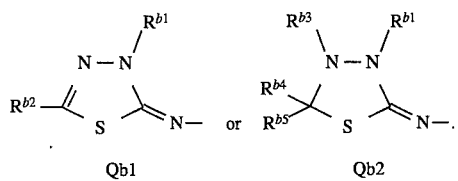
16. The herbicidal composition of claim 13 wherein Q, in said compound of the formula (I), is
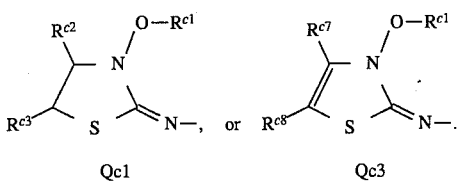
17. The herbicidal composition of claim 13 wherein Q, in said compound of the formula (I), is
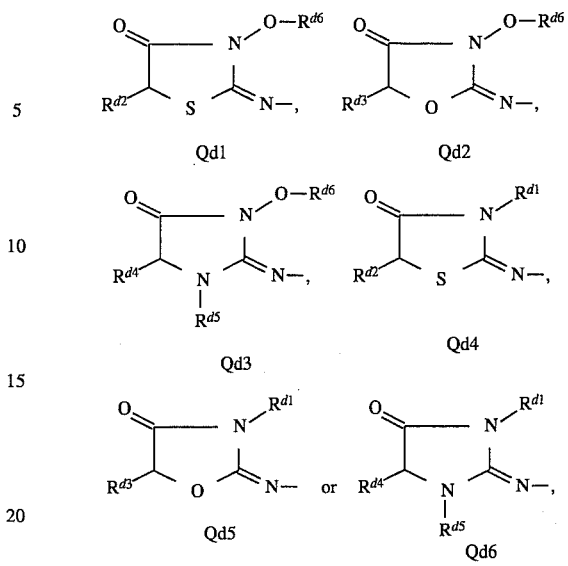
18. The herbicidal composition of claim 13 wherein Q, in said compound of the formula (I), is
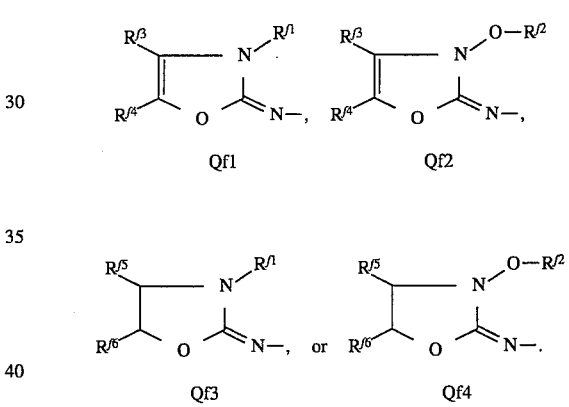
* * * * *

UNITED STATES PATENT AND TRADEMARK OFFICE
CERTIFICATE OF CORRECTION

PATENT NO. : 5,500,406
DATED : March 19, 1996
INVENTOR(S) : Kenzi MAKINO et al.

It is certified that error appears in the above-indentified patent and that said Letters Patent is hereby corrected as shown below:

On the title page, Item [54], the title is incorrect, and in Column 1, lines 1-2, the title is incorrect. It should read:

--[54] IMINOSULFONYLUREA DERIVATIVES AND HERBICIDES--

Signed and Sealed this

Fourth Day of June, 1996

Attest:

BRUCE LEHMAN

Attesting Officer

Commissioner of Patents and Trademarks